(12) United States Patent
Wallace et al.

(10) Patent No.: US 12,310,688 B2
(45) Date of Patent: May 27, 2025

(54) ROBOTIC DELIVERY SYSTEM FOR CARDIAC IMPLANTS

(71) Applicant: Capstan Medical Inc., Santa Cruz, CA (US)

(72) Inventors: Daniel T. Wallace, Waikato (NZ); Travis Schuh, Boulder Creek, CA (US); Neal Tanner, Austin, TX (US); Thomas Nixon, San Jose, CA (US); Evelyn Hayes, Santa Cruz, CA (US); Peter Gregg, Santa Cruz, CA (US)

(73) Assignee: Capstan Medical Inc., Santa Cruz, CA (US)

( * ) Notice: Subject to any disclaimer, the term of this patent is extended or adjusted under 35 U.S.C. 154(b) by 0 days.

(21) Appl. No.: 18/634,439

(22) Filed: Apr. 12, 2024

(65) Prior Publication Data
US 2024/0341872 A1 Oct. 17, 2024

Related U.S. Application Data

(60) Provisional application No. 63/557,392, filed on Feb. 23, 2024, provisional application No. 63/495,978, (Continued)

(51) Int. Cl.
*A61B 34/30* (2016.01)
*A61B 34/00* (2016.01)
(Continued)

(52) U.S. Cl.
CPC ............ *A61B 34/30* (2016.02); *A61F 2/2427* (2013.01); *A61B 2034/301* (2016.02); (Continued)

(58) Field of Classification Search
CPC .............. A61B 34/30; A61B 2034/301; A61B 2034/303; A61B 2034/715; A61F 2/2427; A61M 25/0113; A61M 25/0147
See application file for complete search history.

(56) References Cited

U.S. PATENT DOCUMENTS

| 11,197,755 B1 | 12/2021 | Wallace et al. |
| 11,246,726 B1 | 2/2022 | Wallace et al. |

(Continued)

OTHER PUBLICATIONS

International Search Report and Written Opinion issued in International Application No. PCT/US2024/024401, mailed on Sep. 11, 2024, 12 pages.

*Primary Examiner* — Sarah W Aleman
*Assistant Examiner* — Rachel S Highland
(74) *Attorney, Agent, or Firm* — Dorsey & Whitney LLP

(57) ABSTRACT

A system for delivery of cardiac implants includes a catheter having a handle assembly including a cable control assembly. The handle assembly further includes a tubular body assembly extending distally from the handle assembly and deflectable by operation of the cable control assembly. The system also includes a robot having a linear displacement platform and a carriage coupled to the linear displacement platform. The carriage includes a drive motor assembly and is at least one of linearly displaceable along the linear displacement platform and rotatable relative to the linear displacement platform. The handle assembly is coupled to the carriage such that the cable control assembly interfaces with the drive motor assembly of the carriage to facilitate operation of the cable control assembly by the robot.

30 Claims, 79 Drawing Sheets

Related U.S. Application Data filed on Apr. 13, 2023, provisional application No. 63/543,815, filed on Oct. 12, 2023.

(51) Int. Cl.
  *A61F 2/24* (2006.01)
  *A61M 25/01* (2006.01)

(52) U.S. Cl.
  CPC ... *A61B 2034/303* (2016.02); *A61B 2034/715* (2016.02); *A61M 25/0113* (2013.01); *A61M 25/0147* (2013.01)

(56) References Cited

U.S. PATENT DOCUMENTS

| | | | |
|---|---|---|---|
| 11,654,024 B1 | 5/2023 | Wallace | |
| 11,759,319 B2 | 9/2023 | Wallace et al. | |
| 12,048,639 B2 | 7/2024 | Wallace et al. | |
| 2002/0095175 A1* | 7/2002 | Brock | A61B 34/20 |
| | | | 606/1 |
| 2005/0222554 A1* | 10/2005 | Wallace | A61B 8/12 |
| | | | 606/1 |
| 2010/0312055 A1* | 12/2010 | Konstorum | A61B 1/00066 |
| | | | 600/131 |
| 2018/0311473 A1* | 11/2018 | Laby | A61B 34/30 |
| 2019/0374342 A1* | 12/2019 | Gregg | A61F 2/2439 |
| 2021/0393340 A1* | 12/2021 | Beckman | A61B 17/072 |
| 2023/0108161 A1 | 4/2023 | Yu et al. | |

* cited by examiner

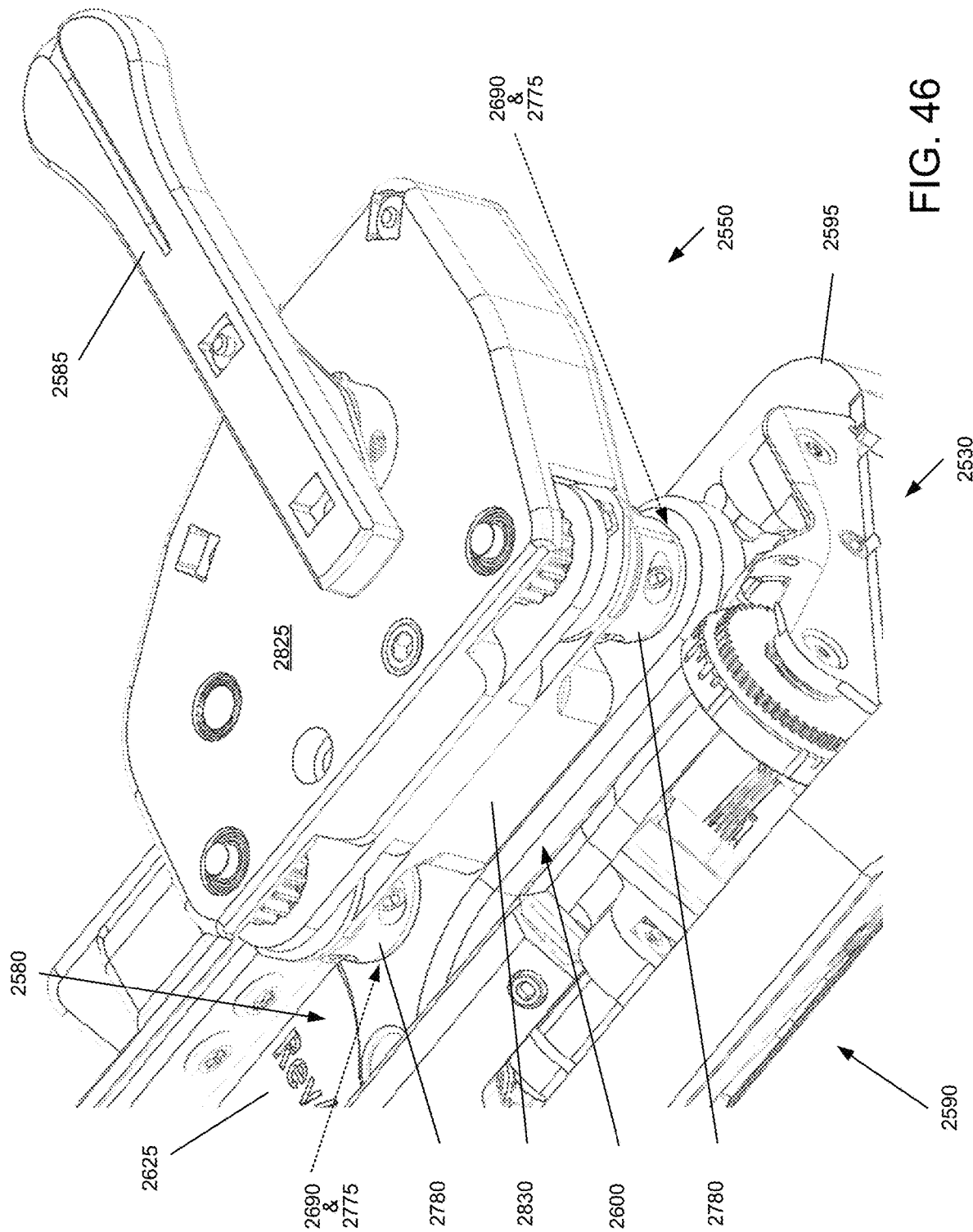

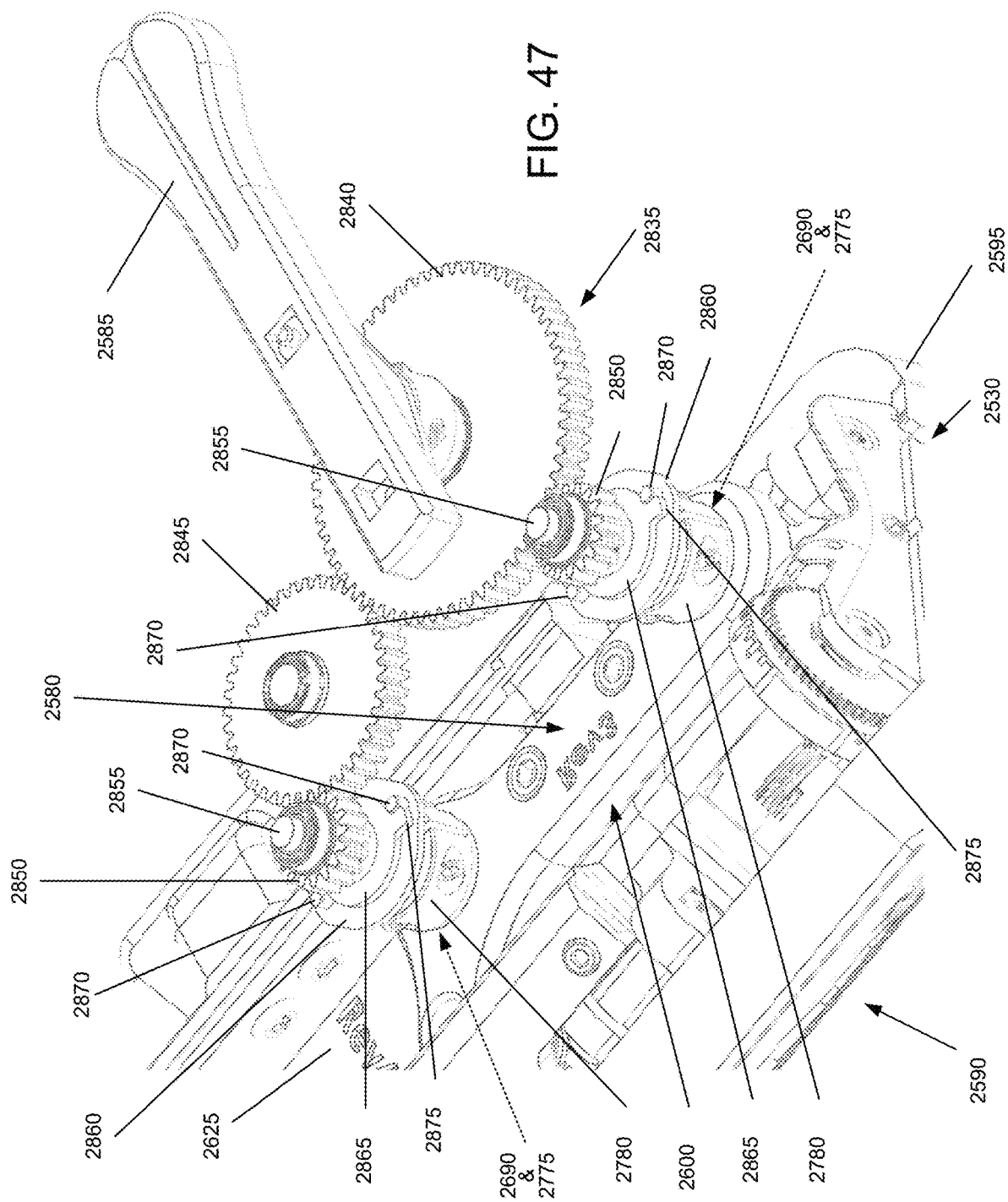

ROBOTIC DELIVERY SYSTEM FOR CARDIAC IMPLANTS

CROSS-REFERENCE TO RELATED APPLICATIONS

This application claims priority to, and incorporates by reference in their entirety, U.S. Provisional Patent Application 63/557,392, which was filed Feb. 23, 2024, and titled "Drive and Control of Robotic Implantation Systems for Cardiac Implants"; U.S. Provisional Patent Application 63/495,978, which was filed Apr. 13, 2023, and titled "Robotic Delivery System for Cardiac Implants"; and U.S. Provisional Patent Application 63/543,815 titled "Robotic Delivery System for Cardiac Implants", which was filed Oct. 12, 2023.

TECHNICAL FIELD

Embodiments of the present disclosure generally relate to delivery systems for surgical implants and, in particular, to robotic transcatheter delivery systems particularly suited for delivery of intracardiac implants, such as mitral valve replacement implants.

BACKGROUND

This disclosure relates generally to a robotic delivery system for medical implants with particular applicability to minimally invasive delivery and deployment of heart valve repair and replacement implants.

Valvular heart disease is a significant burden to patients and healthcare systems, with a prevalence of 2-3% worldwide, and with an increasing prevalence in aging populations. Valvular disease may result from a variety of etiologies, including autoimmune, infective and degenerative causes. The epidemiology of valvular disease also varies with the affected valve, with rheumatic heart disease being the cause worldwide of primary mitral regurgitation and mitral stenosis, but with secondary mitral disease from left ventricular dysfunction being more common in developed countries.

Surgical repair and replacement of cardiac valves present challenges due to the relatively limited workspace for such procedures, the criticality of precision to avoid damage to the heart or impedance of cardiac function, and the tortuous path associated with certain delivery approaches (e.g., transcatheter delivery of mitral valve implants).

Modern robotic surgical systems have proven benefits regarding precision, repeatability, and control culminating in improved patient outcomes (e.g., shorter hospitalizations, reduced pain and discomfort, reduced risks of infection due to smaller incision sites, etc.). Despite these benefits, the application of robotics remains limited in the area of cardiac valve implants and, in particular, transcatheter-based delivery systems.

BRIEF SUMMARY

In one aspect of the present disclosure, a system for delivery of cardiac implants is provided. The system includes a catheter having a handle assembly including a cable control assembly. The handle assembly further includes a tubular body assembly extending distally from the handle assembly and deflectable by operation of the cable control assembly. The system also includes a robot having a linear displacement platform and a carriage coupled to the linear displacement platform. The carriage includes a drive motor assembly and is at least one of linearly displaceable along the linear displacement platform and rotatable relative to the linear displacement platform. The handle assembly is coupled to the carriage such that the cable control assembly interfaces with the drive motor assembly of the carriage to facilitate operation of the cable control assembly by the robot.

In another aspect of the present disclosure, a catheter is provided. The catheter includes a handle assembly and a tubular body assembly extending distally from the handle assembly. The handle assembly further includes a plurality of cable control assemblies, each cable control assembly of the plurality of cable control assemblies operable to deflect a respective portion of the tubular body assembly. The handle assembly is further configured to be selectively coupleable to a robot such that, when coupled to the robot, the cable control assembly interfaces with a drive motor assembly of the robot to facilitate operation of the cable control assembly to deflect the portion of the tubular body.

In yet another aspect of the present disclosure, a robot for use in a catheter-based surgical system is provided. The robot includes a linear displacement platform and a carriage coupled to the linear displacement platform. The carriage is linearly displaceable along the linear displacement platform and rotatable relative to the linear displacement platform and the carriage includes a drive motor assembly such that, when a handle assembly of a catheter is received by the carriage, the drive motor assembly interfaces with a cable control assembly of the catheter.

BRIEF DESCRIPTION OF THE DRAWINGS

FIG. 46 is perspective view of a proximal end of the handle assembly with the manual pull wire assembly interfaced with the top side of the handle assembly.

FIG. 47 is the same view as FIG. 46, except with the housing of the manual pull wire assembly removed for clarity purposes.

DETAILED DESCRIPTION

Figure 1:
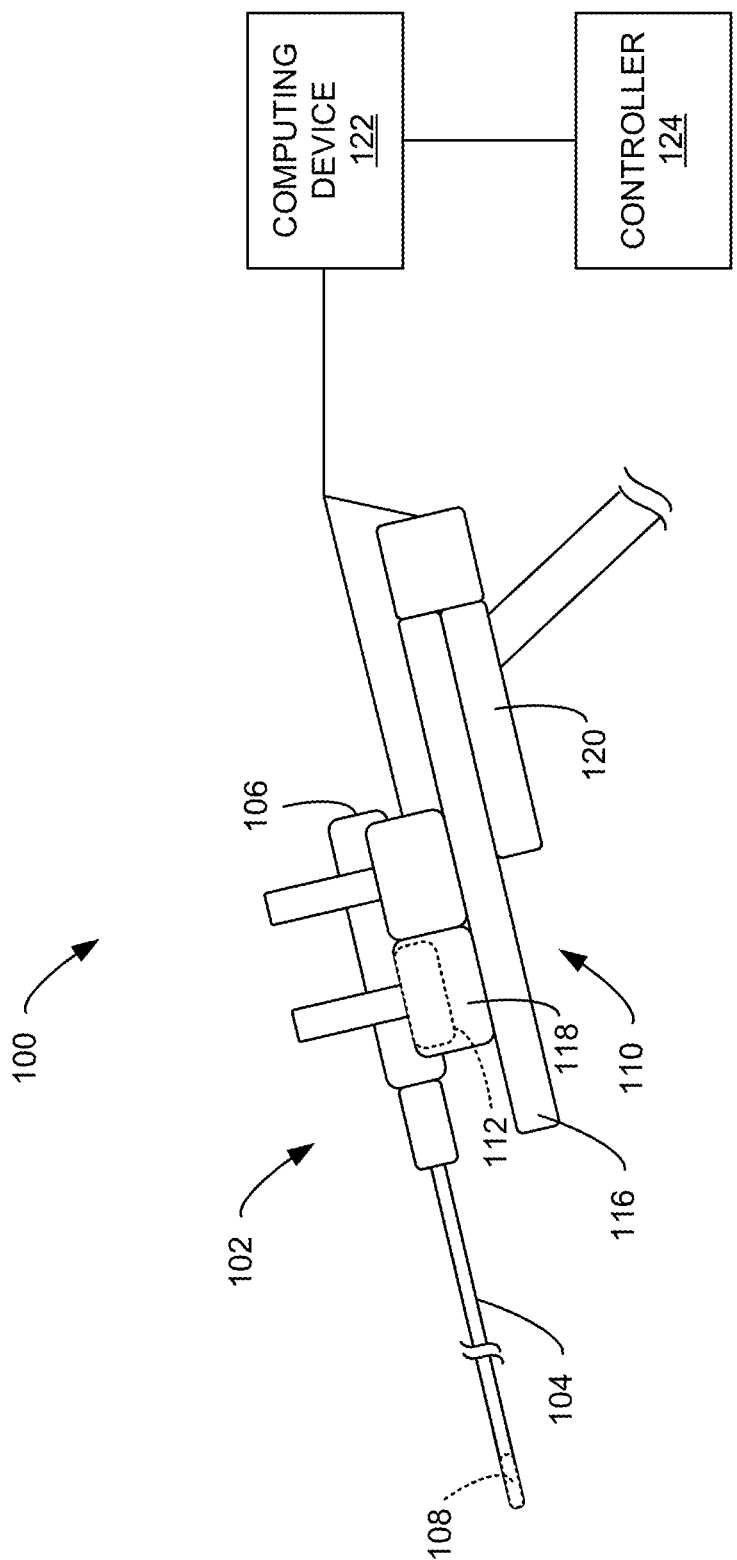
FIG. 1 is a schematic illustration of a robotic implant delivery system according to one implementation of the present disclosure.

Before the embodiments of the present disclosure are described in further detail, it is to be understood that this disclosure is not limited to the specific embodiments described, but rather is extends to equivalents and extensions of those embodiments as would be recognized by those having ordinary skill in the relevant arts. It should also be understood that terminology employed in this disclosure is used for the purpose of describing particular embodiments only and is not intended to be limiting.

Certain aspects of the present disclosure are related to subject matter of other patent filings. For example, aspects of the delivery system of this disclosure and, in particular, elements of the catheter assembly included in implementations of this disclosure are discussed in each of U.S. Pat. No. 11,246,726, which is titled "Systems, Devices and Methods for Delivery Systems", and which was filed on Feb. 18, 2021, and granted on Feb. 15, 2022; and U.S. patent application Ser. No. 17/670,403, which is similarly titled "Systems, devices and methods for delivery systems", and which was filed on Feb. 11, 2022. While not limited to such implants, implementations of this disclosure are particularly suitable for delivery and implantation of heart valve replacement implants, such as the implants of U.S. Pat. No. 11,197,755, which is titled "Systems, devices and methods for folded unibody heart valve stents" and which was filed on Oct. 28, 2020, and granted on Dec. 14, 2021; and U.S. patent application Ser. No. 17/549,690, which is titled "Systems, devices and methods for folded unibody heart valve stents" and was filed Dec. 13, 2021. The entire contents of each of the foregoing patent filings are incorporated by reference into this disclosure in their entirety.

A. OVERVIEW OF TRANSCATHETER IMPLANT DELIVERY

This disclosure includes various systems and methods for a robotic surgical system. The primary implementations discussed relate to catheter-based systems and, in particular, robotic delivery systems configured for transcatheter cardiac implant delivery, such as transcatheter mitral valve replacement delivery.

While specific steps for transcatheter mitral valve replacement implant procedures may vary depending on the implant and equipment being used, the process generally involves delivering the implant via a transfemoral approach. Such approaches involve making an incision in the femoral vein and delivering a guidewire along the femoral vein and into the right atrium via the inferior vena cava. The guidewire is then made to puncture the atrial septum and enter the left atrium.

Following insertion and placement of the guidewire, the valve implant is delivered to the left atrium with a transcatheter delivery device aided by the guidewire. The implant is typically disposed on a distal end of the transcatheter deliver device. To ensure proper placement of the implant, the distal end makes a series of bends as it navigates to the implantation location within the left atrium. More specifically, following insertion of the distal end into right atrium via the inferior vena cava, a proximal steering section of the distal end is bent along the lateral plane as the distal end is advanced toward and through the atrial septum and into the left atrium. This proximal bend is typically approximately 90 degrees such that the tip of the distal end including the implant points in approximately lateral direction following entry into the left atrium. Once in the left atrium, a distal steerable section of the distal end may then be bent along the lateral plane such that the distal tip and implant is oriented to point in a direction approximately normal to the mitral annulus. A clinician may then advance, deploy, and release the implant within the mitral annulus and withdraw the transcatheter delivery device from the patient.

The foregoing is a broad generalization of mitral valve implant delivery. Due to the inherent complexities and variations of the heart, proper alignment of the implant for delivery generally requires not only the macro-level bends noted above, but subtle changes to insertion and roll of the delivery device, bending of the distal end in directions other than the lateral plane, and similar adjustments.

B. SYSTEM OVERVIEW

FIG. 1 is a schematic illustration of a robotic implant delivery system 100 according to one implementation of the present disclosure. Robotic implant delivery system 100 includes an implant delivery assembly 102 including a catheter assembly 104 and a handle assembly 106. During operation, an implant 108, such as a cardiac valve replacement or repair implant, is coupled to a distal end of catheter assembly 104 for delivery to an implantation location within a patient. Catheter assembly 104 is actuatable by manipulating control elements of handle assembly 106. For example, in certain implementations, catheter assembly 104 is cable-driven and handle assembly 106 includes control elements for retracting, paying out, or otherwise modifying tension on cables of catheter assembly 104 to drive catheter assembly 104. Handle assembly 106 may further include additional control elements for changing insertion of catheter assembly 104, extension and retraction of elements of catheter assembly 104 (e.g., sheaths for covering the distal end of catheter assembly 104 and implant 108 during delivery of implant 108 and catheter assembly 104 during extraction of catheter assembly 104 following implantation of catheter assembly 104), and controls for manipulating implant 108 during implantation (e.g., for selective furling or unfurling of implant 108 during deployment and placement).

Robotic drive and control of handle assembly 106 and its various control elements is facilitated by a drive assembly 110. Drive assembly 110 includes one or more motors configured to engage and drive at least some of the control elements of handle assembly 106 and corresponding controllers, drives, and other electronic components for facilitating operation of the motors. For example, in certain implementations, handle assembly 106 includes multiple spools, each spool coupled to and corresponding to a cable for manipulating catheter assembly 104. In such implementations, drive assembly 110 includes a motor for driving a respective one of the spools of handle assembly 106. To the extent handle assembly 106 include other control elements as noted above, drive assembly 110 can include additional motors for manipulating such control elements; however, this disclosure contemplates that at least some of the control elements of handle assembly 106 can be manually controlled as opposed to being motor driven.

In at least certain implementations of this disclosure, drive assembly 110 includes one or more motor modules, such as motor module 112, such that robotic implant delivery system 100 may be readily adapted for use with different implant delivery systems and other robotic surgical devices. In implementations including multiple motor modules, each motor module may be a modular assembly including at least one motor, motor drive and control electronics for the at least one motor, and mechanical features for coupling to control elements of handle assemblies, such as handle assembly 106.

Whether including one or multiple motor modules, drive assembly 110 may further include a carriage base 116 and one or more carriages, such as carriage 118. In general, each carriage is configured to couple to and support a corresponding motor module of drive assembly 110. In implementations in which drive assembly 110 includes multiple motor modules (e.g., motor module 112), drive assembly 110 may include a carriage for each motor module. So, for example, in an implementation including two motor modules, drive assembly 110 can include two carriages, each coupled to and supporting a respective one of the motor modules.

During an implantation or other surgical procedure, carriage base 116 is generally maintained stationary during use, such as by coupling carriage base 116 to a structural mount 120, e.g., a mechanical arm configured to be mounted to a patient bed or other equipment in the operating room. Carriages of drive assembly 110, however, may be configured to be moved relative to carriage base 116. For example, in certain implementations, the carriages slide longitudinally along carriage base 116. Such sliding along carriage base 116 can be used to establish an initial spacing between carriages to accommodate different handle assembly configurations during setup of robotic implant delivery system 100. During the implantation procedure, longitudinal translation of carriages relative to carriage base 116 can also allow a clinician to change insertion of catheter assembly 104.

While this disclosure contemplates that carriage base 116 may be non-motorized and rely on manual adjustment of the carriages, implementations of this disclosure generally include some motorized functionality of carriage base 116 to translate carriages relative to carriage base 116 under computer control. For example, carriage base 116 may include respective and independently controllable screw drives for each carriage. In such implementations, carriage base 116 includes a motor and a threaded shaft coupled to the motor and extending along a length of carriage base 116. The threaded shaft threadedly engages a nut or similar structure coupled to the carriage such that rotation of the threaded shaft by the motor translates the carriage. Accordingly, by actuating a particular screw drive, the longitudinal position of the corresponding given carriage relative to carriage base 116 can be adjusted.

In addition to longitudinal position, certain implementations of this disclosure also permit rotation of carriages. For example, in certain implementations and for each carriage, carriage base 116 can include a motor coupled to and configured to drive a splined shaft. The splined shaft, in turn, engages a splined surface of the carriage such that actuation of the motor results in rotation of the carriage.

Each carriage can be coupled to a first shaft or other drive for translating the carriage relative to carriage base 116 and a second shaft or other drive for rotating the carriage, each drive powered by a corresponding motor. Alternatively, a single motor can be used to control both translation and drive by selectively switching which shaft is driven by the motor.

Robotic implant delivery system 100 further includes a computing device 122 in communication with and configured to control drive assembly 110. Among other things, computing device 122 generates and transmits control signals to actuate the motors of drive assembly 110. Computing device 122 is further configured to receive and process sensor data collected from various sensors of robotic implant delivery system 100, including, but not limited to sensors for measuring tension on spools and other components of handle assembly 106, detecting position and movement of components of catheter assembly 104 (e.g., a distal portion of catheter assembly 104 including implant 108), and detecting various fault and failure scenarios.

In addition to communicating with drive assembly 110, computing device 122 is further configured to present an interface for interacting with robotic implant delivery system 100. So, for example, computing device 122 may include various output devices, such as a display or speakers, for communicating information to the clinician.

Computing device 122 may further include various input devices for receiving commands from the clinician. In addition to conventional input devices (e.g., keyboards, microphones, computer mice, etc.), computing device 122 can include a controller 124 configured for intuitive operation of robotic implant delivery system 100 and, in particular, manipulation and control of catheter assembly 104 to facilitate delivery and implantation of implant 108.

In certain implementations, computing device 122 receives data from and communicates with other operating room capital equipment. For example, computing device 122 can connect to and communicate with imaging equipment such as, but not limited to, ultrasonography and fluoroscopy machines, e.g., by receiving images and imaging-related data from such equipment. Imaging-related data may include, for example, position and orientation information for the imaging equipment to provide additional detail regarding a given image. During operation, computing device 122 can present the images and imaging-related data collected from the imaging equipment to the clinician.

In at least certain implementations, multiple carriages may support a single handle assembly. In such cases, the carriages coupled to and supporting the handle assembly may be locked relative to each other such that translation, rotation, or other similar manipulation of the carriages occurs simultaneously. In manual implementations, locking of the carriages may be by virtue of the handle assembly extending between and coupling to each of the carriages. Alternatively, the carriages to be locked can include mating components or be configured to receive respective portions of a coupling. In computer-controlled implementations, control and movement of the carriages may be locked within software such that the same control commands are sent to the motors driving the carriages simultaneously.

Figure 2:
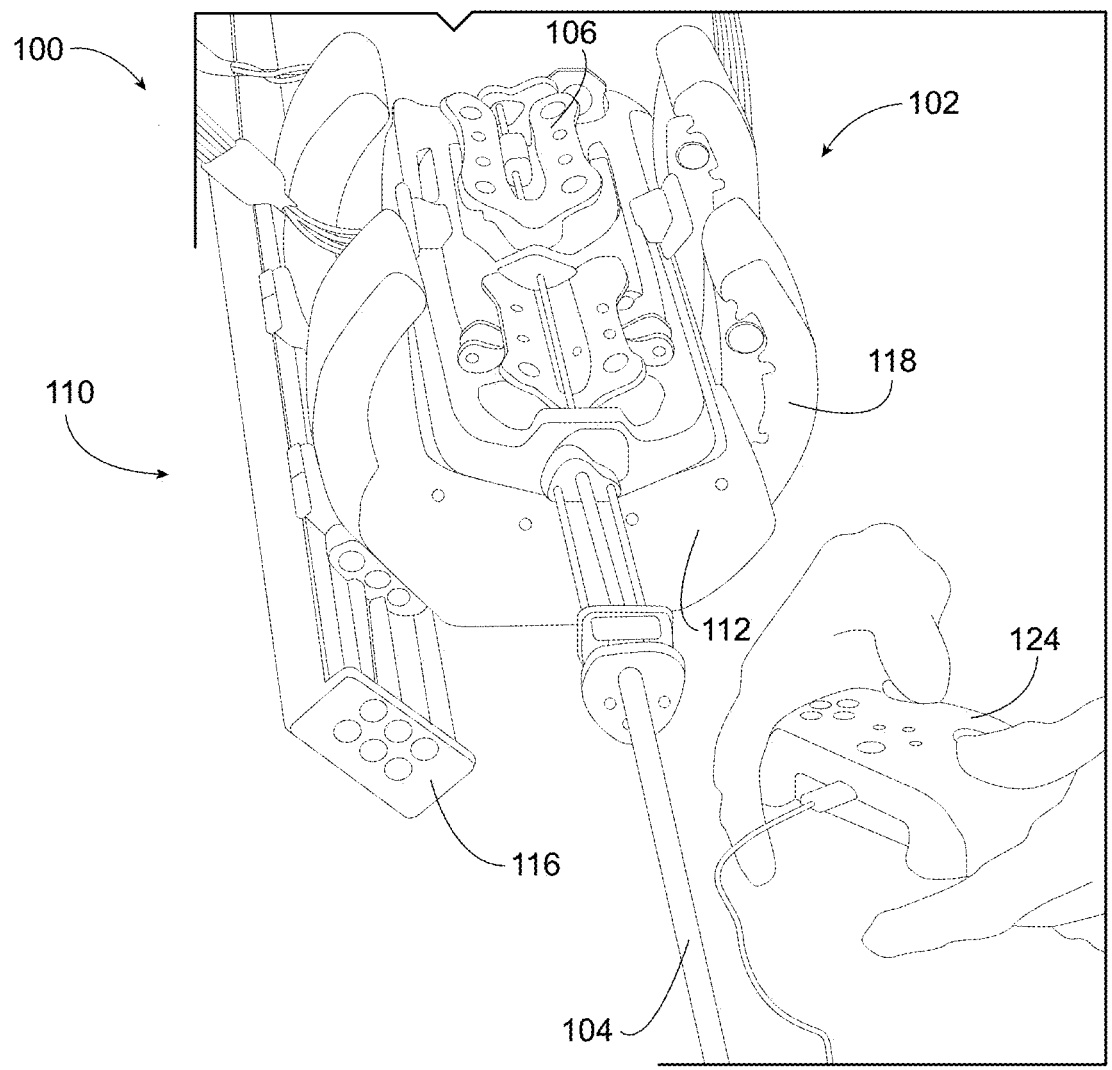
FIG. 2 is a perspective view of another implementation of a robotic implant delivery system according to this disclosure.

FIG. 2 is a perspective view an implementation of robotic implant delivery system 100. As shown, robotic implant delivery system 100 includes implant delivery assembly 102, which further includes each of catheter assembly 104 and handle assembly 106. Handle assembly 106 is coupled to and supported by drive assembly 110 and, more specifically, by a pair of motor modules (e.g., motor module 112). Each motor modules is further coupled to and supported by a respective carriage (e.g., carriage 118) with each carriage coupled to and supported by carriage base 116. As previously discussed, each carriage is both longitudinally translatable along carriage base 116 and rotatable. In the implementation shown in FIG. 2, handle assembly 106 spans two motor modules and carriages. Accordingly, translation and rotation of the carriages to which handle assembly 106 is coupled is configured to occur simultaneously in response to control signals received from computing device 122 (not shown in FIG. 2). As illustrated, computing device 122 may generate such control signals in response to commands input by a user/clinician using controller 124.

C. IMPLANT DELIVERY ASSEMBLY—CATHETER AND HANDLE ASSEMBLIES

Figure 3:
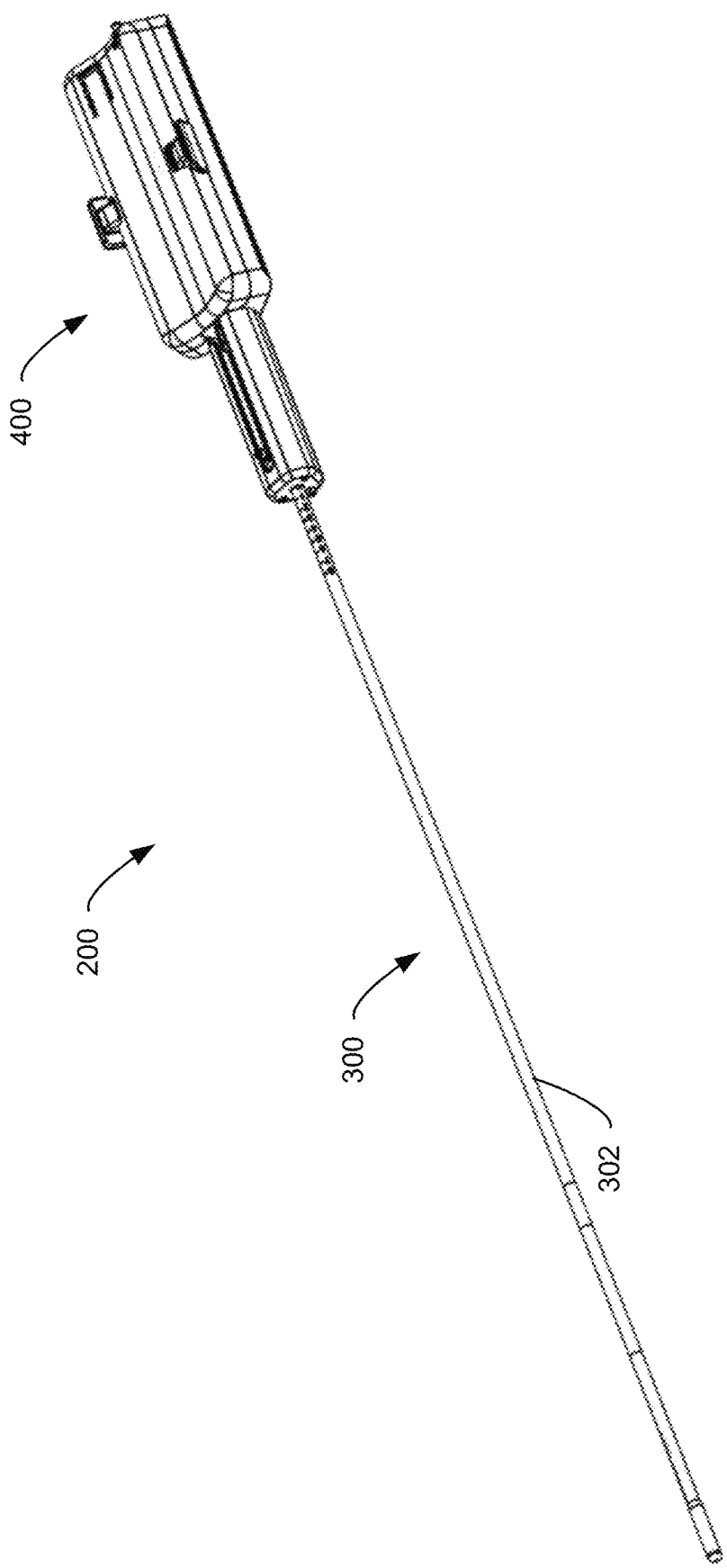
FIG. 3 is an isometric view of an example implant delivery assembly according to the present disclosure.

FIG. 3 is an isometric view of an example implant delivery assembly 200 according to the present disclosure. Implant delivery assembly 200 generally corresponds to implant delivery assembly 102, discussed above. As illustrated, implant delivery assembly 200 includes each of a catheter assembly 300 and a handle assembly 400 with catheter assembly 300 supported by and extending distally from handle assembly 400. As noted above in the context of FIGS. 1 and 2, handle assembly 400 is configured to be coupled to a motor assembly and includes various components controllable by the motor assembly to actuate catheter assembly 300.

In at least certain implementations, catheter assembly 300 may be substantially similar to the catheter assembly included in the implant delivery system disclosed in each of U.S. Pat. No. 11,246,726 (the '726 patent) and U.S. patent application Ser. No. 17/670,403, which are incorporated herein by reference, albeit with the mechanical controls disclosed in those filings substantially replaced with the robotic control systems of the present disclosure.

As described in detail in the '726 patent, catheter assembly 300 generally includes an internal catheter surrounded by an external sheath. The catheter is semi-rigid with the exception of an articulable distal end. In certain implementations, the articulable distal end may include two independently articulable sections, which are referred to in this disclosure as the distal steering portion and the proximal steering portion.

Each steerable portion of the catheter is actuatable by applying tension to cables extending from handle assembly 400 to the steerable portions of the catheter. For purposes of this disclosure and to distinguish them from other cables and tension members that may be included in robotic implant delivery system 100, cables used for articulating the catheter of catheter assembly 300 are referred to in this disclosure as "tendons".

Tendons in implementations of this disclosure are generally provided in antagonistic pairs to provide controlled movement and increased responsiveness of the steerable catheter portions. Tendons of a given antagonistic pair are disposed on and extend along opposite sides of the catheter to their respective steerable sections. Bending of the catheter is achieved by applying tension to and retracting a first tendon of the antagonistic pair in the direction of the desired bend. As the first tendon is retracted, the second tendon may be extended to account for lengthening of the outside of the bend. Notably, extension of the second tendon is preferably done while maintaining tension on the second tendon (e.g., by controlled unspooling) to improve control of bending and to improve responsiveness to a change in bending direction by reducing or eliminating slack in the second tendon.

Each steerable portion of the catheter is configured to bend along one or more planes, with each plane corresponding to a bending degree-of-freedom (DOF) for the catheter. Individual steerable portions may be bendable along multiple planes and, as a result, may correspond to multiple bending DOFs of the catheter. For example, in certain implementations of robotic implant delivery system 100 discussed in this disclosure, the distal section of catheter assembly 300 may include a two-way bending distal steerable portion and a one-way bending proximal steerable portion. More specifically, the distal steerable portion may be configured to bend in each of a lateral plane and an anterior/posterior plane orthogonal to the lateral plane while the proximal steerable portion may be configured to also bend in the lateral plane. Examples of catheter constructions for achieving such articulation are described in detail in the '726 patent.

As discussed in further detail below, robotic implant delivery system 100 may include DOFs in addition to the bending DOFs of catheter assembly 300. For example, robotic implant delivery system 100 may have a DOF corresponding to extension and retraction of the external sheath of catheter assembly 300 and a DOF corresponding to furling/unfurling or similar actuation of the implant to be delivered by robotic implant delivery system 100. As discussed below in further detail, in the example implementations of this disclosure, the DOFs corresponding to sheath extension/retraction and implant actuation are provided by electronically controlled motors coupled to handle assembly 400 and corresponding components of handle assembly 400 (e.g., gears and shafts) configured to convert actuation of the motors to corresponding movement of robotic implant delivery system 100 in the corresponding DOF.

Additional DOFs may correspond to the base or assembly on which implant delivery assembly 200 is mounted, e.g., drive assembly 110, shown in FIG. 1). For example, handle assembly 400 may be coupled to and supported by a drive assembly capable of changing each of insertion and rotation of handle assembly 400 and, by extension catheter assembly 300, thereby providing at least two additional DOFs for the robotic implant delivery system. So, for example, an example implementation in which catheter assembly 300 includes three bending DOFs, a sheath extension/retraction DOF, an implant articulation (e.g., furl/unfurl) DOF, and each of a roll and insertion DOF provided by the drive assembly would include a total of seven DOFs. This disclosure also contemplates that additional DOFs may be provided by structural equipment to which robotic implant delivery system 100 is coupled, such as mounting arms or similar actuatable structures.

Figure 4:
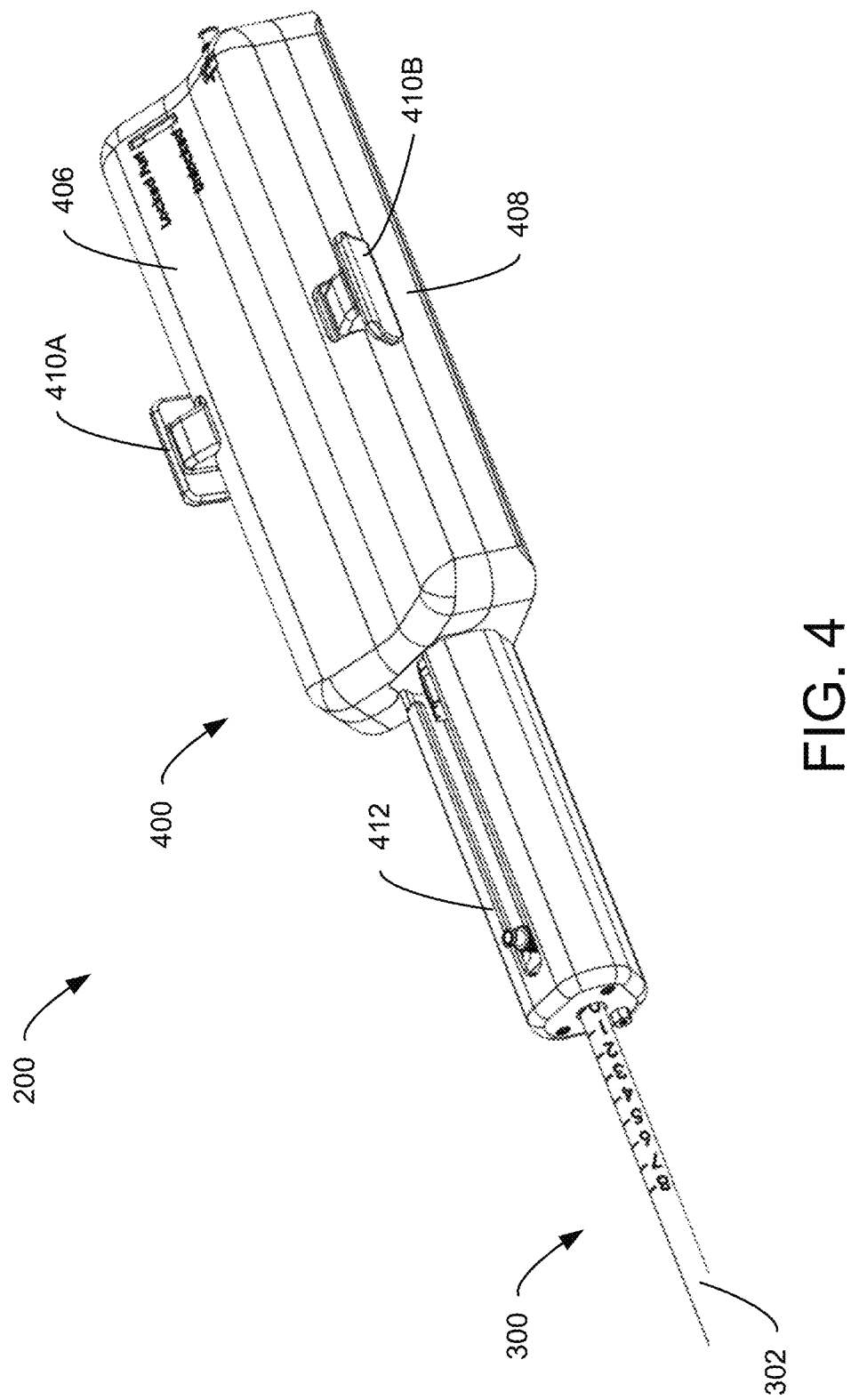
FIG. 4 is a detailed view of a handle assembly of the example implant delivery assembly of FIG. 3.
Figure 5:
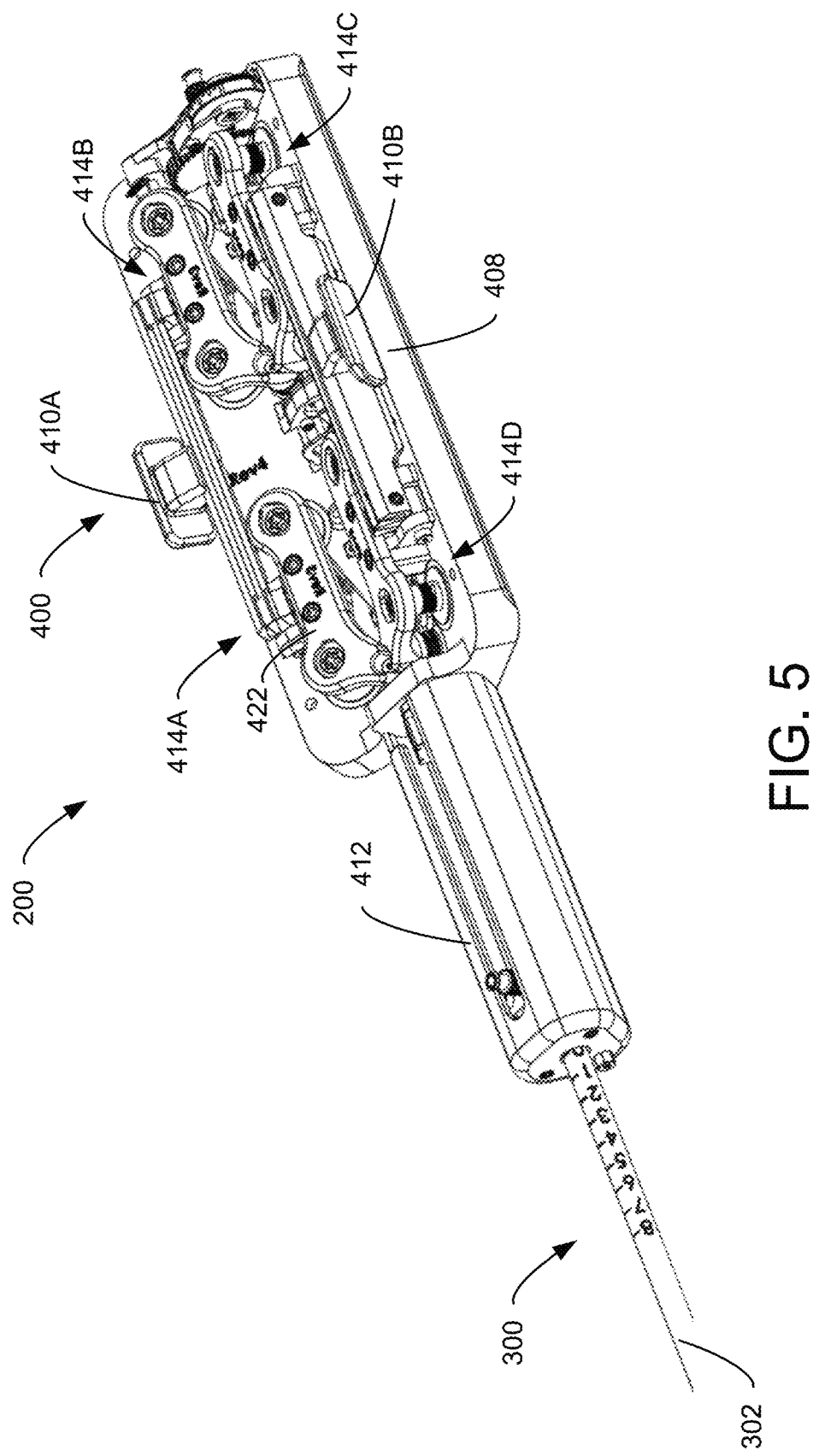
FIG. 5 is an alternative detailed view like FIG. 4 with a cover of the handle assembly removed.
Figure 6:
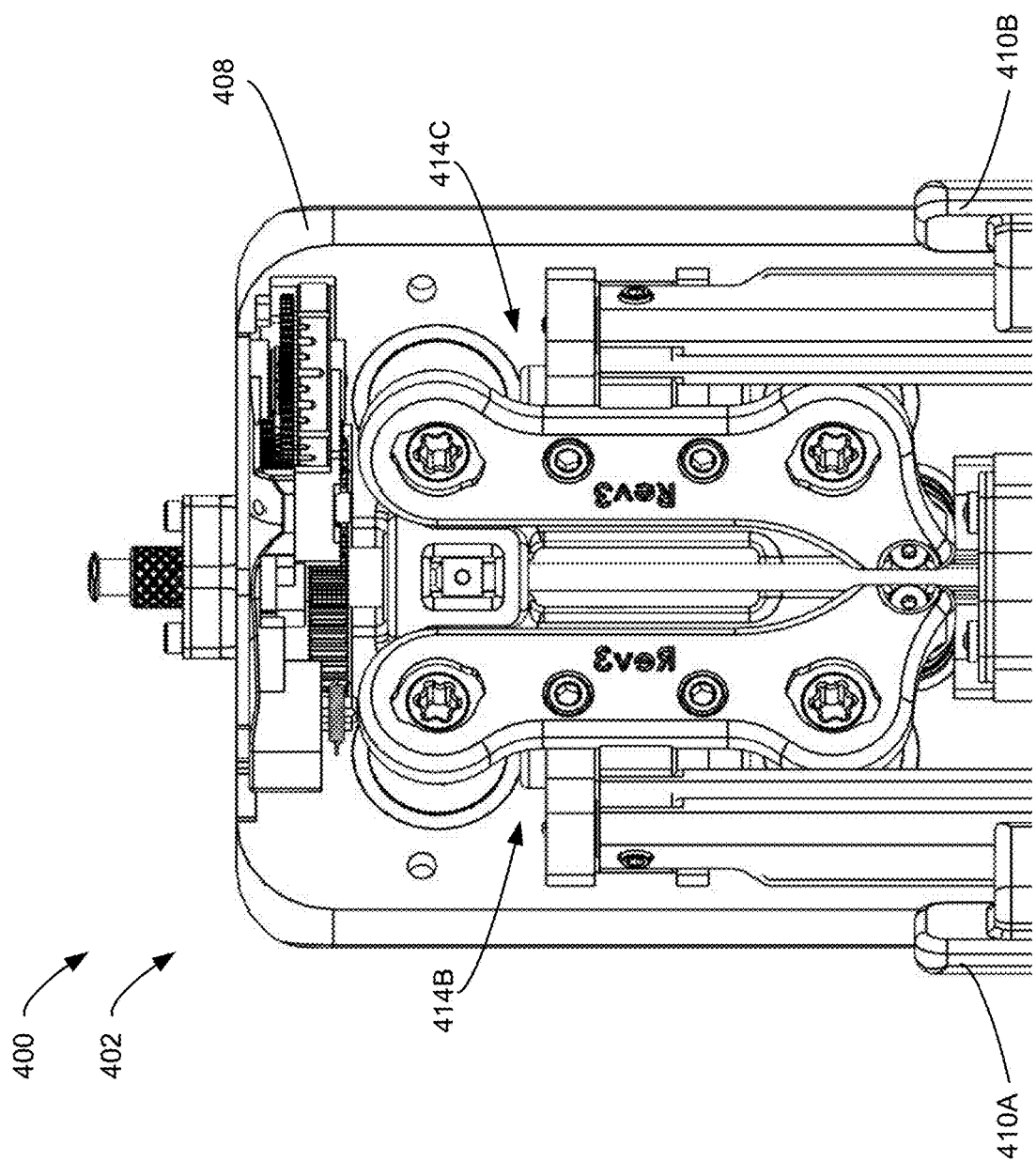
FIG. 6 is a partial top view of a proximal portion of the handle assembly of FIG. 4 with the cover removed.
Figure 7:
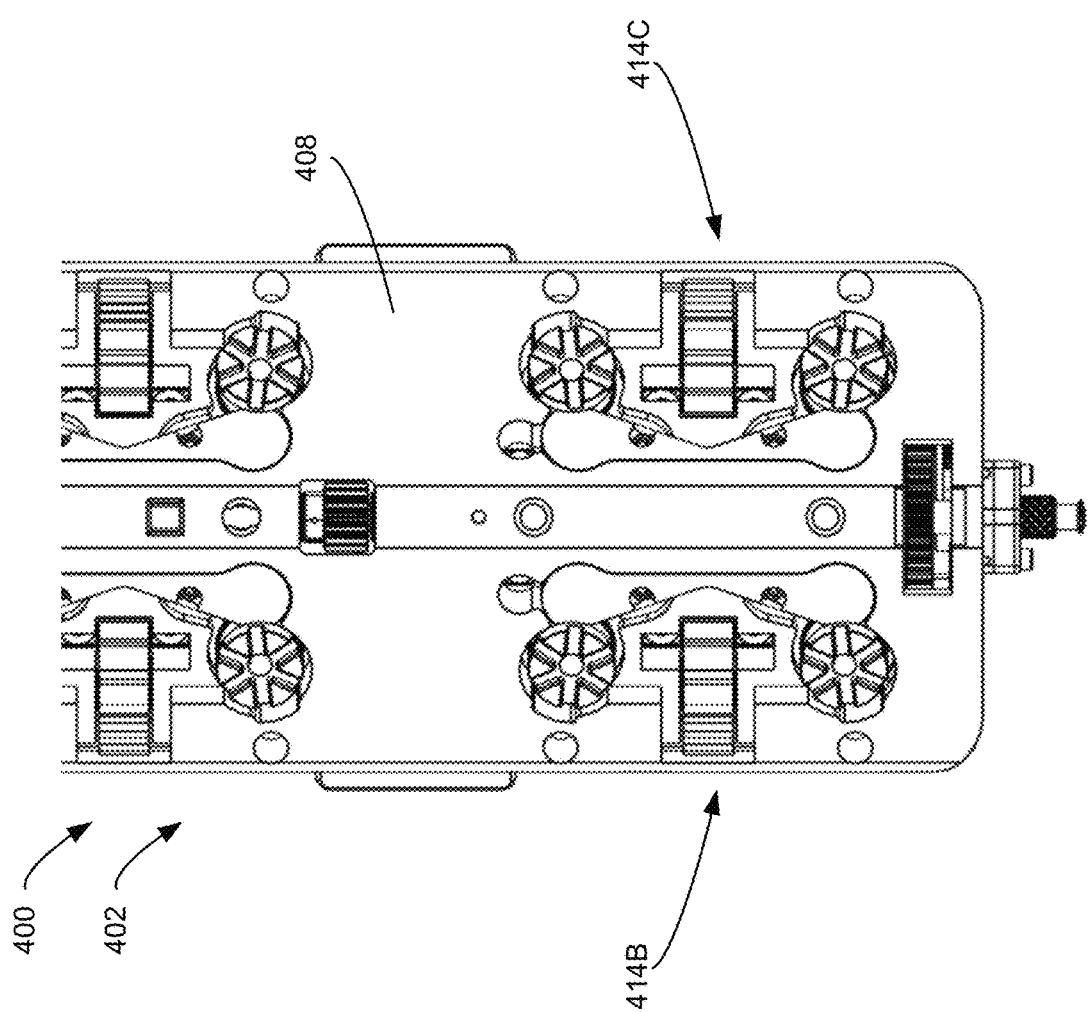
FIG. 7 is a partial bottom view of the proximal portion of the handle assembly of FIG. 4.
Figure 8:
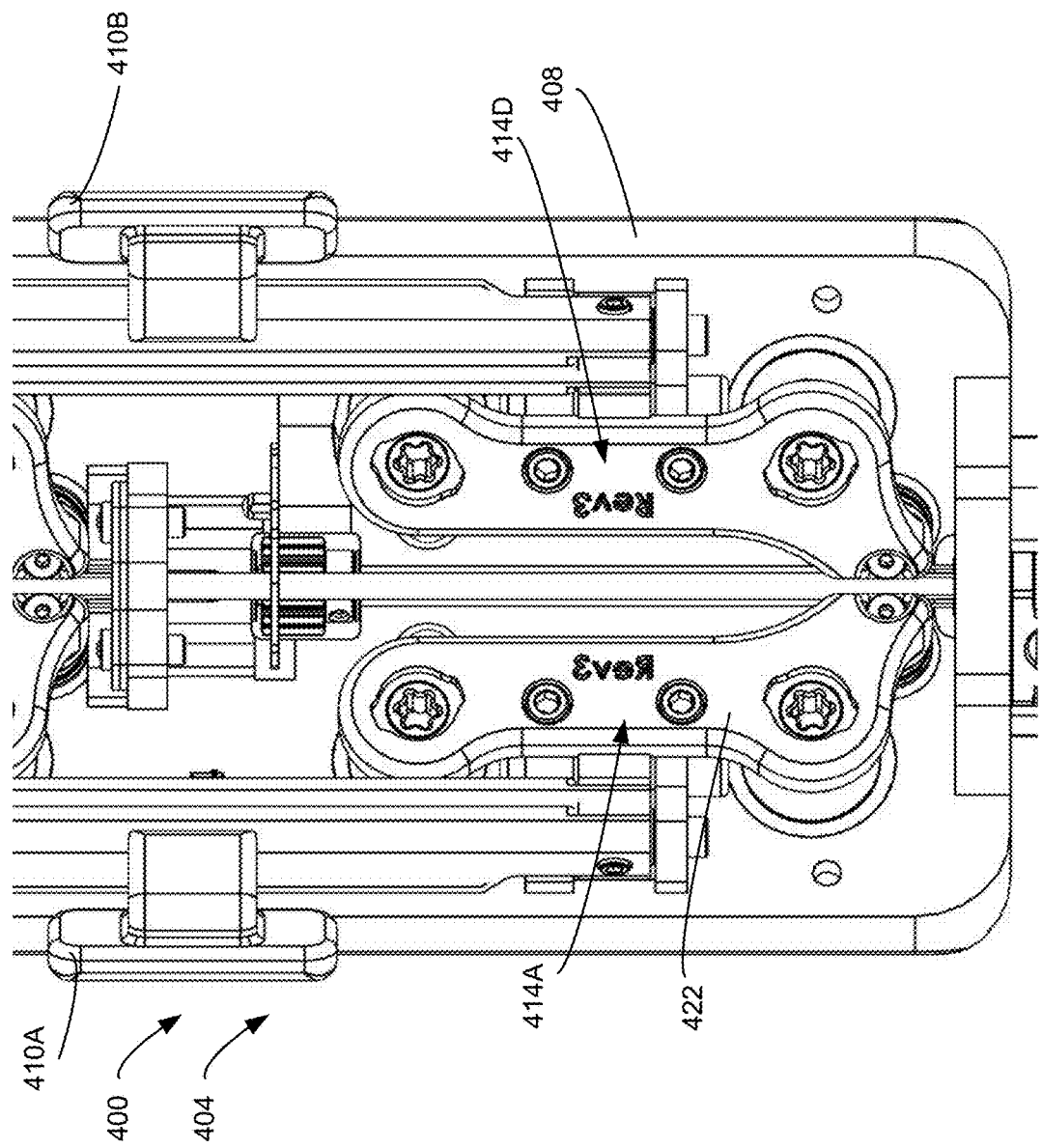
FIG. 8 is a partial top view of a distal portion of the handle assembly of FIG. 4 with the cover removed.
Figure 9:
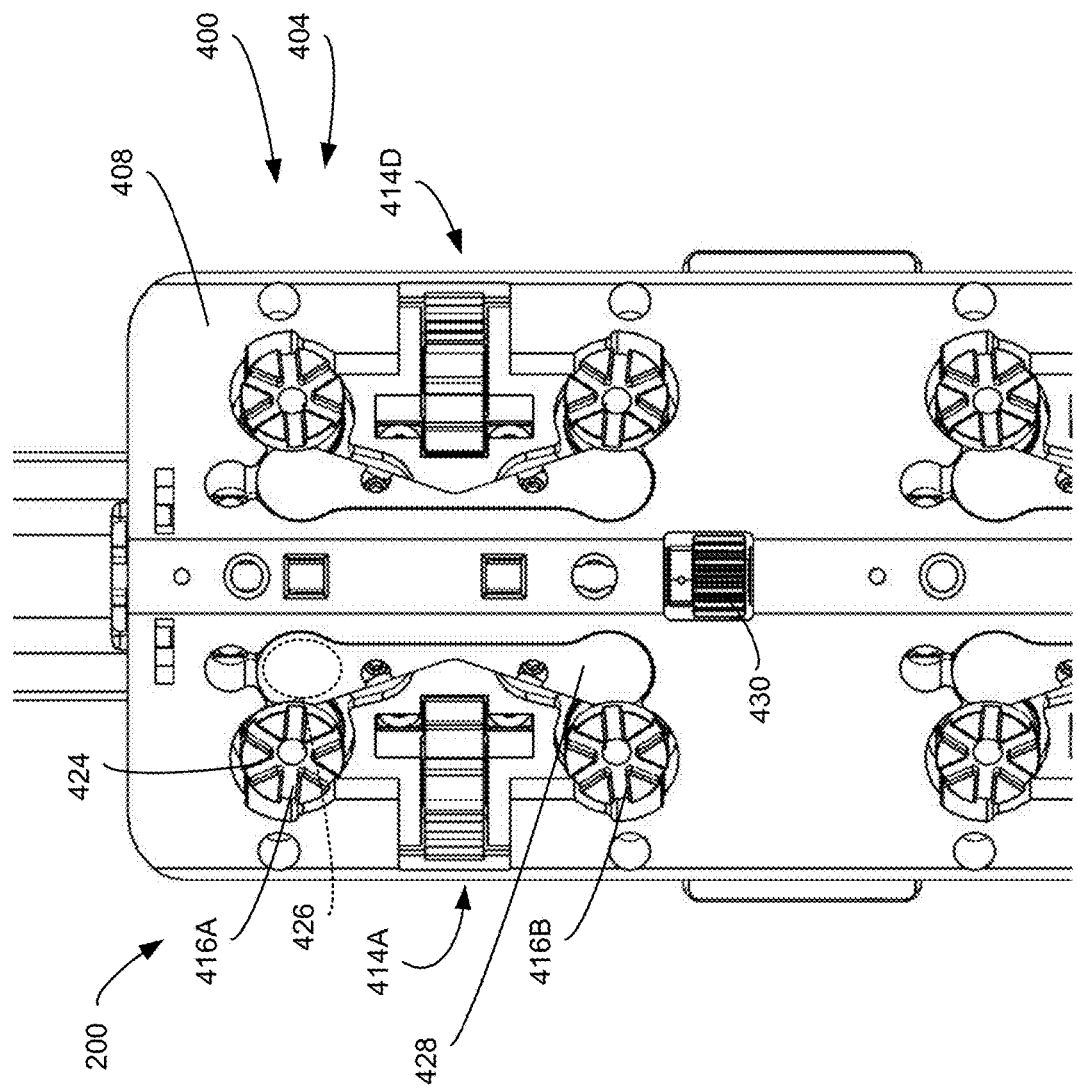
FIG. 9 is a partial bottom view of the distal portion of the handle assembly of FIG. 4.
Figure 10:
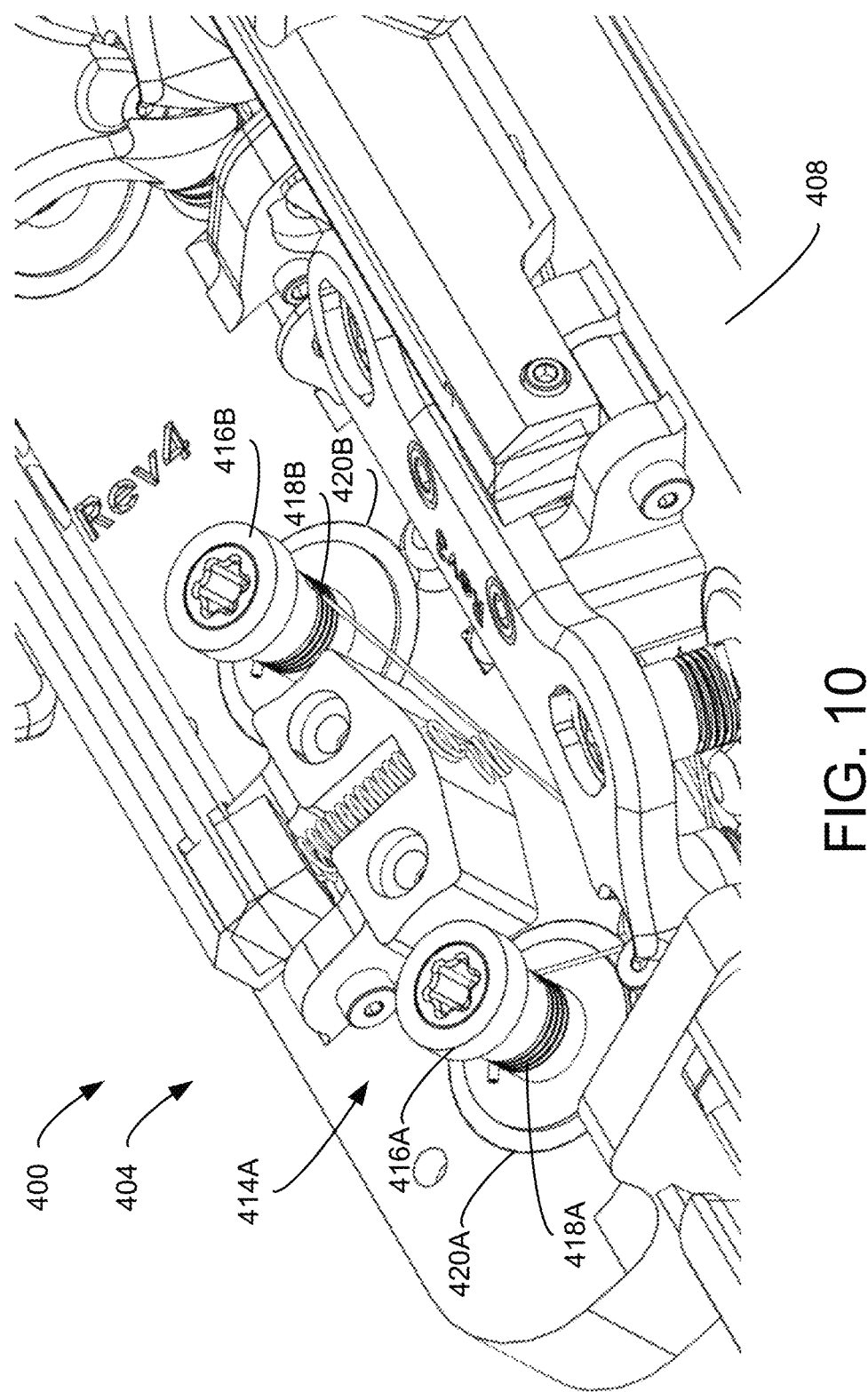
FIG. 10 is an isometric view of the distal portion of the handle assembly of FIG. 4.

FIGS. 4-10 illustrate one implementation of handle assembly 400 in further detail. More specifically, FIGS. 4 and 5 are detailed isometric views of handle assembly 400 in each of a covered and uncovered state. FIGS. 6 and 7 are top and bottom views, respectively, of a proximal portion 402 of handle assembly 400 while FIGS. 8 and 9 are similar top and bottom views, respectively of a distal portion 404 of handle assembly 400. FIG. 10 is a detailed isometric view of distal portion 404.

Referring first to FIG. 4, handle assembly 400 is shown in a fully assembled state in which a cover 406 is disposed on and coupled to a base 408. Handle assembly 400 further includes a first latch mechanism 410A and a second latch mechanism 410B for selectively coupling and decoupling handle assembly 400 to a motor assembly. For example, each of first latch mechanism 410A and second latch mechanism 410B may be spring-loaded or otherwise biased into a latched state. In certain implementations, a clinician or other user may couple handle assembly 400 to the drive assembly by simply pressing handle assembly 400 onto the drive assembly such that first latch mechanism 410A and second latch mechanism 410B snap into engagement with the drive assembly. Alternatively, the user may depress each of first latch mechanism 410A and second latch mechanism 410B inwardly to open the latching mechanism. The user then places handle assembly 400 onto the drive assembly while continuing to depress the latch mechanisms and releases the latch mechanisms such that the latch mechanisms close and retain handle assembly 400 on the motor assembly.

As shown in FIG. 4, handle assembly 400 further includes a distal extension 412 that supports catheter assembly 300. Distal extension 412 and its components are discussed below in further detail in the context of FIG. 11-13, which illustrate the sheath actuation mechanism of handle assembly 400.

FIG. 5 is the same view of handle assembly 400 shown in FIG. 4 albeit with cover 406 removed to illustrate the internal components of handle assembly 400. FIGS. 6 and 7 illustrate top and bottom detailed views of a proximal portion 402 of handle assembly 400 while FIGS. 8 and 9 similarly illustrate top and bottom views of a distal portion 404 of handle assembly 400. FIG. 10 provides a detailed isometric view of handle assembly 400 with cover 406 and a bearing cap removed to illustrate components and arrangements of a spindle assembly of handle assembly 400.

As illustrated in FIGS. 5-9, handle assembly 400 includes a collection of spools for controlling the tendons used for actuating catheter assembly 300. For example, handle assembly 400 includes a first spool assembly 414A for controlling bending a proximal steering portion of the distal end of catheter assembly 300 along a lateral plane, a second spool assembly 414B for controlling bending of a distal steering portion of a distal end of catheter assembly 300 along a lateral plane, and a third spool assembly 414C for controlling bending of the distal steering portion along an anterior/posterior plane. As shown, handle assembly 400 further includes an optional fourth spool assembly 414D for controlling additional bending DOFs of catheter assembly 300, such as bending of catheter assembly 300 along an anterior/posterior plane. The following description of the spindle assemblies is made with reference to first spool assembly 414A and its components. In general, the other spool assemblies are substantially similar to first spool assembly 414A and the description of first spool assembly 414A will generally apply to the other spindle assemblies as well with the exception of the other spindle assemblies being configured to manipulate different DOFs of catheter assembly 300.

First spool assembly 414A includes a first spindle 416A and a second spindle 416B. As shown in FIG. 10, a first tendon 418A is wrapped around and extends from first spool assembly 414A while a second tendon 418B is wrapped around and extends from second spindle 416B. First tendon 418A and second tendon 418B form an antagonistic pair of tendons for controlling a bending DOF of catheter assembly 300. For purposes of the present discussion, the DOF corresponding to first spool assembly 414A will be bending of the proximal steering section along the lateral plane; however, first spool assembly 414A may be configured to operate any suitable bending DOF of catheter assembly 300 by coupling first tendon 418A and second tendon 418B to a corresponding portion of catheter assembly 300.

In general, rotating first spindle 416A to spool first tendon 418A results in bending of the proximal steering section in a first direction. Stated differently, spooling of first tendon 418A about first spindle 416A pulls on and shortens a first side of catheter assembly 300, resulting in catheter assembly 300 bending. During spooling of first tendon 418A, second spindle 416B also rotates to unspool second tendon 418B to account for extension of a second side of catheter assembly 300 resulting from the bend, the second side being generally opposite the first, shortened side. In certain implementations, unspooling by second spindle 416B may be controlled to maintain tension on second tendon 418B to reduce slack developing in second tendon 418B. Among other things, reducing slack and maintaining tension in second tendon 418B facilitates controlled bending motion while increasing responsiveness to a change in bending direction.

Similar rotation of second spindle 416B to spool second tendon 418B provides bending of the proximal steering section in a direction opposite that resulting from spooling of first tendon 418A by first spindle 416A. During spooling of second tendon 418B, first spindle 416A may unspool first tendon 418A to account for extension of the side of catheter assembly 300 opposite the bend. Like during unspooling second tendon 418B, unspooling of first tendon 418A may be performed under tension to facilitate controlled bending and improved responsiveness.

Referring to FIG. 10, first spindle 416A is disposed within a first spindle bore 420A defined in base 408 while second spindle 416B is disposed within a second spindle bore 420B defined in base 408. A suitable bearing (not shown) may also be disposed in each of first spindle bore 420A and second spindle bore 420B to support, maintain alignment, and facilitate rotation of first spindle 416A and second spindle 416B, respectively. As shown in FIGS. 5 and 8, a bearing cap 422 may extend between and couple first spindle 416A to second spindle 416B to provide additional structural support and further maintain alignment of first spindle 416A and second spindle 416B.

FIG. 9 illustrates a bottom view of distal portion 404 of handle assembly 400, including first spool assembly 414A. As illustrated in FIG. 9, the bottom surface of each of first spindle 416A and second spindle 416B may include a coupling surface (e.g., coupling surface 424) to facilitate engagement and alignment with motors of the motor assembly, as discussed below in further detail. Handle assembly 400 may also include springs or similar tensioning members for maintaining tension of its spindles. For example, FIG. 9 illustrates a constant torque spring 426 disposed under a spring cap 428 and that extends around first spool assembly first spindle 416A to maintain torque on first spindle 416A and, as a result, tension on first tendon 418A.

Figure 11:
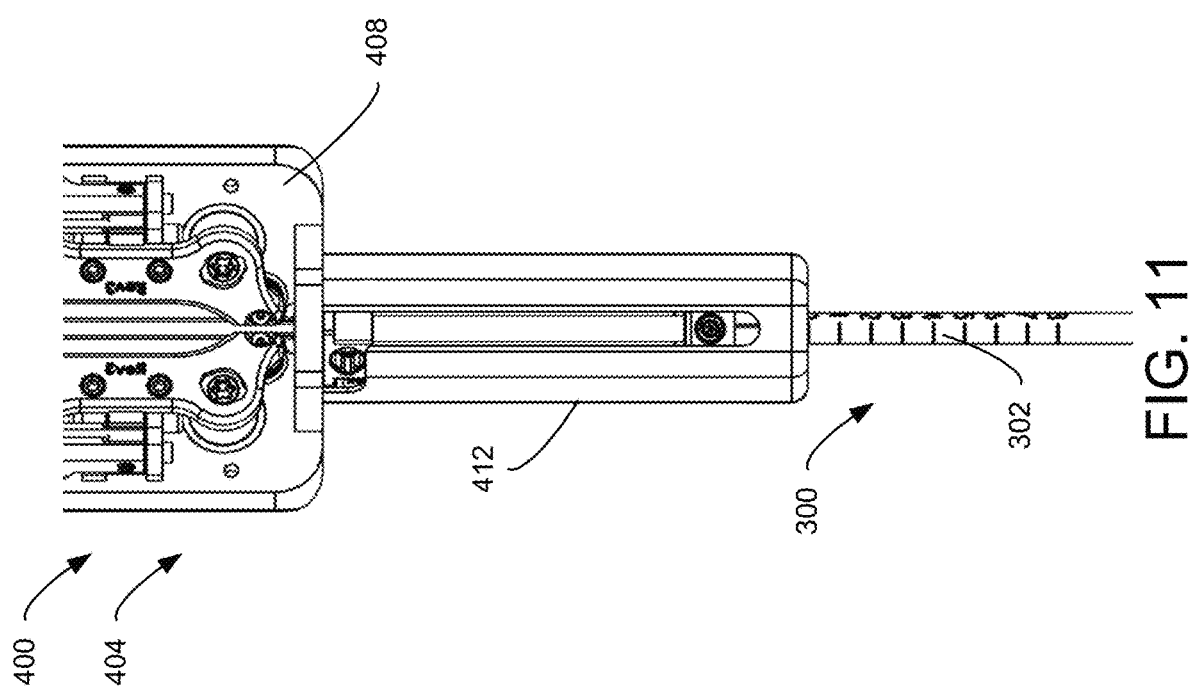
FIG. 11 is a top view of a distal extension of the handle assembly of FIG. 4.

As previously discussed, in certain implementation of this disclosure, handle assembly 400 may perform bending of catheter assembly 300 but may also facilitate extension and retraction of a protective sheath. FIGS. 4 and 11, for example, illustrate handle assembly 400 including a distal extension 412 that supports catheter assembly 300 including sheath 302. During delivery of an implant, sheath 302 may be extended to cover the distal end of catheter assembly 300 including the implant. Following positioning of the distal end of catheter assembly 300 within the left atrium and general alignment of the distal end of catheter assembly 300 with the mitral annulus, sheath 302 may be retracted to expose and allow unfurling and deployment of the implant. Following deployment and release of the implant, sheath 302 may be extended over the distal end of catheter assembly 300 to facilitate removal of catheter assembly 300 from the patient.

Figure 12:
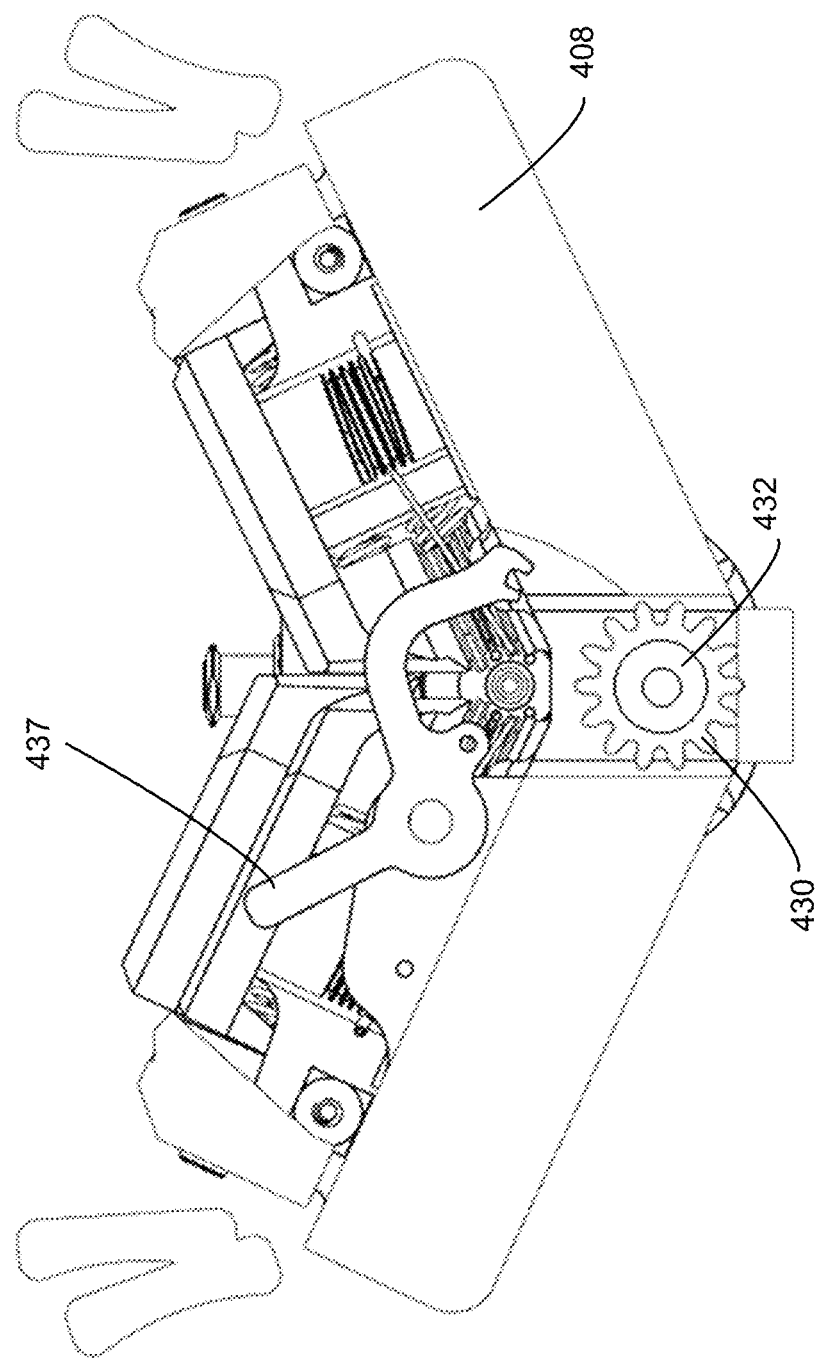
FIG. 12 is a lateral cross-sectional view of the handle assembly of FIG. 4.
Figure 13:
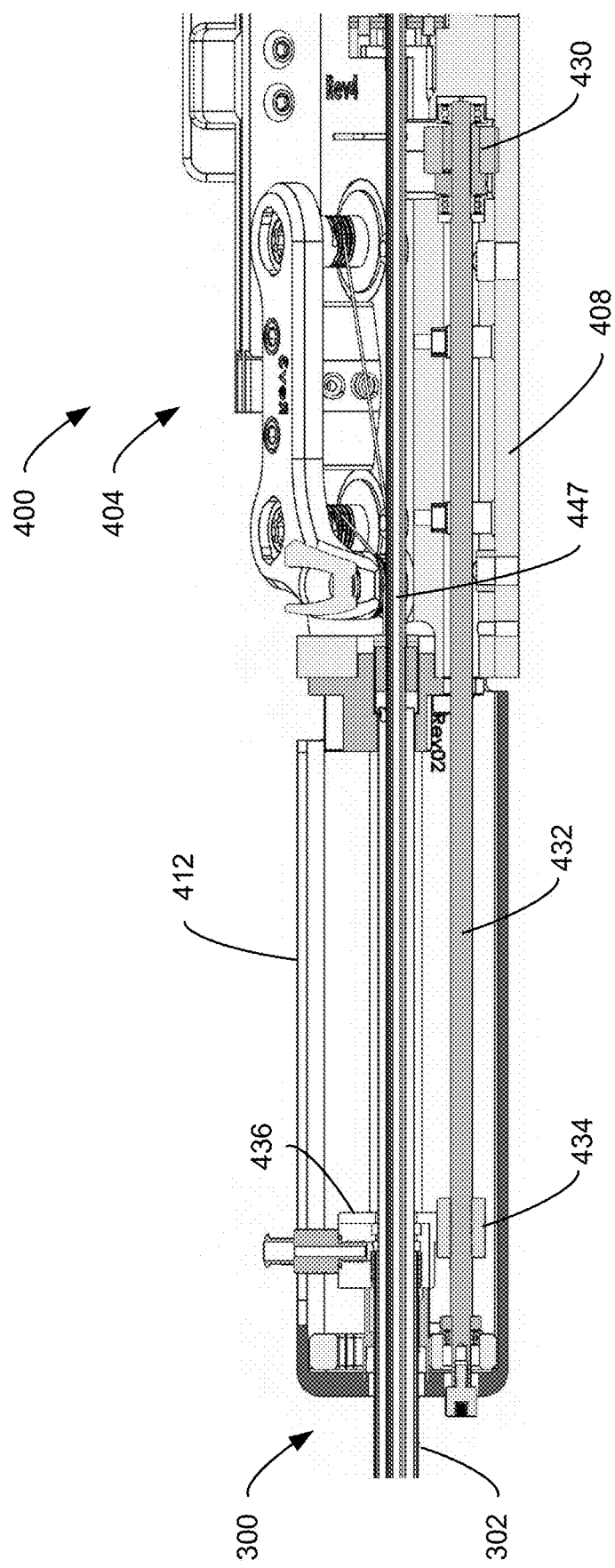
FIG. 13 is a longitudinal cross-sectional view of a distal portion of the handle assembly of FIG. 4 and its distal extension.

While this disclosure contemplates that actuation of sheath 302 may be achieved in various ways, handle assembly 400 includes one example mechanism that relies on a rotating shaft to selectively drive sheath 302. More specifically, as shown in FIGS. 9, 12, and 13 (the latter of which are cross-sectional views of handle assembly 400), handle assembly 400 may include a rotatable spline 430. When handle assembly 400 is coupled to a motor assembly, rotatable spline 430 may engage a motor or drive shaft of the motor assembly to selectively rotate rotatable spline 430. As shown in FIG. 13, rotatable spline 430 is further coupled to a sheath drive shaft 432 including a threaded section 434. Threaded section 434 is threadedly engage to a sheath block 436 supported within distal extension 412 and to which sheath 302 is coupled. In this configuration, rotation of rotatable spline 430 turns sheath drive shaft 432 and threaded section 434, which causes translate of sheath block 436 and corresponding extension and retraction of sheath 302.

As shown most clearly in FIG. 12, handle assembly 400 may include a sheath lock 437 adapted to engage and prevent rotation of rotatable spline 430, thereby preventing unintended extension or retraction of sheath 302.

Figure 14:
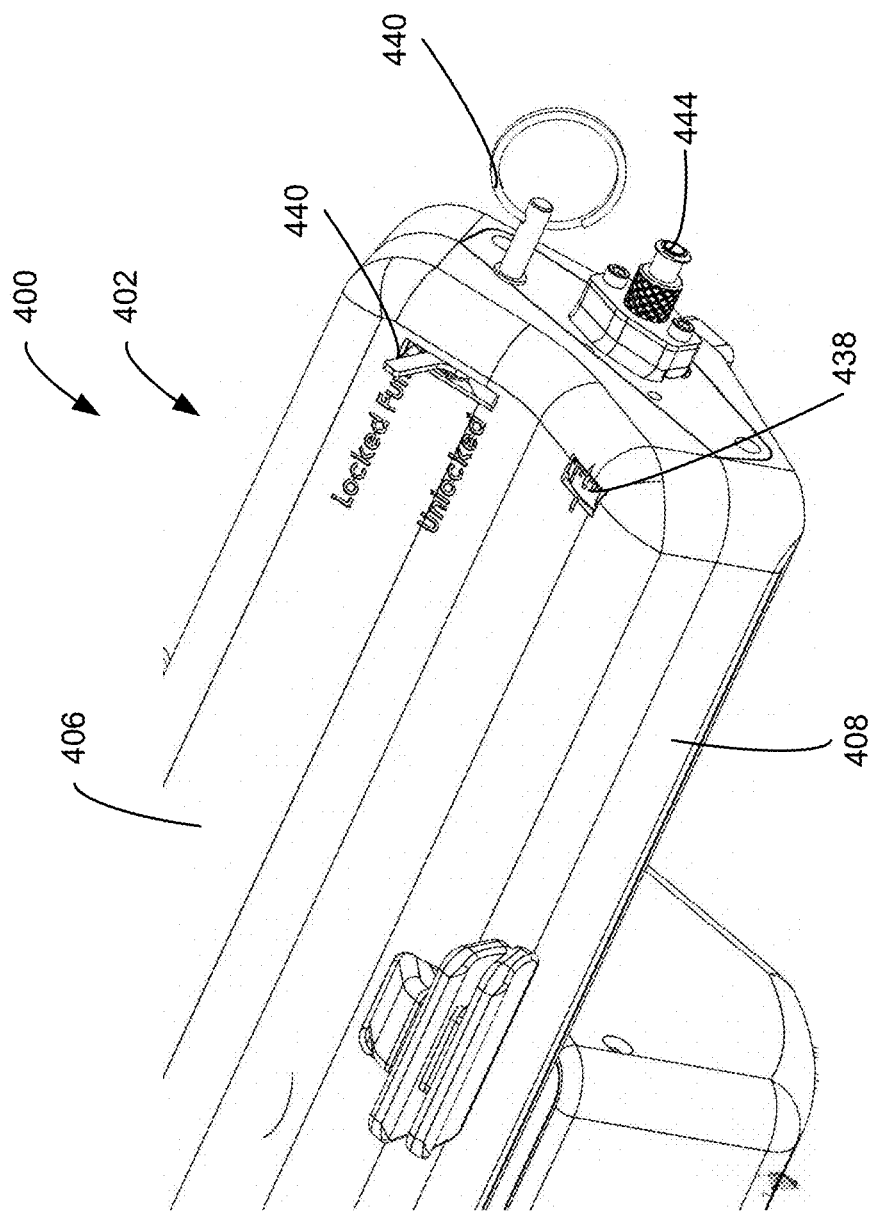
FIG. 14 is an isometric view of a proximal portion of the handle assembly of FIG. 4.
Figure 15:
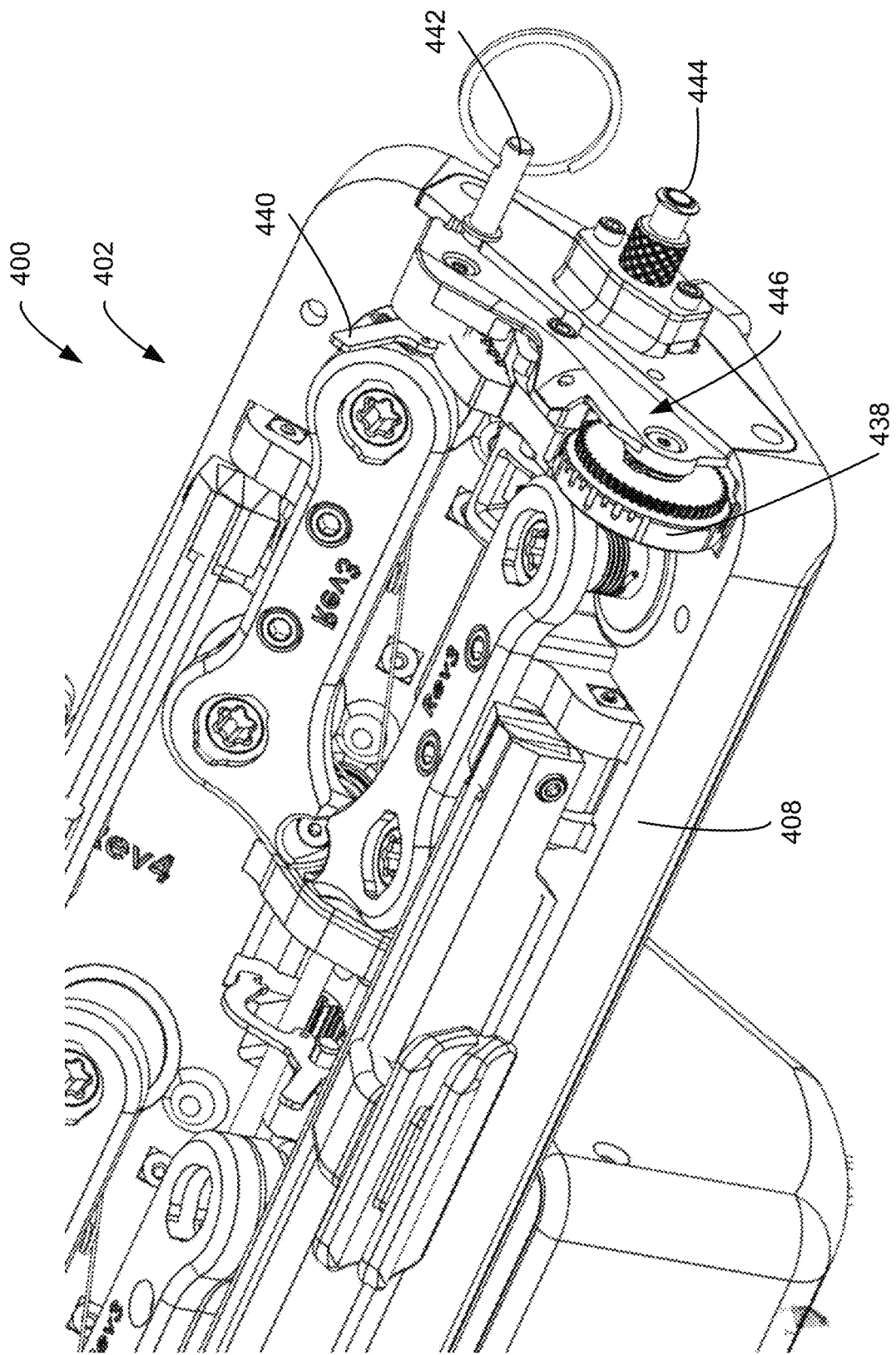
FIG. 15 is an isometric view of a proximal portion of the handle assembly of FIG. 4 like FIG. 14 but with a cover removed.
Figure 16:
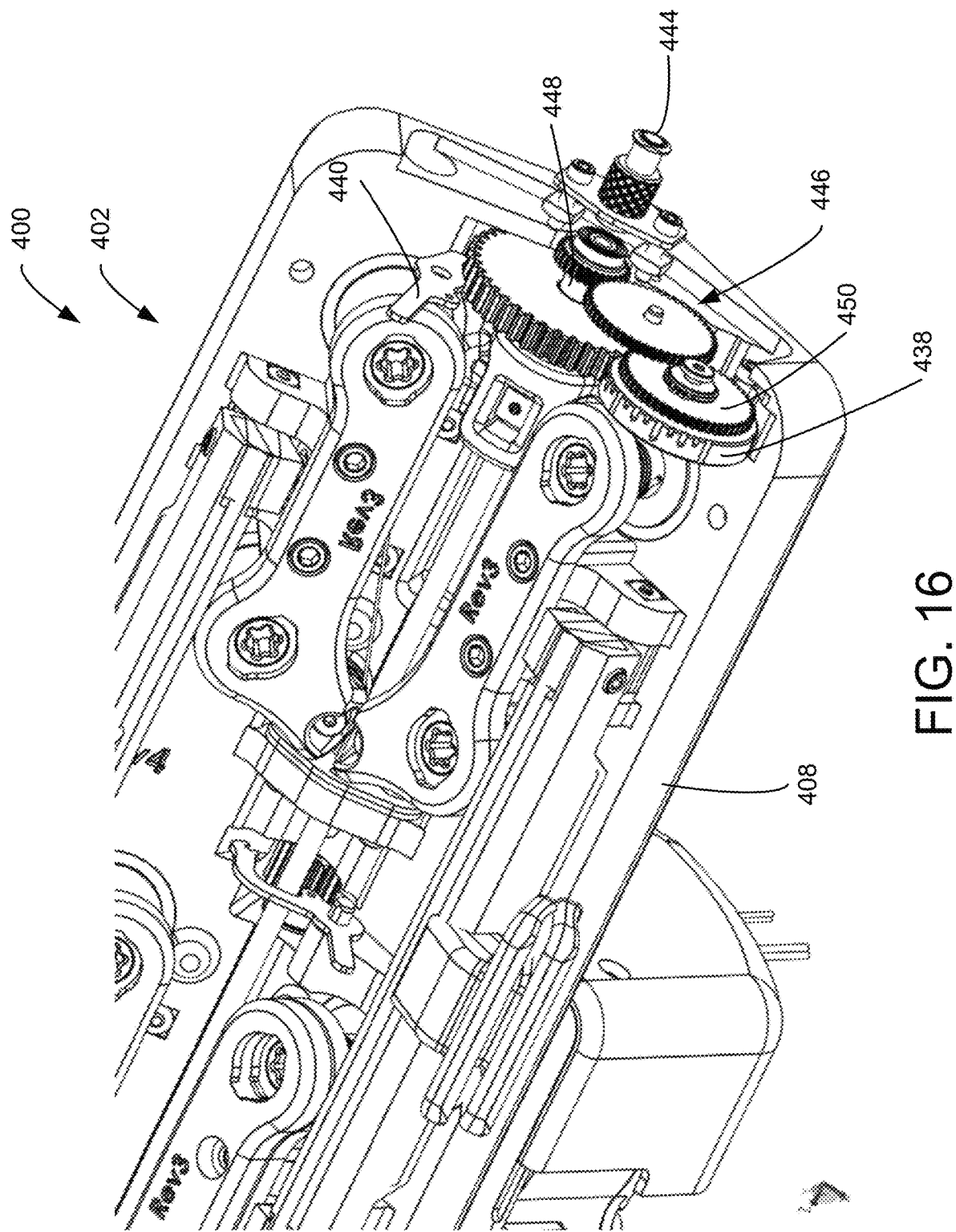
FIG. 16 is another isometric view of the proximal portion of the handle assembly like FIG. 15 with additional components removed to illustrate a sheath furling assembly.

FIGS. 14-16 are isometric views of proximal portion 402 of handle assembly 400 and, in particular, controls for furling of an implant coupled to catheter assembly 300. As previously discussed, implementations of this disclosure may facilitate delivery of various types of implants including, but not limited to, the mitral valve replacement implant of U.S. Pat. No. 11,197,755 (the '755 patent) using delivery techniques and mechanisms of U.S. Pat. No. 11,246,726 (the '726 patent). As disclosed in the '726 patent, implants (like those of the '755 patent) may be selectively expanded (i.e., unfurled) and contracted (i.e., furled) by controlling tension, payout, and retraction of a tension line extending about the implant. To that end, implementations of this disclosure may include various mechanisms for such control of the implant during delivery.

Referring first to FIG. 14, handle assembly 400 is shown with cover 406 in place. Among other things, handle assembly 400 is shown as including each of a furl indicator 438, a furl lock 440, and a furl locking pin 442. Each of furl lock 440 and furl locking pin 442 are mechanical stops to prevent inadvertent or unintended unfurling of an implant prior to positioning and alignment within the atrium. While not relevant to furling, FIG. 14 also includes a fitting 444 through which a guide wire or similar guide element may be disposed to guide catheter assembly 300 during use. FIG. 15 illustrates handle assembly 400 with cover 406 removed while FIG. 16 further removes additional structural elements to illustrates a furling gear assembly 446.

During operation, furling gear assembly 446 engages a computer-controlled motor or drive shaft 447 (shown in FIG. 13) actuatable to selectively furl or unfurl the implant. More specifically, furling gear assembly 446 includes a furling hub 448 to which a tension line (not shown) extending to the implant is coupled such that rotation of furling hub 448 by actuation of furling gear assembly 446 results in selective spooling and unspooling of the tension line from furling hub 448. Furling gear assembly 446 further includes gear train ending in an indicator gear 450, that includes indicators visible through cover 406 for communicating the current state of the implant.

D. IMPLANT DELIVERY ASSEMBLY—DRIVE ASSEMBLY

As discussed in the context of FIG. 1, robotic implant delivery system 100 generally includes implant delivery assembly 102 including catheter assembly 104 and handle assembly 106 and which is coupled to drive assembly 110. Drive assembly 110 may include multiple motor modules (such as motor module 112), each of which may be supported a respective carriage (e.g., carriage 118). Drive assembly 110 may further include a carriage base 116 including a carriage drive system for modifying insertion and rotation of each carriage (e.g., by translating each carriage along carriage base 116 or rotating each carriage relative to carriage base 116).

Figure 17:
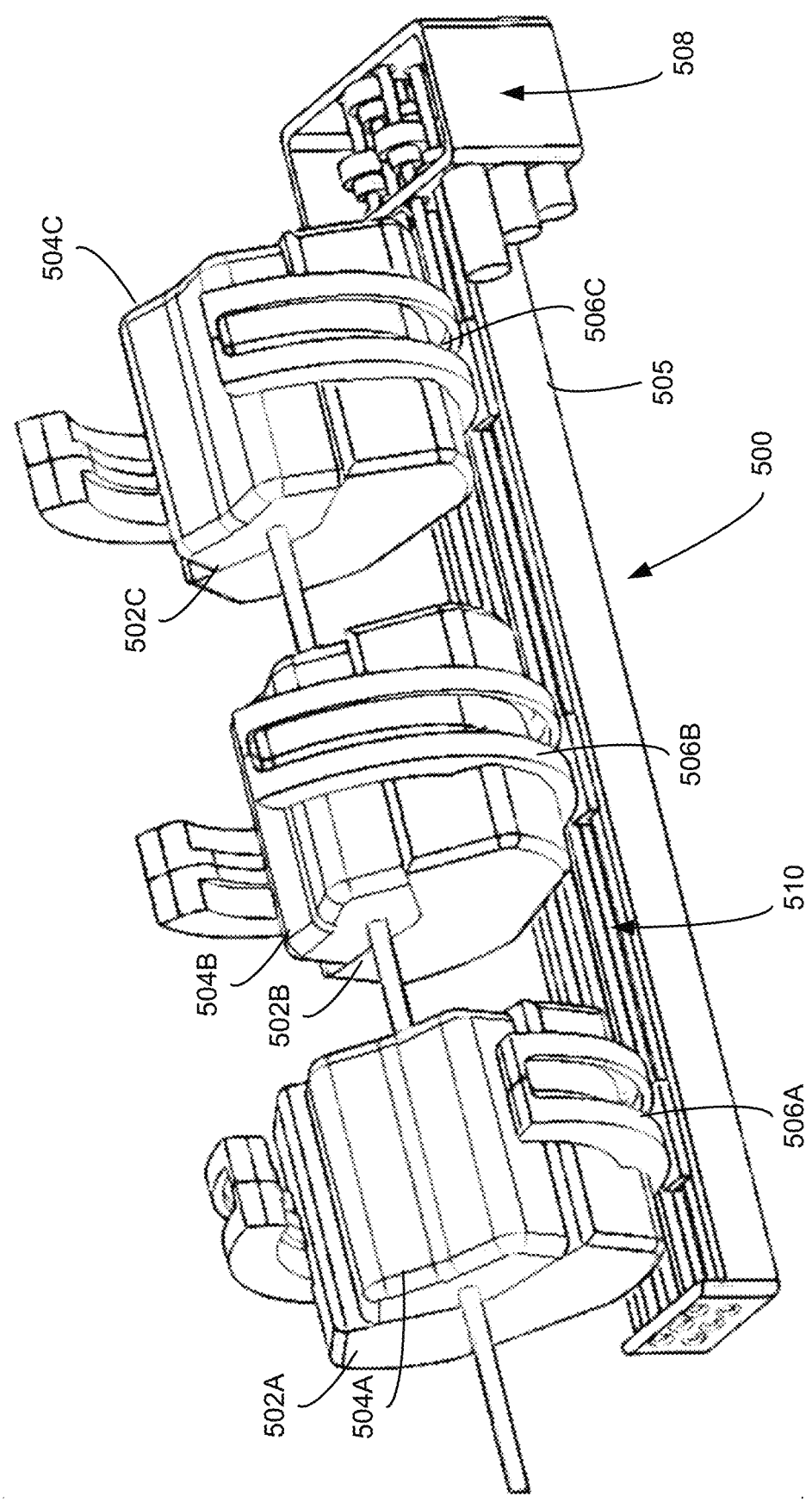
FIG. 17 is an isometric view of an example drive assembly according to the present disclosure.

With the foregoing in mind, FIG. 17 is an isometric view of an example drive assembly 500 according to the present disclosure. As shown, drive assembly 500 includes three motor modules (e.g., a distal motor module 502A, an intermediate motor module 502B, and a proximal motor module 502C). In the specific implementation shown in FIG. 17, each motor module is coupled to and supports a respective handle assembly (e.g., motor module 502A is coupled to and supports a distal handle assembly 504A, motor module 502B is coupled to and supports a medial handle assembly 504B, and motor module 506C is coupled to and supports a proximal handle assembly 504C) and is further coupled to a corresponding carriage (e.g., motor module 502A is coupled to a distal carriage 506A, motor module 502B is coupled to a medial carriage 506B, and motor module 506C is coupled to a proximal carriage 502C). Each motor module is configured to mate with its respective handle assembly such that motors and other computer-controllable elements of the motor modules mate with corresponding control elements (e.g., spools) of the handle assemblies to permit actuation of the control elements.

As shown in FIG. 17, drive assembly 500 includes a carriage base 505 that supports each carriage. Carriage base 505 further includes a motor assembly 508 and drive shafts 510 for actuating carriages 506A-506C. For example, for each carriage, drive shafts 510 may a first shaft drivable by a motor of motor assembly 508 to control longitudinal translation of the carriage and a second shaft drivable by a motor of motor assembly 508 to control rotation of the carriage.

Figure 18:
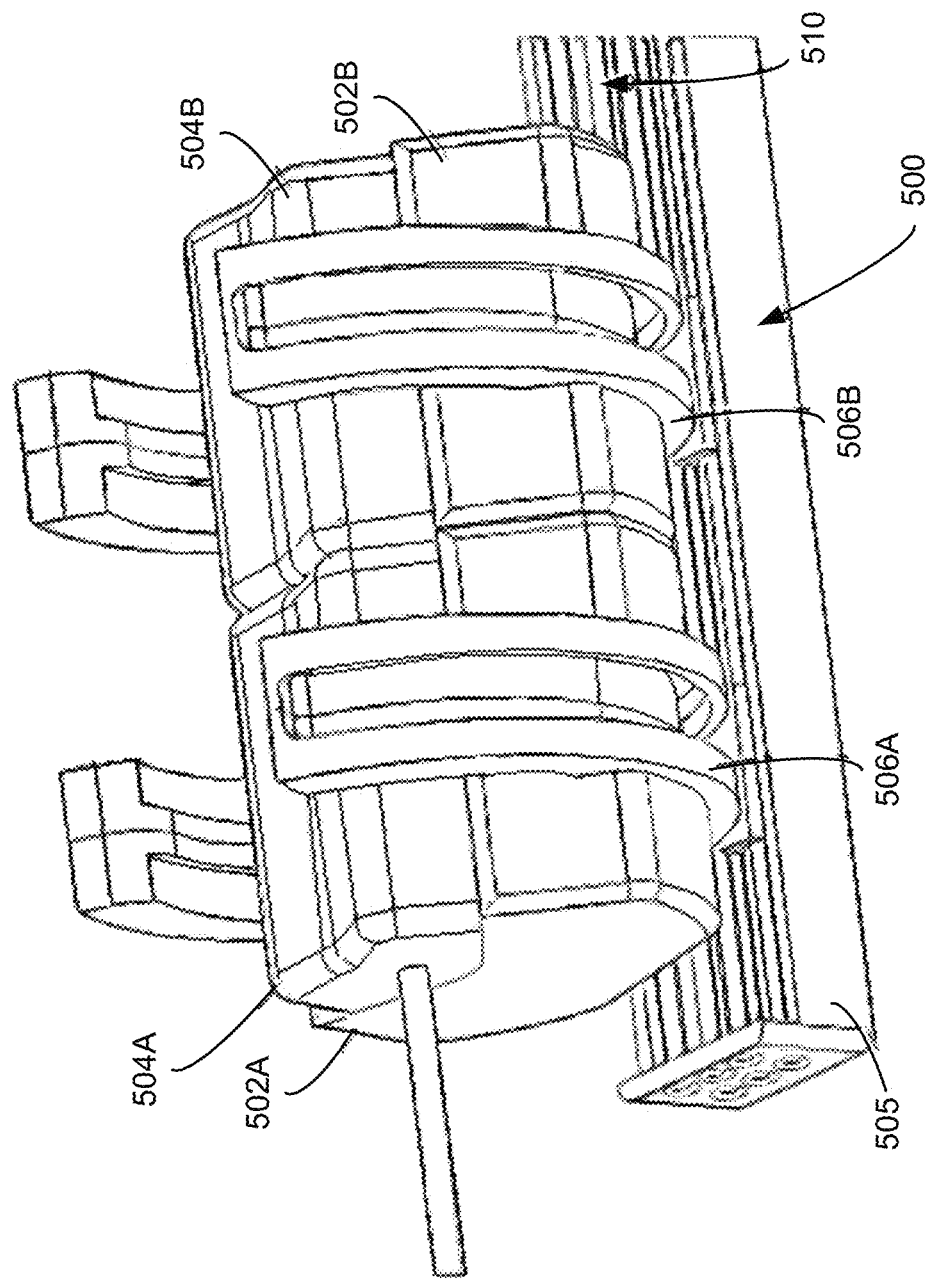
FIG. 18 is an alternative isometric view of the drive assembly of FIG. 17 including paired carriages.

As shown in FIG. 18, drive assembly 500 may be configured such that multiple carriages and, by extension, multiple motor modules may be paired. For example, FIG. 18 illustrates motor module 502A and carriage 506A paired with motor module 502B and carriage 506B. When paired in this way, drive assembly 500 may control the paired motor modules and carriages in tandem, e.g., by simultaneously translating and rotating each paired carriage in response to received control commands. As illustrated in FIG. 18, each carriage and motor module includes a respective handle assembly; however, in implementations of this disclosure handle assemblies may be configured to span multiple motor module/carriage units. For example, handle assembly 400 of FIG. 4 is configured to span two motor module/carriage units.

Figure 19:
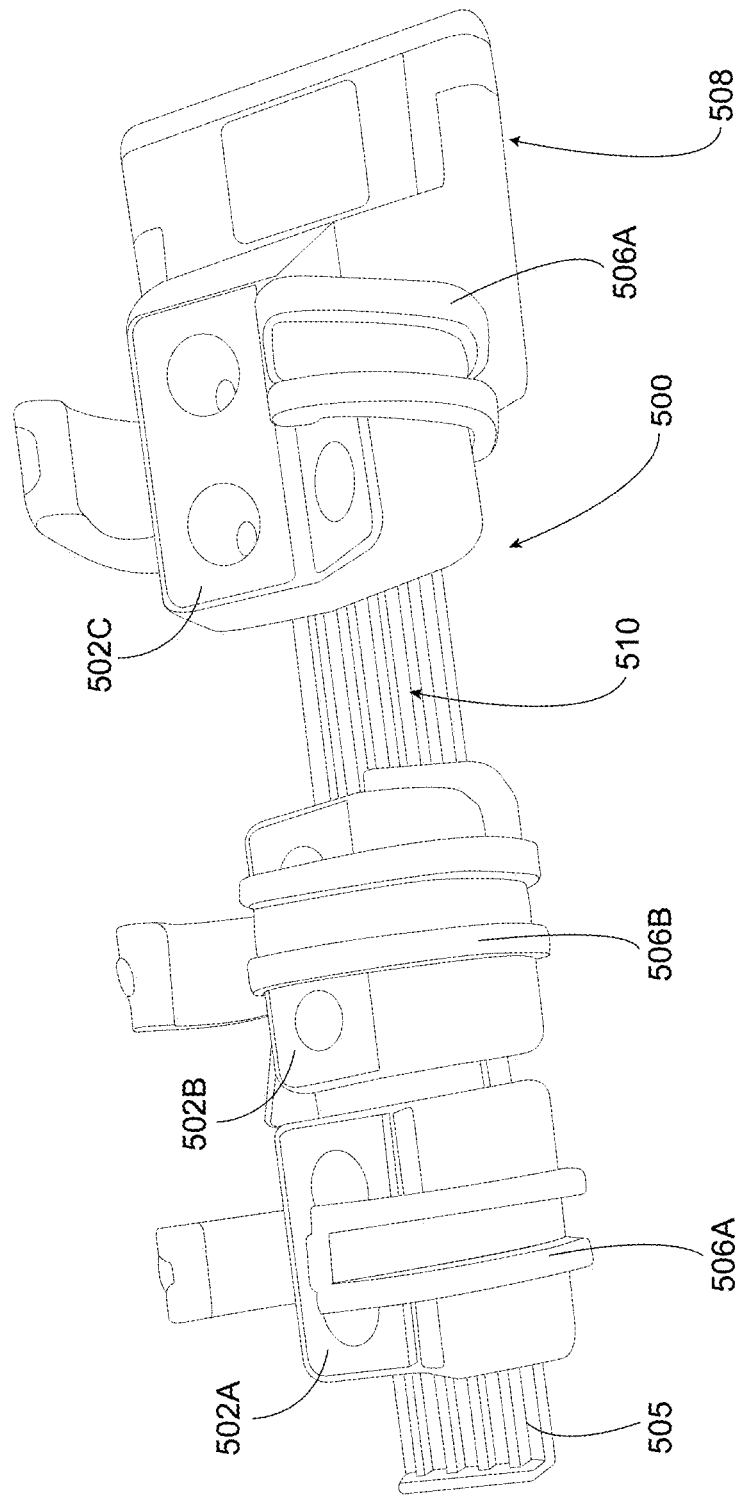
FIG. 19 is a perspective view of a drive assembly according to this disclosure with a handle assembly removed.
Figure 20:
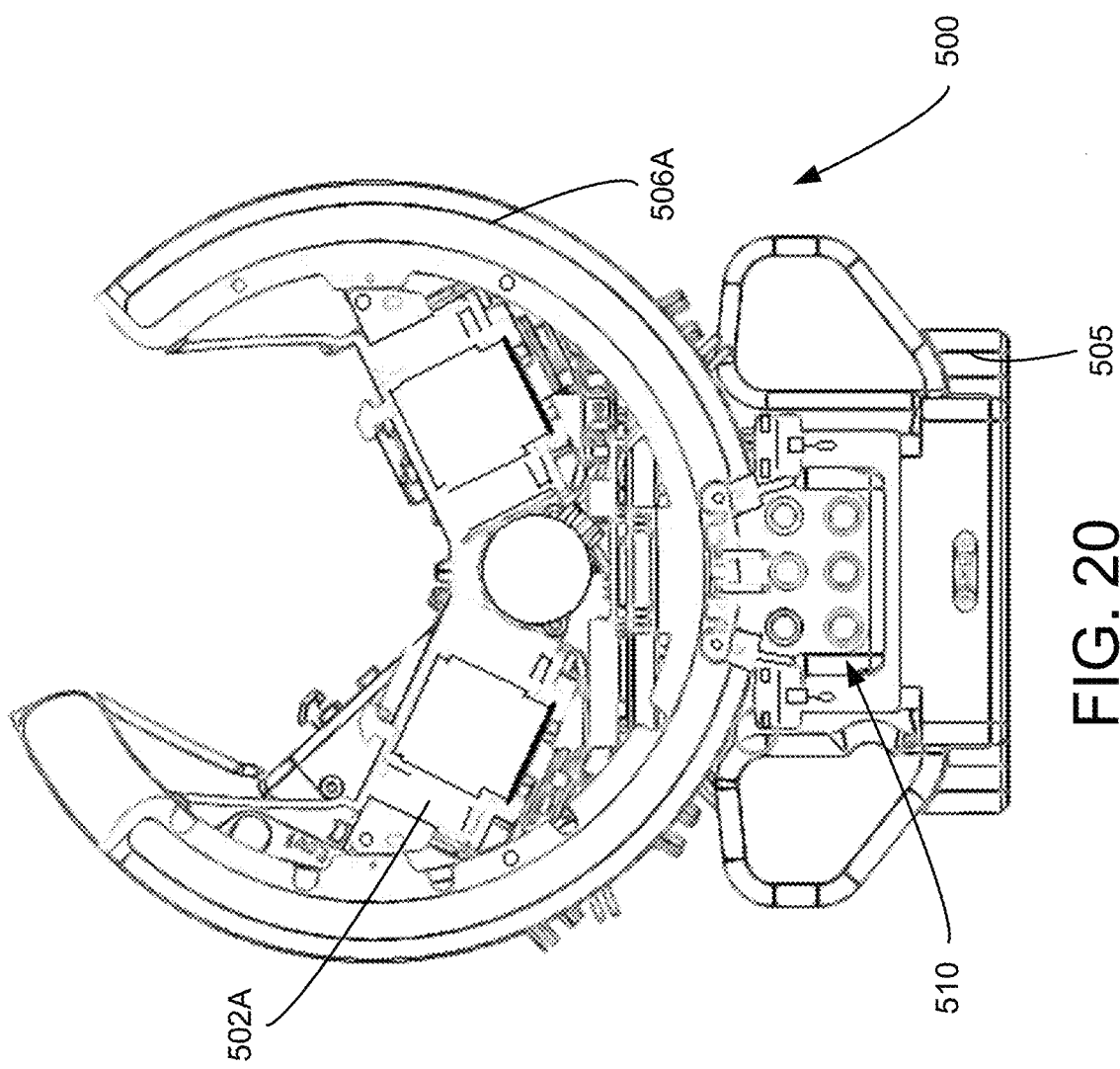
FIG. 20 is a lateral cross-sectional view of an example drive assembly according to this disclosure.

FIGS. 19 and 20 provide additional views of drive assembly 500. In particular, FIG. 19 is a perspective view of drive assembly 500 with handle assemblies omitted and FIG. 20 is a cross-sectional view of drive assembly 500 taken through motor module 502A.

Figure 21:
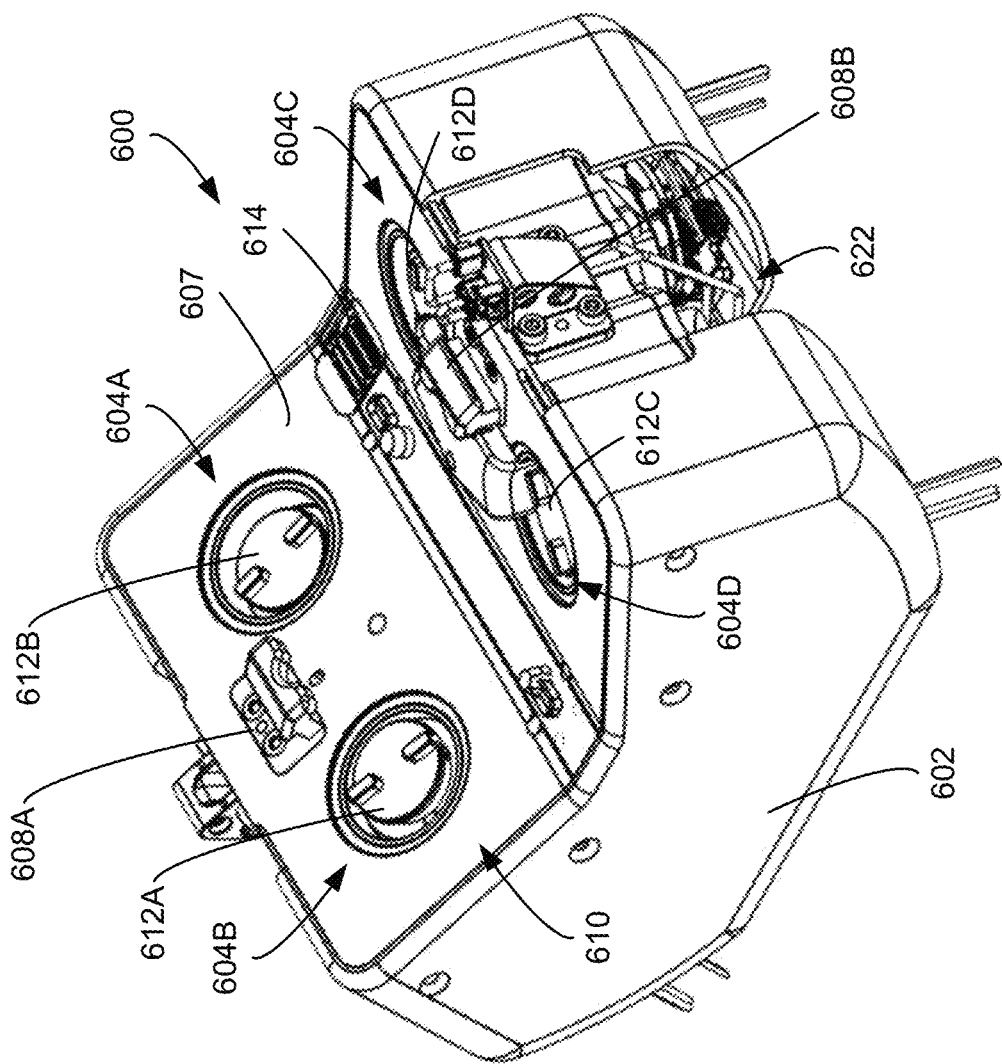
FIG. 21 is an isometric view of an example motor module for use in drive assemblies of this disclosure.

FIG. 21 is an isometric view of an example motor module 600, which may generally correspond to any of motor modules 502A-502C of FIG. 17. Motor module 600 is specifically configured to provide a flexible architecture suitable for a wide range of handle assemblies; however, the following discussion uses handle assembly 400 as a primary example of a handle assembly suitable for use with motor module 600. While a single motor module 600 may be configured to provide functionality for a handle assembly, handle assembly 400 specifically relies on a pair of adjacent motor modules 600 to be fully supported and actuated.

Motor module 600 includes a body 602 containing multiple motors and drive electronics for operating each motor. More specifically motor module 600 includes motors 604A-604D, e.g., for independently controlling respective spools of handle assembly 400, and a motor 606 (shown in FIG. 23) that provides an auxiliary drive. In the context of handle assembly 400, the auxiliary drive of a first, distally mounted motor module is used to drive rotatable spline 430 to control extension/retraction of sheath 302 while the auxiliary drive of a second, proximally mounted motor module actuates furling gear assembly 446 to control implant deployment.

In general, body 602 is shaped and configured to be coupled to a carriage, such as carriage 506A, and includes an interface 610 for coupling motor module 600 to a handle assembly. As illustrated in FIG. 21, interface 610 generally includes an interface surface 607 shaped to receive the handle assembly. Among other things, interface 610 includes retention features 608A, 608B adapted to engage with latches (e.g., first latch mechanism 410A and second latch mechanism 410B of handle assembly 400) or similar retention elements of the handle assembly.

Interface 610 further includes couplings 612A-612D corresponding to each of motors 604A-604D, which are adapted to mate with and engage control elements of the handle assembly. For example, each of couplings 612A-612D is configured to engage a bottom surface of a respective spindle of handle assembly handle assembly 400. In the specific implementation shown, couplings 612A-612D and their counterpart surfaces of the spindles of handle assembly 400 are Oldham couplings. Interface 610 further includes a gear 614 in mechanical communication with and driven by motor 606 to provide the auxiliary drive functionality noted above.

Figure 22:
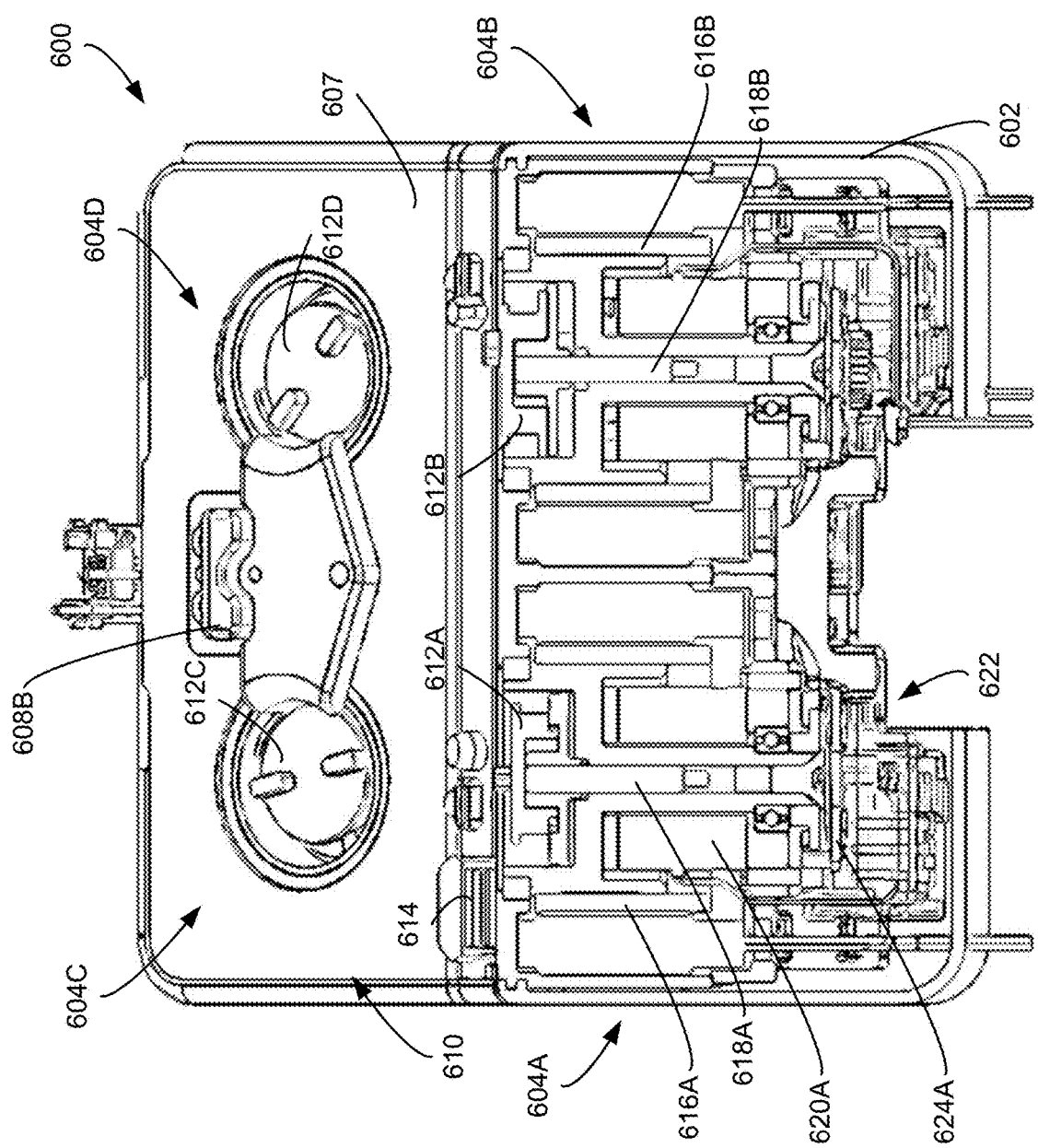
FIG. 22 is a first cross-sectional view of the motor module of FIG. 21 illustrating cable-driving motors of the motor module.

As illustrated in FIG. 21, motor module 600 is generally shown as being arranged as two angled motor hubs. FIG. 22 is a cross-sectional view of motor module 600 through the hub including motor 604A and 604B and bisecting the motors. The following description focuses on motor 604A and motor 604B, but generally applies to any of motors 604A-604D, unless otherwise noted.

As shown, motor 604A includes a motor body 616A, a motor shaft 618A, and a coupling 612A coupled to an interface side of motor shaft 618A. Similarly, motor 604B includes a motor body 616B, a motor shaft 618B, and a coupling 612B to an interface side of motor shaft 618B. To facilitate engagement of the motor shafts with their respective spindles of handle assembly 400, the motor shafts may be spring loaded and biased into an extended/engageable position. Motor 604B illustrates motor shaft 618B in the extended state. In certain implementations and as discussed below in the context of bailout procedures, the motor shafts may also be latched in a depressed or disengage configuration, as shown by motor shaft 618A. Among other things, such latching can selectively disengage spools of handle assembly 400 from their respective motors, permitting manual movement of the spools, e.g., in the event of a motor failure or other error.

FIG. 21 illustrates each coupling directly attached or engaged with the motor shaft of its respective motor. However, in other implementations, couplings may be attached to a coupling shaft drivable by the motor shaft. For example, a gear box or similar transmission element may be disposed between the motor shaft and the coupling shaft to transmit output of the motor to the coupling shaft. Among other benefits, such an arrangement permits locating the coupling adjacent to the motor shaft, which allows a smaller form factor as compared to configurations in which the coupling is stacked/coaxial with the motor shaft.

As further discussed in the context of safety and bailout procedures, motors of motor module 600 may include brakes configured to lock rotation. For example, motor 604A includes brake 620A. In certain implementations, brake 620A may be in the form of a magnet and motor module 600 may be configured to default into a first, engaged position that magnetically locks rotation of motor shaft 618A. During normal operation of motor module 600, a solenoid or similar actuator may translate brake 620A into a disengaged position, thereby permitting rotation of motor shaft 618A. In the event motor 604A fails, loses power, or is commended to lock due to failure or loss of power in another system element, brake 620A defaults into the engage position and locks rotation of motor shaft 618A.

Motor module 600 further includes an electronics assembly 622 disposed within body 602. Among other things electronics assembly 622 can include motor drives, controllers, and similar electronics for controlling operation of the motors of motor module 600. Electronics assembly 622 may also include various sensors for measuring and monitoring operation of the motors. In certain implementations, sensors of electronics assembly 622 may include current or similar sensors capable of measuring current draw of each motor and, by extension, tension applied by the motors. Sensors of electronics assembly 622 may also include but are not limited to relative and/or absolute encoders (e.g., absolute encoder 624A), which can be used to measure rotational position, velocity, and acceleration of each motor. In at least some implementations, electronics assembly 622 may include multiple sensors for a given measurement (e.g., multiple absolute encoders for measuring rotational position of a motor shaft). Such configurations may be used to improve fault detection, to provide redundancy in the event of a sensor failure, to improve measurement accuracy (e.g., by providing multiple values for a given measurement that can then be averaged or otherwise combined), and the like. This disclosure also contemplates that multiple sensors for a given measurement may be of the same type (e.g., multiple optical encoders) or may include sensors of different types (e.g., an optical encoder and a hall effect sensor for measuring shaft rotation).

Figure 23:
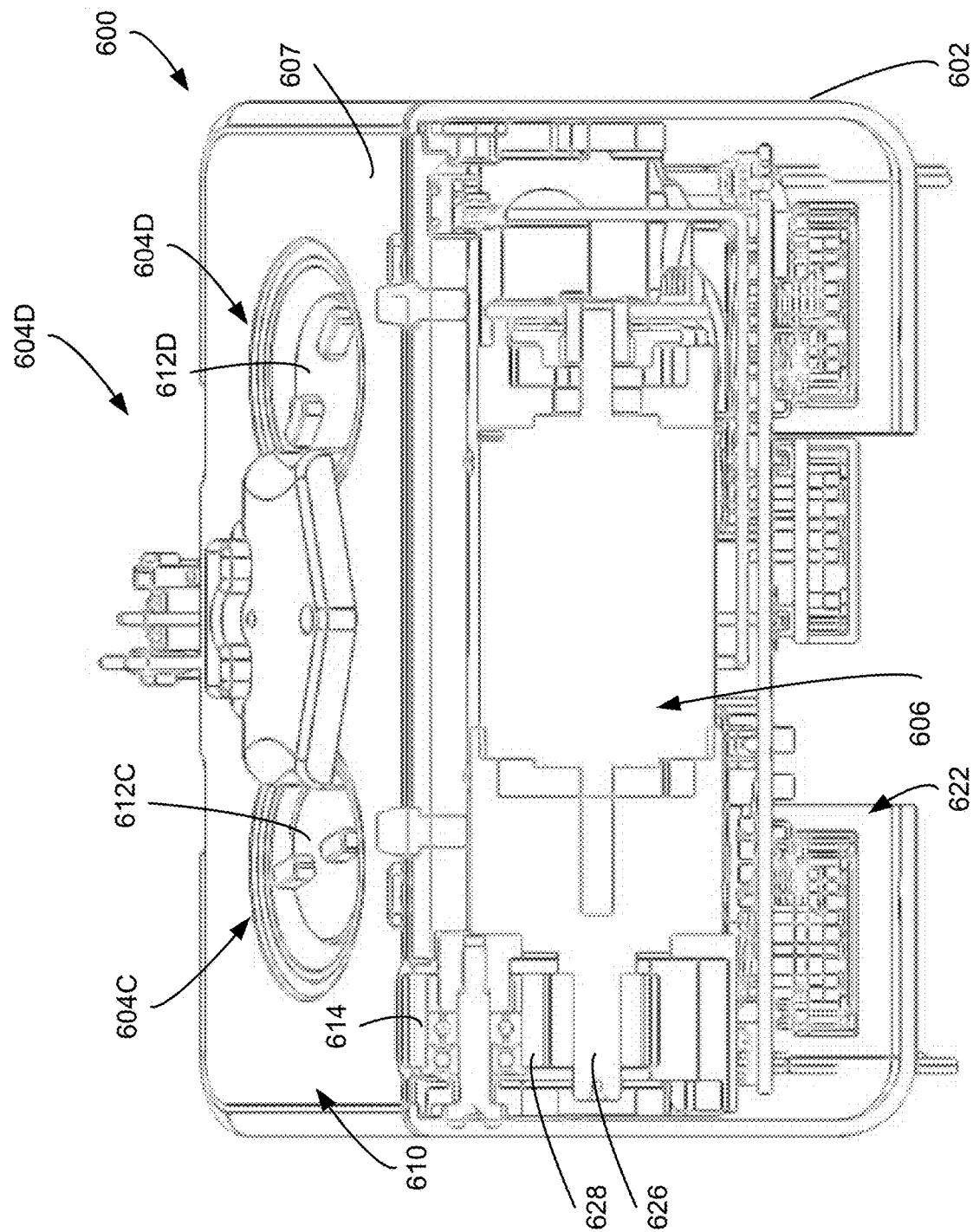
FIG. 23 is a second cross-sectional view of the motor module of FIG. 21 illustrating an auxiliary motor of the motor module.

FIG. 23 is a cross-sectional view of motor module 600 along a mid-line of motor module 600. Among other things, the view of FIG. 23 shows motor 606. Motor 606 includes a shaft 626 including a splined surface 628. Splined surface 628 is engaged with gear 614 such that actuation of motor 606 drives rotation of gear 614 to facilitate the various auxiliary functions described herein.

E. ENHANCED DISTAL ARTICULATION SENSING

Precise movement and control of robotic systems requires precise measurement and understanding of the location of movable components of the robotic system during operation. Determining the position and orientation of flexible robotic devices, such as robotic catheters, is complicated by the inherit lack of stiffness in such devices. Such determinations are further complicated by drive system friction (e.g., friction between cables and internal surfaces of the catheter, friction of the cable against itself when spooled, etc.) and changes in cable strain as tension on the cables changes during catheter actuation.

With reference to robotic implant delivery systems of the current disclosure, these issues, can present substantial challenges in determining the bending angles of articulable catheter sections and, ultimately, the end point of the device corresponding to the location of the implant during delivery. To address the foregoing issues, among others, implementations of the present disclosure may include improved positional measurement systems including multiple positional sensors.

Figure 24:
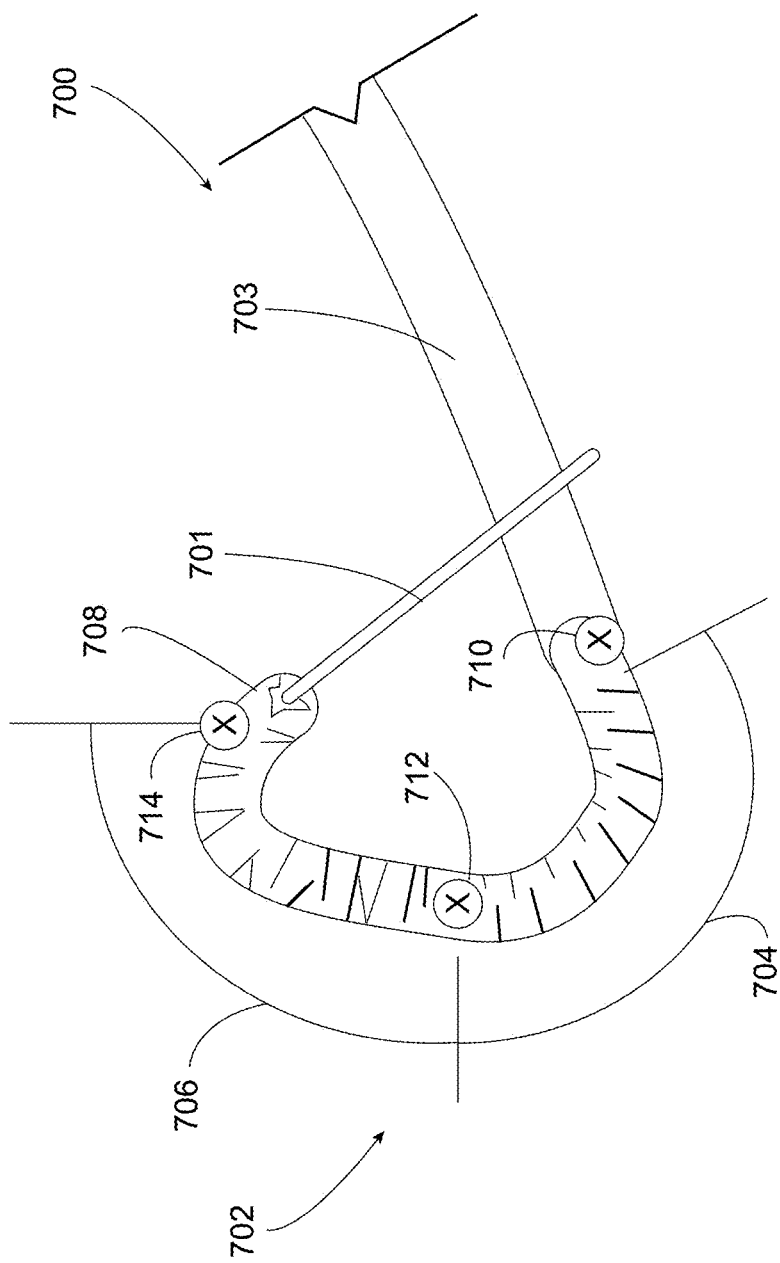
FIG. 24 is a perspective view of a catheter assembly for use with implant delivery systems of this disclosure.

FIG. 24 is a perspective view of a catheter assembly 700 according to the present disclosure and, more specifically, a distal portion 702 of catheter assembly 700 (shown disposed on a guidewire 701). Distal portion 702 includes two steerable sections-a proximal steerable section 704 having a single DOF (e.g., bending along a lateral plane) and a distal steerable section 706 having two DOFs (e.g., bending along each of the lateral plane and an anterior/posterior plane).

Distal portion 702 is shown in FIG. 24 following bending of each of proximal steerable section 704 and distal steerable section 706 resulting in a substantially contorted configuration of distal portion 702. For the reasons noted above, accurate characterization of such a configuration, such as to determine a location of a distal tip 708 of distal portion 702, can be particularly challenging. Nevertheless, such precise locating is necessary for accurate control of catheter assembly 700 and placement of implants in systems of this disclosure.

To improve locating and characterization of distal portion 702, multiple sensors may be integrated into distal portion 702 at different locations along distal portion 702. For example, in one implementation, inertial measuring units (IMUs) and/or electromagnetic (EM) sensors may be positioned at each of a proximal location 710, a medial location 712, and a distal location 714 of distal portion 702. As further discussed below, proximal location 710 generally corresponds to a location at a transition between at the transition between a main catheter body 703 and proximal steerable section 704, medial location 712 generally corresponds to a location at a transition between proximal steerable section 704 and distal steerable section 706, and distal location 714 generally corresponds to a location at a transition between distal steerable section 706 and distal tip 708. During operation, each set of sensor may provide position data or data from which position may be derived (e.g., acceleration data) to facilitate better characterization of the shape and location of distal portion 702 and, in particular distal tip 708.

Both IMUs and EM sensors have certain limitations when measuring absolute position. However, those shortcomings can be significantly reduced by measuring the relative position of sensors with fixed geometric relationship, such as described above. Notably, reliance on the relative position of multiple sensors can also help to address error distortions (e.g., magnetic field distortions of EM sensors) since such errors will apply approximately evenly to the sensors given their close proximity and will therefore be negligible or effectively cancelled out when comparing measurements provided by the sensors.

In at least certain implementations, the positional measurements provided by sensors mounted on distal portion 702 can be supplemented by additional position-related data. For example, and without limitation, such additional data may include device kinematics data (e.g., the known geometric relationship between sensors), tendon displacements (e.g., the length of tendon spooled from spindles for controlling bending of proximal steerable section 704 or distal steerable section 706), and measured tendon tensions. Additional measurement data may be extracted from images of the catheter assembly 700 captured during implant delivery using imaging systems, such as fluoroscopy or echocardiogram systems, and which may be further assisted by radio opaque markers or echo-visible fiducials positioned at distal tip 708, the sensor locations, or any other location of interest along distal portion 702. Any or all of the foregoing measurements can be combined with the data captured directly from sensors mounted on distal portion 702 to create a fused estimate of proximal location 710, medial location 712, and distal location 714, or otherwise characterize the arrangement and orientation of distal portion 702.

As noted above, this disclosure contemplates that in at least some implementations, position measurement of distal portion 702 may rely on IMUs. IMUs are often provided in packages for measuring 3 DOFs, 6 DOFs, or 9 DOFs. For purposes of the present disclosure, 3 DOF IMUs including a gyro or an accelerometer; 6 DOF packages including integrated gyro and accelerometer; and 9 DOF packages including each of a gyro, accelerometer, and magnetometer are generally preferred. Space permitting, higher DOF packages are generally preferred due to the greater amount of data that they provide; however, implementations of this disclosure are not limited to any specific IMU configuration.

In certain implementations, sensors for measuring the position and orientation of distal portion 702 may undergo a calibration process. In certain implementations, the calibration process may occur on startup of the implant delivery system or when the handle assembly including catheter assembly 700 is first loaded onto the drive assembly. During calibration, the drive assembly may actuate the handle assembly into an initial position (e.g., based on a level of tension measured on spools of the handle assembly) and may record the corresponding sensor output to establish a zero position against which subsequent sensor measurements may be compared. Alternatively, system may undergo a factor calibration in which the system is moved into one more configurations and corresponding sensor measurements are recorded and used to establish coefficients, offsets, and other similar parameters for use when measuring position.

In at least some implementations, larger sensor packages may be positioned within a nosecone of distal portion 702. Such a nosecone may be attached following loading of the implant and would require an electrical connection to be made during attachment of the nosecone. In at least one implementation, such a connection may be made by running wires along the length of a guidewire lumen extending through main catheter body 703, the wires terminating in a connection at distal tip 708.

While this section primarily focuses on the use of IMU and EM sensors disposed along distal portion 702, this disclosure more contemplates the use of other sensors that may provide position measurements or data from which position data may be derived. For example, in one implementation, the system may include non-actuated tendons run in parallel with the actuated tendon. The non-actuated tendons may be only lightly tensioned to avoid slack such that by measuring displacement of the non-actuated tendons (e.g., by measuring rotation of a spool to which the non-actuated tendons are coupled), a more reliable displacement/location of the tendon coupling location may be determined.

In alternative implementations, fiber optic shape sensing may be used to determine the shape of the catheter assembly 700 during use. In such implementations fiber optics (e.g., in the form of a multi-core fiber optic cable) may be run along catheter assembly 700 in whole or in part (e.g., along distal portion 702). During operation, light is transmitted through the fiber optics. The location and degree of deformation of the fiber optics and, by extension, any device to which the fiber optics are coupled, may then be determined based on measuring scattering and other changes in the light. Accordingly, fiber optic shape sensing can be used to determine the shape of distal portion 702 and, by extension, the location of key components and locations, such as distal tip 708.

F. BAILOUT-RELATED PROCEDURES AND MANUAL DRIVE SYSTEMS

Robotic systems need to consider how a user can safely finish and/or bail out of a robotic procedure if a motor axis becomes inoperable, a component fails, and/or the system becomes inoperable in whole or in part. While it is possible to design systems with complete redundancy (e.g., as is done in space-related systems), doing so may result in substantial cost for the system and may not be feasible given the size and weight constraints of medical robots.

Robotic systems are commonly able to detect the failure of a motor axis or other component through redundant sensing, and upon detection of such a failure, to put the system into a fault state where unintended and/or uncontrolled motion of the robot is prevented. Once in the fault state, the user may determine whether it is necessary to remove the robot from the patient, whether the robot may be reset or otherwise fixed in place, or if alternative approaches are requires.

The design of robotic delivery systems for structural heart implants brings unique challenges that are not addressed by current robotic fault handling solutions. For example, predicate robotic delivery and surgery systems are generally intended for use in procedures in which, when a fault occurs at the robot, the robot may simply be stopped/powered down to enter a safe state. With the robot in a safe state, the delivery device may then be safely removed from the patient in a limp/back-drivable configuration, occasionally with some form of minimal bailout (e.g., opening up jaws or retention mechanisms).

In contrast, in structural heart implant delivery procedures, there often exists a critical point when a procedure must be seen through to completion. For example, unsheathing of an expandable mitral valve implant within the atrium generally precludes safe removal of the delivery device until after the implant is fully deployed and released from the delivery device. Stated differently, once unsheathed, implant delivery must generally be seen through to completion before the delivery system can be safely removed. So, for example, the delivery system must provide for some measure of manual control to complete the implantation procedure in the event the robotic components fail or become inoperative. Such manual control may also be necessary after the implant is delivered and released to safely navigate the delivery system away without dislocating the implant or damaging cardiac structures.

Prior to unsheathing in structural heart implant delivery procedures, the delivery system may be removed in a limp state, similar to other conventional robotic systems for use in non-cardiac applications. However, de-energizing the robotic components and allowing the robot to go limp may be problematic if the distal end of the delivery device is at or within the heart and runs the risk of puncturing or otherwise damages the wall of the heart or other cardiac structures.

Some faults may be software faults that are recoverable through restarting the system. In such cases, it is often preferable to recover from a software fault and resume normal driving operation before considering going into a bailout mode.

With the foregoing in mind, aspects of this disclosure are directed to enabling control of a robotic implant delivery system after a failure of the robotic capital equipment system driving the robotic delivery system. The failure may be a partial failure in the form of a loss of control of one actuator (e.g., by failing limp through failure of a motor drive or by failing locked through a binding failure of a gear box) or simultaneous failure of multiple actuators (e.g., through loss of power or communication to a motor drive module).

A first aspect of this disclosure relates to maintaining delivery system pose in response to a motor fault in which the motor loses power or is otherwise unable to hold tension on a tendon. In at least certain implementation of this disclosure, the issue of maintaining delivery system pose may be addressed by a failsafe braking mechanism for each motor. For example, FIG. 21 provides an example of a braking system in which a permanent magnet brake 620A is configured to fail into an engaged position that locks rotation of motor shaft 618A to hold the position of the motor.

Locking the pose of the robot may be critical when the delivery device is near or within the heart. In such cases, relaxation of the system may result in various complications including components of the catheter assembly contacting, obstructing, or otherwise impeding normal function of various cardiac structures. For example, relaxing the delivery system while the distal end of the system is positioned within the left atrium may cause the distal tip to inadvertently fall into the mitral valve annulus, impeding function of the mitral valve, obstructing the aortic valve, or causing other similar complications. Such risks are particularly acute following unsheathing and partial deployment of the implant.

Notably, locking the position of the delivery system may be less critical or even unnecessary during other segments of an implant delivery procedure. For example, if a fault occurs during initial delivery of the implant but prior to reaching or entering the heart or during withdrawal of the delivery device after it has cleared the heart, locking the delivery device pose on fault may not be necessary due to the relative compliance of the vasculature between the incision site and inferior vena cava and relatively low possibility of the delivery device damaging tissue as it undergoes relaxation.

With the foregoing in mind, fault-driven locking of the delivery device may be selectively engaged based on progress of the delivery procedure. So, for example, during initial delivery of the implant but prior to the implant reaching the heart, fault-driven locking of the delivery device motors may be disabled. During subsequent and more critical segments of the procedure, such as when the delivery device and/or implant is disposed within the heart and, in particular, when the implant is unsheathed but not yet released within the valve annulus, fault-driven locking of the delivery device motors may be enabled. Following release of the implant and retraction of the delivery device from the heart, fault-driven locking may again be disabled given the reduced risks presented by a fault after the delivery device is outside of the heart.

In general, when systems according to this disclosure encounter software-related faults, locking movement of the robot and diagnosing and clearing the faults without resetting the robotic system is generally preferred. Locking the robot reduces potential injury to the patient, particularly when the delivery system is within or near the heart, and generally permits the procedure to continue as planned once the fault is cleared.

In certain extreme cases, however, clearing software-related faults may require rebooting the computer systems of the robot, such as by performing a full power cycle of the robot and its associated computing systems. While locking the robot in such circumstances is possible, resuming a procedure may be challenging or impossible due to critical data being stored in non-volatile memory that is erased on loss of power. If the critical data includes start position or relative position data for components of the delivery system, for example, the robot may effectively lose its understanding of where its components are in space, presenting substantial risk of injury to the patient for any post-reboot actuation of the system. If the delivery system is disposed within the patient, the typical homing operations used to resolve such issues may be unavailable. As a result, the implant delivery procedure may need to be abandoned or the clinician may need to take full manual control to complete the procedure.

To support full reboots/power cycling, implementations of this disclosure may include absolute encoders for their motor. For example, FIG. 22 illustrates absolute encoder 624A, which measures absolute rotational position of motor shaft 618A of motor 604A. Each of motors 604B-604D of motor module 600 may also have absolute encoders for measuring rotation of their respective motor shafts.

In implementations including absolute encoders, loading and initialization of the robotic system may include establishing a starting motor angle relative to a fixed zero point of the encoder. As part of the initialization process, the robotic system further collects starting position data for the delivery device and its components and correlates that data with the zero-point data collected from the encoders. The zero-position data is then stored in non-volatile memory such that, if the system is restarted with the delivery device still installed, the user can resume driving and operation of the device without the need to redo a homing procedure (which often requires the device be in a straight or otherwise predefined configuration).

In certain implementations, the system may store commanded states/poses of the device to know where to pick up from on reboot. Alternatively, the system may be configured to use a current position of the absolute encoders and the known zero position stored in non-volatile to determine the closest valid device position. Control may then be resumed based on the closest valid device position.

G. OVERVIEW OF ROBOTIC IMPLANTATION SYSTEM

Figure 25:
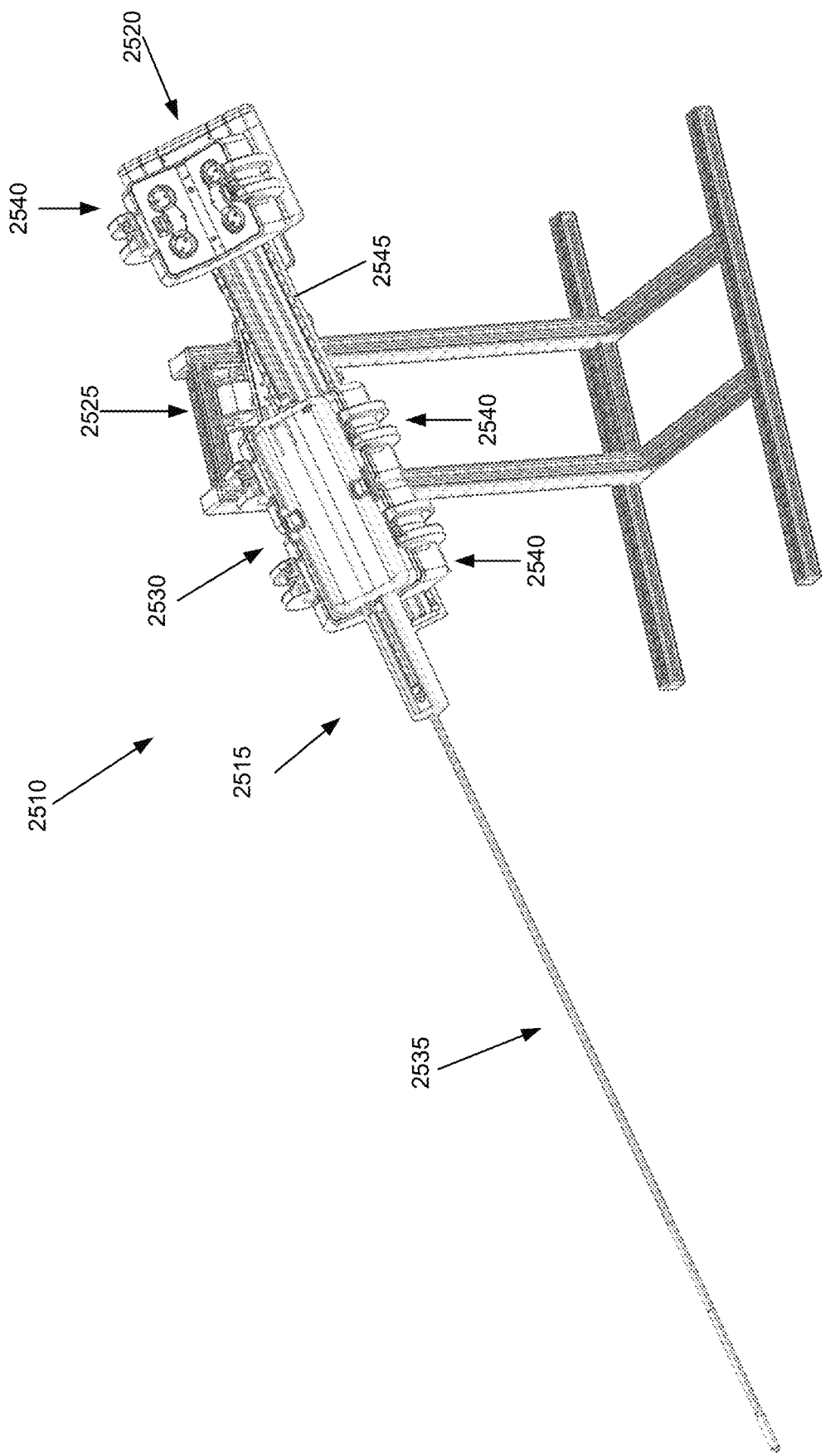
FIG. 25 is a front perspective view of robotic implantation system.
Figure 26:
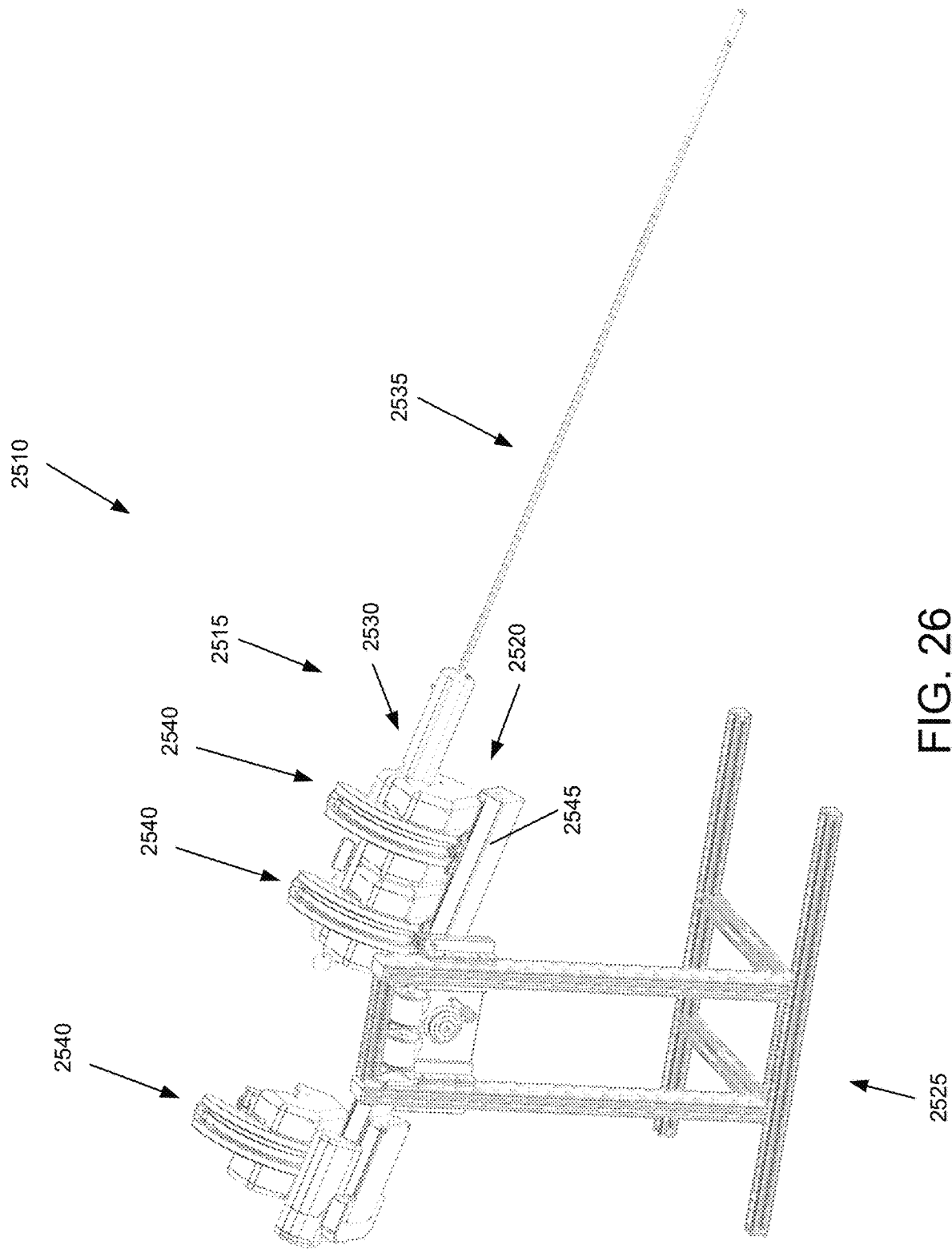
FIG. 26 is a back perspective view of the robotic implantation system.

FIGS. 25 and 26 are respectively front and back perspective views of a robotic implantation system 2510 including a catheter 2515, a robot 2520 and a stand 2525 and according to one specific implementation of this disclosure. The catheter 2515 includes a handle assembly 2530 and a tubular body assembly 2535 extending distally from the handle assembly. While the robotic implantation system 2510 disclosed herein is discussed in the context of transcatheter cardiac implant delivery, in some embodiments it may be employed for the implantation of other types of implants or the performance of other surgical procedures.

The robot 2520 includes one or more carriages 2540 and a linear displacement platform 2545. The carriages 2540 are supported on the linear displacement platform 2545 and are both rotatable relative to, and linearly displaceable along, the linear displacement platform.

The stand 2525 is coupled to the linear displacement platform 2545 and adjustable with respect to the height of the robot 2520 above the floor.

While the following discussion focuses on the specific implementation of the robotic implantation system 2510, this disclosure contemplates that certain features and functions of the robotic implantation system 2510 may be modified, omitted, or adapted in other implementations and that such implementations are within the scope of this disclosure.

H. CATHETER INTERFACED WITH CARRIAGE OF ROBOT

Figure 27:
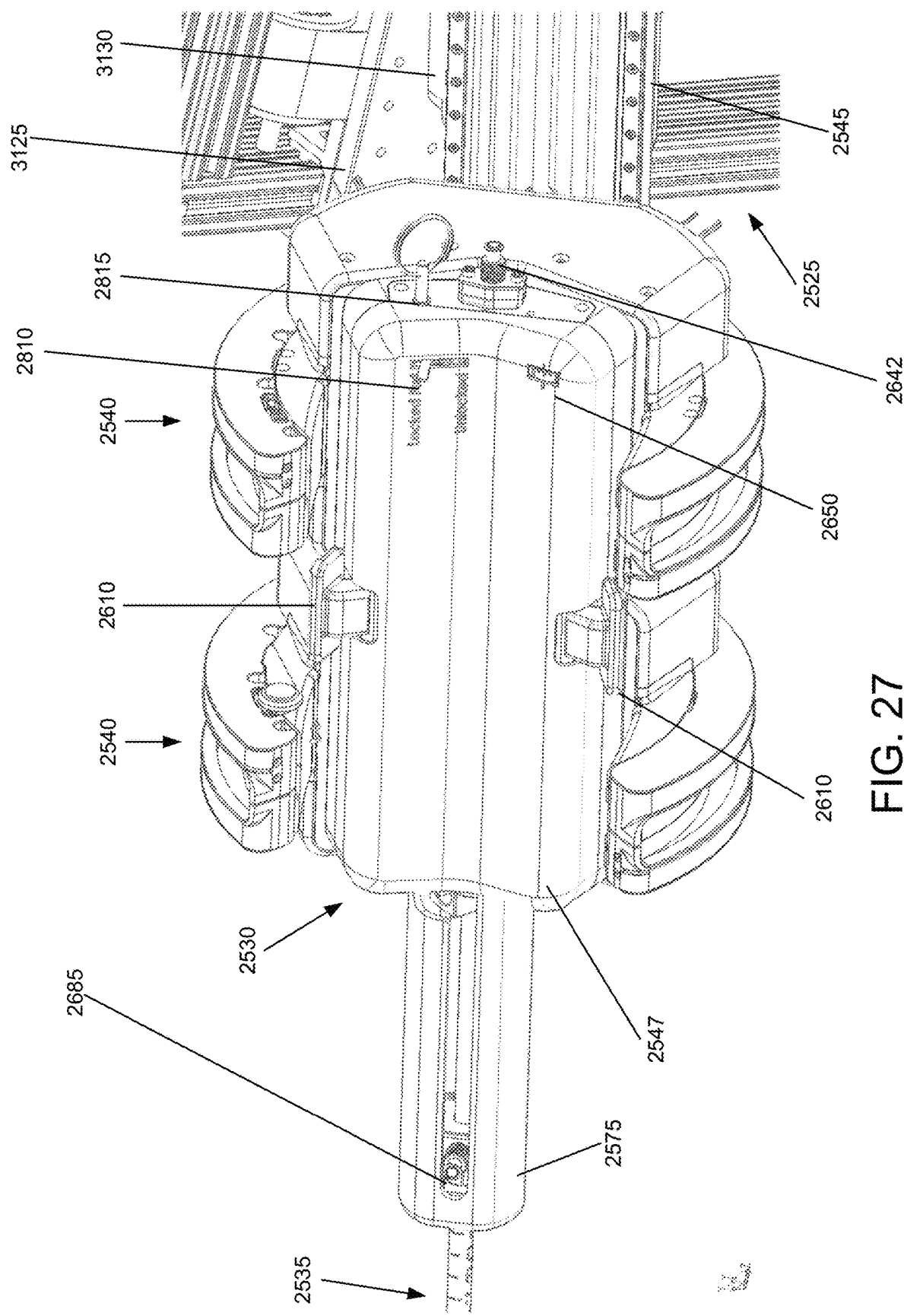
FIG. 27 is an enlarged top perspective view of the handle assembly nested against two carriages of the robot as depicted in FIG. 1.

FIG. 27 is an enlarged top perspective view of the handle assembly 2530 and two carriages 2540 as depicted in FIG. 25. As shown in FIG. 27, the handle assembly 2530 nests against the carriages 2540 such that the powered mechanisms of each carriage can drive the corresponding mechanical mechanisms of the handle assembly 2530, which in turn manipulates the functions of the tubular body assembly 2535. The handle assembly 2530 is enclosed by a removable housing shell 2547.

Figure 28:
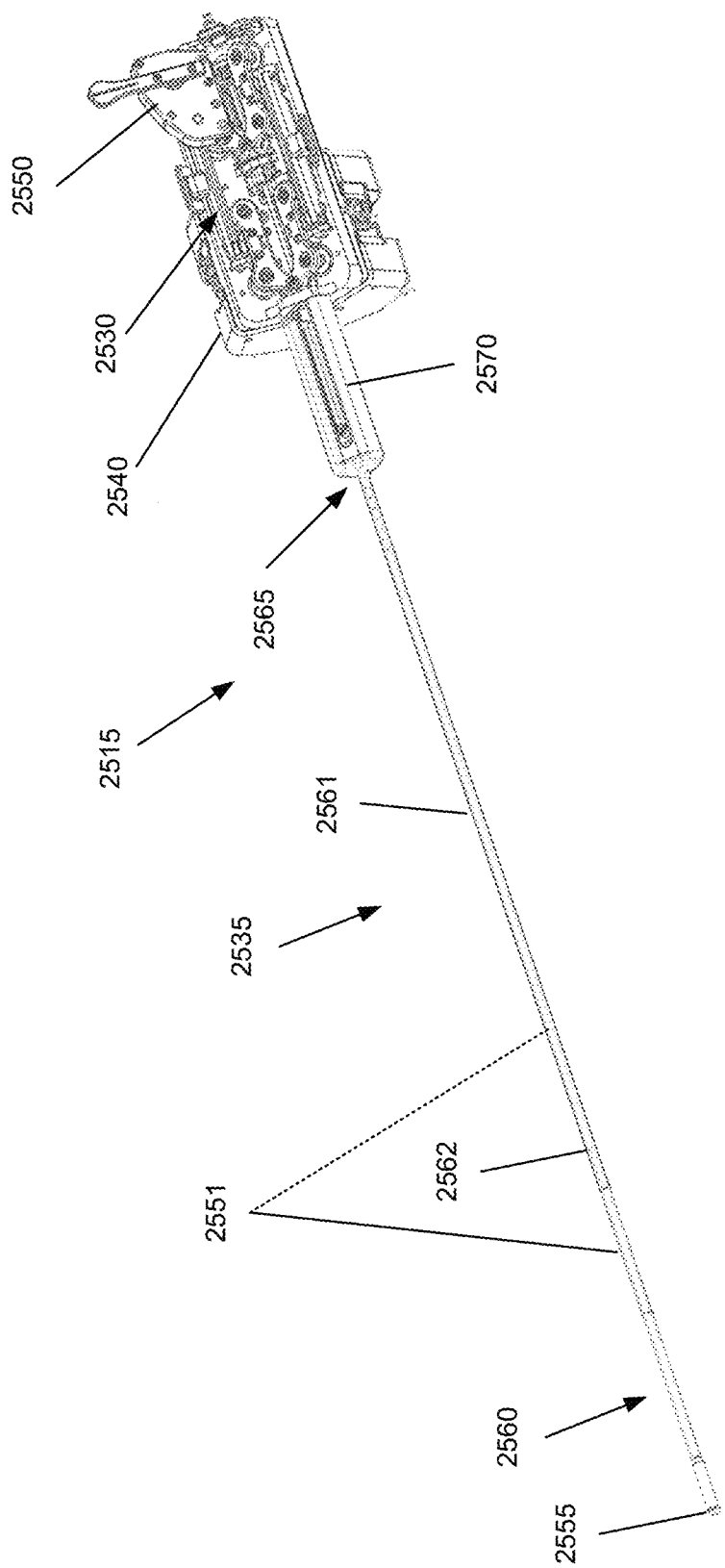
FIG. 28 is a top perspective view of the catheter with its handle assembly nested with an example carriage, a housing shell of the handle assembly removed, and a manual pull wire assembly interfaced with the handle assembly.
Figure 29:
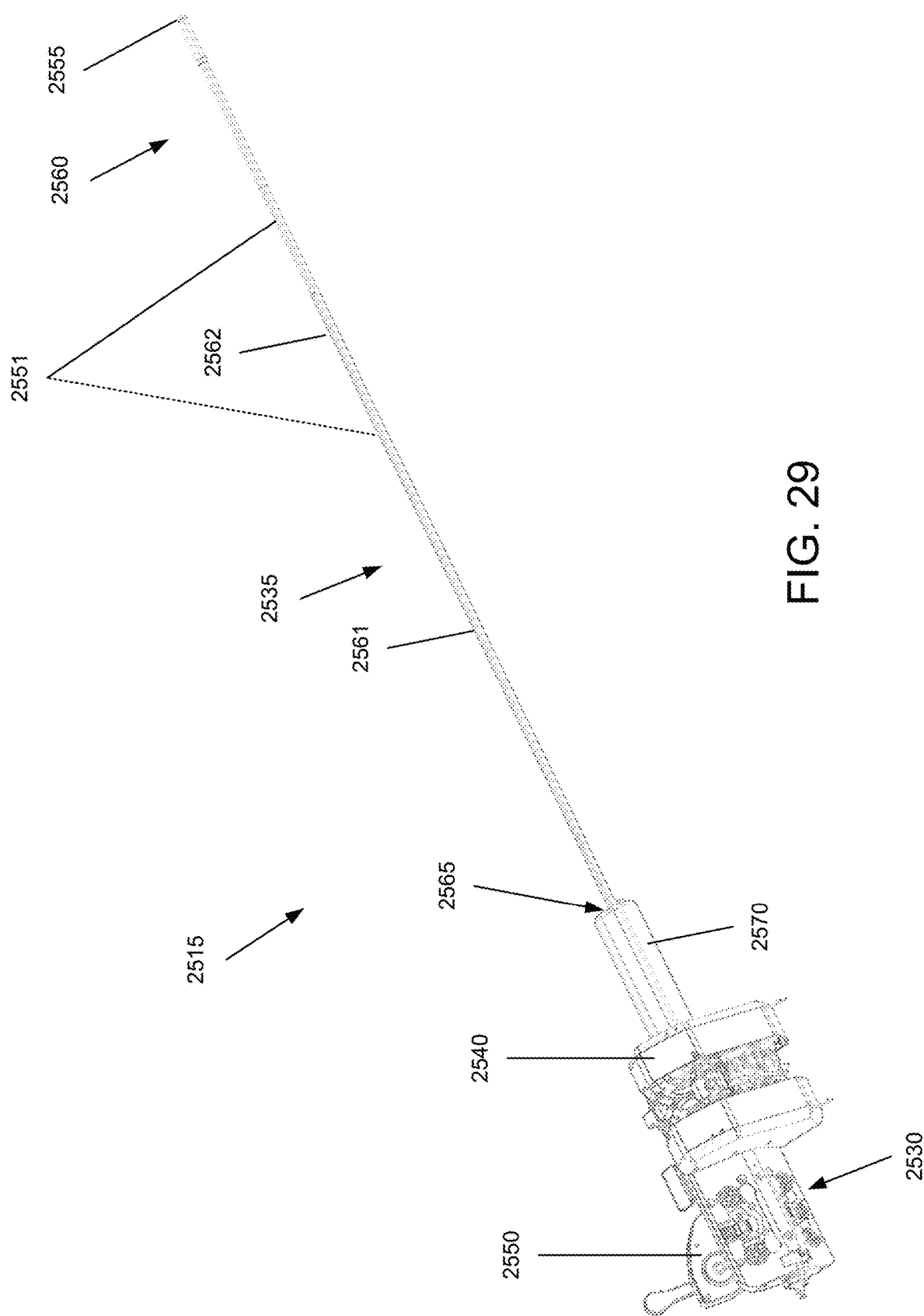
FIG. 29 is a bottom perspective view of the same elements depicted in FIG. 28.

FIGS. 28 and 29 are respectively top and bottom perspective views of the catheter 2515 with its handle assembly 2530 nested with an example carriage 2540, the housing shell 2547 of the handle assembly removed, and a manual pull wire assembly 2550 interfaced with the handle assembly. As indicated in FIGS. 28 and 29, the tubular body assembly 2535 includes an inner tubular body 2551 with a distal tip 2555 and a deflectable region 2560 extending for a distance proximal of the distal tip. The deflectable region is deflectable by operation of the mechanical mechanisms of the handle assembly 2530, as discussed in detail below.

A sheath 2561 is coaxially supported about the inner tubular body 2551 and is linearly displaceable along the inner tubular body distally/proximally such that a distal end 2562 of the sheath is distally/proximally displaceable relative to the distal tip 2555 of the inner tubular body 2551 via operation of the mechanical mechanisms of the handle assembly 2530 as discussed in detail below.

A proximal end 2565 of the tubular body assembly 2535 couples to a sheath retraction assembly 2570 forming a distal region of the handle assembly 2530.

Figure 30:
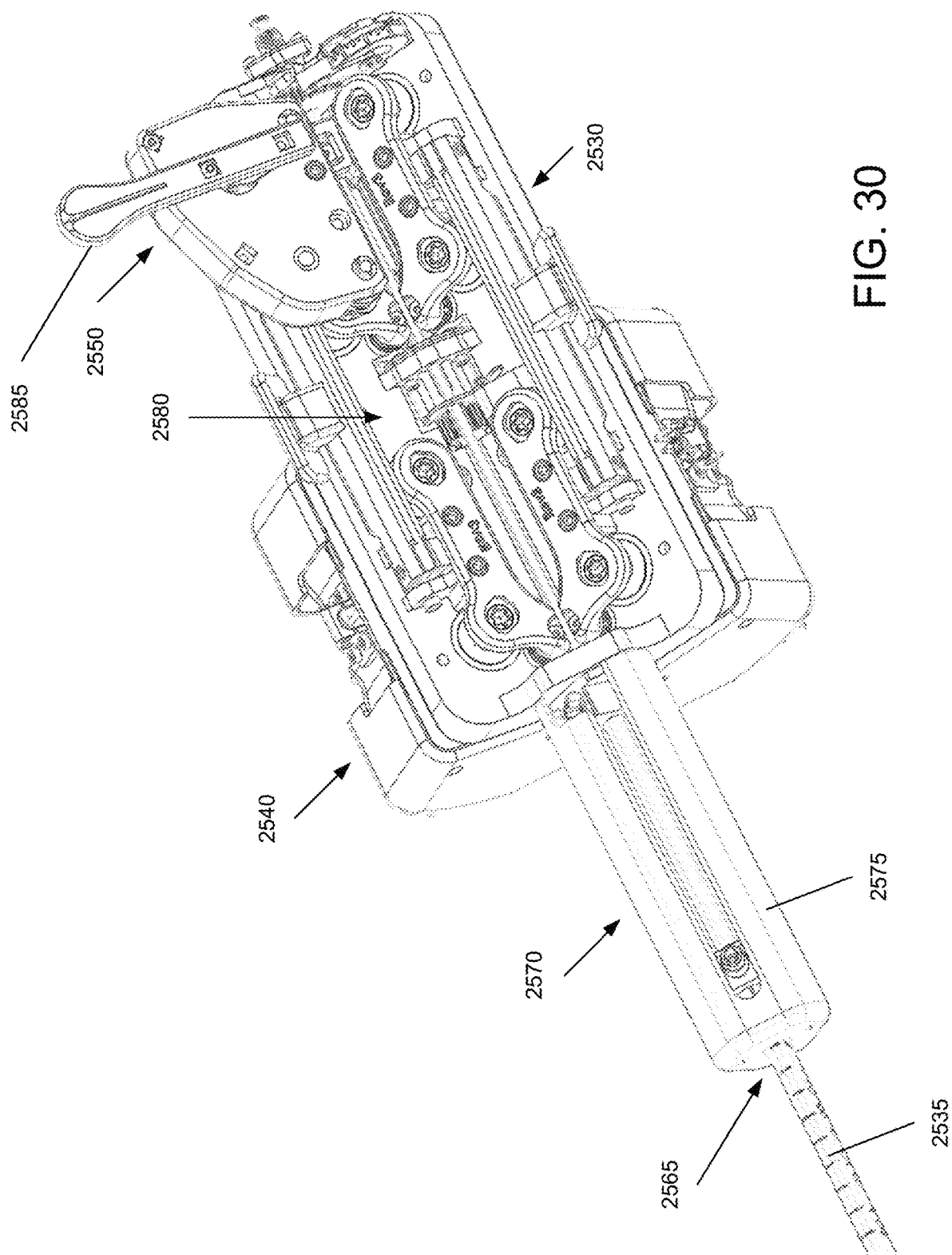
FIGS. 30 and 31 are enlarged views of the handle assembly according to the same respective views shown in FIGS. 28 and 29.
Figure 31:
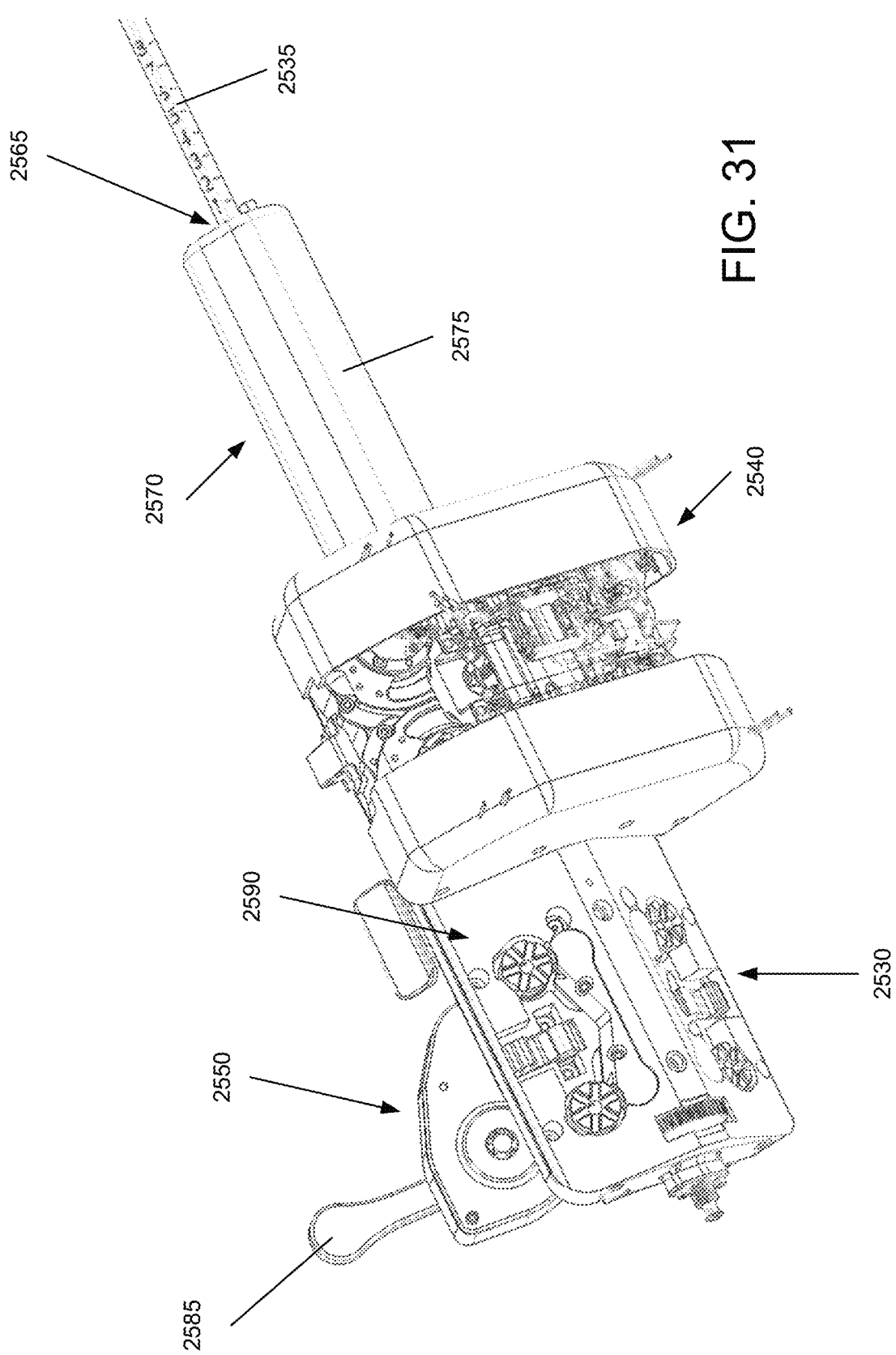

FIGS. 30 and 31 are enlarged views of the handle assembly 2530 according to the same respective views shown in FIGS. 28 and 29. As can be understood from FIGS. 30 and 31, the handle assembly 2530 has space to nest with a second carriage 2540 as shown in FIG. 27. The carriage 2540 depicted in FIGS. 28-31 is shown without its C-arm, which is discussed in detail below.

The sheath retraction assembly 2570 is enclosed by a housing 2575. As described in greater detail later in this Detailed Description, upon removal of the housing shell 2547 (shown in FIG. 27), the manual pull wire assembly 2550 can mechanically interface with drive features in an top side 2580 of the handle assembly 2530, as depicted in FIGS. 30 and 31. With the manual pull wire assembly 2550 so interfaced with the handle assembly, an interventional cardiologist or other medical professional can use a handle 2585 of the manual pull wire assembly 2550 to manually manipulate the mechanical mechanisms of the handle assembly 2530 to manipulate the tubular body assembly 2535 as desired should there be a problem with the robot 2520.

As can be understood from FIG. 31, a bottom side 2590 of the handle assembly 2530 mechanically interfaces with coupling and drive features of a nesting side 2587 of the carriage 2540 (see FIGS. 49 and 50), thereby allowing the handle assembly 2530 to nest with one or more carriages, as illustrated in FIGS. 25-27. With the handle assembly 2530 so interfaced with the nesting side of the carriage 2540, the robot can drive the mechanical mechanisms of the handle assembly to manipulate the tubular body assembly as desired.

I. HANDLE ASSEMBLY OF CATHETER

Figure 32:
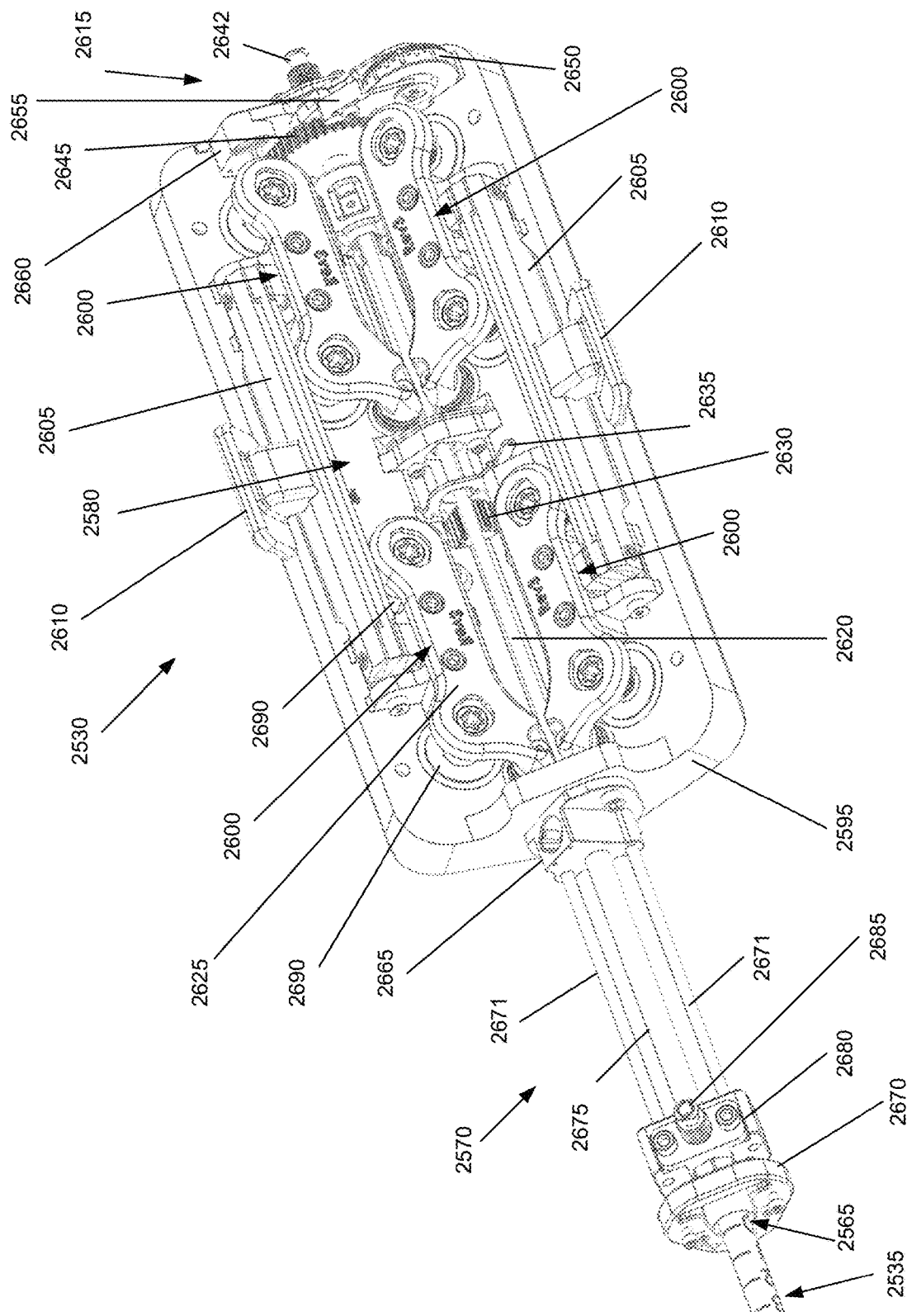
FIGS. 32 and 33 are enlarged views of the handle assembly according to the same respective views shown in FIGS. 24 and 29, but with the sheath retraction assembly housing, the manual pull wire assembly, and the carriage having been removed.
Figure 33:
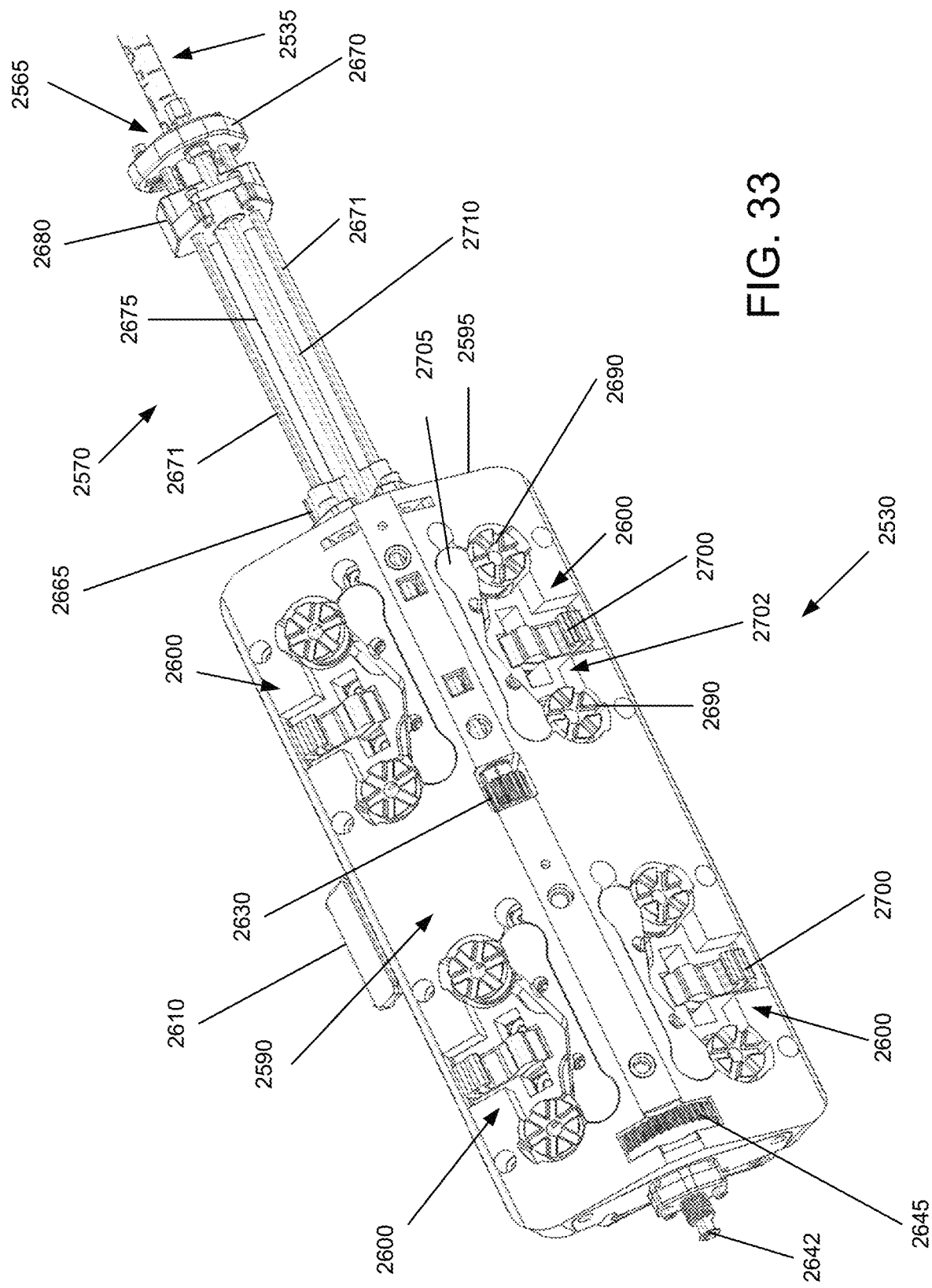

FIGS. 32 and 33 are enlarged views of the handle assembly according to the same respective views shown in FIGS. 28 and 29, but with the sheath retraction assembly housing 2575, the manual pull wire assembly 2550, and the carriage having been removed 2540. As indicated in FIGS. 32 and 33, the handle assembly 2530 includes a handle frame 2595 that supports cable control assemblies 2600, latch tie bars 2605 each having a handle latch pad 2610, a furl assembly 2615, a stator 2620, a lead screw gear 2630, a sheath lock plate 2635, a working channel fitting (e.g., the proximal fitting 2642), and the sheath retraction assembly 2570 extending distally from the handle frame 2595.

As can be understood from FIG. 27, each handle latch pad 2610 works with the removable housing shell 2547 to couple the removable housing shell to the handle assembly 2530.

Additionally, handle latch pad 2610 and its respective latch tie bar may be coupled to one or more respective handle latches disposed on an underside of the handle assembly 2530 (e.g., handle latches 2700, which are indicated in FIG. 33, which is coupled to tie bar 2605). The handle latches may be spring-loaded or otherwise biased to retain the handle assembly 2530 on carriages of a corresponding robot and configured to release when the corresponding tie latch bar is depressed (e.g., by depressing the corresponding handle latch pad). In implementations including multiple handle latches coupled to a single latch tie bar, operation of a latch tie bar (e.g., by depressing a handle latch pad of the latch tie bar) may simultaneously release the multiple handle latches.

As shown in FIGS. 32 and 33, each cable control assembly 2600 includes a bearing cap 2625, two cable control spindles 2690, a handle latch 2700, a plate receiving recess 2702, and a bottom spring cap 2705. In this embodiment of the handle assembly 2530 there are four cable control assemblies 2600. In other embodiments, the handle assembly may have more or fewer cable control assemblies.

As discussed in detail below, the cable control assemblies 2600 are driven by electromechanical aspects of the carriages 2540 of the robot 2520 when the handle assembly 2530 is nested with the carriages as shown in FIGS. 25-31. Alternatively, a manual pull wire assembly 2550 can be interfaced with a cable control assembly if the robot is not available or not desired, as shown in FIGS. 28-31. Either way and as discussed in detail below, each cable control assembly 2600 allows for the deflection of the deflectable region 2560 of the inner tubular body 2551 via pairs of actuation cables 2720 (e.g., see FIG. 35).

The furl assembly 2615 includes a capstan gear 2645, a furl dial 2650, a furl inside plate 2655, and a furl back plate 2660. The inside and back furl plates support the rotating elements of the furl assembly. As shown in FIG. 27, the furl dial 2650 is visible through an opening in the removable housing shell 2547, thereby allowing the medical professional to monitor and measure the extent to which furling/unfurling of the implant has occurred at the distal tip 2555 of the inner tubular body 2551 on account of operation of the mechanisms of the handle assembly 2530.

Again, referring to FIGS. 32 and 33, the sheath retraction assembly 2570 is coupled to the handle frame 2595 by a shaft mount 2665. Distally opposite the shaft mount is a sheath nose block 2670, which forms the distal end of the retraction assembly. Guide shafts 2671, a capstan steering shaft 2675 and an ultra-precision lead screw 2710 extend between the shaft mount and the sheath nose block. In one embodiment, the ultra-precision lead screw 2710 may be a single start or multi-start leadscrew, a leadscrew such as those employed in a threadless ball screw assembly, or other types of leadscrews for other leadscrew arrangements.

Figure 34:
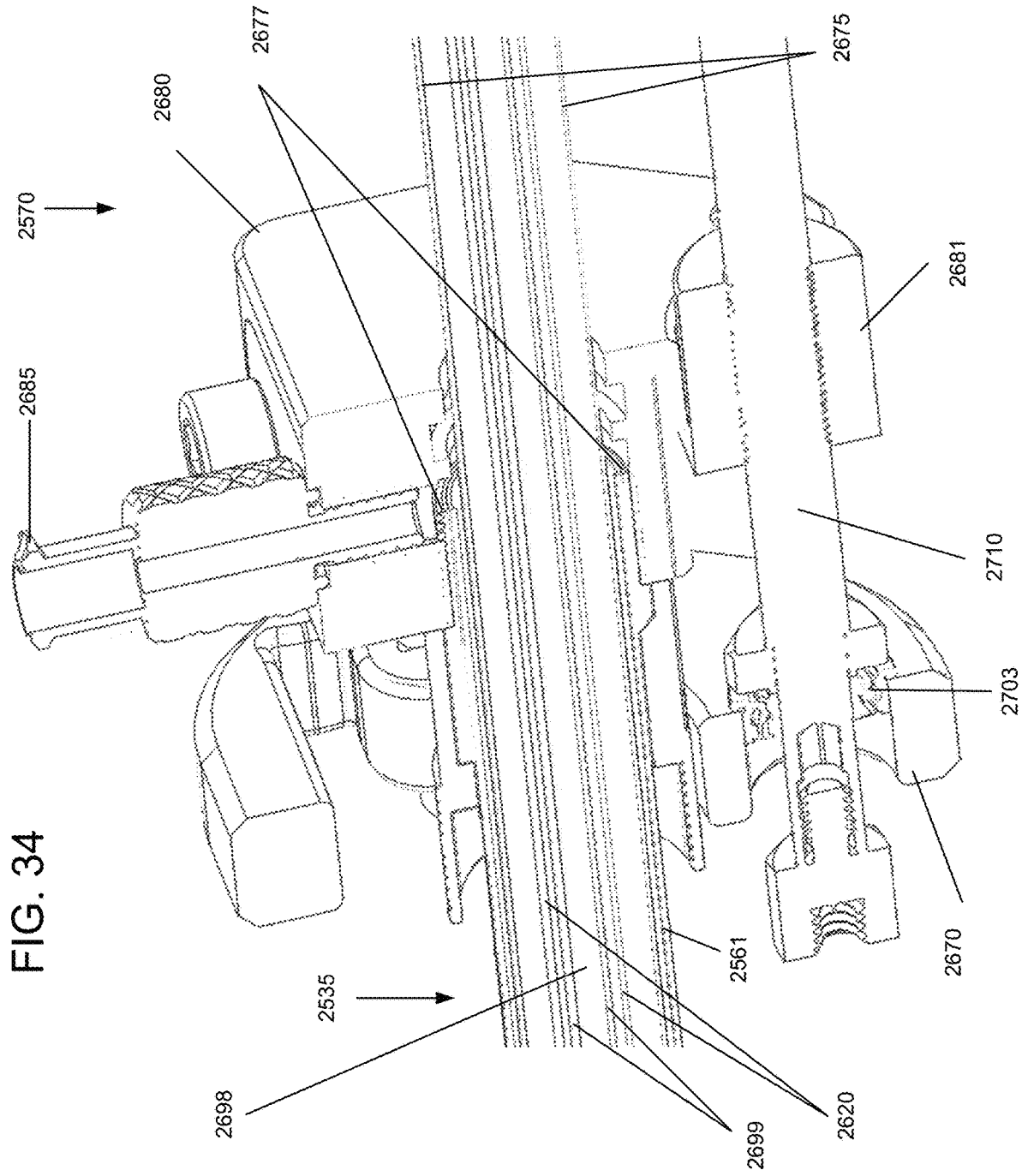
FIG. 34 is longitudinal sectional elevation taken along the capstan steering shaft and the ultra-precision lead screw and through the sheath nose block and a sheath mount block near the distal end of the sheath retraction assembly.

FIG. 34 is longitudinal sectional elevation taken along the capstan steering shaft 2675 and the ultra-precision lead screw 2710 and through the sheath nose block 2670 and a sheath mount block 2680 near the distal end of the sheath retraction assembly 2570. As can be understood from FIG. 32-34, a proximal end 2677 of the of the sheath 2561 is coupled to the sheath mount block 2680. The sheath mount block 2680 slides distal/proximal along the capstan steering shaft 2675 and guide shafts 2671 driven by clockwise/counterclockwise rotation of the ultra-precision lead screw 2710 received therethrough by a fast travel flange 2681. Because the mechanical interaction between the ultra-precision lead screw and the fast travel flange is at a minimum thread-like regardless of whether these elements are indeed threaded or threadless (e.g., threadless ball screw assembly), clockwise/counterclockwise rotation of the ultra-precision lead screw 2710 drives the fast travel flange 2681 distal/proximal. As a result, the sheath mount block is driven distal/proximal relative to the rest of the sheath retraction assembly 2570, thereby driving the sheath distal end 2562 distal/proximal to the distal tip 2555 of the inner tubular body 2551 to cause the sheath 2561 to extend/retract to cover/uncover the distal tip 2555 and deflectable region 2560 of the inner tubular body 2551 (see FIGS. 28 and 29).

As illustrated in FIGS. 32 and 34, the sheath mount block 2680 includes a distal fitting 2685. In one embodiment, the proximal fitting 2642 may be a Tuohy-Borst connector and the distal fitting 2685 may be in the form of a Luer lock fitting. A Tuohy-Borst connector may allow a guidewire to be passed therethrough while still allowing for the introduction of flushing fluids.

In other embodiments, these fittings 2642 and 2685 may be both or alternatively Tuohy-Borst, Luer or other quick connect/disconnect fittings. Regardless, these fittings 2642 and 2685 are used to couple to a piece of medical equipment used to effectuate the medical procedure and/or to couple to a medical lumen through which a medical fluid (e.g., saline, $CO_2$, etc.) flows into the fittings 2642, 2685. Both fittings 2642, 2685 are visible when the housing shells 2547, 2575 are in place over their respective assemblies, as depicted in FIG. 27.

Figure 35:
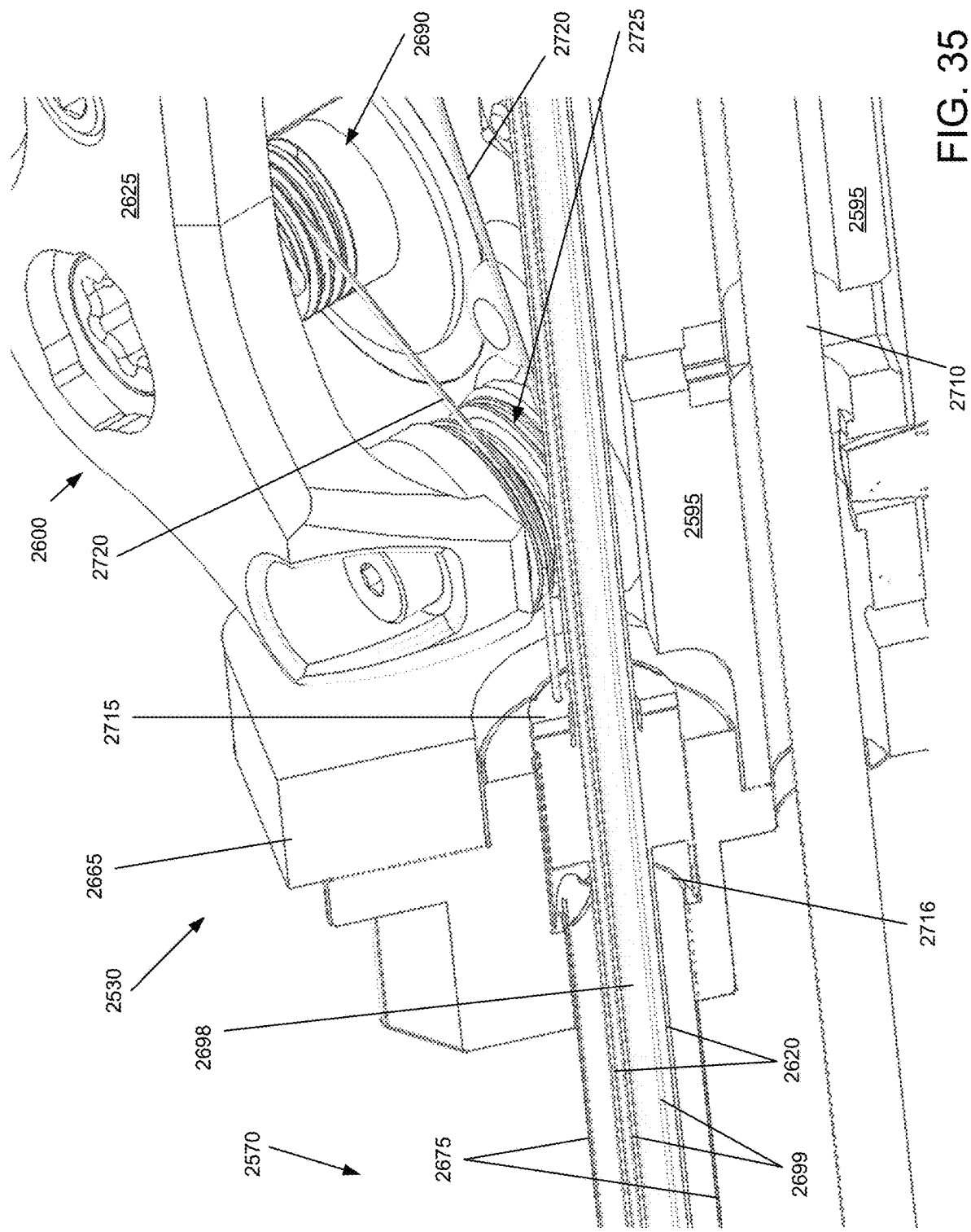
FIG. 35 is longitudinal sectional elevation taken along the capstan steering shaft and the ultra-precision lead screw and through the shaft mount near the intersection between the proximal end of the sheath retraction assembly and the distal end of the handle frame.

FIG. 35 is longitudinal sectional elevation taken along the capstan steering shaft 2675 and the ultra-precision lead screw 2710 and through the shaft mount 2665 near the intersection between the proximal end of the sheath retraction assembly 2570 and the distal end of the handle frame 2595. As illustrated in FIGS. 28, 29, 34 and 35 and starting inwardly and working outwardly from the center of the tubular body assembly 2535, the tubular body assembly is a coaxial arrangement of tubular bodies with its center being a center or working lumen 2698 that is a lumen of a rotor 2699. The rotor 2699 is coaxially surrounded by the stator 2620, which is coaxially surrounded by the capstan steering shaft 2675. The capstan steering shaft 2675 is surrounded by the sheath 2561. The rotor 2699 is configured to rotate clockwise/counterclockwise within the stator 2620 to unfurl or furl an implant carried by the tubular body assembly 2535 at its distal tip 2555. An example of such an implant can be found in: U.S. Pat. No. 11,197,755, which is titled "Systems, Devices and Methods for Folded Unibody Heart Valve Stents" and has a filing date of Oct. 28, 2020, and a grant date of Dec. 14, 2021; and U.S. patent application Ser. No. 17/549,690, which is titled "Systems, Devices and Methods for Folded Unibody Heart Valve Stents" and has a filing date of Dec. 13, 2021. The disclosures of these patents/applications are all fully incorporated by reference in their entireties into this present disclosure. The working lumen 2698 of the rotor 2699 may receive a medical device (e.g., guidewire, stylet, catheter, etc.) therethrough and/or a medical fluid (e.g., saline, $CO_2$, etc.).

It should be noted that the robotic implantation system 2510 disclosed herein may also be used to implant other types of implants with little or no further adaptation of the system 2510, depending on the implant and location in the body. The rotor 2699 can be configured to facilitate deployment of any implant with rotation-based actuation. For example, the robotic implantation system 2510 may be used to implant a clip-style implant similar to that disclosed in U.S. Pat. No. 11,654,024, which is titled "Heart Valve Clip" and has a filing date of Nov. 22, 2022, and a grant date of May 23, 2023.

As can be understood from FIGS. 32-34 and discussed in greater detail below, the proximal end 2677 of the sheath 2561 is couple to the sheath mount block 2680, and the sheath 2561 distally terminates at the sheath distal end 2562. The sheath 2561 is longitudinally displaceable distal/proximal about the capstan steering shaft 2675. The capstan steering shaft 2675 extends from within the handle assembly 2530, through the sheath retraction assembly 2570, and through the inner tubular body 2551 to a distal portion thereof, as described in: U.S. Pat. No. 11,246,726, which is titled "Systems, Devices and Methods for Delivery Systems", and has a filing date of Feb. 18, 2021 and a grant date of Feb. 15, 2022; and U.S. patent application Ser. No. 17/670,403, which is similarly titled "Systems, Devices and Methods for Delivery Systems" and has a filing date of Feb. 11, 2022. The disclosures of these patents/applications are all fully incorporated by reference in their entireties into this present disclosure.

As can be understood from FIGS. 32, 33 and 35, the rotor 2699 and stator 2620 both extend distally and coaxial from within the handle assembly 2530. The rotor and stator further extend through a cable passthrough plate 2715 and the shaft mount 2665. The rotor and stator then pass into and through the sheath retraction assembly 2570 and the capstan steering shaft 2675 of the inner tubular body 2551 to a distal portion thereof, as described in: U.S. Pat. No. 11,246,726, which is titled "Systems, Devices and Methods for Delivery Systems", and has a filing date of Feb. 18, 2021 and a grant date of Feb. 15, 2022; and U.S. patent application Ser. No. 17/670,403, which is similarly titled "Systems, Devices and Methods for Delivery Systems" and has a filing date of Feb. 11, 2022. As noted above, the disclosures of these patents/applications are all fully incorporated by reference in their entireties into this present disclosure. A proximal end 2716 of the capstan steering shaft 2675 is secured to the shaft mount 2665.

As illustrated in FIGS. 32-35, the ultra-precision lead screw 2710 extends from within the handle assembly 2530, through the fast travel flange 2681 of the sheath mount block 2680 to terminate at the sheath nose block 2670 via a ball bearing assembly 2703 mounted in the sheath nose block.

As can be understood from FIGS. 32 and 33, the lead screw gear 2630 and capstan gear 2645 protrude through the surfaces of the top side 2580 and bottom side 2590 of the handle frame 2595. On account of protruding through the surface of the bottom side 2590 of the handle frame 2595, the lead screw gear 2630 and capstan gear 2645 can respectively mechanically interface with a drive gear 2712 of a first carriage 2540 and a drive gear 2712 of a second carriage 2540 when the handle assembly 2530 employs and nests with two paired carriages 2540 as shown in FIG. 27. As discussed below in greater detail with respect to FIGS. 49 and 50, the drive gear 2712 of each carriage 2540 protrudes through the nesting side 2587 of each carriage 2540.

As depicted in FIG. 35, a pair of actuation cables 2720 can be seen to extend from corresponding cable control spindles 2690 and across an idler pulley 2725 to pass through the cable passthrough plate 2715. While not depicted in this figure or others for purposes of picture clarity, this pair of actuation cables 2720, and other pairs of actuation cables extending from other cable control assemblies 2600, then extend from the cable passthrough plate 2715 down the capstan steering shaft 2675 between its inner circumferential and the outer circumference of the stator 2620. The distal ends of these actuation cables 2720 anchor to features within the deflectable region 2560 of the inner tubular body 2551 to allow a medical professional to use the handle assembly 2530 to bring about a desired deflection of the deflectable region of the tubular body assembly. For more detail regarding these cables as they exist and operate within the tubular body assembly 2535, see U.S. Pat. No. 11,246,726, which is titled "Systems, Devices and Methods for Delivery Systems", and has a filing date of Feb. 18, 2021 and a grant date of Feb. 15, 2022; and U.S. patent application Ser. No. 17/670,403, which is similarly titled "Systems, Devices and Methods for Delivery Systems" and has a filing date of Feb. 11, 2022. As noted above, the disclosures of these patents/applications are all fully incorporated by reference in their entireties into this present disclosure.

Figure 36:
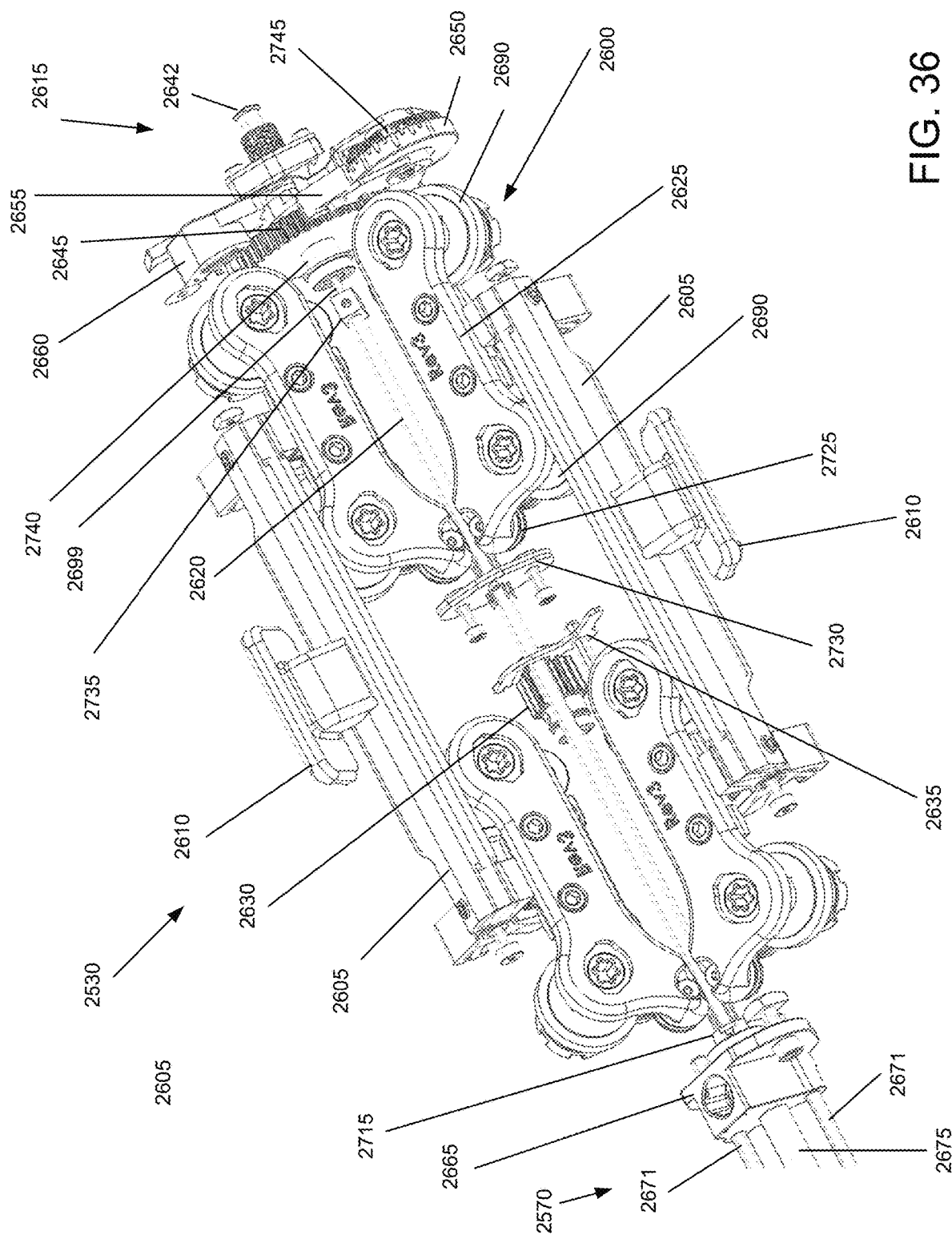
FIGS. 36 and 37 are the same respective views as FIGS. 32 and 33, except the handle frame has been removed for clarity purposes.
Figure 37:
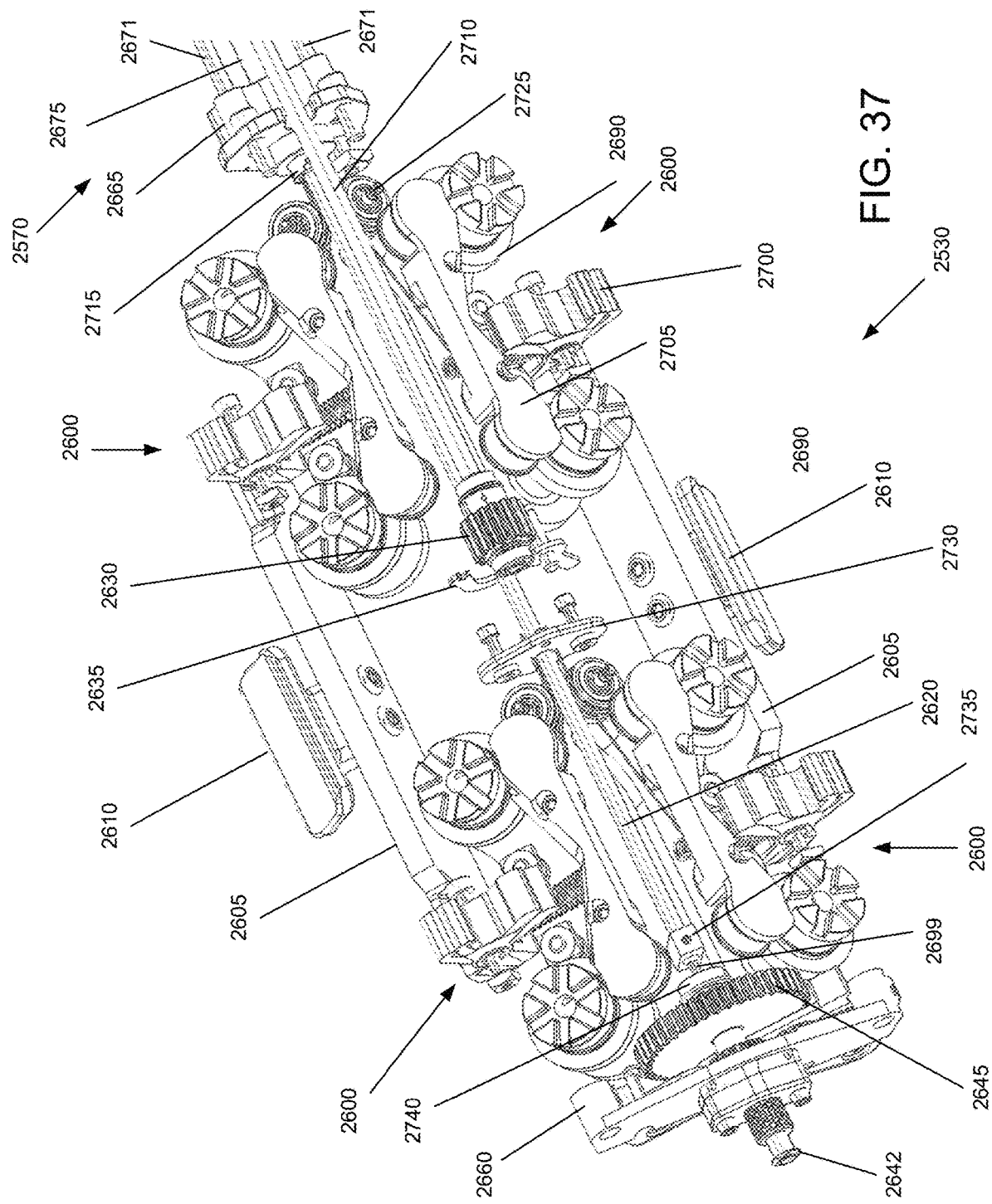

FIGS. 36 and 37 are the same respective views as FIGS. 32 and 33, except the handle frame 2595 has been removed for clarity purposes. As more clearly depicted in these figures, each cable control assembly 2600 includes a bearing cap 2625, two cable control spindles 2690, a handle latch 2700, a bottom spring cap 2705, and an idler pulley 2725. Each cable control assembly 2600 includes a pair of actuation cables 2720, one actuation cable coming off of one of the two cable control spindles 2690 of the specific cable control assembly 2600 and the other actuation cable coming off of the other of the two cable control spindles 2690.

While not actually depicted along their full length through the handle assembly 2530 for purposes of figure clarity, in the case of the actuation cables 2720 of either of the two most proximal cable control assemblies 2600, the two actuation cables extend from their respective cable control spindles 2690 to pass across the idler pulley 2725 of the specific cable control assembly 2600 before passing through a proximal cable passthrough plate 2730. From the proximal cable passthrough plate 2730 the two actuation cables then pass through the distal cable passthrough plate 2715 before entering the capstan steering shaft 2675 on the way to the deflectable region 2560 of the inner tubular body 2551. In the case of the actuation cables 2720 of either of the two most distal cable control assemblies 2600, the two actuation cables extend from their respective cable control spindles 2690 to pass across the idler pulley 2725 of the specific cable control assembly 2600 before passing through the distal cable passthrough plate 2715 and entering the capstan steering shaft 2675 on the way to the deflectable region 2560 of the inner tubular body 2551.

As illustrated FIGS. 36 and 37, a stator key 2735 forms a proximal end of the stator 2620 such that the stator does not enclose the rotor 2699 proximal of the stator key. Just proximal of a proximal side of the stator key 2735 is a furl hub 2740. In FIG. 36, a furl gear 2745 can be seen immediately adjacent the furl dial 2650 as part of the furl assembly 2615.

Figure 38:
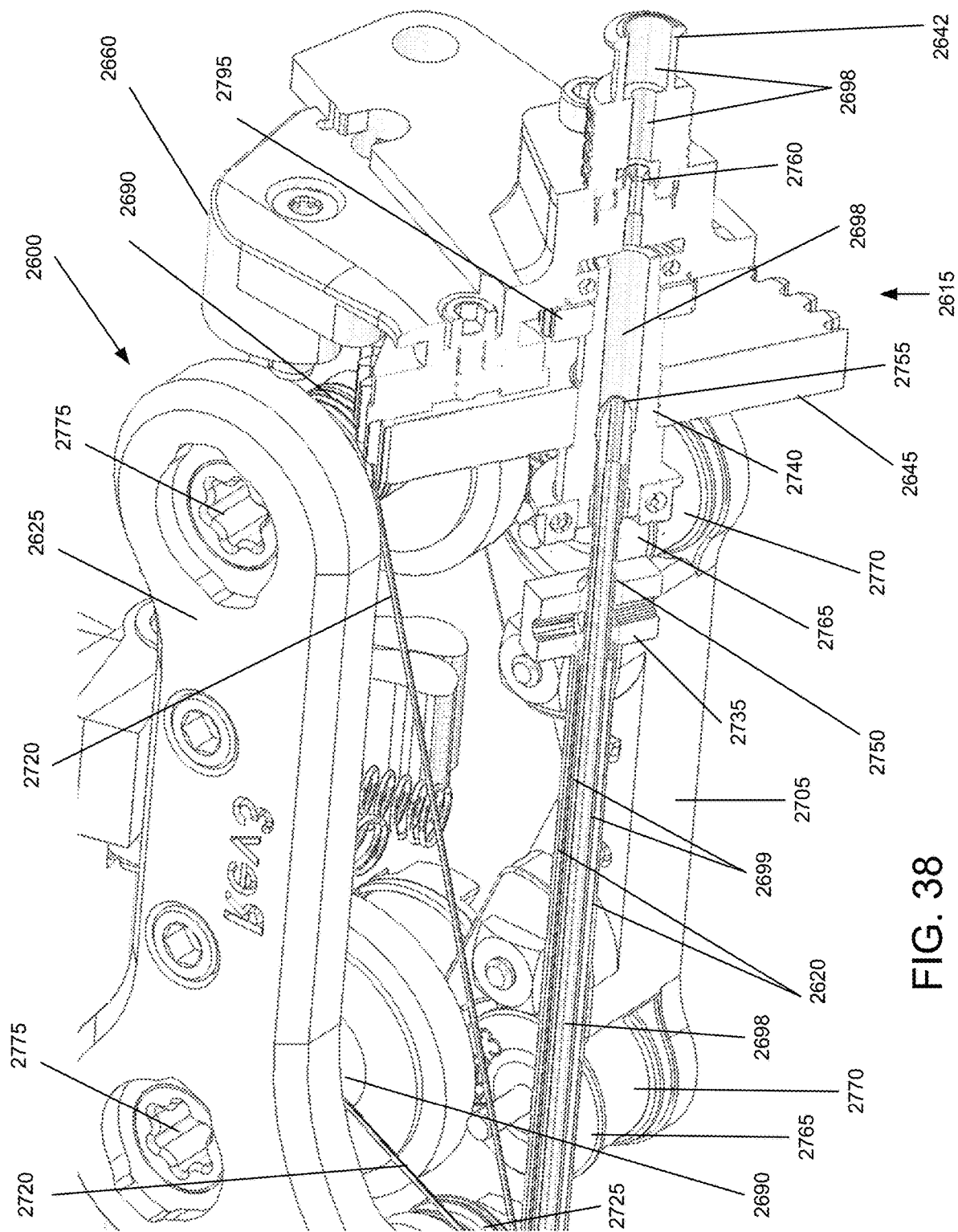
FIG. 38 is longitudinal sectional elevation taken along the stator, rotor, stator key, furl hub and proximal fitting.

FIG. 38 is longitudinal sectional elevation taken along the stator 2620, rotor 2699, stator key 2735, furl hub 2740 and proximal fitting 2642. As depicted in FIG. 38, the furl hub 2740 serves as the rotational hub for the capstan gear 2645. A proximal end 2750 of the stator 2620 terminates at a proximal side of the stator key 2735. A proximal end 2755 of the rotor 2699 terminates within the furl hub 2740. A guidewire disk 2760 is located proximal the furl hub 2740 and partially within and distal the proximal fitting 2642. Although not shown in FIG. 38, a tube attaches to a distal end of the guidewire disk 2760 extending distally therefrom to nest within the lumen of the rotor 2699. This tube plus each of the rotor, furl hub, guidewire disk and proximal fitting are hollow to define a segment of the working lumen 2698. Thus, as can be understood from FIGS. 34, 35 and 38 and as explained in the accompanying discussions above, the working lumen 2698 extends through the rotor 2699, tube (not shown), the furl hub 2740, the guidewire disk 2760, and the proximal fitting 2642, thereby allowing a medical professional to introduce a medical device (e.g., guidewire, stylet, catheter, etc.) therethrough and/or a medical fluid (e.g., saline, $CO_2$, etc.). As a result, the introduced medical device and/or medical fluid can enter the proximal fitting and pass through the working lumen 2698 all the way to the distal tip 2555 of the inner tubular body 2551 (see FIGS. 28 and 29).

As can be understood from FIGS. 32, 33 and 38, each cable control spindle 2690 is supported with a bearing assembly of its bearing cap 2625 on one side and a bearing assembly of the handle frame 2595 on the other side. Each cable control spindle 2690 is paired with a torque spring spool 2765 with a torque spring 2770 extending between the cable control spindle 2690 and the paired torque spring spool 2765.

Figure 39:
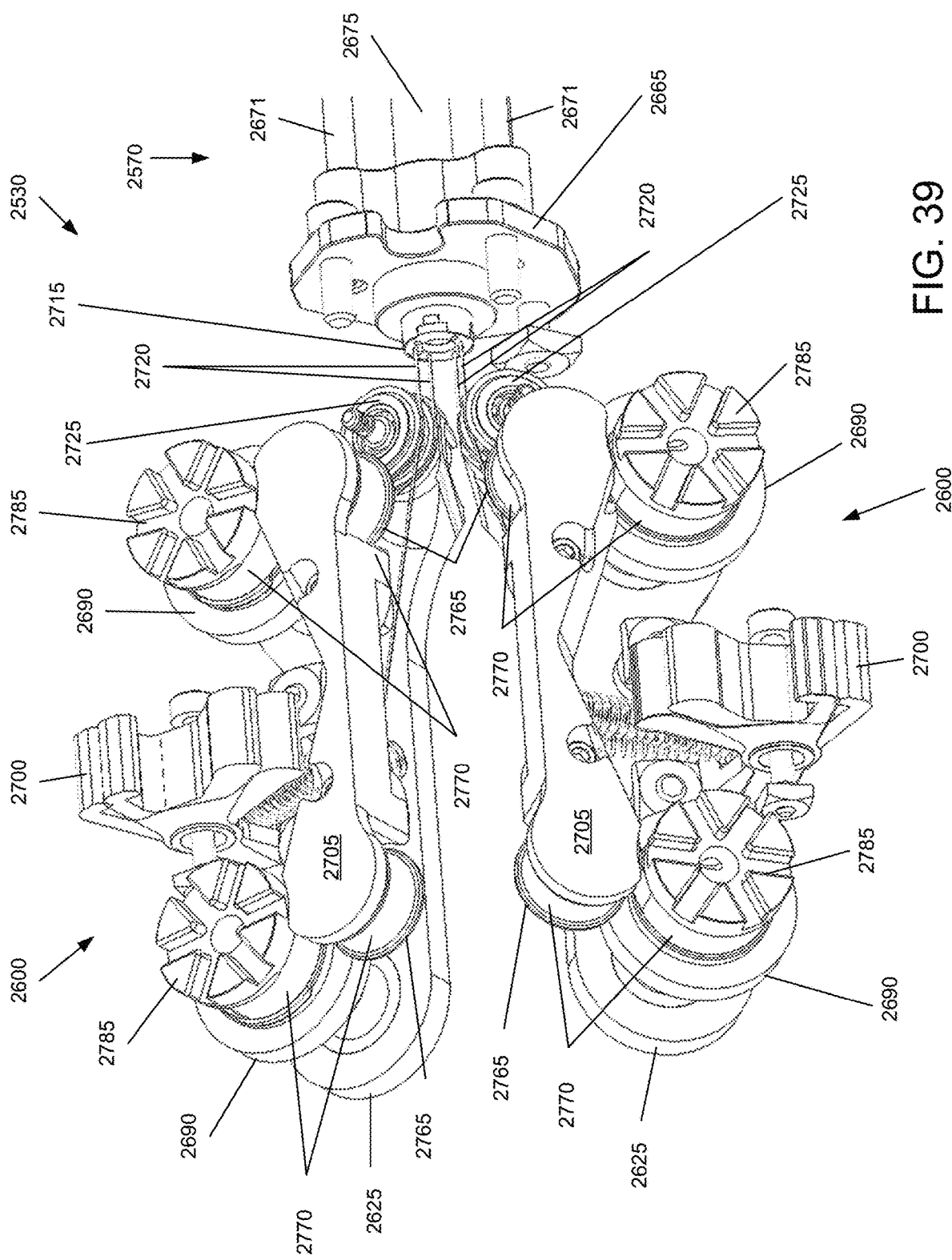
FIG. 39 is the same view as FIG. 37, except showing only the two distal cable control assemblies and certain elements of the sheath retraction assembly.
Figure 40:
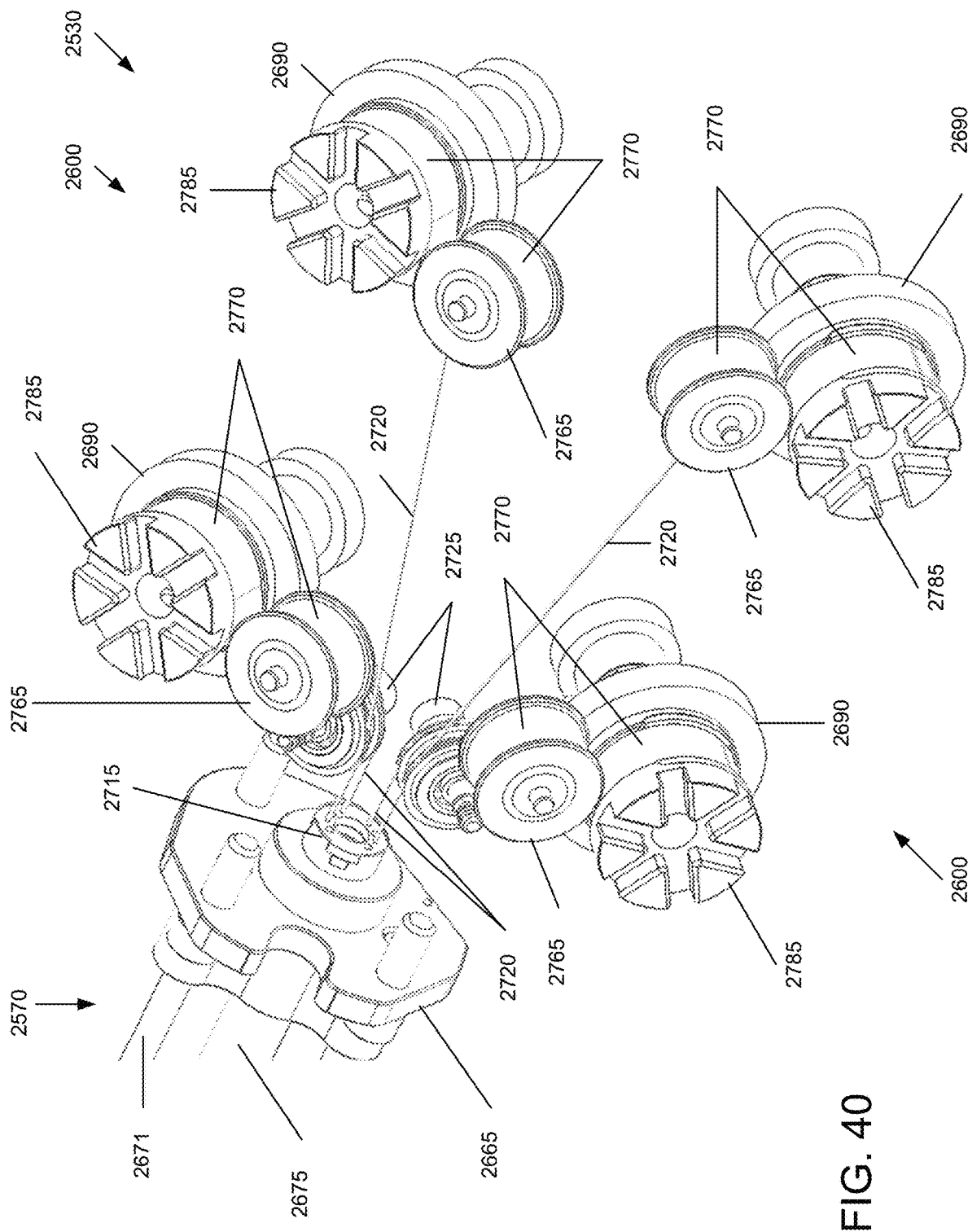
FIGS. 40 and 41 are perspective views of the same elements as FIG. 39, except with the bearing caps, handle latches, and bottom spring caps hidden for clarity purposes.
Figure 41:
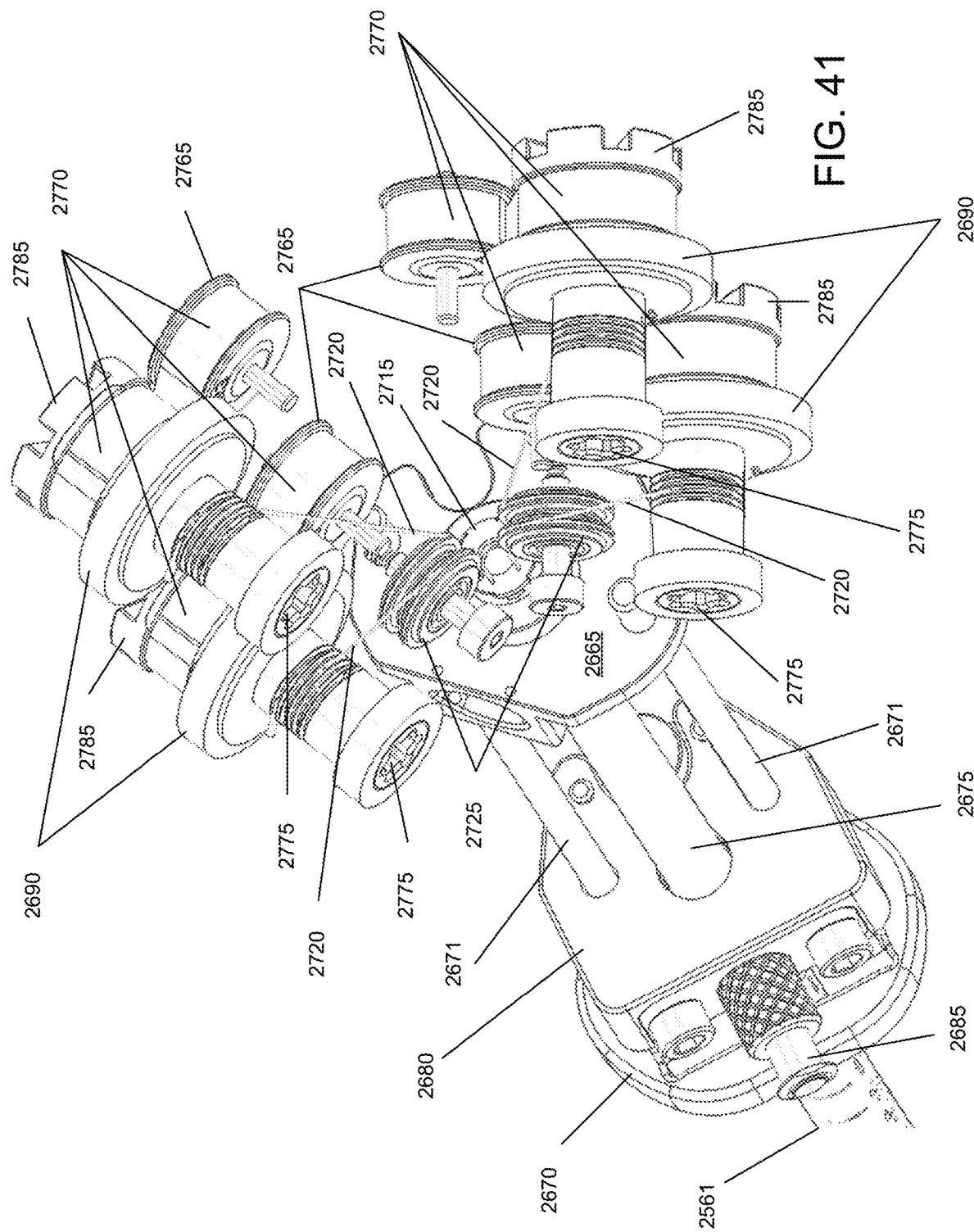

FIG. 39 is the same view as FIG. 37, except showing only the two distal cable control assemblies 2600 and certain elements of the sheath retraction assembly 2570. FIGS. 40 and 41 are perspective views of the same elements as FIG. 39, except with the bearing caps 2625, handle latches 2700, and bottom spring caps 2705 hidden for clarity purposes.

As illustrated in FIGS. 36-41, each actuation cable 2720 is paired with another actuation cable 2720 as part of a single cable control assembly 2600, and each of these actuation cables 2720 extends to a dedicated cable control spindle 2690 that is paired with a dedicated torque spring 2770 extending between the cable control spindle 2690 and a torque spring spool 2765.

Thus, each cable control assembly 2600 includes a pair of cable control spindles, a pair of torque spring spools, a pair of torque springs, a pair of actuation cables and a pair of idler pullies 2725 across which the pair of actuation cables extend. Each pair of pullies are mounted on a common shaft, but independently rotatable relative to each other. Each pulley of the pair of pullies 2725 has a groove that receives therein one actuation cable of the pair of actuation cables 2720, as best understood from FIGS. 35 and 39-41.

The pair of actuation cables 2720 of a single cable control assembly 2600 are operationally opposed to each other such that displacement of a first actuation cable of the pair of actuation cables results in an opposite displacement of the second actuation cable of the pair of actuation cables. Torque remains constant across the operation of the actuation cables and their respective cable control spindles and torque springs on account of the actuation cables being opposed in operation and acting between respective opposed cable control spindles and torque springs, as can be understood from FIGS. 38-41. This constant torque is the case regardless of whether a carriage 2540 of the robot 2520 is driving the cable control spindles 2690 of a cable control assembly 2600 (see FIGS. 25-27) or the cable control spindles are driven by the manual pull wire assembly 2550 (see FIGS. 28-31). Further, this constant torque maintains minimal cable tension when the handle assembly 2530 is off the robot 2520 and a physician is back driving the tubular body assembly 2535. While not shown in detail in the figures, each proximal cable control assembly 2600 employs the same elements in operationally the same way to achieve the same constant torque as described herein with respect to the distal cable control assemblies 2600 depicted in FIGS. 39-41.

Each cable control assembly 2600 is constant torque in its functionality as described above. In some embodiments, such assemblies may employ constant torque spring arrangements. However, in some embodiments, each spring may not be truly constant torque but will be adequately so as long as the spring has a sufficiently low spring constant and enough range of travel such that the variation in torque over the range of travel is low enough (e.g., less than 25% variation). One example of such a torque spring that is not truly constant torque but is sufficient adequate for the purpose is a spiral torsion (clock) spring or a standard torsional spring with a sufficiently high number of loops.

As called out in FIGS. 38 and 39 and as also visible in FIGS. 30 and 32, each cable control spindle 2690 ends on the top side 2580 of the handle assembly 2530 as a female mechanical coupling 2775. This female mechanical coupling 2775 is configured to mechanically couple with a male mechanical coupling 2780 (see FIGS. 46 and 47) of the manual pull wire assembly 2550 when the manual pull wire assembly is interfaced with the handle assembly 2530 as depicted in FIG. 30. With the couplings 2775, 2780 mechanically coupled together, torque can be transferred from the male mechanical coupling 2780 to the female mechanical coupling 2775 in transmitting rotational power from the male mechanical coupling to the female mechanical coupling. Such transmitting of rotational power drives the cable control spindle, which displaces the associated actuation cable 2720 to deflect the distal tip 2555 and the deflectable region 2560 of the inner tubular body 2551.

While the figures and the above description are given in the context of mechanical coupling 2775 and mechanical coupling 2780 being respectively female and male configurations, in other embodiments, the female/male arrangement could be reversed or each mechanical coupling 2775, 2780 may be a combination of male and female elements such that neither is fully female or fully male. Exemplary couplings 2775, 2780 include dog coupling, magnetic coupling, face spline, friction coupling, or etc.

As called out in FIGS. 39-41 and as also visible in FIGS. 31 and 33, each cable control spindle 2690 ends on the bottom side 2590 of the handle assembly 2530 as a female mechanical coupling 2785. This female mechanical coupling 2785 is configured to mechanically couple with a male mechanical coupling 2790 (see FIGS. 25 and 26) of the nesting side 2587 of the carriage 2540 (see FIGS. 49 and 50) when the handle assembly 2530 is nested with the carriage 2540 as depicted in FIGS. 27, 30 and 31. With the couplings 2785, 2790 mechanically coupled together, torque can be transferred from the male mechanical coupling 2790 to the female mechanical coupling 2785 in transmitting rotational power from the male mechanical coupling to the female mechanical coupling. Such transmitting of rotational power drives the cable control spindle, which displaces the associated actuation cable 2720 to deflect the distal tip 2555 and the deflectable region 2560 of the inner tubular body 2551.

As can be understood from FIGS. 39-41, the female mechanical coupling 2785 and the male mechanical coupling 2790 may take the respective form of a slotted Oldham floating disk 2785 and a ribbed Oldham floating disk 2790. Of course, in other embodiments, this female/male arrangement could be reversed. Also, in yet other embodiments, each mechanical coupling 2785, 2790 may be a combination of male and female elements such that neither is fully female or fully male. Besides the Oldham floating disc, other exemplary couplings 2785, 2790 include a spline, tapered fit, keyed, magnetic coupling, face spline, or etc.

Figures 42, 43:
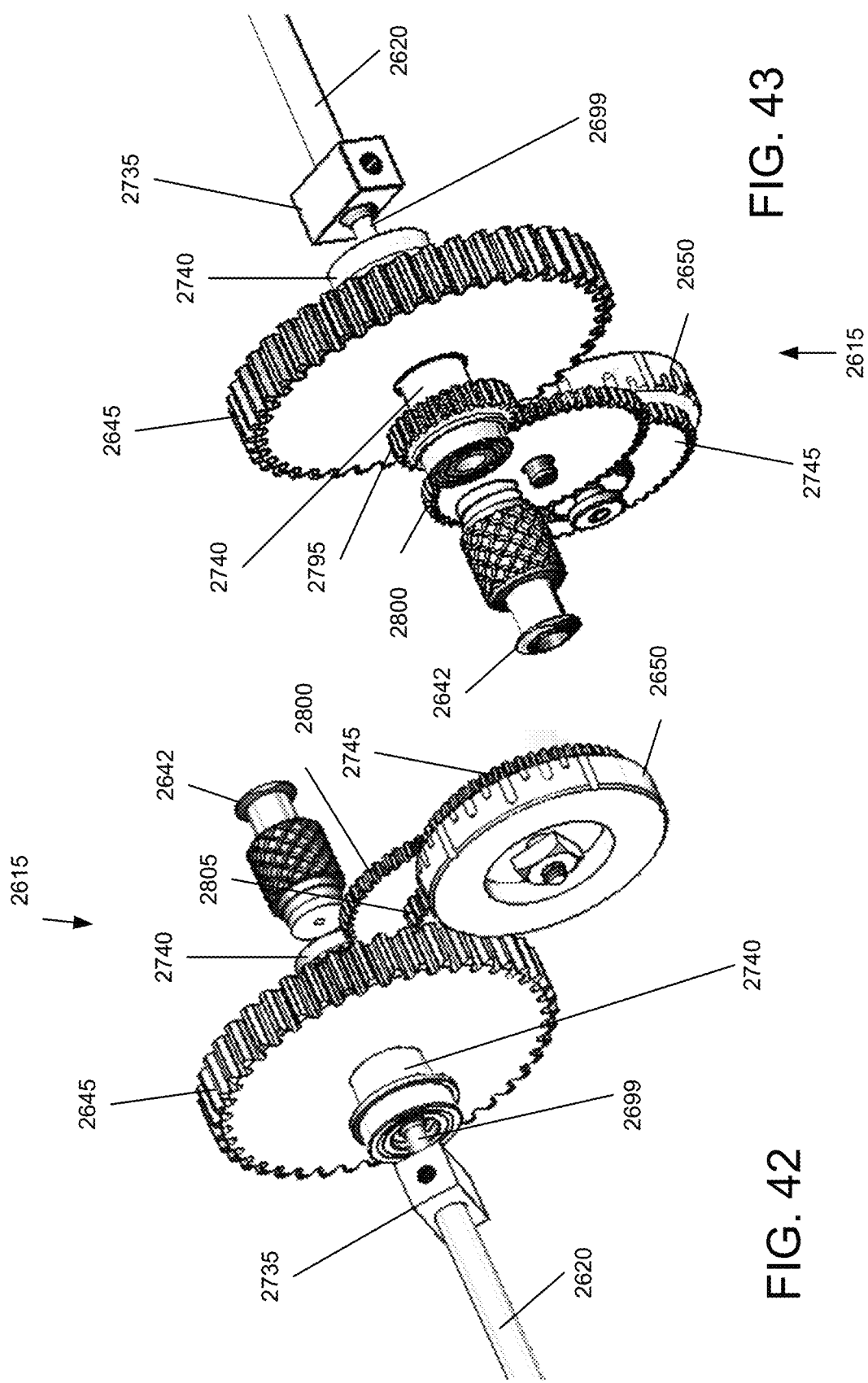
FIGS. 42 and 43 are opposite perspective views of the furl assembly that exists between the proximal fitting and the stator key.

FIGS. 42 and 43 are opposite perspective views the furl assembly 2615 that exists between the proximal fitting 2642 and the stator key 2735 and includes the capstan gear 2645, furl dial 2650, furl gear 2745, a hub gear 2795, a large intermediate gear 2800 and a small intermediate gear 2805. The capstan gear 2645 protrudes through the bottom side 2590 of the handle assembly 2530 to be mechanically engaged and driven by the drive gear 2712 protruding from the nesting side 2587 of the carriage 2540 (see FIGS. 49 and 50). Since the capstan gear 2645 and hub gear 2795 are both mounted on the furl hub 2740, rotation of the capstan gear 2645 causes the hub gear 2795 to also rotate. The hub gear 2795 interfaces with and drives the large intermediate gear 2800, which interfaces with and drives the small intermediate gear 2805.

The small intermediate gear 2805 interfaces with and drives the furl gear 2745, which drives the furl dial 2650. Thus, rotation of the capstan gear 2645 and the rotor 2699 to which it is coupled can be tracked at the furl dial 2650 on account of the transmission of the rotation of the capstan gear to the furl dial on account of the gears of the furl assembly 2615. By watching the furl dial during the unfurling or furling of the implant carried at the distal tip of the tubular body, the interventional cardiologist can monitor the extent to which the implant has unfurled/furled by operation of the capstan gear in the handle assembly of the catheter. This is particularly helpful during furling of the implant in the loading process.

As shown in FIG. 27, the furl dial 2650 is visible through an opening in the removable housing shell 2547, thereby allowing the interventional cardiologist to monitor and measure the extent to which furling/unfurling of the implant has occurred at the distal tip 2555 of the inner tubular body 2551 on account of operation of the mechanisms of the handle assembly 2530. Near the furl dial is a furl lock lever 2810 and a furl lock release pin 2815, both of which protrude through the housing shell and/or the handle frame. As the furling operation is a critical aspect of implanting the procedure, the furl lock lever 2810 and furl lock release pin 2815 function as a safety to prevent inadvertent unfurling of the implant.

Figure 45:
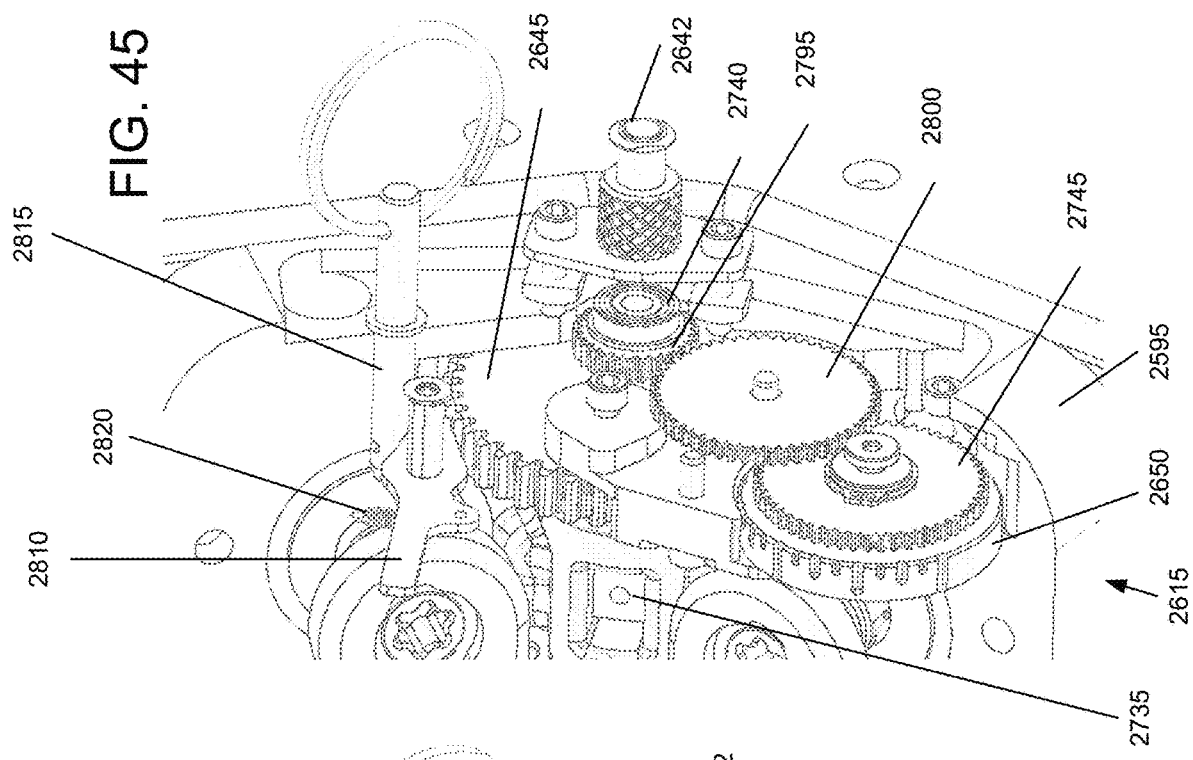
FIGS. 44 and 45 are perspective views of the furl assembly respectively with and without the furl inside plate and furl back plate.
Figure 44:
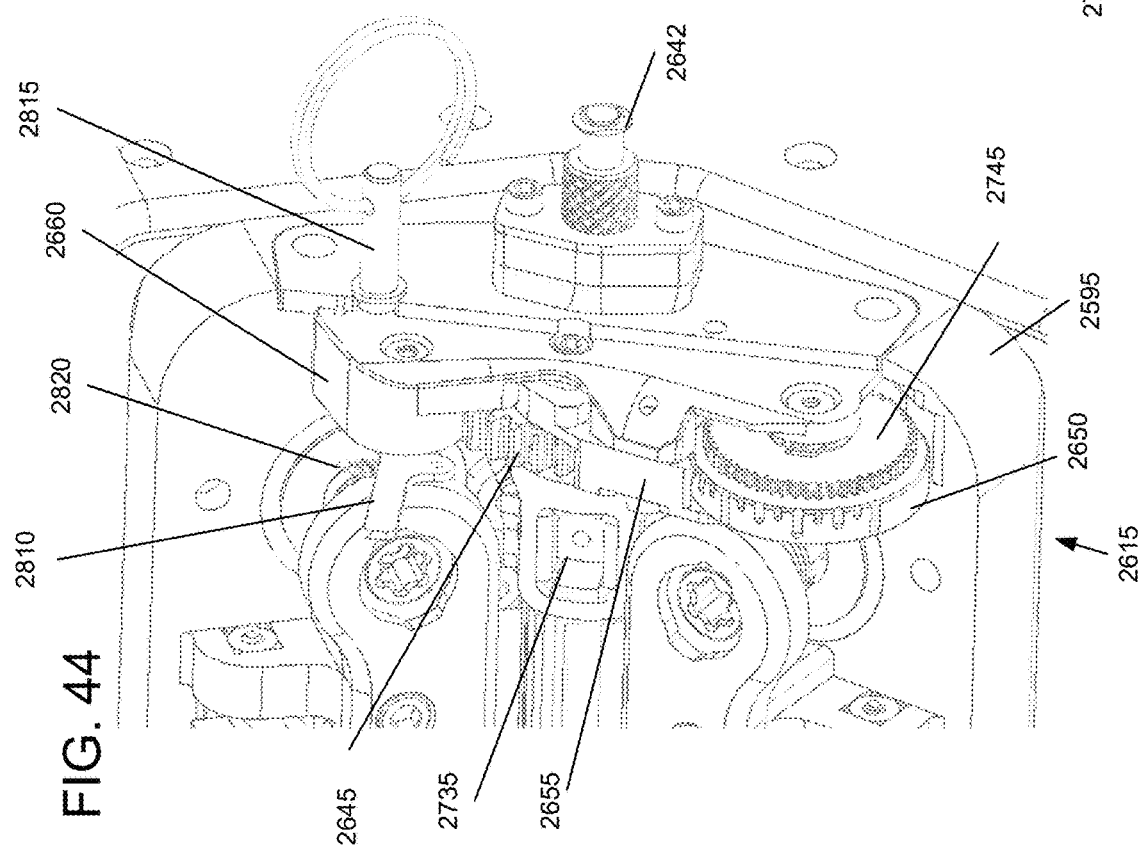

As depicted in FIGS. 44 and 45, which are perspective views of the furl assembly 2615 respectively with and without the furl inside plate 2655 and furl back plate 2660, the furl lock lever 2810 is pivotally secured to the furl back plate 2660 via a pivot point. On one side of the pivot point is a tooth or pawl for engaging the teeth of the capstan gear 2645. On the opposite side of the pivot point is a lever arm of the furl lock lever 2810. A lever spring 2820 extends between the housing shell 2547, handle frame 2595 or other structural aspect of the handle assembly 2530. The lever spring 2820 is mounted in an over-center configuration so the latch is bistable either in the locking/ratchet configuration or the open configuration. The lever spring 2820 biases the tooth or pawl of the furl lock lever 2810 into engagement with the teeth of the capstan gear 2645, thereby placing the furl assembly 2615 in a locked condition whereby unfurling is prevented but manual furling is allowed. To further lock the furl assembly 2615 to prevent both furling and unfurling, the furl lock release pin 2815 is biased inwardly into the furl back plate 2660 to extend across an upper edge of the furl lock lever 2810, thereby preventing the furl lock lever from pivoting in a manner that allows the tooth or pawl to come out of engagement with the teeth of the capstan gear. Pulling proximally on the furl lock release pin 2815 causes it to clear the furl lock lever 2810. With the furl lock release pin so positioned, the lever arm of the furl lock lever can be pushed downward so the furl lock lever 2810 pivots about it pivot so the tooth or pawl of the furl lock lever 2810 is brought out of engagement with the teeth of the capstan gear, thereby allowing manual furling via ratcheting of the tooth or pawl of the furl lock lever 2810 with the teeth of the capstan gear 2645, but preventing unfurling from occurring.

Thus, in summary, the furl lock lever 2810 acts as a ratchet when engaged with the gear teeth of the capstan gear 2645. This ratcheting action prevents unfurling of the implant but allows manual furling of the implant during the process of packing the implant onto the distal end of the tubular body assembly 2535 in preparing for an implantation procedure. Once the furl lock release pin 2815 extends into the furl back plate 2660, the mechanism is fully locked and prevents ratcheting and both furling and unfurling. This locking of the mechanism is done after the implant is fully packed onto the distal end of the tubular body assembly 2535 and before the handle assembly 2530 is loaded onto the robot 2520.

J. MANUAL PULL WIRE ASSEMBLY

FIG. 46 is perspective view of a proximal end of the handle assembly 2530 with the manual pull wire assembly 2550 interfaced with the top side 2580 of the handle assembly 2530. FIG. 47 is the same view as FIG. 46, except with the housing 2825 of the manual pull wire assembly 2550 removed for clarity purposes. The manual pull wire assembly 2550 is removably interfaceable with the handle assembly 2530 in the event the interventional cardiologist finds it necessary to manually manipulate the mechanisms of the handle assembly with manual pull wire assembly 2550 as opposed to relying on the robot 2520 to do so.

As shown in FIG. 46, a base 2830 of the manual pull wire assembly 2550 abuts against the bearing cap 2625 of the cable control assembly 2600 when the manual pull wire assembly 2550 interfaces with the cable control assembly 2600 on the top side 2580 of the handle assembly 2530. As can be understood from FIGS. 46 and 47, when the manual pull wire assembly 2550 interfaces with the cable control assembly 2600, each male mechanical coupling 2780 of the manual pull wire assembly is received within a respective female mechanical coupling 2775 of a respective cable control spindle 2690 of the cable control assembly.

As illustrated in FIG. 47, the manual pull wire assembly 2550 includes a gear train 2835 including a lever gear 2840, an intermediate gear 2845, and a small gear 2850 on the drive shaft 2855 of each respective male mechanical coupling 2780. The handle 2585 is used to rotate the lever gear 2840, which interfaces with, and drives, one of the small gears 2850 and the intermediate gear 2845. The intermediate gear 2845 interfaces with, and drives, the other small gear 2850. Thus, rotation of the handle 2585 in one direction or the other will transmit through the gear train 2835 and male mechanical couplings 2780 to the female mechanical couplings 2775 to cause the cable control spindles 2690 of the cable control assembly 2600 to rotate in one direction or the other, thereby displacing the actuation cables 2720 to effectuate displacement of the distal tip 2555 and a deflectable region 2560 of the inner tubular body 2551.

As depicted in FIG. 47, each drive shaft 2855 includes a dog plate arrangement with a driving dog plate 2860 and a driven dog plate 2865. Each driving dog plate 2860 includes a pair of pins 2870 projecting upward and radially offset by 180 degrees from each other. Each driven dog plate 2865 includes a pair of tabs 2875 facing radially outward and offset by 180 degrees from each other.

In operation, the driving dog plate 2860 is configured such that when the handle 2585 is actuated in one direction, one actuation cable 2720 of a pair of actuation cables 2720 of the associated cable control assembly 2600 is immediately engaged as the tension cable (see FIGS. 40 and 41). This tension cable will stretch under load, causing the back cable (i.e., the second actuation cable 2720 of the pair of actuation cables 2720 of the associated cable control assembly 2600) to potentially go slack if there was no dog plate and there was instead 1:1 gearing.

If the handle assembly 2530 is disengaged from the robot 2520, or at least the drive mechanisms of the handle assembly 2530 are decoupled from the drive mechanisms of the robot 2520, the dog plate 2860 allows for the off-robot torque spring 2770 to maintain a minimum tension in the tension cable and therefore maintain tension in the system by allowing the spring to pull the input beyond the dog plate, such that the dog pins are no longer touching the dog plate.

To decouple the drive mechanisms of the handle assembly 2530 from the drive mechanisms of the robot 2520, the handle assembly 2530 could simply be disengaged from the robot 2520 by physically unlatching it.

Alternatively, to decouple the drive mechanisms of the handle assembly 2530 from the drive mechanisms of the robot 2520 while the handle assembly 2530 remains latched to the robot 2520, a tool could be inserted through a hollow version of the drive shaft 2855 of each respective male mechanical coupling 2780 of the manual pull wire assembly 2550 and into the associated hollow shaft of the female mechanical coupling 2775 and slotted Oldham floating disk 2785 to contact and push out the sprung input (i.e., the ribbed Oldham floating disk 2790) to decouple the two Oldham floating disks 2785, 2790. In such an embodiment, the ribbed Oldham floating disk 2790 would be biased outwards to project towards the slotted Oldham floating disk 2785 to be in torque transmitting engagement with the slotted Oldham floating disk 2785. Using the tool to push the ribbed Oldham floating disk 2790 inwards away from the slotted Oldham floating disk 2785 and out of engagement therewith would allow the handle assembly 2530 to remain in place on the robot 2520 but disengage the drive mechanisms of the handle assembly from the drive mechanisms of the robot 2520. In a play on this last embodiment, the tool could be replaced by an adaptation of the drive shaft 2855 which could be configured to telescopically displace towards the ribbed Oldham floating disk 2790 to bring about the decoupling of the two Oldham floating disks 2785, 2790 as described above in this paragraph with respect to the tool.

K. OVERVIEW OF ROBOT

Figure 48:
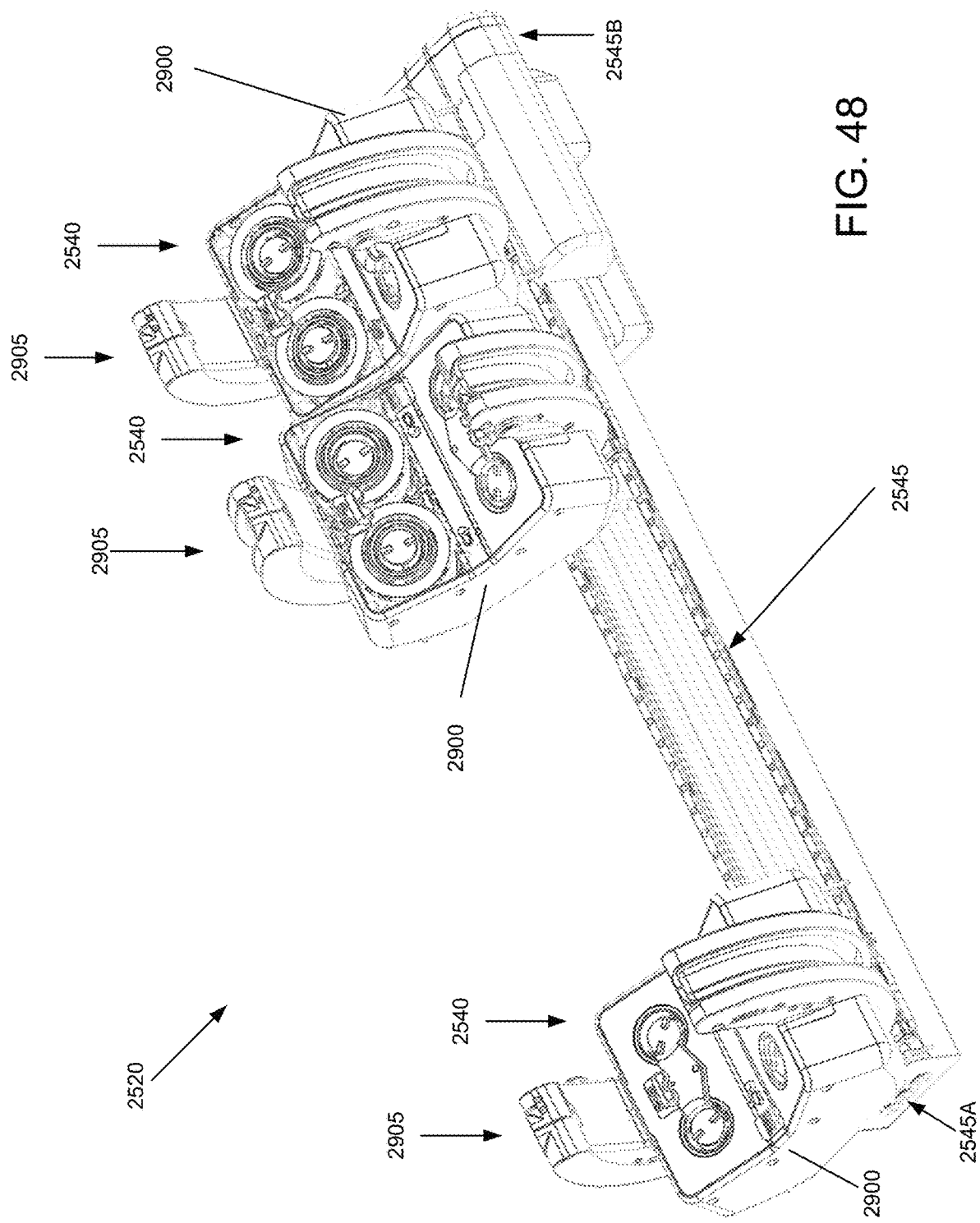
FIG. 48 is a top perspective view of the robot of the robotic implantation system depicted in FIG. 25.

FIG. 48 is a top perspective view of the robot 2520 of the robotic implantation system 2510 depicted in FIG. 25. The robot 2520 includes one or more carriages 2540 and a linear displacement platform 2545. The carriages 2540 are supported on the linear displacement platform 2545 and are both rotatable relative to, and linearly displaceable along, the linear displacement platform. More specifically, each carriage 2540 is independently positionable along the linear displacement platform from the other carriages, and each carriage is independently rotatable relative to the linear displacement platform from the other carriages. For purposes of the following discussion, the linear displacement platform 2545 can be considered to have a distal end 2545A and a proximal end 2545B, which may also be called a motor end 2545B.

L. CARRIAGES OF ROBOT

Figure 49:
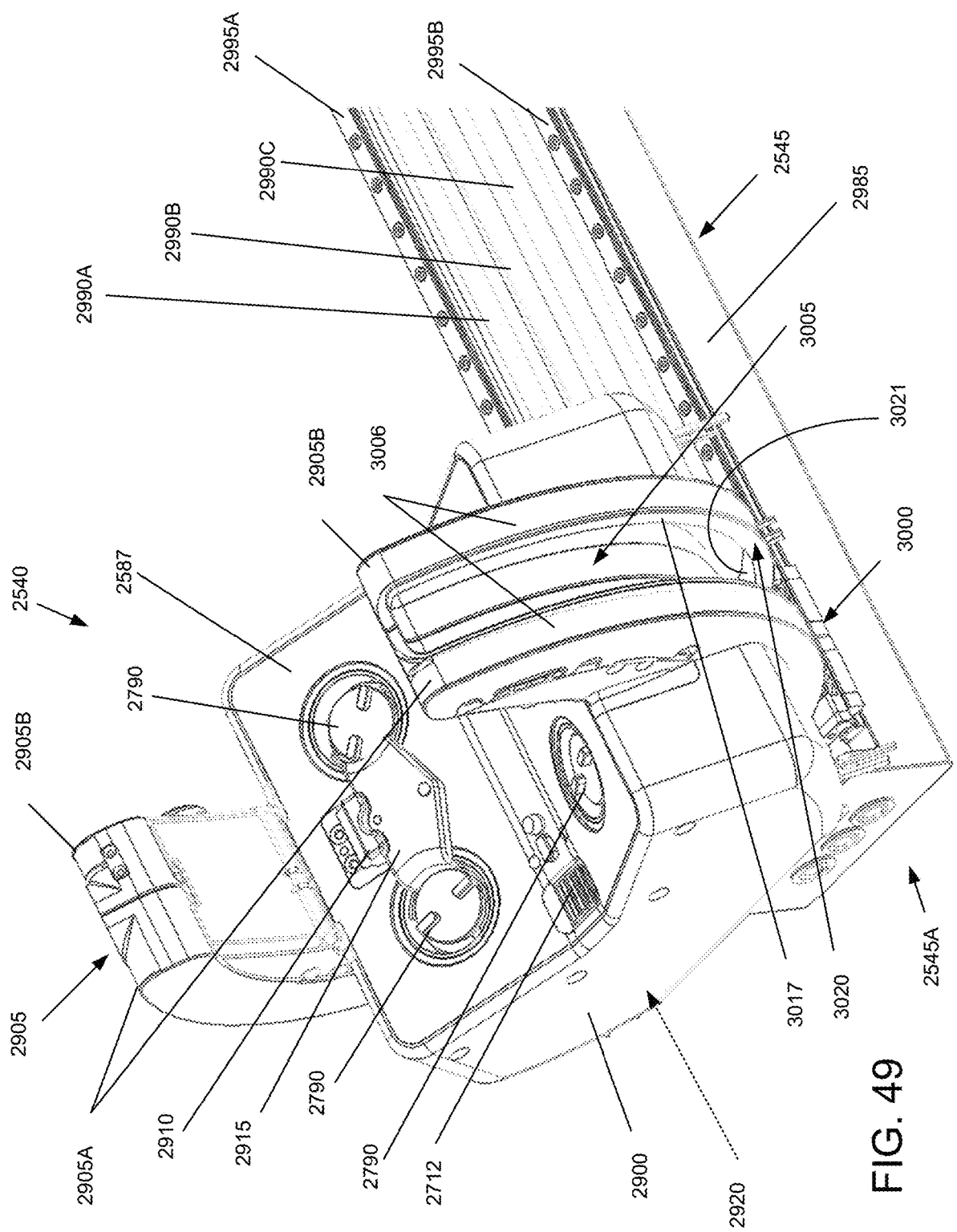
FIGS. 49 and 50 are opposite top perspective views of a carriage at the distal end of the linear displacement platform of the robot of FIG. 48.
Figure 50:
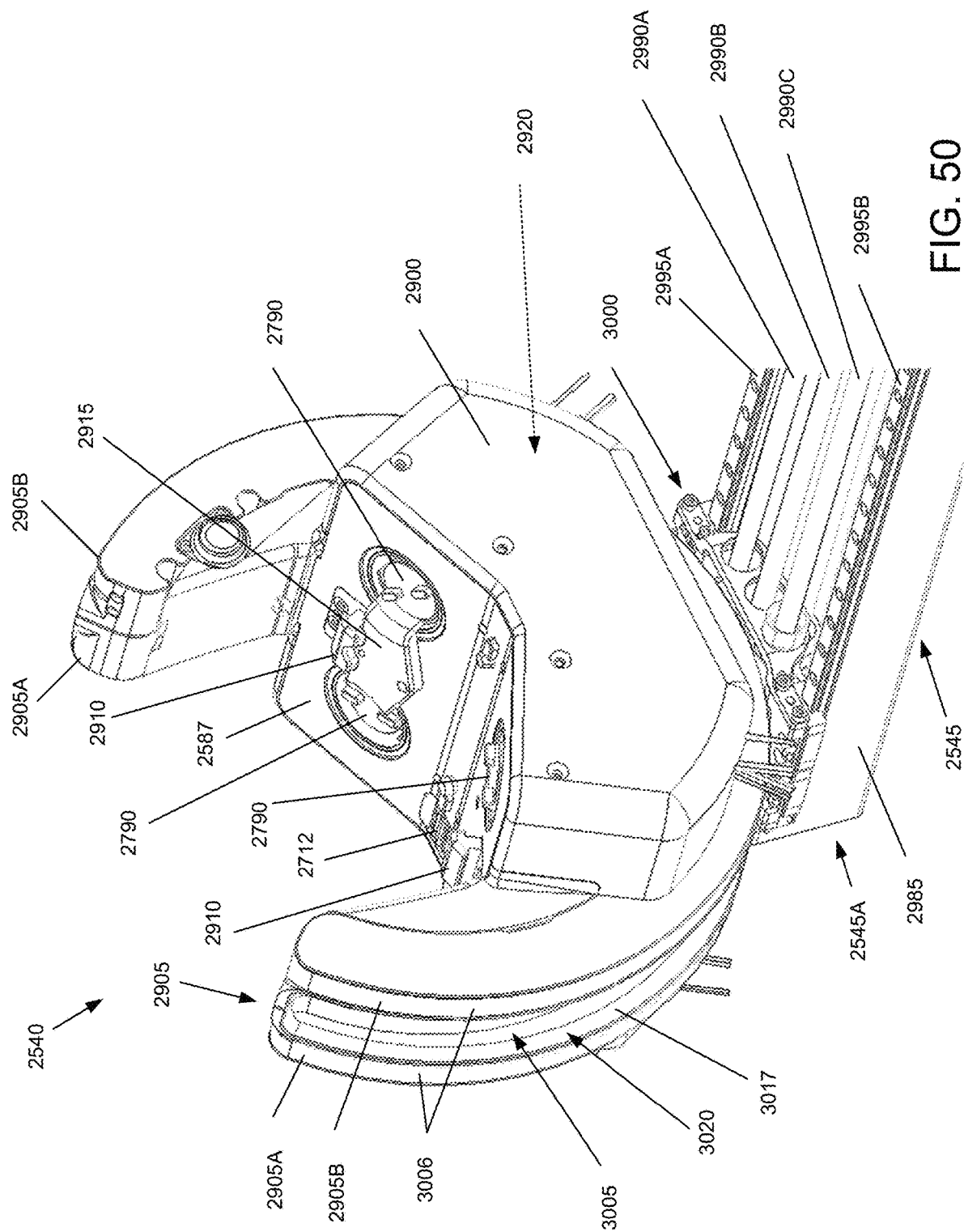

FIGS. 49 and 50 are opposite top perspective views of a carriage 2540 at the distal end 2545A of the linear displacement platform 2545 of the robot 2520 of FIG. 48. As can be understood from FIGS. 48-70B, each carriage 2540 includes a carriage housing 2900 rotatably supported relative to and on the linear displacement platform 2545 by a C-arm 2905.

As can be understood from FIGS. 27, 32 and 33-38 and the accompanying discussion provided above, a working lumen 2698 extends through the tubular body assembly 2535, sheath retraction assembly 2570 and handle assembly 2530. Each carriage 2540 is configured such that when the handle assembly 2530 is nested with one or more carriages as shown in FIGS. 25-27, rotation of the nested combination occurs around an axis of rotation extending coaxially with a longitudinal center axis of the working lumen 2698, at least within the boundaries of the sheath retraction assembly, the handle assembly and the most proximal segment of the tubular body assembly 2535. This axis of rotation is advantageous as it allows the tubular body assembly 2535 to be positioned within the vasculature of the patient and then rotated about the axis of the working lumen 2698 without resulting linear displacement of the tubular body assembly 2535 at the percutaneous access point of the tubular body assembly into the patient, thereby reducing the likelihood of trauma to patient tissue or structures like, for example, the femoral vein. This axis of rotation is also advantageous in that it allows for precise and predictable manipulation of the tubular body assembly 2535 during an implantation procedure.

As indicated in FIGS. 49 and 50, each carriage 2540 includes a nesting side 2587 against which the bottom side 2590 of the handle assembly 2530 is received, as depicted in FIGS. 25-27. As illustrated in FIGS. 49 and 50, the nesting side 2587 includes a drive gear 2712, multiple male mechanical couplings 2790, latch fingers 2910, and disengagement plates 2915. As discussed above, each male mechanical coupling 2790 may take the form of a ribbed Oldham floating disk 2790 that can mechanically interface in a mated fashion with a respective slotted Oldham floating disk 2785 of a cable control spindle 2690 on the bottom side 2590 of the handle assembly 2530. With the couplings 2785, 2790 mechanically coupled together, torque can be transferred from the male mechanical coupling 2790 to the female mechanical coupling 2785 in transmitting rotational power from the male mechanical coupling to the female mechanical coupling. Such transmitting of rotational power drives the cable control spindle, which displaces the associated actuation cable 2720 to deflect the distal tip 2555 and the deflectable region 2560 of the inner tubular body 2551.

As noted above, while the female mechanical coupling 2785 and the male mechanical coupling 2790 may take the respective form of a slotted Oldham floating disk 2785 and a ribbed Oldham floating disk 2790, in other embodiments, this female/male arrangement could be reversed. Also, in yet other embodiments, each mechanical coupling 2785, 2790 may be a combination of male and female elements such that neither is fully female or fully male. Besides the Oldham floating disk, other exemplary couplings 2785, 2790 include a spline, tapered fit, keyed, magnetic coupling, face spline, or etc.

As shown in FIGS. 49 and 50, the drive gear 2712 protrudes through the nesting side 2587 of the carriage 2540. As discussed above with respect to FIGS. 32 and 33, the lead screw gear 2630 and capstan gear 2645 protrude through the surfaces of the top side 2580 and bottom side 2590 of the handle frame 2595. On account of protruding through the surface of the bottom side 2590 of the handle frame 2595, the lead screw gear 2630 and capstan gear 2645 can respectively mechanically interface with a drive gear 2712 of a first carriage 2540 and a drive gear 2712 of a second carriage 2540 when the handle assembly 2530 employs and nests with two paired carriages 2540 as shown in FIG. 27. In other words, due to the drive gears 2712 protruding upwardly through the nesting sides 2587 of the respective carriages 2540 and the lead screw gear 2630 and capstan gear 2645 both protruding downward through the surface of the bottom side of the handle frame 2595, the lead screw gear and capstan gear can mechanically interface with, and be driven by, the respective drive gears 2712 of respective carriages 2540 when the handle assembly 2530 is nested with the carriages 2540, as can be understood from FIG. 27.

As can be understood from FIGS. 33, 49 and 50, when the bottom side 2590 of the handle assembly 2530 is nested against the nesting side 2587 of a carriage 2540 as illustrated in FIGS. 27, 30 and 31, each disengagement plate 2915 on the nesting side 2587 of the carriage 2540 is received in a respective plate receiving recess 2702 (see FIG. 33) of the bottom side 2590 of the handle frame 2595 of the handle assembly 2530 so as to act as a reference in aligning the bottom side 2590 with the nesting side 2587 in nesting the handle assembly 2530 with the carriages 2540. Also, each handle latch 2700 (see FIGS. 33, 37 and 39) latches with a respective latch finger 2910 (see FIGS. 49 and 50), thereby securing the handle assembly 2530 against the nesting side 2587 of the carriage 2540 in a selectively releasable manner.

In decoupling the handle assembly 2530 from the carriages 2540, the handle latches 2700 are actuated such that a foot of each such handle latch pushes down on the respective disengagement plate 2915. The disengagement plates in turn depress the sprung inputs such that the male mechanical couplings 2790 are caused to move away from the female mechanical couplings 2785, thereby ending the Oldham coupling arrangement that existed in the interface between the nesting side 2587 of the carriage 2540 and bottom side 2590 of the handle assembly 2530. Without first removing the sprung Oldham inputs, the handle assembly 2530 could be locked onto the robot 2520 depending on an angle of articulation between the components of the Oldham inputs. For example, depending on the rotation angle of the inputs, the bar of an Oldham input could be angled like a V, resulting in the handle assembly being locked onto the robot.

Figure 51:
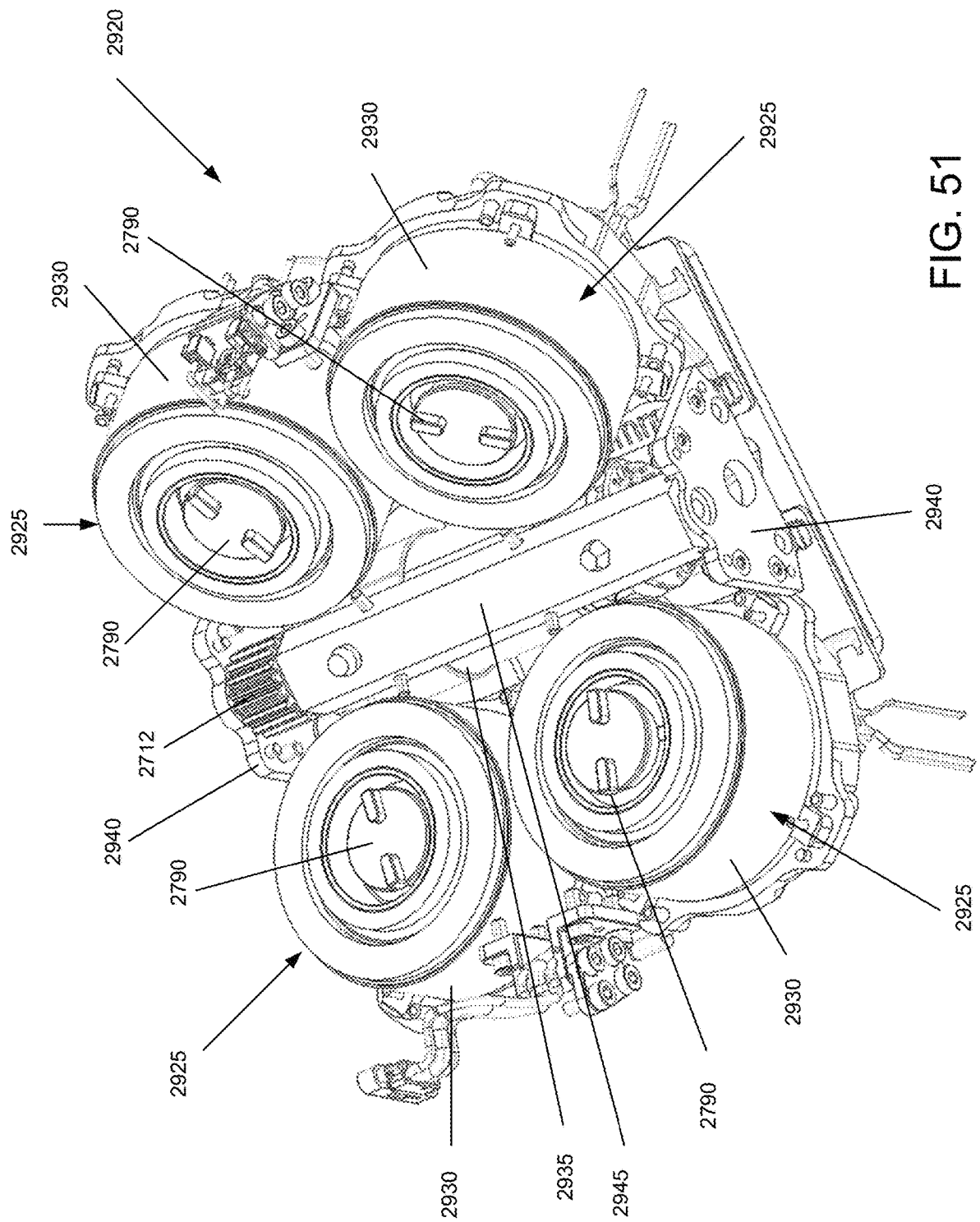
FIG. 51 is a top perspective view of a carriage electromechanical assembly substantially contained within the confines of the carriage housing shown in FIGS. 49 and 50, wherein the carriage housing is hidden for clarity purposes.

FIG. 51 is a top perspective view of a carriage electromechanical assembly 2920 substantially contained within the confines of the carriage housing 2900 shown in FIGS. 49 and 50, wherein the carriage housing is hidden for clarity purposes. As indicated in FIG. 51, each male mechanical coupling 2790 forms an upward extent of a drive motor assembly 2925, the electromechanical components of which are housed within a motor housing 2930. As is well-known with Oldham coupling arrangements, the male mechanical coupling 2790 is sprung relative to the drive motor assembly 2925 to float relative to the drive motor assembly 2925, thereby being capable of translating inward/outward in the direction of the female mechanical coupling 2785, This floating capability supports the engagement of the male mechanical coupling 2790 with the female mechanical coupling 2785 if the handle assembly 2530 is loaded onto a carriage 2540 of the robot 2520 without these couplings 2785, 2790 already aligned. On account of this floating arrangement, the input (i.e., male mechanical coupling 2790) is sprung down until the robot 2520 rotates the male mechanical coupling 2790 until it aligns with, and is received by, the female mechanical coupling 2785 in a proper Oldham coupling arrangement.

Still referring to FIG. 51, the carriage electromechanical assembly 2920 also includes a combination motor gear box 2935 that drives the drive gear 2712. The combination motor gear box 2935 and drive gear 2712 are supported between a pair of end plates 2940. The combination motor gear box 2935 is at least partially hidden by a cover 2945.

Figure 52:
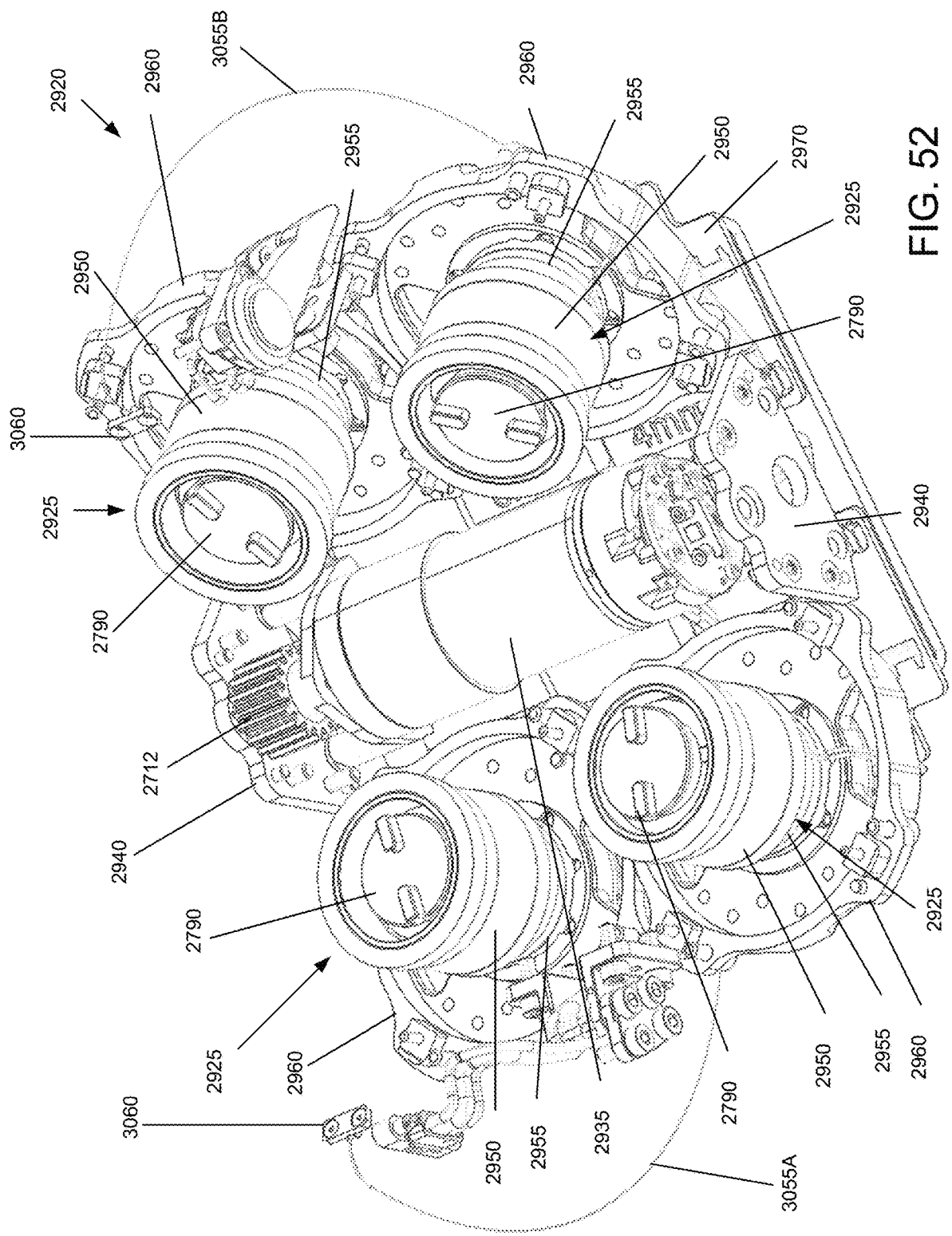
FIGS. 52 and 53 are top perspective views of the carriage electromechanical assembly with the motor housing and cover hidden for clarity purposes.
Figure 53:
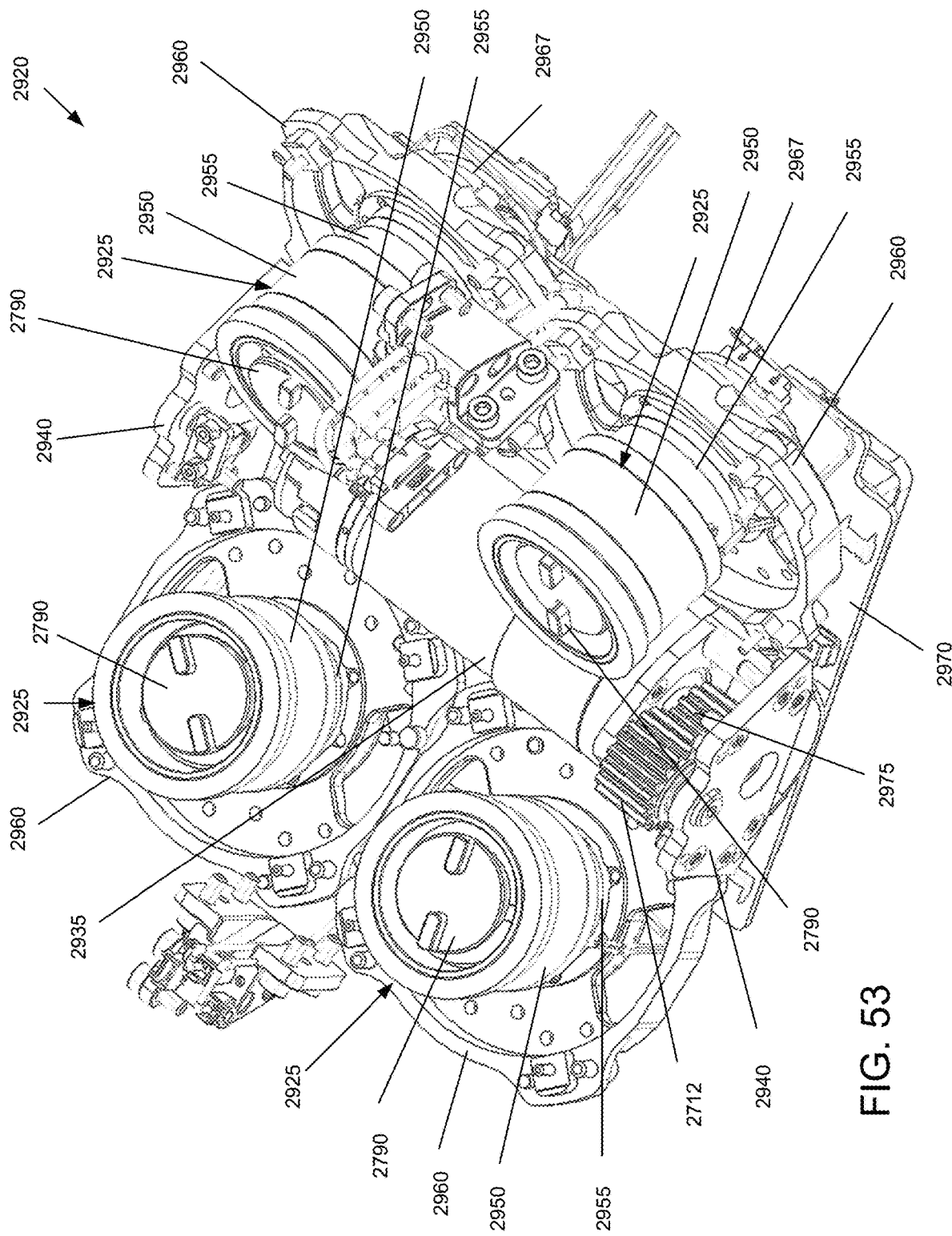
Figure 54:
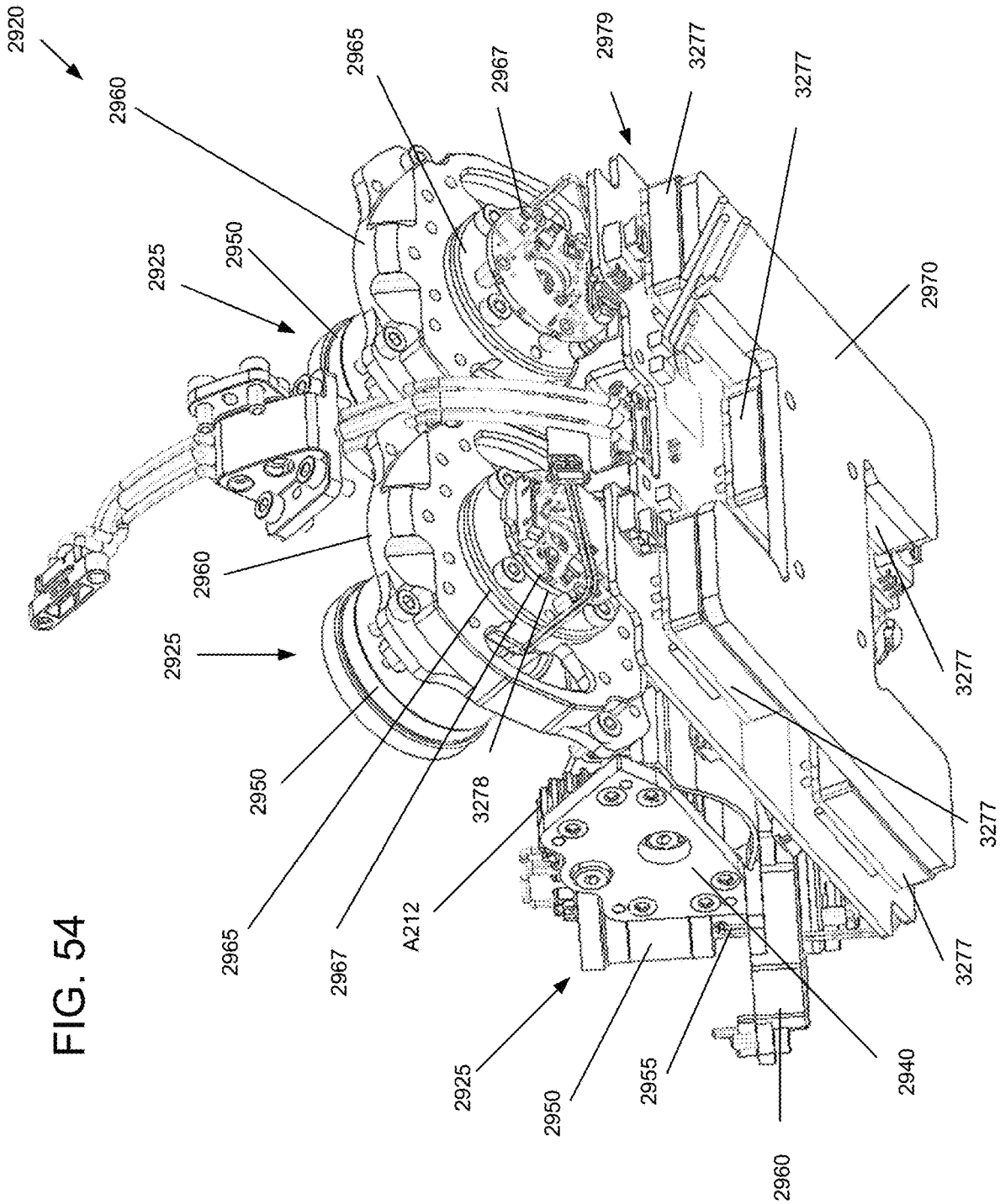
FIG. 54 is a bottom perspective view of the carriage electromechanical assembly with the motor housing and cover hidden for clarity purposes.

FIGS. 52 and 53 are top perspective views of the carriage electromechanical assembly 2920 with the motor housing 2930 and cover 2945 hidden for clarity purposes. FIG. 54 is a bottom perspective view of the carriage electromechanical assembly 2920 with the motor housing 2930 and cover 2945 hidden for clarity purposes.

As shown in FIGS. 52-54, each drive motor assembly 2925 includes a cable axis rotor 2950, a brake 2955, a motor back plate 2960, a motor encoder mount plate 2965, encoder read circuitry 2967, and an encoder read disk 3278 mounted to the motor axis. The drive motor assemblies 2925 and combination motor gear box 2935 are supported off of the housing 2900 hidden in FIGS. 52-54 but illustrated in FIGS. 49 and 50. Each cable axis rotor 2950 drives its male mechanical coupling 2790 and the associated brake 2955 brakes this driving, the driving and the braking occurring according to the dictates of the respective motor control circuit assemblies 3277.

Depending on the embodiment, braking can be actuated via control logic, or braking can be achieved via a STO (safe torque off) configuration. Thus, if the robot 2520 faults, then power is removed from the motor and the brake, resulting in brake engagement because the brake is a power off brake). This design ensures that the robotic implantation system 2510 fails to a safe state (holding its position) during a fault scenario that renders the robot unable to continue control.

Once the robot 2520 is in a safe faulted condition holding position on the handle assembly 2530, then the clinician can install the manual pull wire assemblies 2550, which will disengage the sprung inputs and enable manual control of the catheter for either safely finishing the procedure or safely aborting the procedure. A process by which braking would be engaged in the robot 2520 in the event of a fault, the operation of the handle assembly 2530 then transitioning from the robot to manual control, is discussed below in reference to FIG. 68.

Five motor control circuit assemblies 3277 are supported on the heat sink 2970, the four corner motor control circuit assemblies 3277 being for the four drive motor assemblies 2925 and the center one being for the combination motor gear box 2935, as illustrated in FIG. 54. Each motor encoder mount plate 2965 secures its respective encoder read circuitry 2967 to the respective drive motor assembly 2925. Each motor back plate 2960 secures its respective drive motor assembly 2925 to the housing 2900.

As indicated in FIG. 53, an output gear 2975 is mounted on an output drive shaft of the combination motor gear box 2935. The output gear 2975 is mechanically interfaced with the drive gear 2712 such that the output gear 2975 transmits rotational power from the combination motor gear box 2935 to the drive gear 2712, thereby driving the drive gear.

As depicted in FIG. 54, a carriage printed circuit board (PCB) 2979 is located between the heat sink 2970 and the rest of the carriage electromechanical assembly 2920. The carriage PCB 2979 controls the overall operation of the carriage electromechanical assembly 2920, sequencing the function of the drive motor assemblies 2925 and pairing them as necessary to bring about the desired performance of the cable control spindles 2690 and the attached tubular body assembly 2535.

M. LINEAR DISPLACEMENT PLATFORM OF ROBOT AND INTERACTION OF CARRIAGE C-ARM WITH SAME

As can be understood from FIGS. 49 and 50, the linear displacement platform 2545 includes an elongated frame 2985, multiple C-arm drive shafts 2990A, 2990B, 2990C extending longitudinally within the elongated frame 2985, multiple drive lead screws 3040A, 3040B, 3040C extending longitudinally within the elongated frame 2985, and linear slide rails 2995A, 2995B extending longitudinally along the tops of sidewalls of the elongated frame. Each carriage 2540 sits on a linear displacement block 3000, which is supported on, and travels along, the linear slide rails 2995A, 2995B as discussed in greater detail below. Further, each of the carriages are similarly arranged to linearly displace along the linear slide rails, as can be understood from FIG. 46 and discussed in greater detail below.

Figure 56:
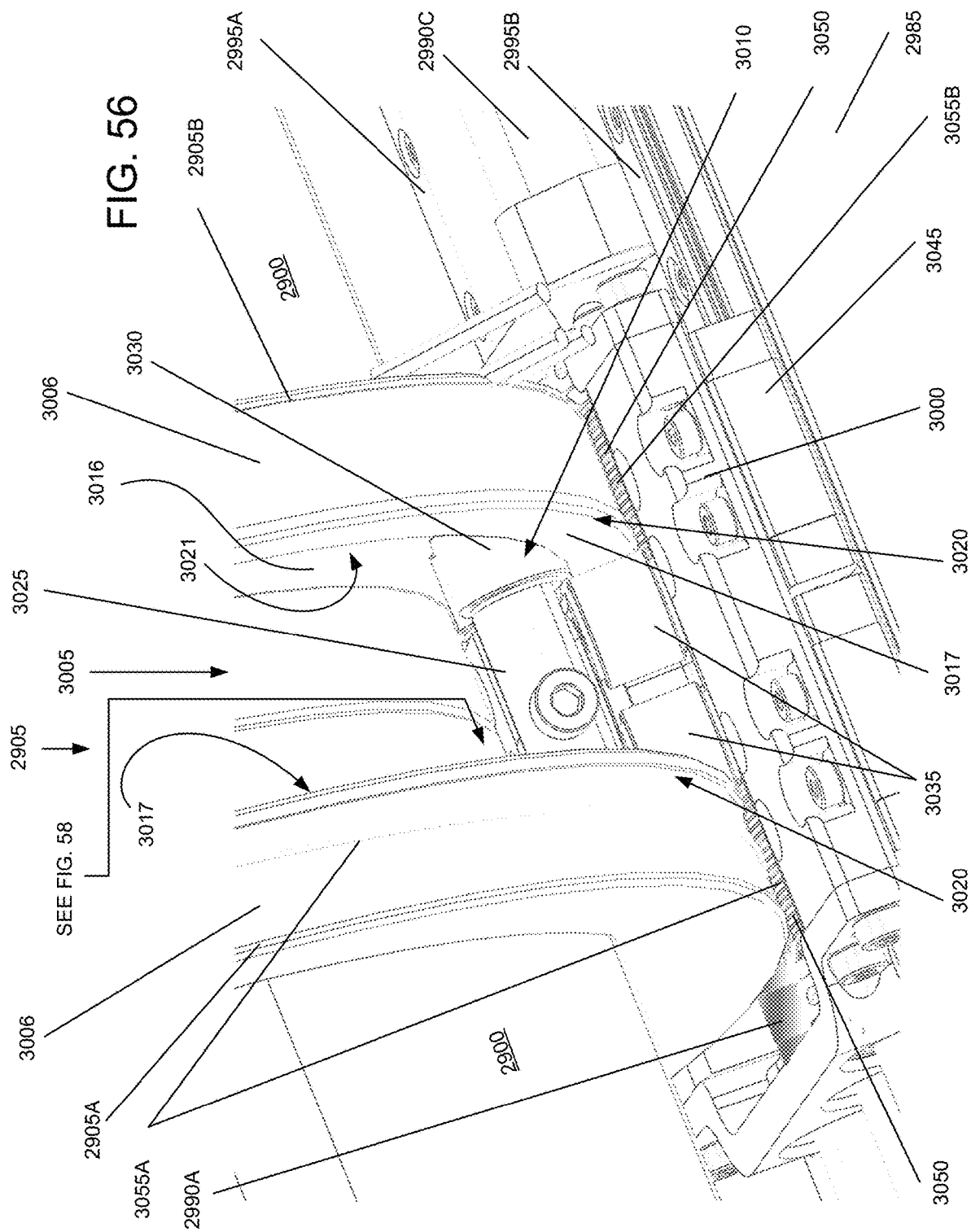
FIG. 56 is an enlarged perspective view of the interface region between the rollers of the roller assembly and the arcuate sides of the arcuate channel of the C-arm.
Figure 58:
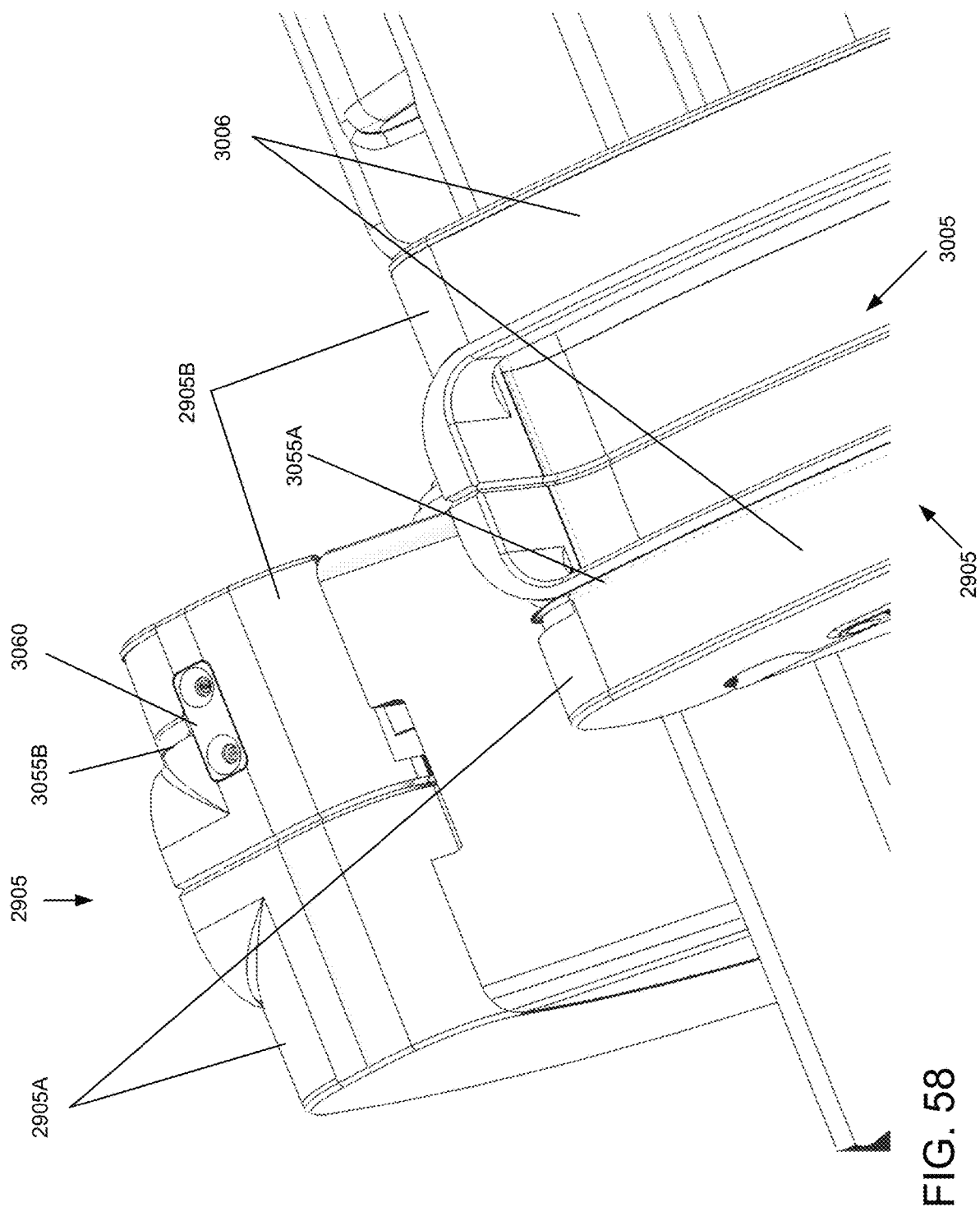
FIG. 58 is a top perspective view of the upper ends of the C-arm.

As illustrated in FIGS. 47 and 48, the C-arm 2905 includes halves 2905A, 2905B that mate together to form the overall C-arm 2905. In doing so, halves 2905A, 2905B define an arcuate channel 3005 that opens outwardly and extends nearly an entire outer circumferential surface 3006 of the C-arm 2905, as also depicted in FIGS. 56 and 58 discussed in greater detail below.

Figure 55:
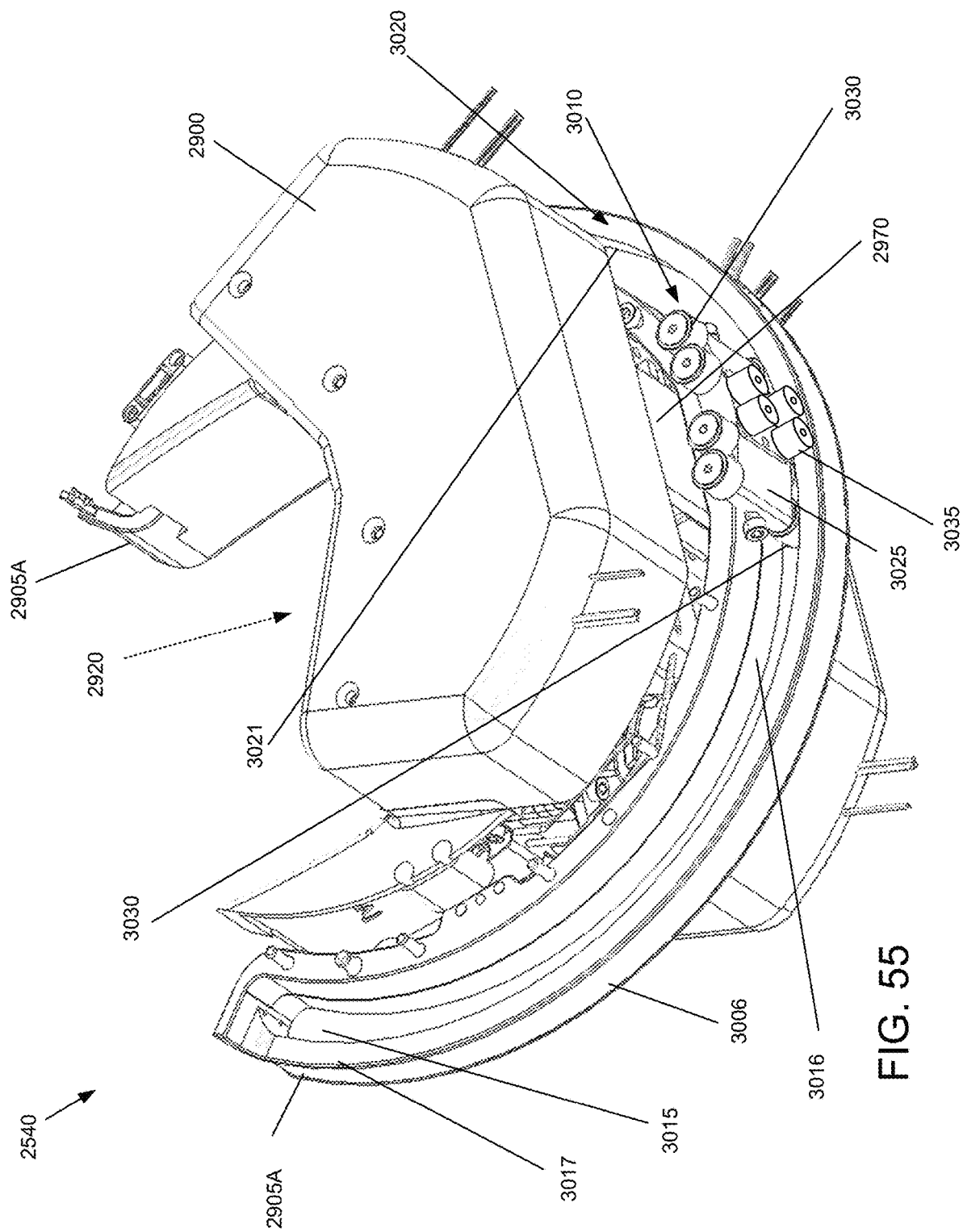
FIG. 55 is a bottom perspective view of the carriage of FIGS. 49 and 50, except with one of the two halves of the C-arm removed for clarity purposes.

FIG. 55 is a bottom perspective view of the carriage of FIGS. 49 and 50, except with one half 2905B of the two halves 2905A, 2905B of the C-arm 2905 removed for clarity purposes. As can be understood from FIG. 55, the two halves 2905A, 2905B of the C-arm 2905 are coupled to the housing 2900, and a roller assembly 3010 is configured to roll along the two halves 2905A, 2905B of the C-arm 2905 as discussed in greater detail below.

A C-arm roller channel 3015 is defined in an inward facing side 3017 of the half 2905A visible in FIG. 55, and the C-arm roller channel is arcuate, spaced radially inward from the outer circumferential surface 3006 of the visible half 2905A, and extends nearly the entire circumference of the visible C-arm half 2905A. Although the other C-arm half 2905B is hidden in FIG. 55, it also has such a C-arm roller channel 3015 defined in its inward facing side 3017, as can be understood from FIGS. 56-57B discussed in greater detail below. The opposed inward facing sides 3017 are visible in FIGS. 49 and 50.

As shown in FIGS. 49 and 55, for each C-arm half 2905A, 2905B, an outer flanged rim 3020 is defined between each C-arm roller channel 3015 and the adjacent outer circumferential surface 3006. A radially inward facing rolling surface 3021 of the outer flanged rim 3020 opposite the exterior circumferential surface 3006 is arcuate, faces radially inward and extends the length of the C-arm roller channel 3015. Similarly, but oppositely, a radially outward facing rolling surface 3016 faces radially outward, and with the radially inward facing rolling surface 3021, define the inner and outer arcuate boundaries of the C-arm roller channel 3015.

Figure 59:
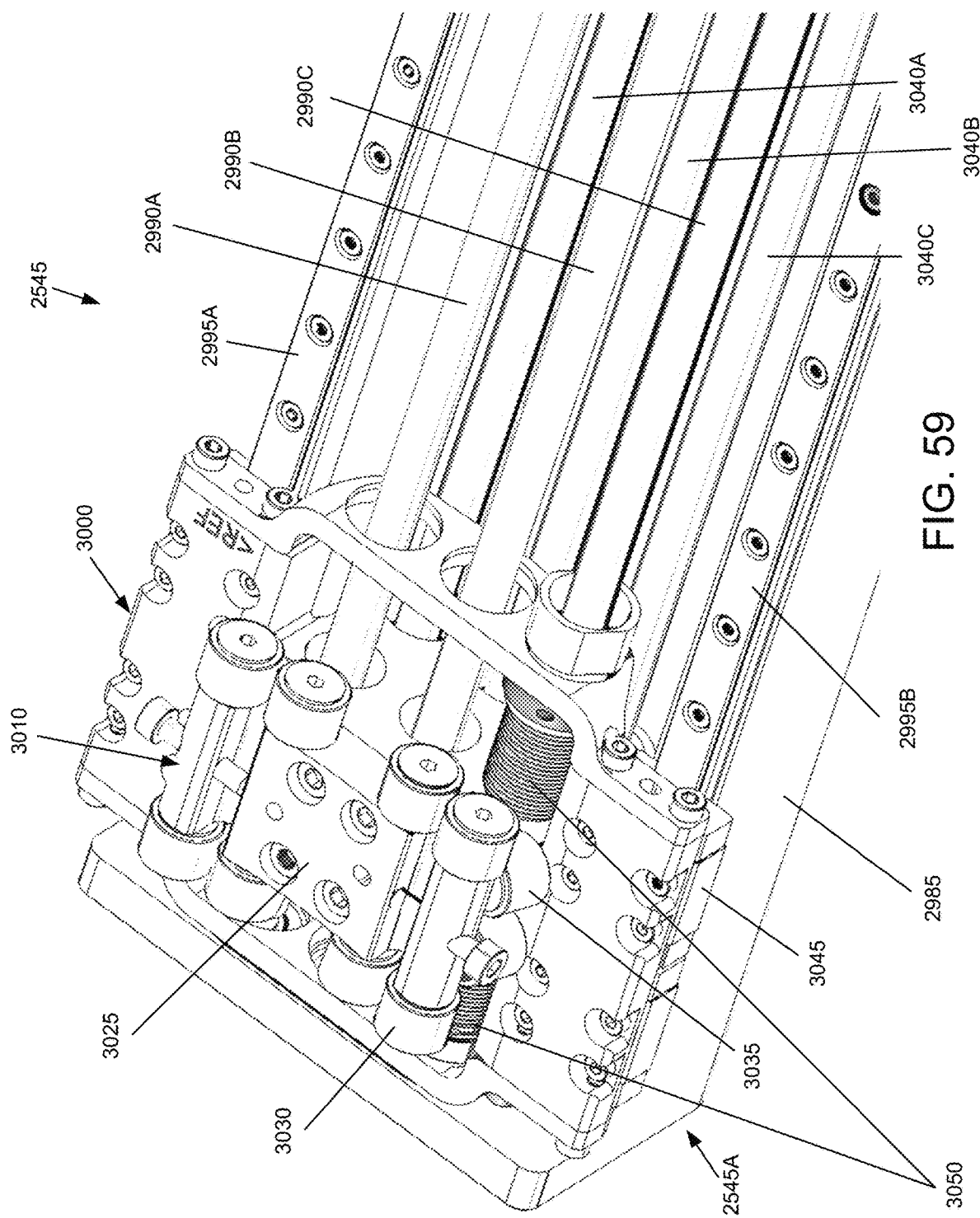
FIG. 59 is a top perspective view of the linear displacement platform and linear displacement block of FIGS. 49 and 50 with the carriage hidden for clarity purposes.

As indicated in FIG. 55 and also in FIG. 59, which is a top perspective view of the linear displacement platform 2545 and linear displacement block 3000 of FIGS. 49 and 50 with the carriage 2540 hidden for clarity purposes, the roller assembly 3010 includes a roller block 3025 and multiple side free rollers 3030 on each side of the roller block. The roller assembly 3010 also includes multiple bottom free rollers 3035. Further, the roller assembly 3010 is coupled to the linear displacement block 3000. The arrangements of elements described with respect to FIGS. 55 and 59 are also representative of the other carriages 2540 shown in FIG. 48, including their respective roller assemblies and linear displacement platforms.

FIG. 56 is an enlarged perspective view of the interface region between the rollers 3030, 3035 of the roller assembly 3010 and the sides of the arcuate channel 3005 of the C-arm 2905.

As can be understood from FIGS. 55 and 56, the bottom free rollers 3035 project downward into the arcuate channel 3005 of the C-arm 2905 from the roller block 3025 to roll along the inward facing sides 3017 of the outer flanged rims 3020. Because the roller assembly 3010 is coupled to the linear displacement block 3000 and the bottom free rollers 3035 are sandwiched between the opposite inward facing sides 3017 of the spaced apart outer flanged rims 3020 of the C-arm 2905, the C-arm 2905 and the rest of its carriage 2540 move with the linear displacement block 3000 as a unit along the linear slide rails 2995A, 2995B of the elongated frame 2985 despite the C-arm 2905 being capable of rolling against elements of the linear displacement block 3000, as discussed below.

Figure 60:
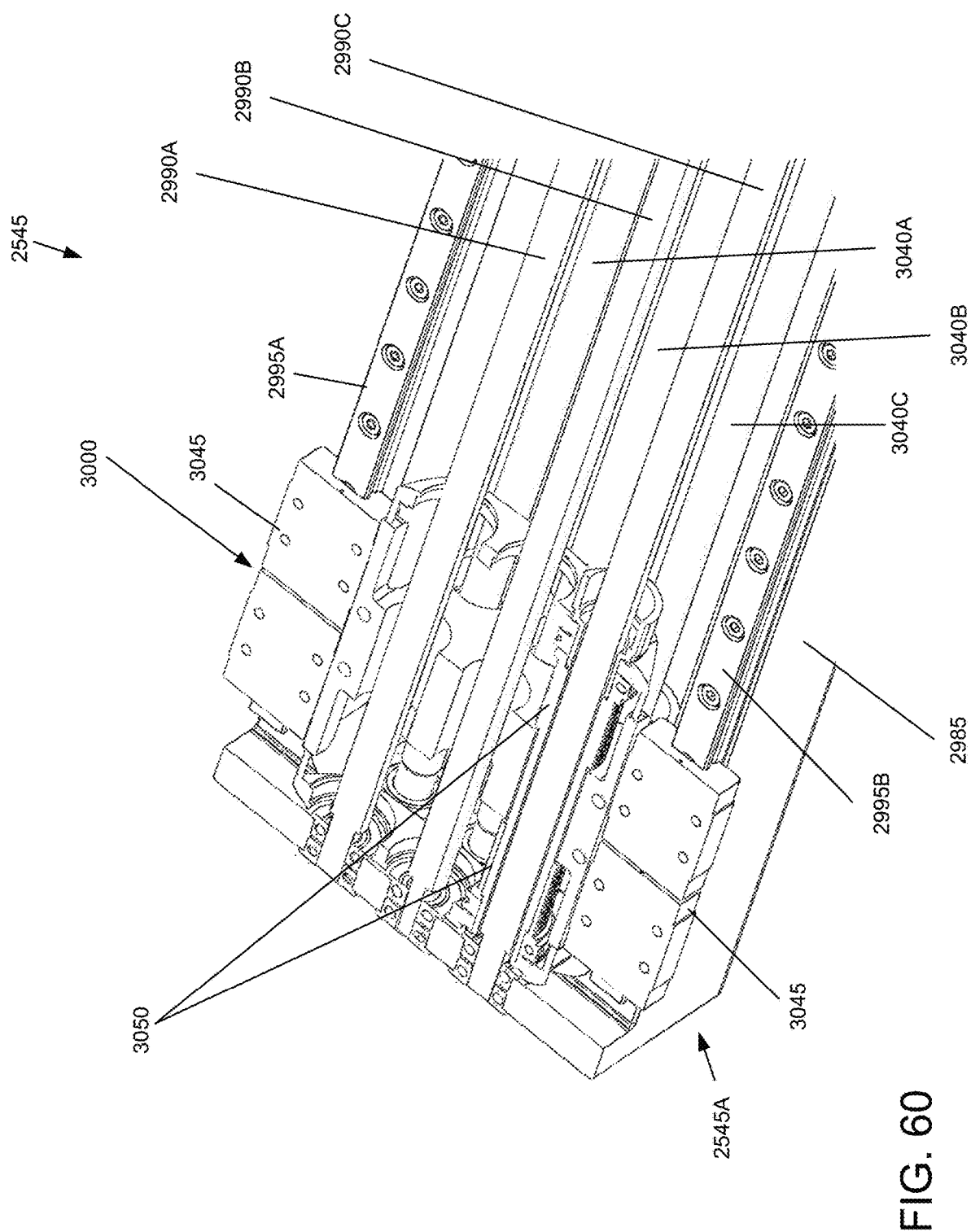
FIG. 60 is the same view as FIG. 59 but is a cross section through elements of the linear displacement block and the C-arm drive shafts as taken along the longitudinal axes of the C-arm drive shafts.

FIG. 60 is the same view as FIG. 59 but is a cross section through elements of the linear displacement block 3000 and the C-arm drive shafts 2990A, 2990B, 2990C as taken along the longitudinal axes of the C-arm drive shafts. The linear displacement block 3000 shown in FIGS. 59 and 60 belongs to the most distal of the three carriages 2540 depicted in FIG. 48. As shown in FIGS. 59 and 60, the linear displacement platform 2545 includes multiple drive lead screws 3040A, 3040B, 3040C extending longitudinally within the elongated frame 2985. Each side of the linear displacement block 3000 is supported in a sliding displacement manner on a respective linear slide rail 2995A, 2995B of the elongated frame 2985 via a slide block 3045. Each carriage 2540 of the robot 2520 of FIG. 48 has an identical sliding interface between its linear displacement block 3000 and the elongated frame 2985. As a result, each carriage 2540 of the robot 2520 via its respective linear displacement block 3000 can slide along the elongated frame 2985 when driven by its respective drive lead screw 3040A, 3040B, 3040C, as discussed below.

As can be understood from FIG. 60, two C-arm drive shafts 2990A, 2990B of the three extend through the linear displacement block 3000 without contacting or otherwise interacting with the linear displacement block. However, as shown in FIGS. 59 and 60, the remaining C-arm drive shaft 2990C includes a C-arm drive drum 3050 located within, and rotatably coupled to, the linear displacement block 3000 such that the C-arm drive drum 3050 rotates with its supporting C-arm drive shaft 2990C when this drive shaft is caused to rotate about its longitudinal axis within the elongated frame 2985. Each of the three C-arm drive shafts 2990A, 2990B, 2990C and the three drive lead screws 3040A, 3040B, 3040C are rotatably supported at their extreme distal and proximal ends by bearing assemblies in the ends 2545A, 2545B of the elongated frame 2985, as best understood from FIGS. 60, 63 and 64.

Depending on the embodiment, each of the drive shafts 2990A, 2990B, 2990C may be a spline shaft (e.g., such as the SS Series Spline Shafts offered by Haydon Kerk Pittman). In other embodiments, these drive shafts may be a ball spline.

Reference is again made to FIG. 61 in discussing the components of the most distal of the three carriages 2540 depicted in FIG. 48. As can be understood from FIG. 60, a nut (not shown) is coupled to the C-arm drive drum 3050 to couple the rotation of the C-arm drive drum 3050 to the associated C-arm drive shaft 2990C independent of the insertion position (i.e., distal-proximal location) of the associated linear displacement block 3000 and its carriage 2540 (i.e., in this instance, the most distal of the three carriages 2540 depicted in FIG. 48) along the distal-proximal length of the linear displacement platform 2545 of the robot 2520. This arrangement is advantageous in that it allows insertion (i.e., distal-proximal location along the linear displacement platform 2545) and rotation of the C-arm drive drum 3050 to be decoupled.

As a result, and as discussed in greater detail below in reference to FIGS. 62 and 63, a lead screw motor 3070C and its drive lead screw 3040C drive the insertion position of the most distal C-arm drive drum 3050 (depicted in FIGS. 59 and 60), and a C-arm motor 3065C and its C-arm drive shaft 2990C rotate this most distal C-arm drive drum 3050. Because of this arrangement, these motors 3065C and 3070C, plus the other four associated with the middle and most proximal carriages 2540 depicted in FIG. 48, can be co-located at the proximal or motor end 2545B of the linear displacement platform 2545. This proximal location of the motors reduces the distal mass of the linear displacement platform as well as makes the robot smaller distally.

Figure 61:
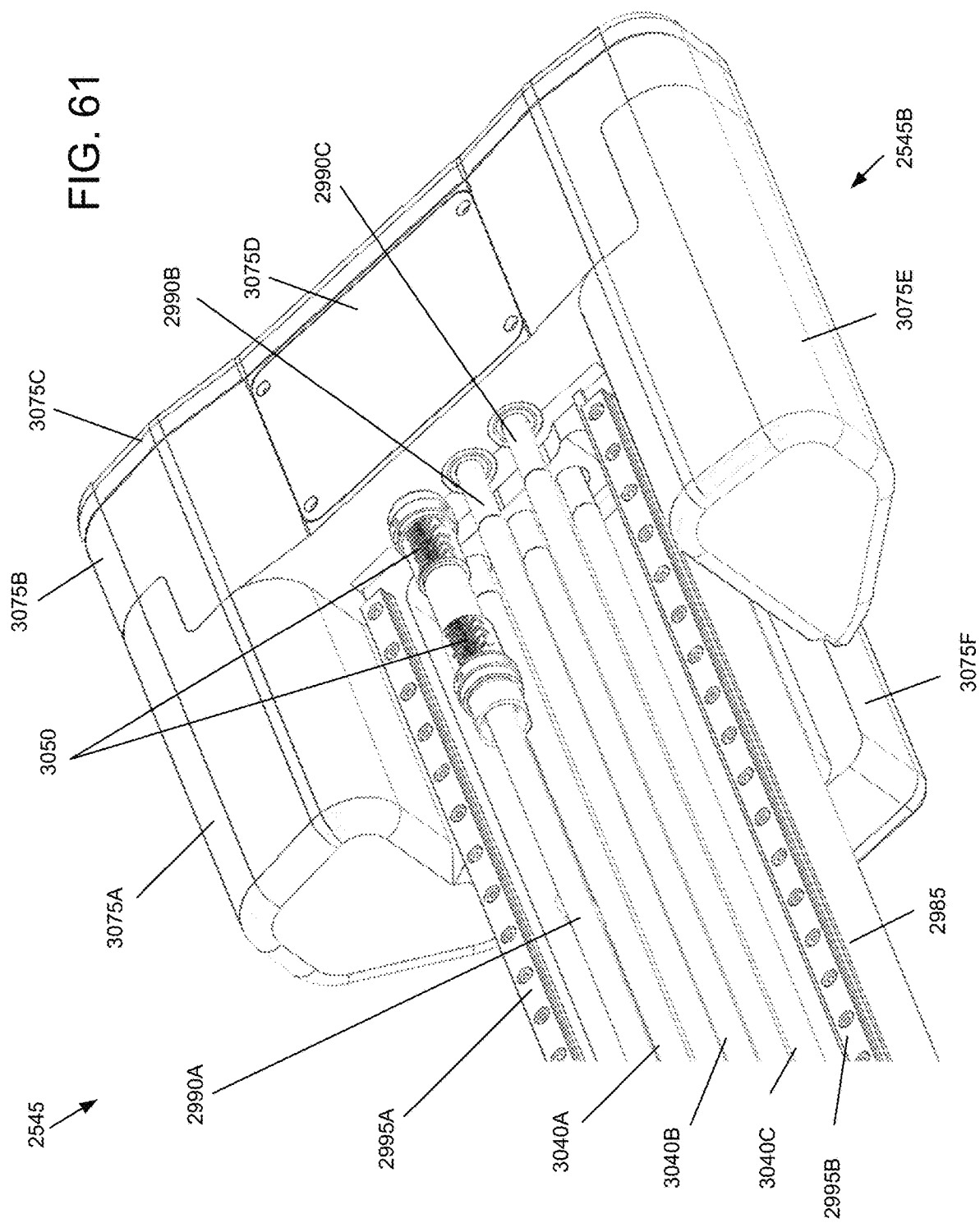
FIG. 61 is a top perspective view of the proximal or motor end of the linear displacement platform of the robot of FIG. 48.
Figure 62:
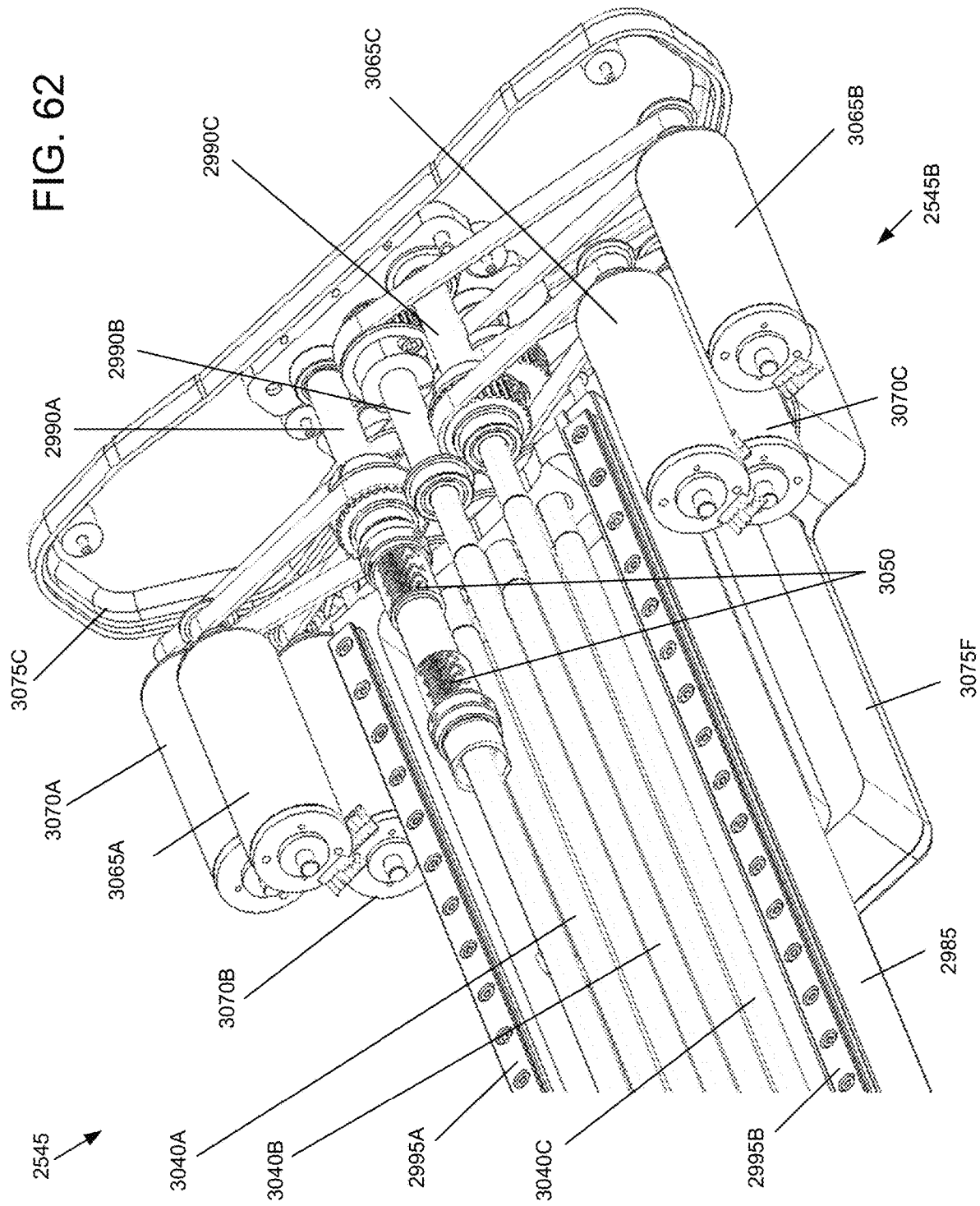
FIG. 62 is the same view as FIG. 61, except the housings have been removed to show the motors and pulleys of the proximal or motor end of the linear displacement platform.

As can be understood from FIGS. 61 and 62, which are top perspective views of the proximal or motor end 2545B of the linear displacement platform 2545 of the robot 2520 of FIG. 48, a C-arm drive drum 3050 is also supported on C-arm drive shaft 2990A. Although the linear displacement block 3000 of the most proximal of the three carriages 2540 depicted in FIG. 48 is not illustrated in FIGS. 61 and 62 for clarity purposes, the C-arm drive drum 3050 on C-arm drive shaft 2990A is also located within, and rotatably coupled to, a linear displacement block 3000 as described above with respect to FIGS. 59 and 60. Also, just as discussed above, a lead screw motor 3070A and its drive lead screw 3040A drive the insertion position of the most proximal C-arm drive drum 3050 (depicted in FIGS. 61 and 62), and a C-arm motor 3065A and its C-arm drive shaft 2990A rotate this most proximal C-arm drive drum 3050. As already noted, such an arrangement is advantageous in that it allows insertion (i.e., distal-proximal location along the linear displacement platform 2545) and rotation of the C-arm drive drum 3050 to be decoupled.

Although not shown in any figures, an identical C-arm drive drum 3050 is also supported on C-arm drive shaft 2990B, and this C-arm drive drum 3050 on C-arm drive shaft 2990B is also located within, and rotatably coupled to, a linear displacement block of the middle of the three carriages 2540 depicted in FIG. 48. Also, just as with the most distal and most proximal of the three carriages 2540 depicted in FIG. 48 and described above, the middle of the three carriages 2540 also is has a similar component arrangement. Specifically, a lead screw motor 3070B and its drive lead screw 3040B drive the insertion position of the middle C-arm drive drum 3050 (not shown, but identical to those already described herein), and a C-arm motor 3065B and its C-arm drive shaft 2990B rotate this middle C-arm drive drum 3050. As already noted, such an arrangement is advantageous in that it allows insertion (i.e., distal-proximal location along the linear displacement platform 2545) and rotation of the C-arm drive drum 3050 to be decoupled.

Figure 57A:
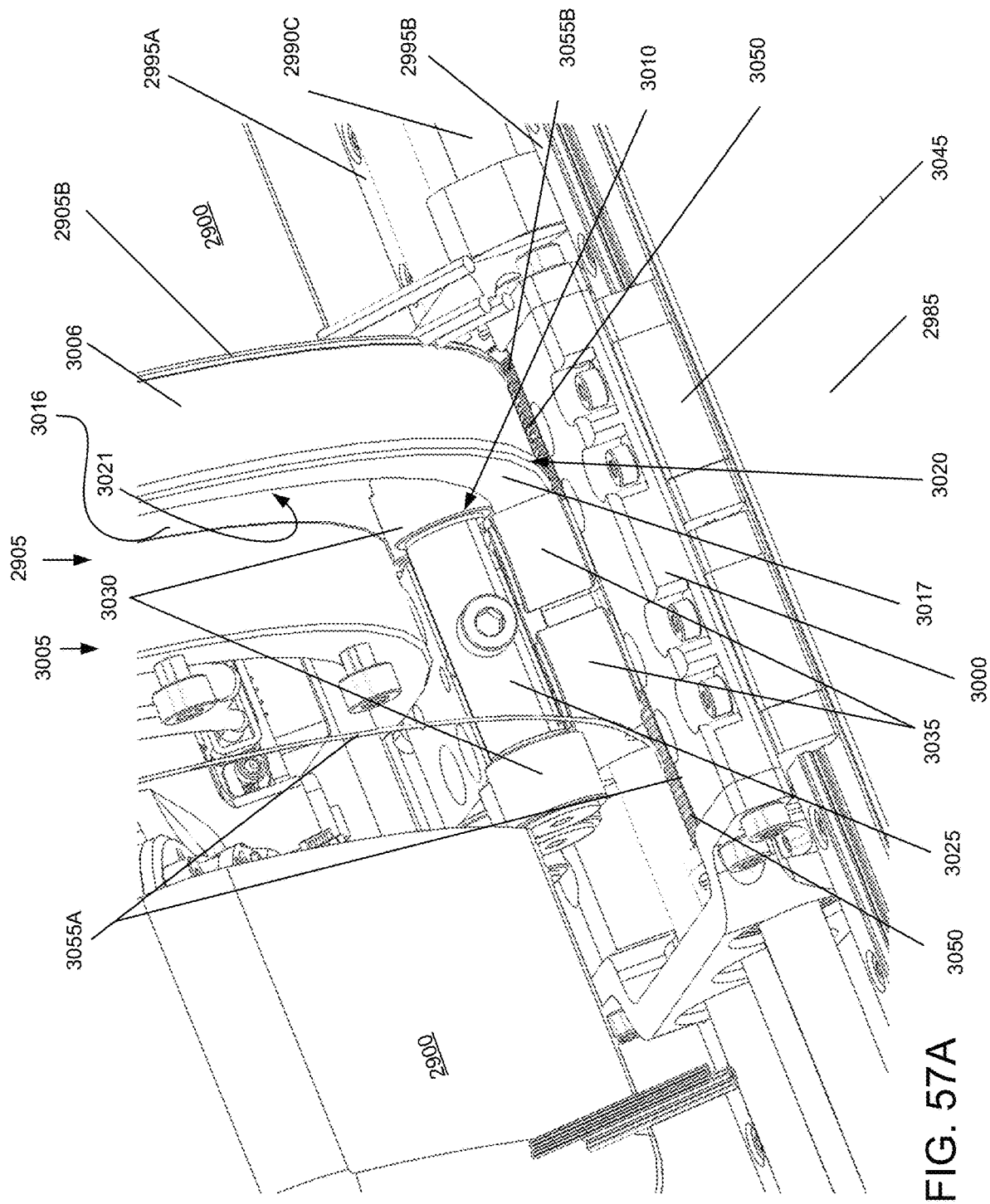
FIG. 57A is the same view as FIG. 56, except one of the two halves of the C-arm is hidden for clarity purposes.
Figure 57B:
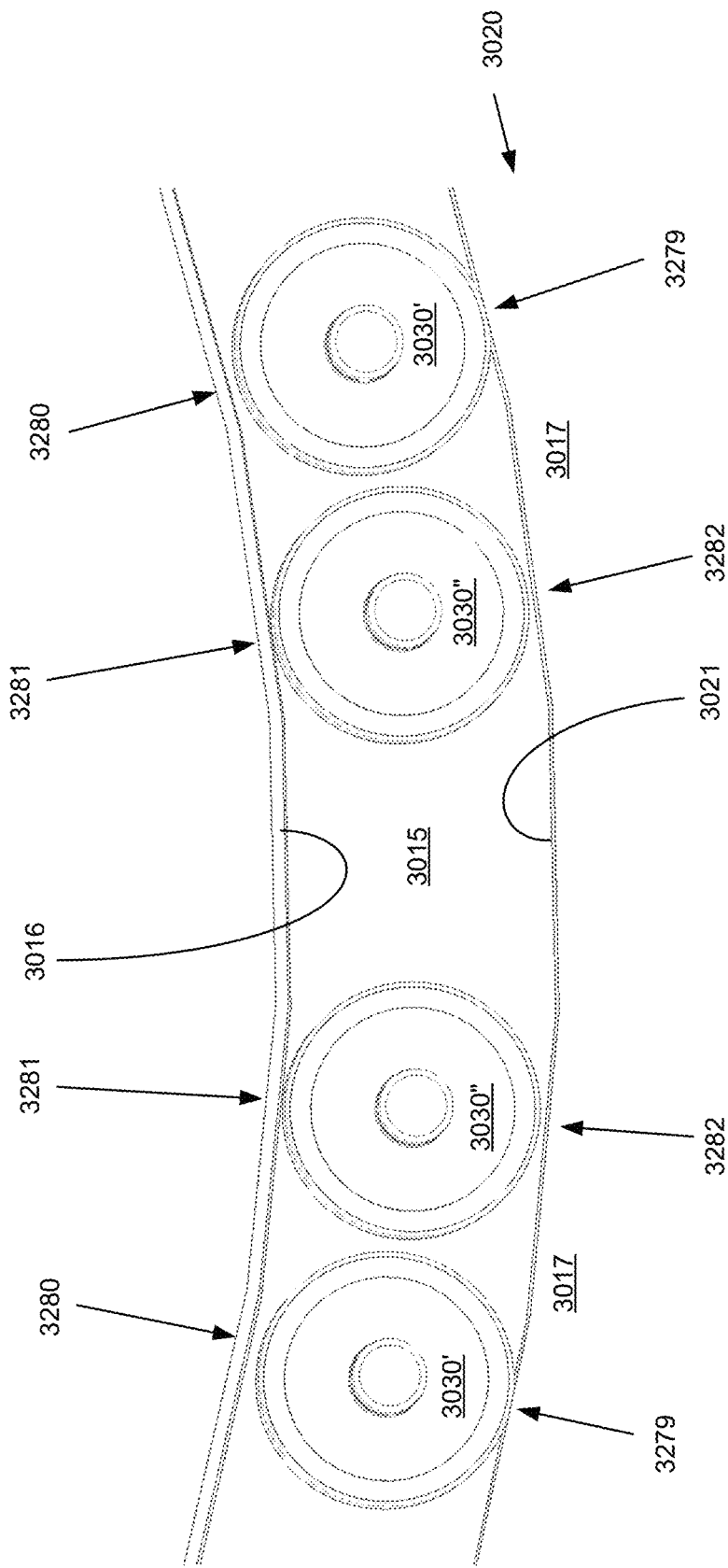
FIG. 57B is an elevational view of a C-arm roller channel viewed normal to the inward facing side of one half of the two halves of a C-arm, as indicated by the view arrow in FIG. 56.

FIG. 57A is the same view as FIG. 56, except one of the two halves 2905A, 2905B of the C-arm 2905 is hidden for clarity purposes. FIG. 57B is an elevational view of a C-arm roller channel 3015 viewed normal to the inward facing side 3017 of one half 2905B of the two halves 2905A, 2905B of a C-arm 2905, as indicated by the view arrow in FIG. 56. As can be understood from FIGS. 56-57B, multiple side free rollers 3030 of a roller block 3025 occupy each C-arm roller channel 3015, some of those side free rollers 3030 rolling against a radially outward facing rolling surface 3016 and other side free rollers 3030 rolling against a radially inward facing rolling surface 3021. These rolling interfaces between these side free rollers 3030 and the rolling surfaces 3016, 3021 prevent the C-arms 2905 from displacing closer to or further away from the linear displacement block 3000.

Figure 57C:
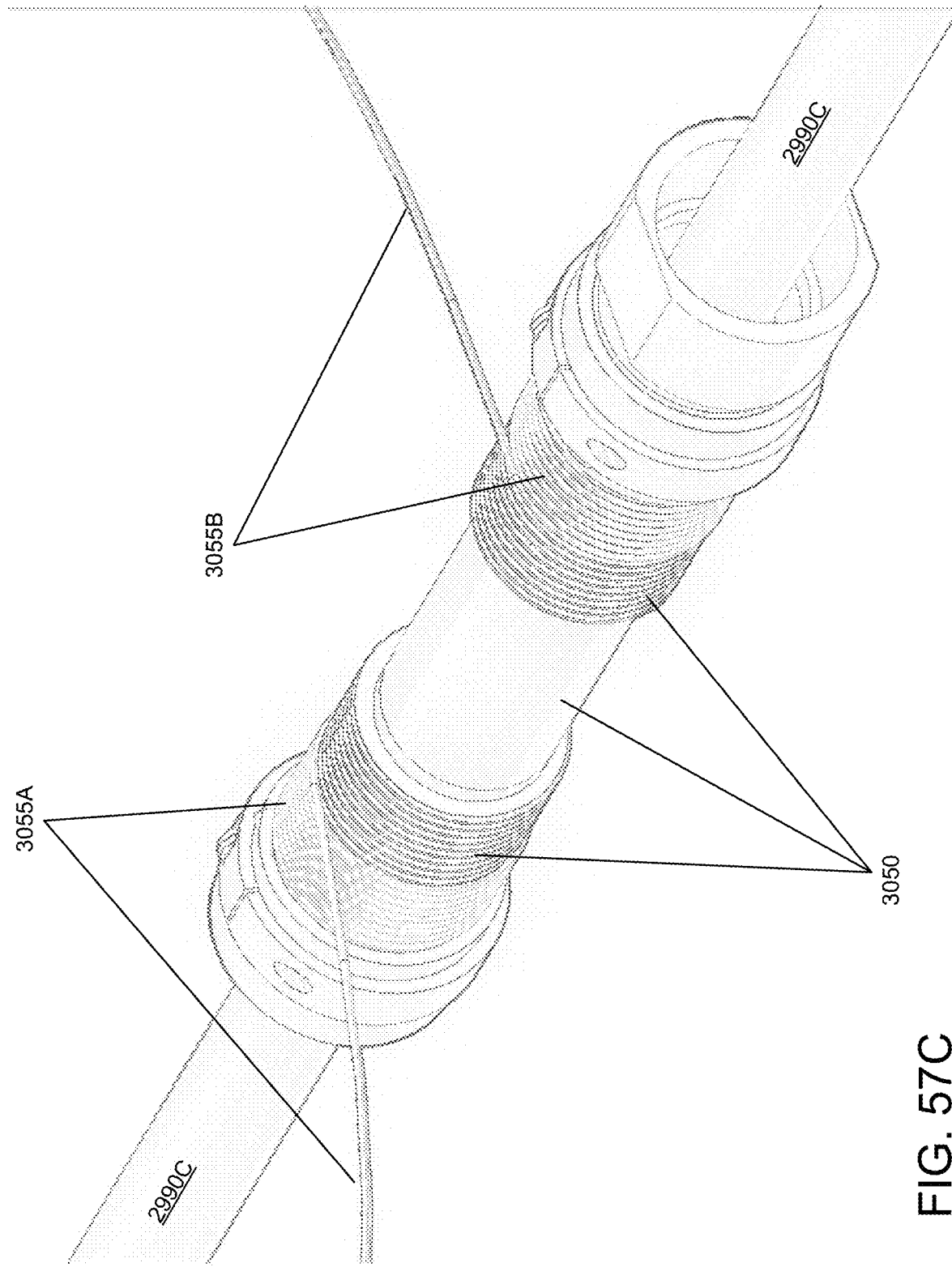
FIG. 57C is an isolated enlarged perspective view of a C-arm drive drum mounted on a C-arm drive shaft.

FIG. 57C is an isolated enlarged perspective view of the C-arm drive drum 3050 mounted on C-arm drive shaft 2990C, as also depicted in FIGS. 56 and 57A. As shown in FIGS. 56, 57A and 57C, and discussed in greater detail below, distal, and proximal portions of the C-arm drive drum 3050 respectively wind out/in C-arm rotation cables 3055A, 3055B to effectuate rotation of the C-arm 2905 and the rest of the carriage 2540.

As illustrated in FIGS. 56, 57A and 58, the C-arm rotation cables 3055A, 3055B respectively extend along the outer circumferential surfaces 3006 of the C-arm 2905 to respective attachment points 3060 at the free ends of the C-arm. Thus, as can be understood from FIGS. 56, 57A, 57C and 58, as the C-arm drive shaft 2990C is caused to rotate, the C-arm drive drum 3050 mounted thereon is caused to rotate, the distal and proximal portions of the drive drum 3050 winding out and winding up the cables 3055A, 3055B that extend along the outer circumferential surfaces of the C-arm in rotating the C-arm clockwise or counterclockwise as discussed in detail below. This rotation of the C-arm drive drum 3050 as transmitted to the C-arm via the cables 3055A, 3055B rotates the C-arm 2905 and the rest of the carriage 2540, including the carriage housing 2900 coupled to the C-arm 2905 and the handle assembly 2530 nested with the carriage 2540. This rotation is about the above-discussed axis of rotation that extends coaxially with the longitudinal center axis of the working lumen 2698 of the sheath retraction assembly 2570, the handle assembly 2530 and the most proximal segment of the tubular body assembly 2535.

As the C-arm 2905 rotates, the side free rollers 3030 of the roller block 3025 roll along the radially inward facing rolling surface 3021 and the radially outward facing rolling surface 3016. As can be understood best from FIG. 57B, outer pairs of side free rollers 3030' have rolling points of contact 3279 with the radially inward facing rolling surface 3021 and non-contacting gaps 3280 with the radially outward facing rolling surface 3016. Similarly, but oppositely, inner pairs of side free rollers 3030" have rolling points of contact 3281 with the radially outward facing rolling surface 3016 and non-contacting gaps 3282 with radially inward facing rolling surface 3021. This rolling interface between the pairs of rollers 3030', 3030" and the rolling surface 3016, 3021 secures the C-arm 2905 to the linear displacement block 3000 in an up-down direction, but still allows the carriage 2540 and the handle assembly 2530 nested therein to rotate about the above-discussed axis of rotation. Each C-arm 2905 of each of the three carriages 2540 of the robot 2520 depicted in FIG. 48 has an identical roller arrangement and rolling operation as described above.

FIG. 58 is a top perspective view of the upper ends of the C-arm 2905 for the most distal carriage 2540 depicted in FIG. 48. As shown in FIGS. 56, 57A and 57C, C-arm rotation cables 3055A, 3055B are respectively coiled about distal and proximal portions of the C-arm drive drum 3050. As can be understood from FIGS. 52 and 56, 57A, 57C and 58, from the distal and proximal portions of the C-arm drive drum 3050, the C-arm rotation cables 3055A, 3055B respectively extend along the outer circumferential surfaces 3006 of the C-arm 2905 to respective attachment points 3060 at the free ends of the C-arm. The C-arm drive drum 3050 rotating in a first direction will wind up one C-arm rotation cable 3055A about a distal half of the drive drum 3050 and wind out the other C-arm rotation cable 3055B from a proximal half of the drive drum 3050, thereby causing the rotation of the most distal carriage 2540. Rotating the C-arm drive drum 3050 in a second direction opposite the first direction will wind out one C-arm rotation cable 3055A from about a distal half of the drive drum 3050 and wind up the other C-arm rotation cable 3055B about a proximal half of the drive drum 3050, thereby causing an opposite rotation of the most distal carriage 2540. Each C-arm 2905 of each of the other two carriages 2540 (i.e., the middle and proximal most carriages 2540) of the robot 2520 depicted in FIG. 48 has an identical arrangement of C-arm rotation cables 3055A, 3055B and drive drums 3050 as described here in regards to those same elements of the most distal carriage 2540 in FIG. 48 and as discussed in this paragraph with respect to FIGS. 52 and 56-58.

Figure 63:
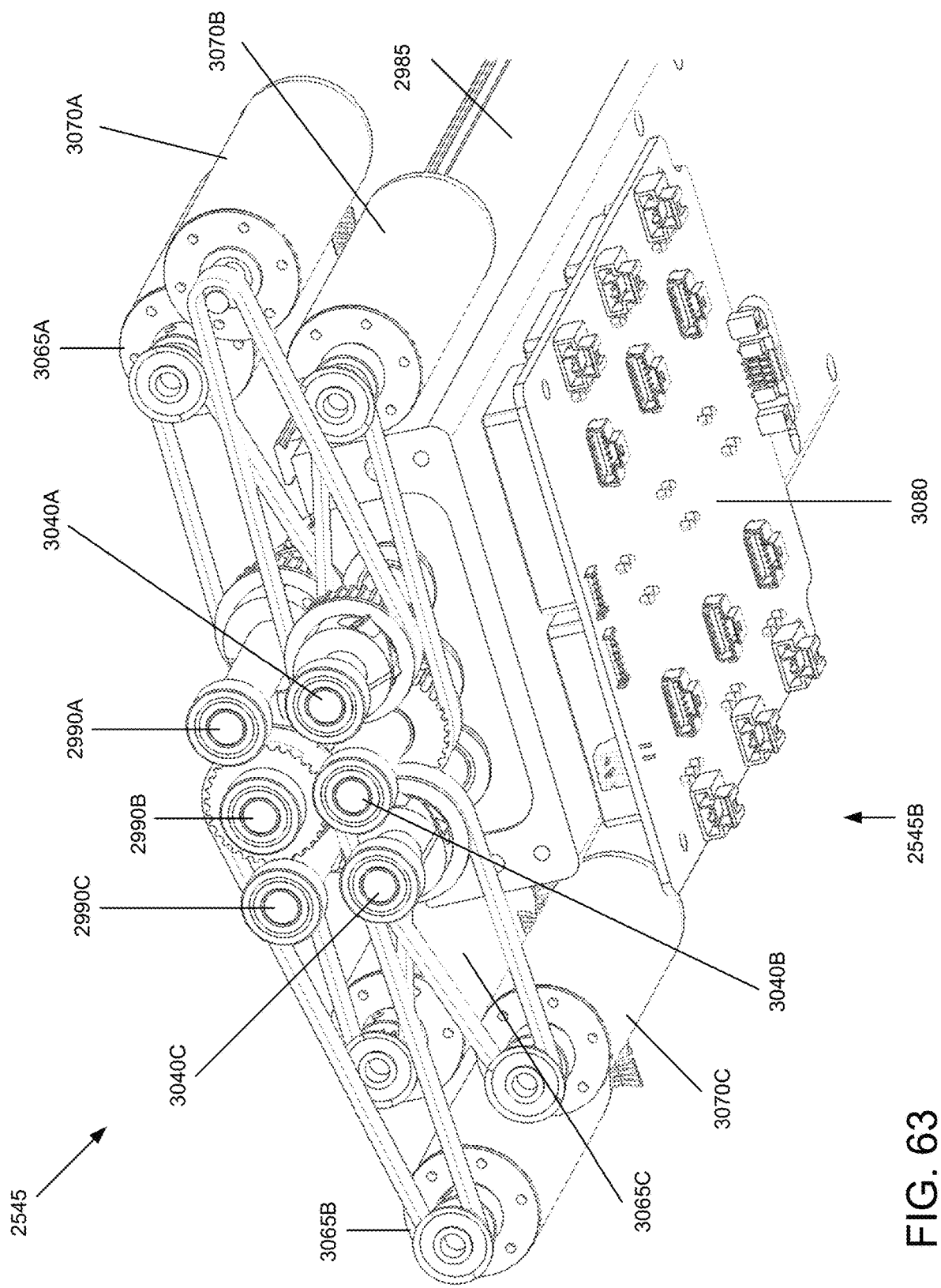
FIG. 63 is a bottom perspective view of the proximal or motor end of the linear displacement platform of the robot of FIG. 48 with the housings removed to show the motors and pulleys of the proximal or motor end of the linear displacement platform.

As depicted in FIG. 62 and also in FIG. 63, which is a bottom perspective view of the proximal or motor end 2545B of the linear displacement platform 2545 of the robot 2520 of FIG. 48, the proximal or motor end 2545B of the linear displacement platform 2545 of the robot 2520 of FIG. 48 includes C-arm motors 3065A, 3065B, 3065C that respectively drive C-arm drive shafts 2990A, 2990B, 2990C via pulley and belt arrangements. The proximal or motor end 2545B of the linear displacement platform 2545 also includes lead screw motors 3070A, 3070B, 3070C that respectively drive lead screws 3040A, 3040B, 3040C via pulley and belt arrangements. While pulley and belt arrangements are shown as mechanisms for transferring rotational energy from the above-described motors to the above-described shafts/screws, in other embodiments, rotational energy can be transferred via mechanisms made entirely of gears or even simply using the output shaft of the motor, or any extension thereof, as the above-described shaft/screw.

As indicated in FIG. 63, a printed circuit board (PCB) 3080 is secured to the bottom of the elongated frame 2985 of the linear displacement platform 2545. This PCB 3080 controls the functions and operation of the lead screw motors and the C-arms motors.

As depicted in FIG. 61, the proximal or motor end 2545B of the linear displacement platform 2545 of the robot 2520 of FIG. 48 includes upper housing elements 3075A, 3075B, 3075C, 3075D, 3075E and a lower housing element 3075F. As can be understood from FIGS. 62 and 63, these upper and lower housing elements can be removed to access aspects of the proximal or motor end of the linear displacement platform hidden beneath the housing elements.

For example, the above-described motors and associated pulley and belt arrangements are hidden below the upper housing elements, and the PCB 3080 is hidden by the lower housing element.

N. MOVING THE CARRIAGES ALONG THE LINEAR DISPLACEMENT PLATFORM

As can be understood from FIGS. 48-50 and 59-63, actuation of the lead screw motor 3070C and its drive lead screw 3040C in a first rotational direction will cause the associated linear displacement block 3000 and its associated carriage 2540 (i.e., the most distal carriage 2540 in FIG. 48) to distally displace along the linear slide rails 2995A, 2995B of the linear displacement platform 2545. Actuation of the lead screw motor 3070C and its drive lead screw 3040C in a second rotational direction opposite the first rotational direction will cause the associated linear displacement block 3000 and its associated carriage 2540 to proximally displace along the linear displacement platform 2545.

Similarly, actuation of the lead screw motor 3070B and its drive lead screw 3040B in a first rotational direction will cause the associated linear displacement block 3000 and its associated carriage 2540 (i.e., the most middle carriage 2540 in FIG. 48) to distally displace along the linear slide rails 2995A, 2995B of the linear displacement platform 2545. Actuation of the lead screw motor 3070B and its drive lead screw 3040B in a second rotational direction opposite the first rotational direction will cause the associated linear displacement block 3000 and its associated carriage 2540 to proximally displace along the linear displacement platform 2545.

Finally, actuation of the lead screw motor 3070A and its drive lead screw 3040A in a first rotational direction will cause the associated linear displacement block 3000 and its associated carriage 2540 (i.e., the most proximal carriage 2540 in FIG. 48) to distally displace along the linear slide rails 2995A, 2995B of the linear displacement platform 2545. Actuation of the lead screw motor 3070A and its drive lead screw 3040A in a second rotational direction opposite the first rotational direction will cause the associated linear displacement block 3000 and its associated carriage 2540 to proximally displace along the linear displacement platform 2545.

By such mechanisms and operations, each of the carriages 2540 may be positioned at a variety of locations along the linear displacement platform, either moved individually or together with one or two other carriages. As indicated in FIG. 48, each of the carriages may be placed in a position spaced apart from the other carriages or placed abutting with one or more of the other carriages.

O. ROTATING THE CARRIAGES ABOUT THEIR AXES OF ROTATION

As can be understood from FIGS. 48-50, 56, 57A, 57C, and 59-63, actuation of the C-arm motor 3065C and its C-arm drive shaft 2990C in a first rotational direction will cause the associated C-arm drive drum 3050 to rotate in a first direction to wind up a C-arm rotation cable 3055A about a distal half of the drive drum 3050 and to wind out another C-arm rotation cable 3055B from a proximal half of the drive drum 3050, each cable extending along the outer circumference 3006 of the C-arm 2905 of the most distal carriage 2540 in FIG. 48 and as discussed with respect to FIGS. 56, 57A, 57C, and 58. This wind up/wind out of the cables 3055A, 3055B causes the most distal carriage 2540 and its nested handle assembly 2530 (see FIG. 27) to rotate clockwise about the axis of rotation extending coaxially with the longitudinal center axis of the working lumen 2698, at least within the boundaries of the sheath retraction assembly 2570, the handle assembly 2530 and the most proximal segment of the tubular body assembly 2535 (see FIGS. 32-38). Actuation of the C-arm motor 3065C and its C-arm drive shaft 2990C in a second rotational direction opposite the first rotational direction will cause the associated C-arm drive drum 3050 to wind up/wind out the cables 3055A, 3055B along its associated C-arm 2905 such that the most distal carriage 2540 rotates counterclockwise about the axis of rotation extending coaxially with the longitudinal center axis of the working lumen 2698.

Similarly, actuation of the C-arm motor 3065B and its C-arm drive shaft 2990B in a first rotational direction will cause the associated C-arm drive drum 3050 to wind up/wind out the cables 3055A, 3055B along the outer circumference 3006 of the C-arm 2905 of the middle carriage 2540 in FIG. 48. This wind up/wind out of the cables 3055A, 3055B causes the middle carriage 2540 and its nested handle assembly 2530 (see FIG. 27) to rotate clockwise about the axis of rotation extending coaxially with the longitudinal center axis of the working lumen 2698, at least within the boundaries of the sheath retraction assembly 2570, the handle assembly 2530 and the most proximal segment of the tubular body assembly 2535 (see FIGS. 32-38). Actuation of the C-arm motor 3065B and its C-arm drive shaft 2990B in a second rotational direction opposite the first rotational direction will cause the associated C-arm drive drum 3050 to wind up/wind out of the cables 3055A, 3055B along its associated C-arm 2905 such that the middle carriage 2540 rotates counterclockwise about the axis of rotation extending coaxially with the longitudinal center axis of the working lumen 2698.

Finally, actuation of the C-arm motor 3065A and its C-arm drive shaft 2990A in a first rotational direction will cause the associated C-arm drive drum 3050 to wind up/wind out of the cables 3055A, 3055B along the outer circumference 3006 of the C-arm 2905 of the most proximal carriage 2540 in FIG. 48. This wind up/wind out of the cables 3055A, 3055B causes the most proximal carriage 2540 and any nested handle assembly 2530 to rotate clockwise about the axis of rotation extending coaxially with the longitudinal center axis of the working lumen 2698, at least within the boundaries of the sheath retraction assembly 2570, the handle assembly 2530 and the most proximal segment of the tubular body assembly 2535 (see FIGS. 32-38). Actuation of the C-arm motor 3065A and its C-arm drive shaft 2990A in a second rotational direction opposite the first rotational direction will cause the associated C-arm drive drum 3050 to wind up/wind out of the cables 3055A, 3055B along its associated C-arm 2905 such that the most proximal carriage 2540 rotates counterclockwise about the axis of rotation extending coaxially with the longitudinal center axis of the working lumen 2698.

By such mechanisms and operations, each of the carriages 2540 may be rotated at a variety of rotational orientations about the axis of rotation extending coaxially with the longitudinal center axis of the working lumen 2698. Such rotational orientations of a carriage may be achieved either individually or together with one or two other carriages.

P. SUPPORT STAND AND HEIGHT ADJUSTMENT FOR ROBOT

Figure 64:
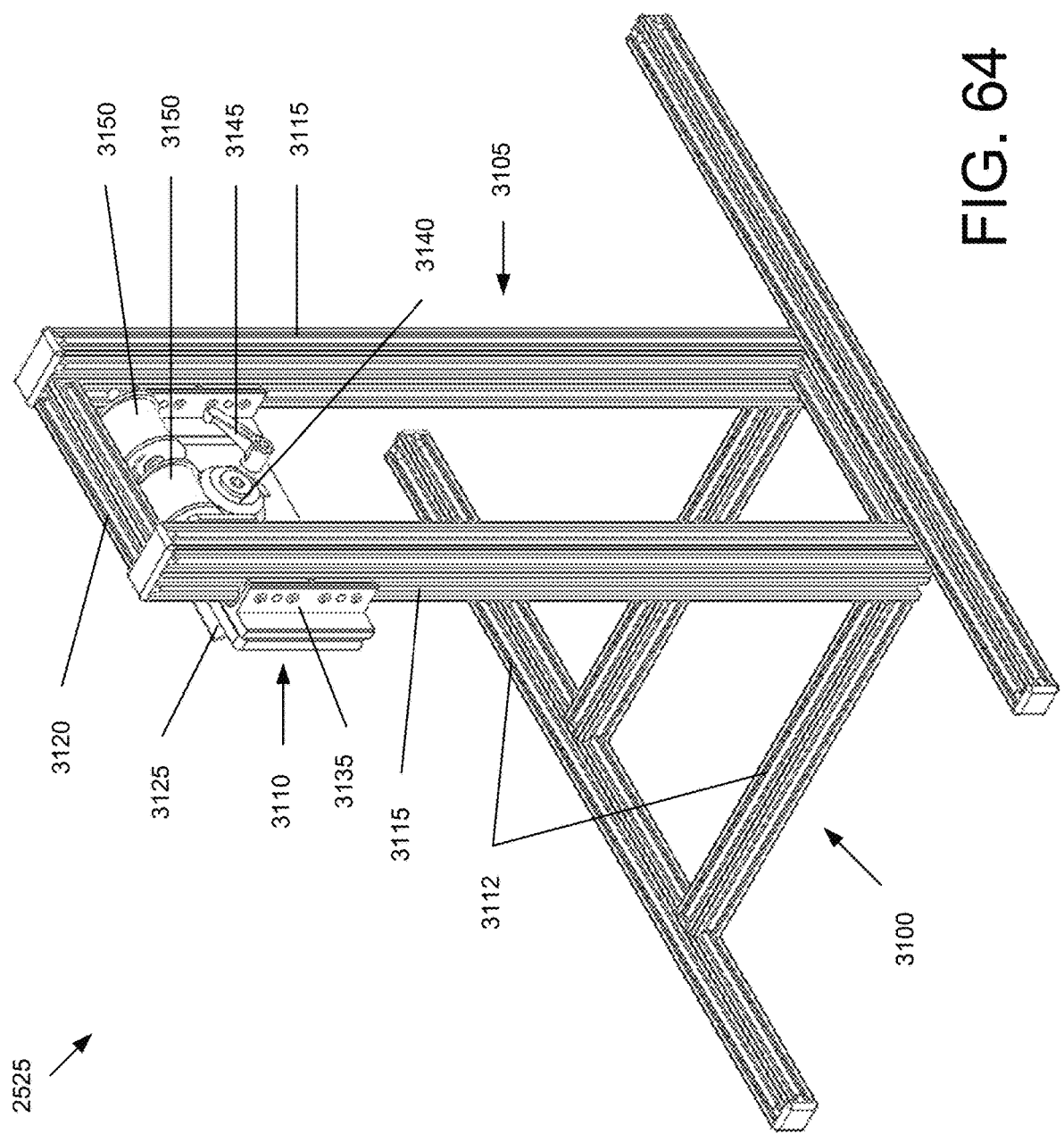
FIGS. 64 and 65 are respectively rear and front perspective views of the stand of the robotic implantation system shown in FIGS. 25 and 26.
Figure 65:
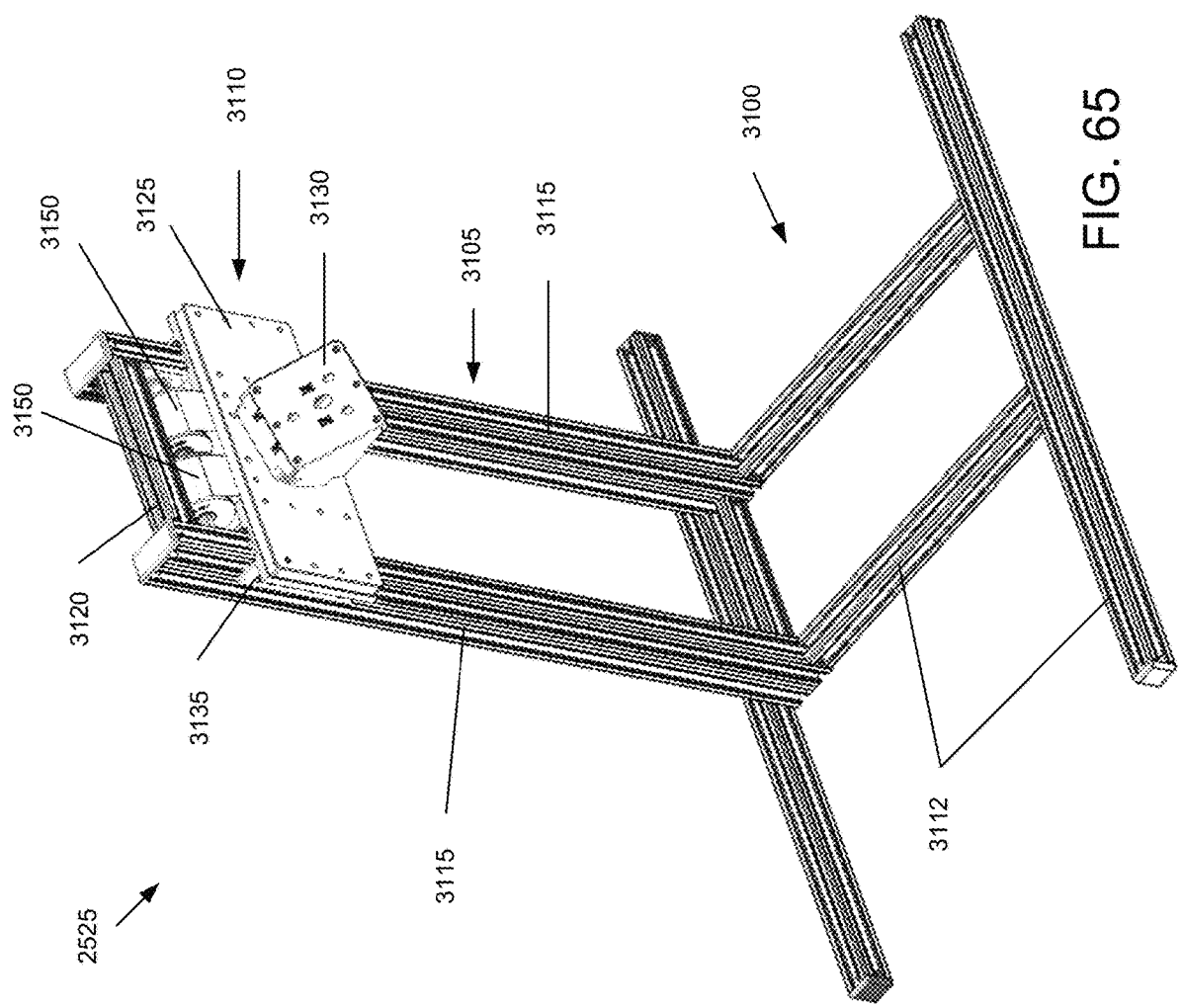

FIGS. 64 and 65 are respectively rear and front perspective views of the stand 2525 of the robotic implantation system 2510 shown in FIGS. 25 and 26. As indicated in FIGS. 64 and 65, the stand 2525 includes a base 3100, a frame 3105, and a mounting assembly 3110. The base 3100 rests on the floor to stabilize and support the robotic implantation system 2510. The base can be formed of horizontally oriented T-slotted members 3112 or other structural members sufficiently rigid and strong to support the robotic implantation system 2510.

The frame 3105 extends vertically upward from the base 3100 and may be formed of a pair of offset vertically oriented T-slotted members 3115 or other structural members sufficiently rigid and strong to support the robotic implantation system 2510. The frame 3105 includes a horizontally oriented T-slotted member 3120 coupling together the tops of the offset vertically oriented T-slotted members 3115 to provide rigidity to the frame.

Figure 66:
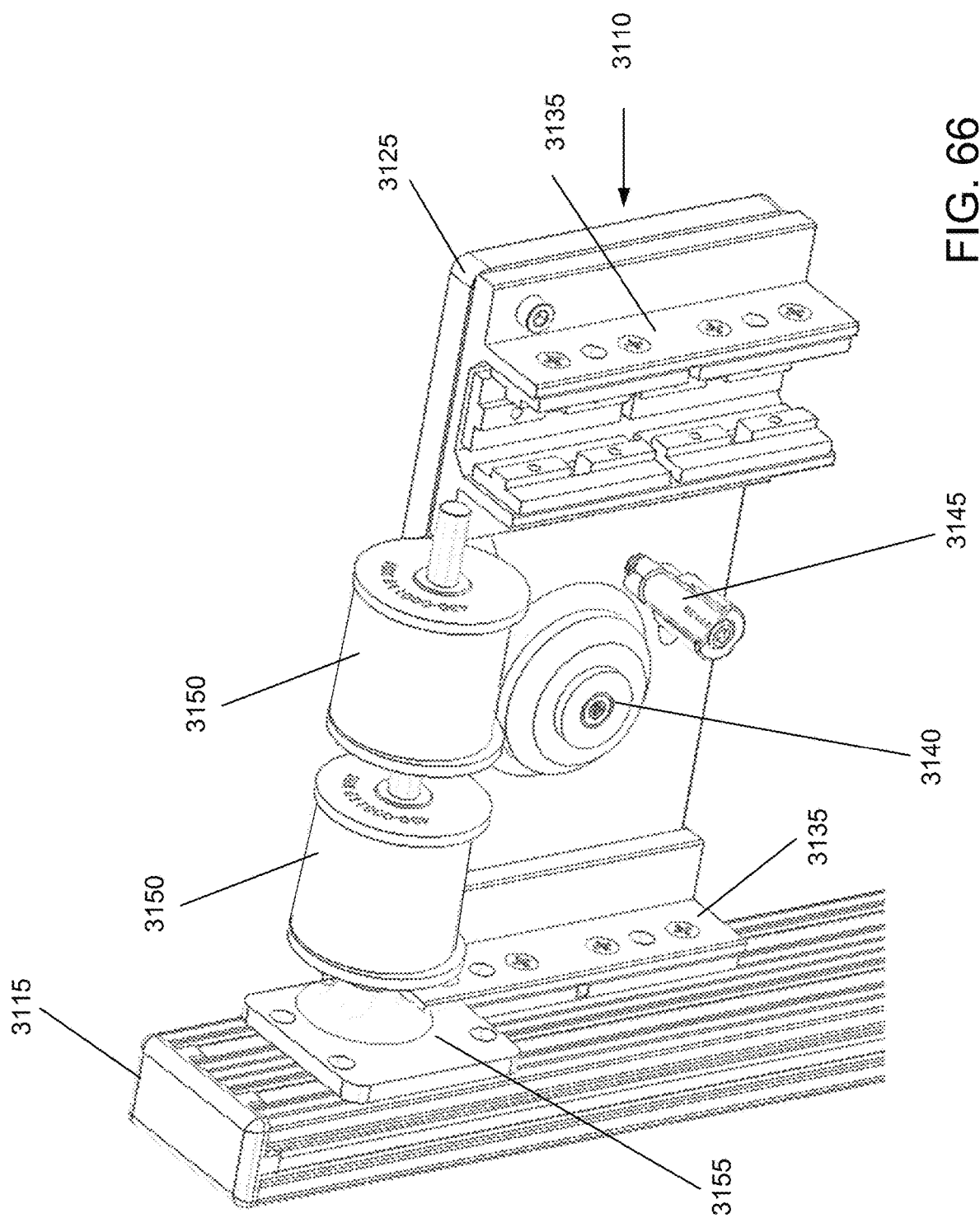
FIGS. 66 and 67 are respectively rear and front perspective views of the mounting assembly with one of the vertically oriented T-slotted members and the horizontally oriented T-slotted member hidden for clarity purposes.
Figure 67:
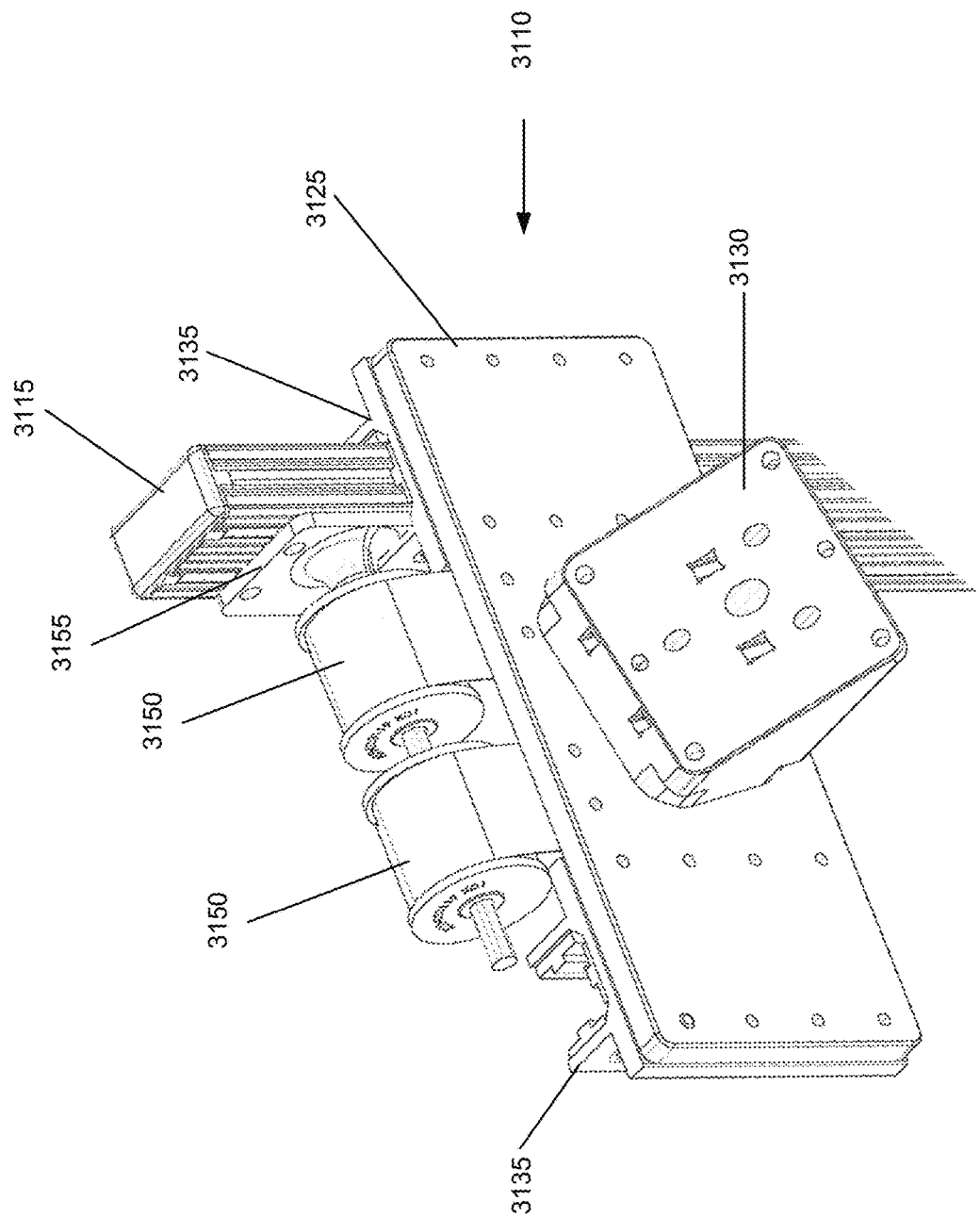

The mounting assembly 3110 extends between, and is secured to, the vertically oriented T-slotted members 3115. As shown in FIGS. 66 and 67, which are respectively rear and front perspective views of the mounting assembly 3110 with one of the vertically oriented T-slotted members 3115 and the horizontally oriented T-slotted member 3120 hidden for clarity purposes, the mounting assembly 3110 includes a mounting plate 3125, a mount 3130, a pair of displacement brackets 3135, a linear motion locking mechanism 3140, a height adjustment locking handle 3145, and a pair of constant force spring assemblies 3150.

As can be understood from FIGS. 64-67, the mounting plate 3125 extends between the vertically oriented T-slotted members 3115. A displacement bracket 3135 is secured to each end of the back side of the mounting plate 3125. Each displacement bracket 3135 is slidingly displaceable along its respective vertically oriented T-slotted members 3115. The mount 3130 is secured to the front of the mounting plate 3125, and the bottom of the linear displacement platform 2545 of the robot 2520 is secured to the mounting plate as can be understood from FIGS. 25-27.

As illustrated in FIGS. 66 and 67, the pair of constant force spring assemblies 3150 is coupled to the vertically oriented T-slotted members 3115 via mount members 3155. The constant force spring assemblies 3150 are coupled to the mounting plate 3125. The constant force spring assemblies 3150 are sized and configured to offset the weight of the robot 2520 and catheter 2515 suspended off of the mount 3130 such that it requires very little force to displace the mounting plate 3125 upward or downward along the vertically oriented T-slotted members 3115 when setting the height of the robot and catheter in preparation for a procedure. The linear motion locking mechanism 3140 is responsible for locking the mounting plate 3125 in place at a desired height along the vertically oriented T-slotted members 3115. The linear motion locking mechanism can be caused to lock or unlock as desired via use of the height adjustment locking handle 3145.

Q. FAULT LEADING TO BRAKING OF ROBOT AND TRANSITION TO MANUAL CONTROL OF HANDLE ASSEMBLY

Figure 68:
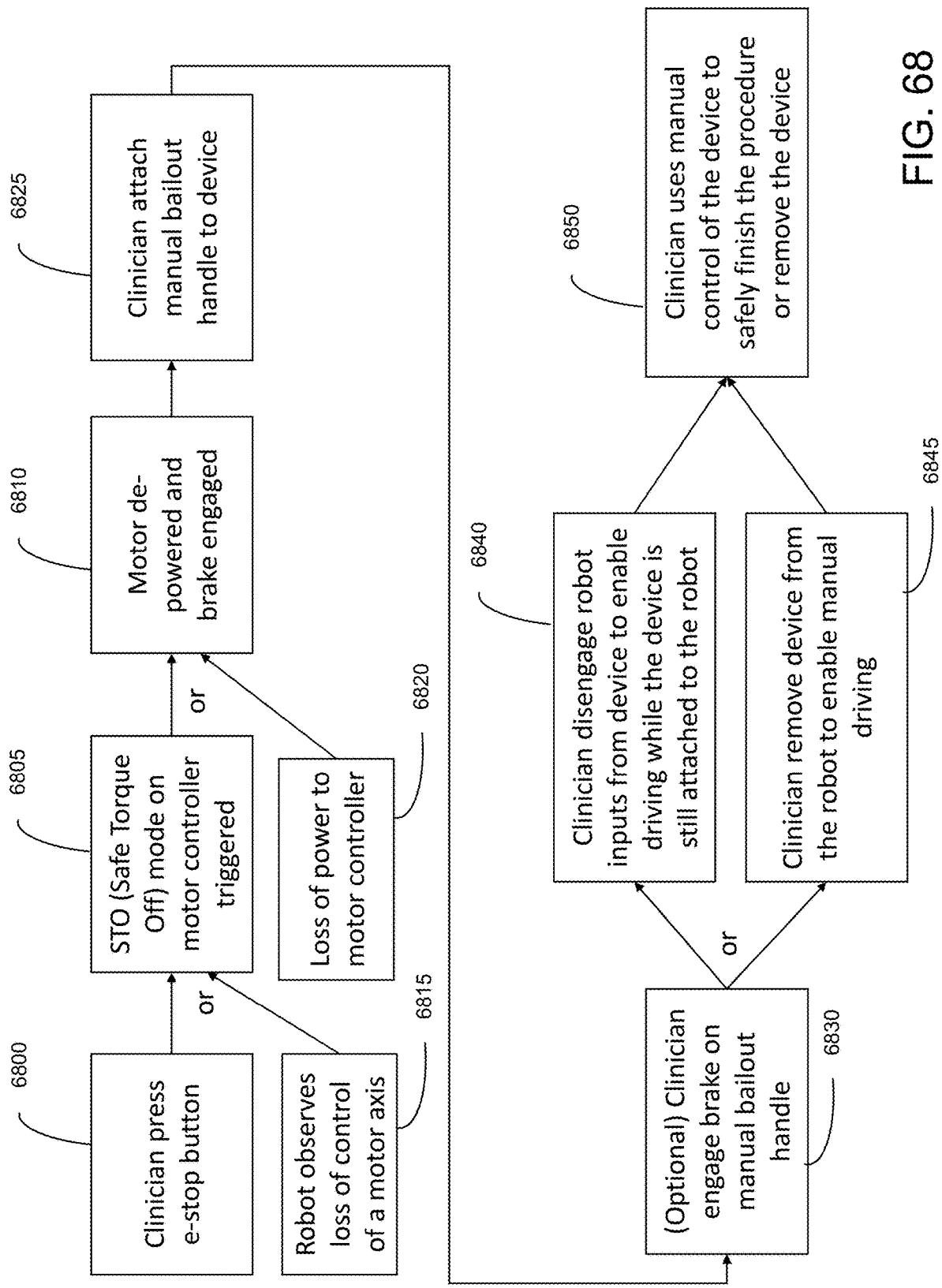
FIG. 68 is a diagram illustrating a procedure by which braking would be engaged in the robot in the event of a fault, the operation of the handle assembly then transitioning from robot control to manual control.

FIG. 68 is a diagram illustrating a procedure by which braking would be engaged in the robot 2520 in the event of a fault, the operation of the handle assembly 2530 then transitioning from robot control to manual control. As shown in FIG. 68, a fault in the robot 2520 or other issue in the implant procedure arises necessitating a transition from the robot 2520 being used to control the handle assembly 2530 to the handle assembly being controlled manually by a clinician. In one such situation, the clinician observes there is an issue necessitating the change in control and presses the emergency stop button (block 6800), which causes the motor controllers for the various motors of the robot to enter a safe torque off (STO) mode (block 6805) and leads to the motors being deenergized and causing the motor brakes to be engaged (block 6810).

In another such situation, the robot 2520 observes a loss of control of a motor axis (block 6815), which causes the motor controllers for the various motors of the robot to enter a safe torque off (STO) mode (block 6805) and leads to the motors being deenergized and causing the motor brakes to be engaged (block 6810).

In another situation, the robot 2520 observes a loss of power to a motor controller (block 6820), which leads to the motors being deenergized and causing the motor brakes to be engaged (block 6810). This sequence ensures that when the handle assembly 2530 is disengaged from the robot 2520, then there is no motion at the catheter distal tip or with the implant supported thereon until the clinician is ready to take over and command motion, either via the robot or the manual pull wire assembly 2550, or via a combination of these mechanisms/approaches.

In some embodiments, the robot does not actively observe the loss of power. Instead, one or more certain motor controllers of the robot lose power and, as a result, one or more motors of the robot associated with the one or more certain motor controllers would be automatically deenergized and the associated brakes then being engaged, the braking may be automatic or manually actuated. In some of these embodiments or under certain circumstances, the loss of power to one or more certain motor controllers of the robot results in all motors of the robot being deenergized and all associated brakes then being engaged, not just those motors of the robot associated with the one or more certain motor controllers.

Depending on the embodiment, the brake function may be a friction brake or toothed brake interacting with the deenergized motor or its associated gear train. In some embodiments, these brake embodiments may be manually actuated by the clinician manipulating a lever, switch, or button. Alternatively, the braking may be automatic and simply occur upon the circuit being deenergized. For example, while electrical power is energizing the circuits of the motor controller and associated motor(s), electrical power is also being provided to the associated brake to hold the brake open (nonengaged). Oppositely, when electrical power is no longer energizing the circuits of the motor controller and associated motor(s), electrical power is also no longer being provided to the associated brake(s) and the brake(s) bias closed (engaged).

Regardless of how the process arrives at block 6810, the clinician can then attach the manual pull wire assembly 2550 to the handle assembly 2530 as depicted in FIGS. 28-31, the manual pull wire assembly 2550 being configured to allow the clinician to manually control the handle assembly 2530 to complete the implantation procedure or to effectuate a manual bailout of the catheter and its implant from the patient (block 6825). Optionally, the clinician may then engage a brake assembly on the manual pull wire assembly 2550 and/or the brake formed in the handle assembly (see furl lock lever 2810 and furl lock release pin 2815 in FIGS. 27, 44 and 45) to lock the operation of the handle assembly and prevent any deflection of the catheter and the implant supported thereon within the patient until the clinician is ready to operate the manual pull wire assembly in completing the implantation procedure or effectuating the bailout (block 6830).

As illustrated in FIG. 68, the clinician may then disengage the robot inputs from the handle assembly to enable the manual pull wire assembly 2550 to be used by the clinician to manually control the handle assembly 2530 while the handle assembly is still attached to the robot 2520 (block 6840). Using this disengagement method allows the clinician to selectively disengage only the catheter control axes (e.g., the cable control assemblies 2600 of the handle assembly 2530 and associated drive motor assemblies 2925 of the robot 2520) that are not working. This selective decoupling of a certain non-functional catheter control axes allows a hybrid bailout where the clinician maintains robotic control of those catheter control axes the robot is still capable of controlling, and then have manual control of the catheter control axes no longer controllable via the robot.

Alternatively, the clinician removes the handle assembly 2530 from the robot 2520 to enable the manual pull wire assembly 2550 to be used by the clinician to manually control the handle assembly 2530 (block 6845). In either case, the clinician can then use the manual pull wire assembly to control the handle assembly to safely finish the implantation procedure or remove the catheter and implant from the patient (i.e., bailout) (block 6850).

R. ELECTROMECHANICAL AND CONTROL SYSTEM OVERVIEW

The following section provides a general description of the electromechanical and control-related components of implant delivery systems according to this disclosure. Such delivery systems include an actuated delivery assembly including or in communication with a primary computing system configured to operate and control actuators of the robotic delivery assembly, to collect and process sensor data from the robotic delivery assembly, to interact with other computing systems and capital equipment, and to perform other related functions.

Figure 69:
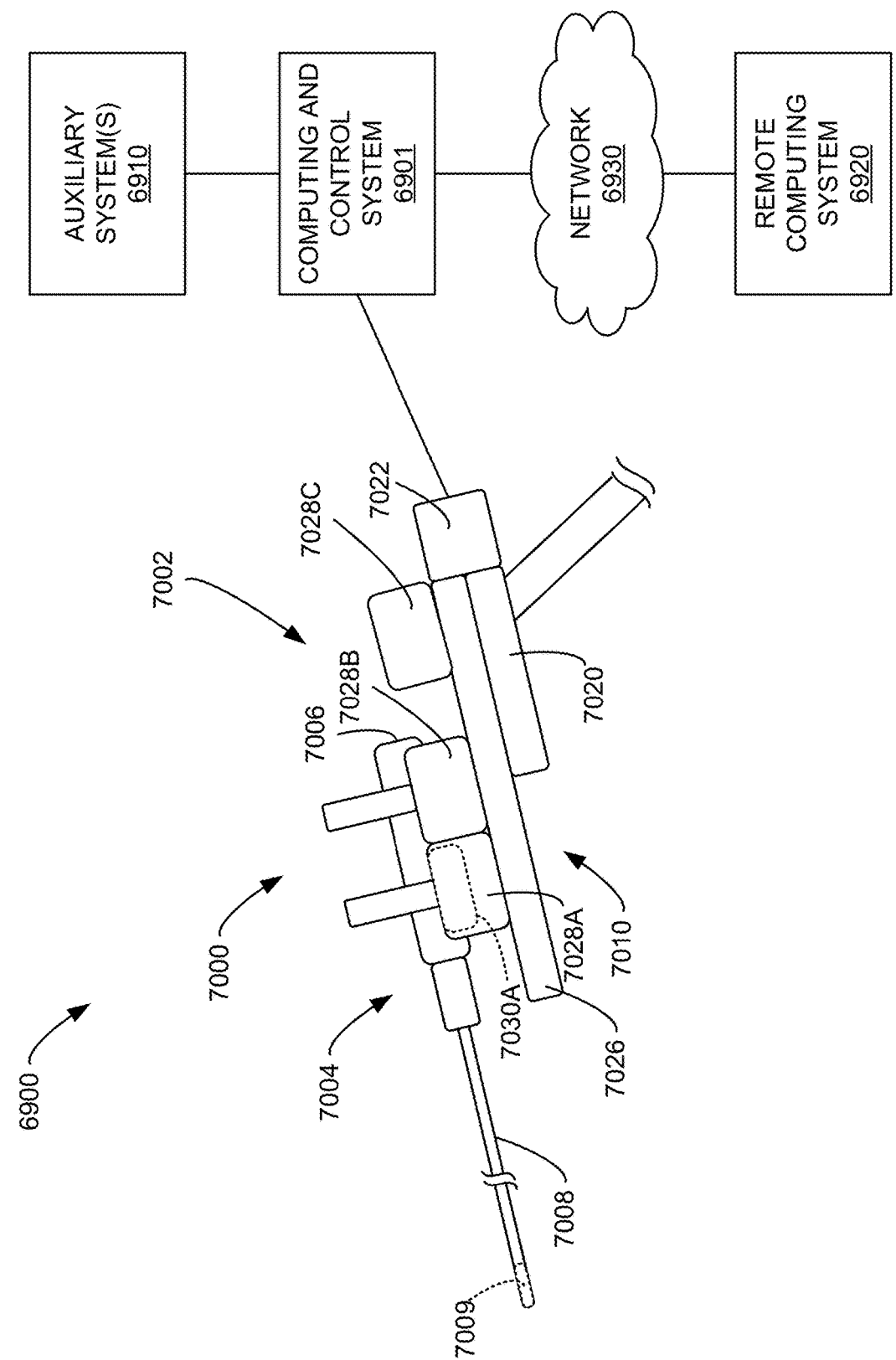
FIG. 69 is an illustration of an example environment including a robotic implantation system according to the present disclosure.

FIG. 69 is a schematic illustration of an environment 6900 including a robotic implantation system 7000 according to one implementation of the present disclosure and generally corresponding to robotic implantation system 2510, which is discussed above in detail. Nevertheless, the following discussion reintroduces certain aspects of and components of robotic implantation system 2510 in a more generalized form for purposes of subsequent discussions related to control and operation of robotic implantation systems according to this disclosure.

Robotic implantation system 7000 includes a robot 7002 and a catheter 7004, with catheter 7004 being generally divided into a handle assembly 7006 and a tubular body assembly 7008. During operation, an implant 7009, such as a cardiac valve replacement or repair implant, is coupled to and/or disposed within a distal end of tubular body assembly 7008 for delivery to an implantation location within a patient. In the illustrated example, tubular body assembly 7008 is steerable by a cable-based system with the steering cables extending from handle assembly 7006 along/through tubular body assembly 7008. Accordingly, handle assembly 7006 includes mechanical elements to facilitate storage and selective retraction, pay out, tensioning, etc. of the cables to steer tubular body assembly 7008.

This disclosure contemplates that handle assembly 7006 may further include additional mechanical elements for manipulating other components of tubular body assembly 7008. For example, in certain implementations, tubular body assembly 7008 may include a selectively retractable sheath for covering implant 7009 during delivery and placement and a distal end of tubular body assembly 7008 following delivery of implant 7009. As another example, handle assembly 7006 may include mechanical elements for selectively manipulating implant 7009, e.g., for facilitating selective furling or unfurling of implant 7009 during implantation.

While not limited to the embodiment shown in FIGS. 25-68, further details regarding mechanical elements that may be incorporated into robotic implantation system 7000, including handle assembly 7006 are provided above in the context of FIGS. 25-28.

Handle assembly 7006 is received and actuatable by robot 7002. More specifically, handle assembly 7006 is supported by one or more carriages, such as carriage 7028A and carriage 7028B, of robot 7002. As illustrated, robot 7002 may include additional carriages, such as carriage 7028C for accommodating alternative handle assembly designs. Each carriage generally includes a corresponding motor assembly, such as motor assembly 7030A of carriage 7028A, configured to be coupled to a handle assembly or similar device and to facilitate actuation of one or more elements of the handle assembly/device. For example, in the illustrated example, handle assembly 7006 is configured to couple to each of carriage 7028A and carriage 7028B that couples with handle assembly 7006 and facilitates actuation of one or more mechanical elements of handle assembly 7006.

Robot 7002 further includes a linear displacement platform 7010 on which each carriage is mounted. Linear displacement platform 7010 generally includes a rail 7026 supported by and coupled to a structural mount 7020 (alternatively referred to herein as a stand). As illustrated, a proximal end of linear displacement platform 7010 includes a housing 7022. Housing 7022 includes various motor assemblies and corresponding control electronics for actuating elements of robot 7002. For example, housing 7022 can include motors configured to linear translate each carriage of robot 7002 and/or roll each carriage of robot 7002 (e.g., by rotating a C-arm of the given carriage). Housing 7022 may further include a control board or similar electronics for interfacing with other computing devices and for receiving and transmitting control signals to the motor assemblies of each individual carriage. Notably, while the illustrated implementation contemplates that motors for controlling insertion and/or roll of handle assembly 7006 are contained within housing 7022, in other implementations, one or more motors for controlling insertion and/or roll may be contained in one or more of the carriages.

Environment 6900 further includes a computing system 6901 in communication with and configured to control robotic implantation system 7000. Among other things, computing system 6901 generates control signals and transmits the generated control signals to robotic implantation system 7000 to actuate robot 7002. Controls signals may be received and processed by a control board or similar electronics assembly within housing 7022. In at least certain implementations. the electronics assembly may be a microcontroller including a dedicated microprocessor and corresponding computing elements (e.g., memory, one or more communication interfaces, etc.); however, this disclosure contemplates that other suitable computing architectures and arrangements of computing components may be implemented to operate robotic implantation system 7000. More generally, computing system 6901 and associated computing components of robotic implantation system 7000 may include one or more computing devices, each of which may be configured to operate in real time or in non-real time and that operate collectively to monitor, control, and otherwise drive functions of robotic implantation system 7000.

In addition to communicating with sensors, actuators, and other components of robotic implantation system 7000, computing system 6901 is configured to present an interface for interacting with the robotic implantation system. So, for example, computing system 6901 may include various output devices, such as a display or speakers, for communicating information to the clinician. In implementations in which computing system 6901 includes a display, the display may be a conventional computer screen or may include a virtual- or augmented reality display, such as a VR headset.

Computing system 6901 may further include various input devices for receiving commands from the clinician. In addition to conventional input devices (e.g., keyboards, microphones, computer mice, etc.), computing system 6901 can include an input device configured for intuitive operation of robotic implantation system 7000 and, in particular, manipulation and control of catheter 7004 to facilitate delivery and implantation of implant 7009. Computing system 6901 may also be in communication with auxiliary systems 6910 (e.g., imaging systems) within the operating environment and/or configured to communicate with a remote computing system 6920 over a network 6930 (e.g., the Internet or a Local Area Network (LAN)).

In certain implementations, computing system 6901 receives data from and communicates with other operating room capital equipment, which is considered to be included in auxiliary systems 6910. For example, computing system 6901 can connect to and communicate with imaging equipment such as, but not limited to, ultrasonography and fluoroscopy machines, e.g., by receiving images and imaging-related data from such equipment. Imaging-related data may include, for example, position and orientation information for the imaging equipment to provide additional detail regarding a given image including, but not limited to a frame of reference for the image. So, for example, computing system 6901 may receive and present images captured by the imaging equipment and present the images to the clinician via a display device of computing system 6901. Other examples of auxiliary systems with which computing system 6901 may interact, from which computing system 6901 collect data, etc., include, without limitation, patient table systems, other robotic capital equipment, and vital sign monitoring systems.

Figure 70A:
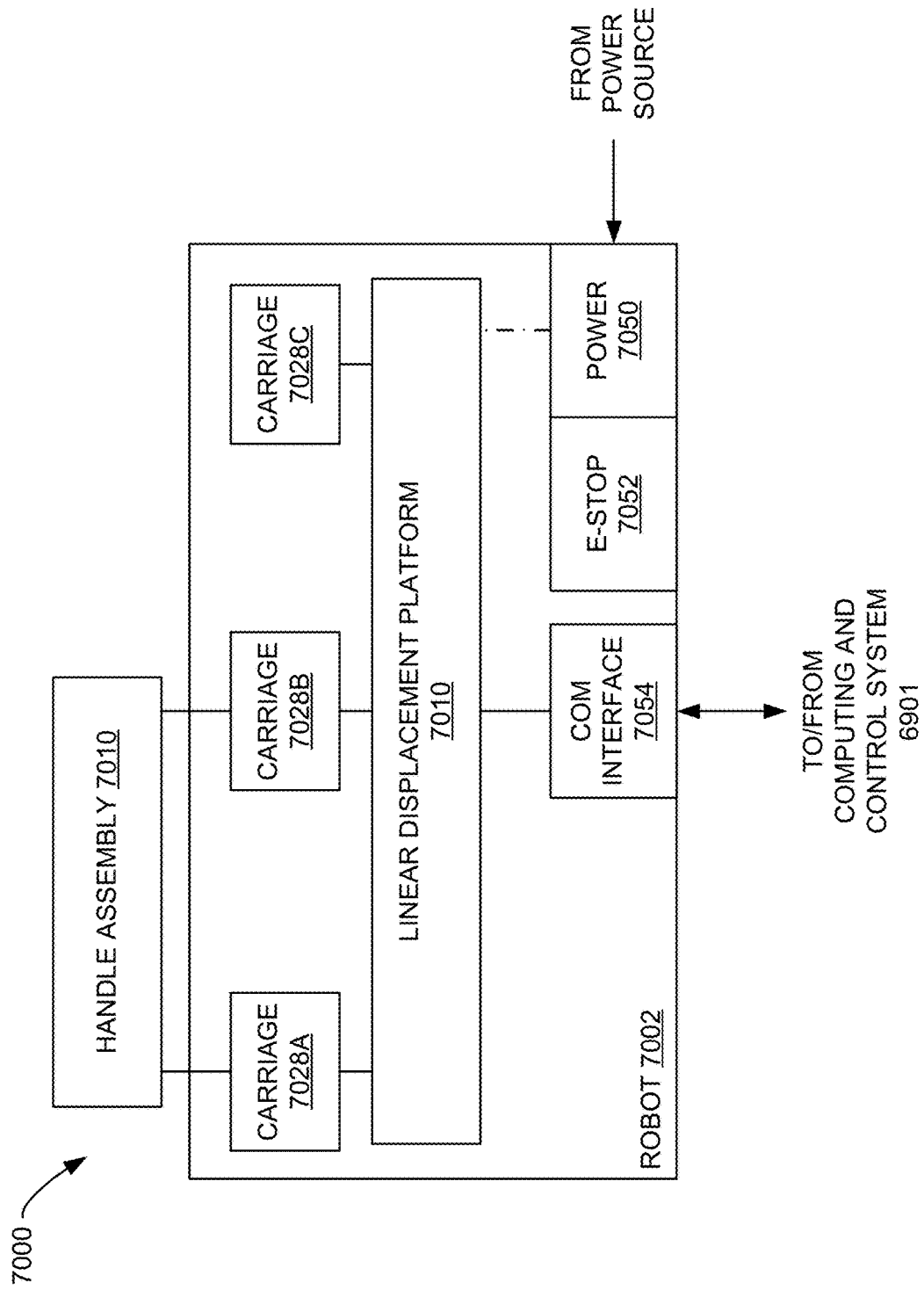
FIGS. 70A and 70B are block diagrams illustrating various aspects of the drive and control system of the robotic implantation system of FIG. 69.
Figure 70B:
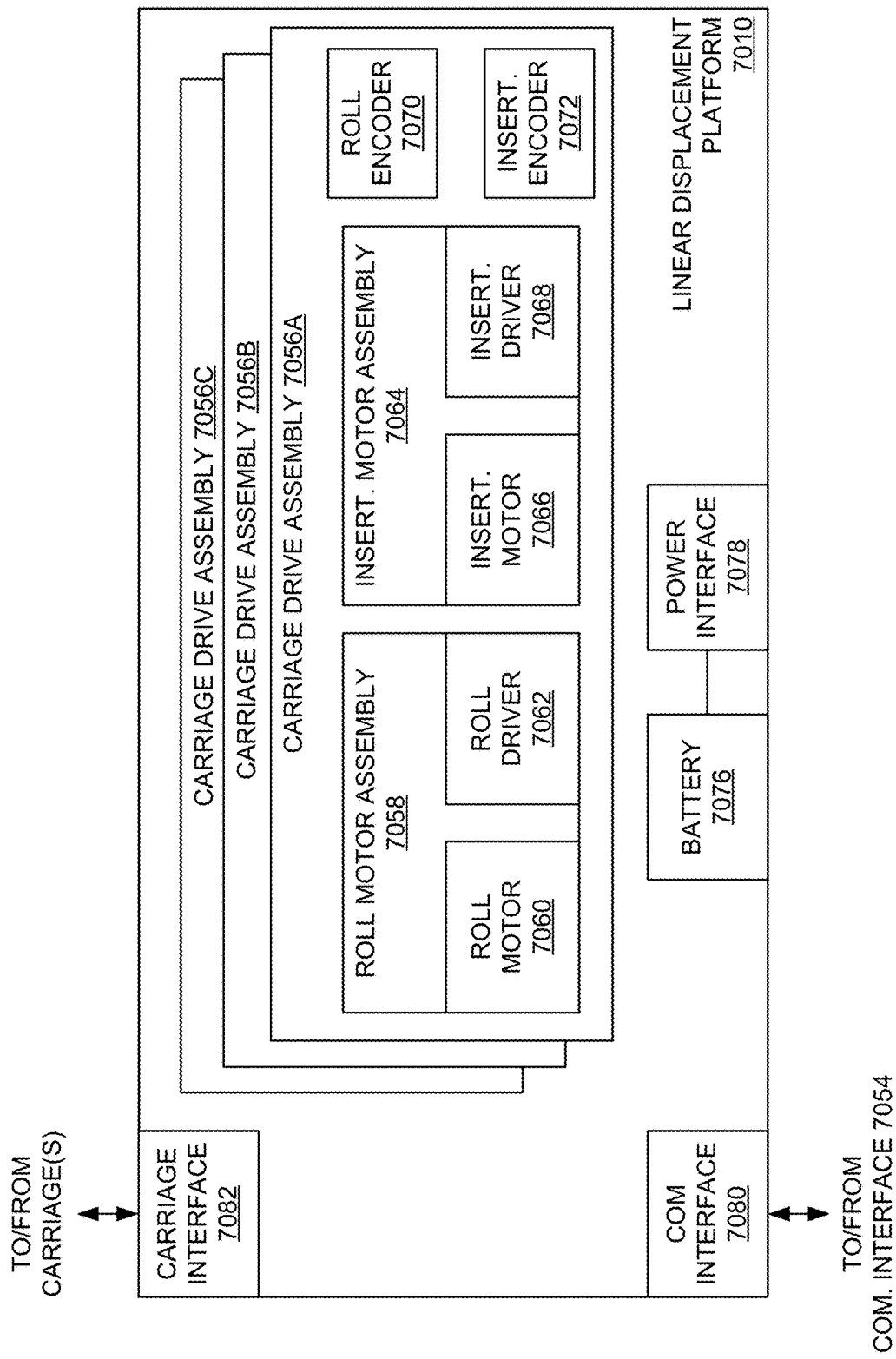
Figure 71:
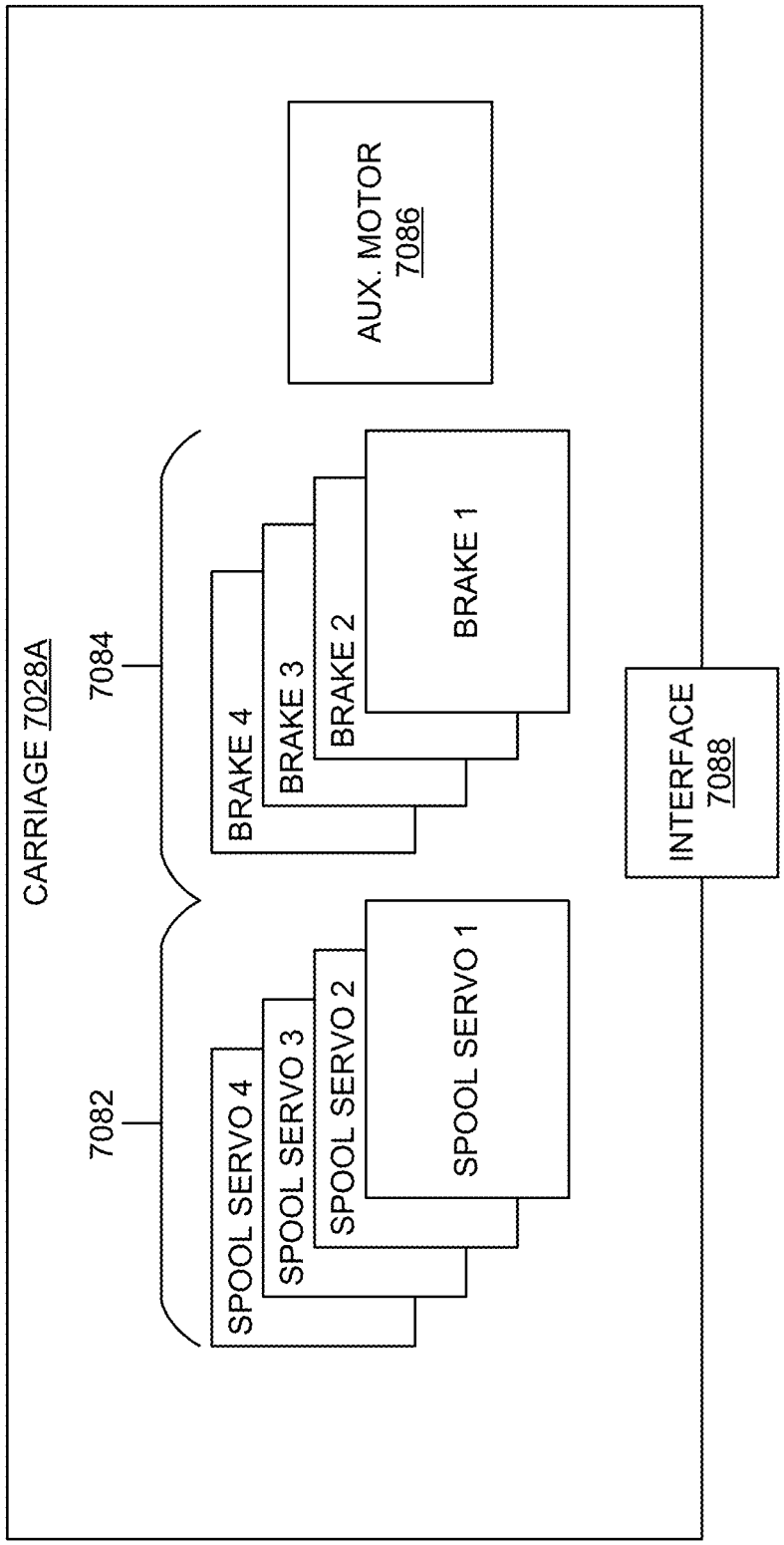
FIG. 71 is a block diagram of a carriage of the robotic implantation system of FIG. 69.

FIGS. 70A, 70B, and 71 are block diagrams illustrating components of robotic implantation system 7000. Turning first to FIG. 70A and consistent with the preceding discussion, robotic implantation system 7000 is illustrated as including robot 7002 which is coupled to and supports linear displacement platform 7010. More specifically, robot 7002 includes linear displacement platform 7010, which in turn is coupled to and supports multiple carriages, such as carriage 7028A, carriage 7028B, and carriage 7028C. As noted above, the specific implementation of FIG. 69 includes a handle assembly configured to interface with and be supported by two carriages; however, this disclosure contemplates that linear displacement platform 7010 may be configured to include any suitable number of carriages to accommodate various handle assemblies.

Linear displacement platform 7010 receives power through a power module 7050. Among other things, power module 7050 may convert power received from the power source into a suitable voltage and current. For example, in at least one specific implementation, power module 7050 may be a 24V DC power supply. In certain implementations power module 7050 or the power source to which it is coupled may further include additional power-related components such as one or more batteries, an uninterruptible power supply, or similar components to maintain power in emergency situations. As shown, power module 7050 may include or otherwise be operable with an emergency stop 7052 configured to immediately cut power to robot 7002.

Robot 7002 further includes a communication interface 7054 configured to connect to and exchange data with computing system 6901. This disclosure contemplates that communication interface 7054 may include one or more interfaces supporting any suitable wired or wireless communication protocol. In at least certain implementations, communication interface may support an automation-related protocol such as Ethernet for Control Automation Technology (EtherCAT). Other example protocols include, but are not limited to EtherNet/IP, ProfiNet, ProfiBus, Modbus RTU/TCP, and the like.

FIG. 70B illustrates linear displacement platform 7010 in further detail. More specifically, FIG. 70B illustrates linear displacement platform 7010 and corresponding components for linearly displacing and rolling each of the carriages. More specifically, linear displacement platform 7010 includes each of a carriage drive assembly 7056A, a carriage drive assembly 7056B, and a carriage drive assembly 7056C for linearly displacing and rolling carriage 7028A, carriage 7028B, and carriage 7028C, respectively. For simplicity and clarity, only the components of carriage drive assembly 7056A are shown in detail; however, carriage drive assembly 7056B and carriage drive assembly 7056C should be assumed to include substantially the same elements albeit for manipulating carriage 7028B and carriage 7028C.

As illustrated, carriage drive assembly 7056A includes a roll motor assembly 7058 for controlling roll of carriage 7028A. More specifically, roll motor assembly 7058 includes a roll motor 7060 for converting drive signals produced by a roll drive 7062. Roll drive 7062, in turn, receives commands through a communication interface 7080. As shown communication interface 7080 is communicatively coupled to or otherwise receives communications from communication interface 7054, which, as shown in FIG. 70A, facilitates communication with computing system 6901. Accordingly, commands from computing system 6901 may be received by roll drive 7062 through communication interface 7054 and communication interface 7080).

Carriage drive assembly 7056A further includes an insertion motor assembly 7064. Like roll motor assembly 7058, insertion motor assembly 7064 includes an insertion motor 7066 and an insertion driver 7068, the latter of which provides drive signals to control operation of insertion motor 7066 based on commands received from computing system 6901 (e.g., through communication interface 7054 and communication interface 7080).

To measure position and movement of carriage 7028A with respect to roll and insertion, carriage drive assembly 7056A includes each of a roll encoder 7070 and an insertion encoder 7072. In at least certain implementations, roll encoder 7070 and insertion encoder 7072 may be absolute encoders such that the absolute roll and insertion of carriage 7028A can be known even if power is lost.

Regarding power, linear displacement platform 7010 includes a power interface 7078 that may be electrically coupled to power module 7050 of robot 7002 (shown in FIG. 70A). While not shown in FIG. 70B, communication interface 7080 may in turn be electrically coupled to and provide power to the various elements of the carriage drive assemblies, such as roll drive 7062 and insertion driver 7068.

As shown, linear displacement platform 7010 may also include one or more batteries, such battery 7076. Among other things, battery 7076 may be configured to provide backup power to the carriage drive assembly components and the carriage motors in the event of power loss at robot 7002. Such backup power may be used, for example, to perform an automated wind-down of the robot components and/or to hold a state of the robot until the power issue can be corrected or the device removed from the patient. As another example, battery 7076 or one or more supplemental batteries may also be used to maintain sensor rotation/absolute position in the case of power loss.

FIG. 71 is a detailed block diagram of carriage 7028A, which is intended to be representative of the carriages of robotic implantation system 7000. As shown, carriage 7028A includes servomotors 7082 and brakes 7084. As discussed previously in this disclosure, servomotors 7082 are generally configured to drive rotation of each pull wire spool of handle assembly 7006 with each servomotor corresponding to a respective spool. Brakes 7084 are configured to arrest rotation of each pull wire spool with each brake corresponding to a respective spool. While not specifically illustrated in the figures, each roll motor assembly (e.g., roll motor assembly 7058 of FIG. 70B) and/or insertion motor assembly (e.g., insertion motor assembly 7064 of FIG. 70B) may also include a corresponding braking system to arrest movement of the corresponding motor. For example, once an operator achieves a desired insertion depth and roll angle, the operator may engage brakes for each of insertion motor assembly 7064 and roll motor assembly 7058 to prevent unwanted drift or movement with respect to insertion and roll.

Carriage 7028A further includes an auxiliary motor 7086, which may be configured to drive additional functions of the handle assembly 7006. For example, as discussed above, handle assembly 7006 may include a furl assembly 2615 including a capstan gear 2645 that may be drivable by auxiliary motor 7086 to selectively furl and unfurl implant 7009. As another example, auxiliary motor 7086 may be configured to drive lead screw gear 2630 to selectively extend and retract sheath 2561. In certain, non-limiting implementations, construction and design of carriage 7028A may be simplified by using substantially the same motors for each of servomotors 7082 and auxiliary motor 7086; however, this disclosure contemplates that different motors may be used for any of servomotors 7082 and auxiliary motor 7086. Also, while not shown in FIG. 71, auxiliary motor 7086, like each of servomotors 7082, may have a corresponding brake to arrest movement of auxiliary motor 7086.

Finally, FIG. 71 illustrates carriage 7028A as including an interface 7088. Interface 7088 facilitates coupling with linear displacement platform 7010 to provide power to carriage 7028A and to facilitate communication between the components of carriage 7028A and linear displacement platform 7010. While shown as a single interface, interface 7088 may include multiple interfaces, e.g., one for power and one for communication.

This disclosure contemplates that communication between robotic implantation system 7000 and computing system 6901 may be achieved using a range of architectures and interfaces. For example, FIG. 70A illustrates robot 7002 as including communication interface 7054 for facilitating communication with computing system 6901. In such implementations, robot 7002 may include suitable components and logic for receiving, processing, and applying communication signals from computing system 6901 as well as generating and transmitting signals back to computing system 6901. In other implementations, computing system 6901 may be communicatively coupled to and in direct communication with one or more sensors or actuators of robotic implantation system 7000. So, for example, computing system 6901 may be wired to the servomotors of the carriages and configured to send and receive signals from the servomotors without an intermediate computing device. As another example, robotic implantation system 7000 may include a wiring harness coupled to one or more connectors and computing system 6901 may be connected to each of the connectors by a suitable cable. This disclosure also contemplates that computing system 6901 and robotic implantation system 7000 and/or computing system 6901 and specific components of robotic implantation system 7000 may communicate wirelessly in addition or as an alternative to wired communication, particularly for exchange of relatively non-critical or non-control related data.

While not illustrated in FIG. 71, carriage 7028A may include additional sensors for providing feedback to robot 7002 and computing system 6901. For example, in certain implementations, carriage 7028A may include a tension sensor for each spool.

S. INTUITIVE DRIVE MODES AND CONTROL INTERFACES

Mitral valve replacement implantation is a particularly challenging procedure that requires substantial training and experience to perform correctly. Conventional catheter-based delivery systems generally include an actuatable catheter having a distal end that is coupled to and supports an implant during delivery. In a transfemoral approach, the distal end including the catheter must be navigated into the right atrium via the inferior vena cava and steered approximately 90-degrees to align with the atrial septum. Following insertion through the atrial septum into the left atrium, the distal end including the implant must be steered again by approximately 90 degrees to provide rough alignment of the implant with the mitral annulus. The clinician must then advance and adjust the implant to align the implant for deployment and release from the distal end of the delivery tool. Even after deployment and detachment of the implant, the clinician must carefully clear the annulus without damaging the implant or surrounding cardiac structures.

Conventionally, mitral valve implants rely on a delivery system including a mechanical handle operable to execute the various bends, rolls, insertions, and other movements necessary to deliver and deploy the implant. Such devices often include multiple knobs, levers, wheels, and similar control elements, each of which is associated with movement of a specific component of the delivery system. In general, each control is associated with a corresponding degree of freedom (DOF) of the delivery system, such that actuation of the control results in a movement or change in that DOF. In some cases, a control element may be bidirectional (e.g., a knob that can be turned in two directions to steer a catheter in two directions along a plane). In other cases, a control element may be actuated to provide unidirectional movement with a second control element providing counter movement. Alternatively, countermovement to a given unidirectional control element may be provided by a spring or similar biasing element that provides countermovement absent force being applied to the control element.

In implant delivery procedures, such as mitral valve replacement implantation procedures, delivery systems often have multiple DOFs, each of which must be carefully controlled to successfully locate, orient, and deploy the implant. By way of example, certain implementations of the delivery system disclosed in U.S. Pat. No. 11,246,726 (incorporated herein by reference) include five DOFs that directly impact location and orientation of a distal end of the system's delivery catheter and, as a result, any implant coupled to the distal end. These DOFs include bending of a distal steerable section of the delivery catheter along a lateral plane, bending of the distal steerable section along an anterior/posterior plane, bending of a proximal steerable section of the catheter along a lateral plane, insertion, and roll. Such implementations may further include DOFs related to longitudinal translation of a sheath for covering/uncovering the distal end of the device and furling/unfurling of the implant.

Certain conventional robotic surgery systems translate the control elements of existing mechanical delivery handles into electronic equivalents. So, for example, levers, knobs, and other mechanical control elements of mechanical delivery handles are often translated into control pads, joysticks, touchscreen icons, buttons, and other similar inputs for an electromechanically driven delivery systems. Stated differently, in many robotic surgery systems, the clinician provides inputs that actuate joints of the delivery device, similar to how the mechanical control elements of manual delivery systems manipulate and articulate joints of corresponding mechanical delivery systems.

Given the DOFs of certain delivery systems, achieving specific intended movements of the distal tip of the delivery system (or similar structure of interest) can be highly unintuitive using joint-based control regardless of whether the delivery system is operated using a mechanical or conventional electromechanical interface with even highly trained and experienced clinicians can have difficulty visualizing what delivery system movement is necessary to achieve a desired result (e.g., a desired movement of the implant coupled to the distal end of the delivery system) and then translating that movement into corresponding inputs to the control interface.

The challenges faced by clinicians are readily illustrated by mitral valve implant procedures. In such procedures, clinicians are often concerned with perpendicularity (i.e., how parallel a longitudinal axis of the implant is to a central axis of the mitral valve annulus), depth, and centrality (i.e., alignment of the implant axis with that of the mitral valve annulus). In total, these dimensions represent at least five DOFs when considered from the perspective of the mitral valve. More specifically and with reference to a plane defined by the mitral valve annulus, perpendicularity corresponds to pitch and yaw relative to a normal extending from the annulus plane, depth corresponds to translation normal to the annulus plane, and centrality corresponds to translation across the annulus plane. In applications in which the implant is asymmetric and requires specific orientation for implantation, roll may also be a DOF of interest and corresponds to rotation about an axis parallel to the normal.

Figure 72C:
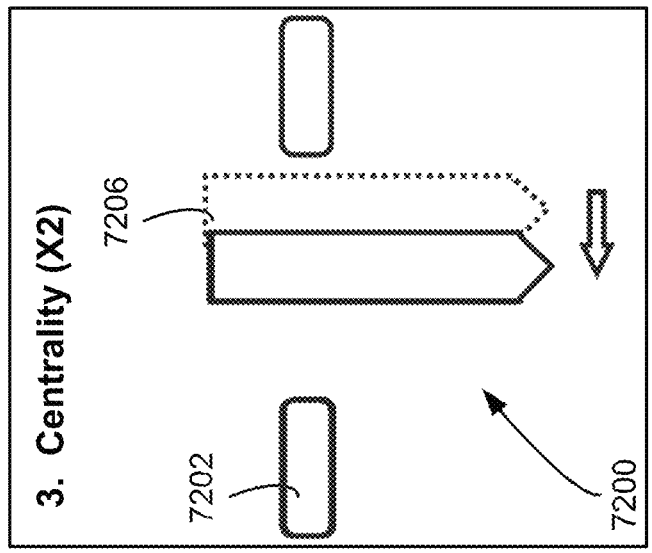
FIGS. 72A-72C illustrate key degrees of freedom relevant to mitral valve implant placement and implantation.
Figure 72B:
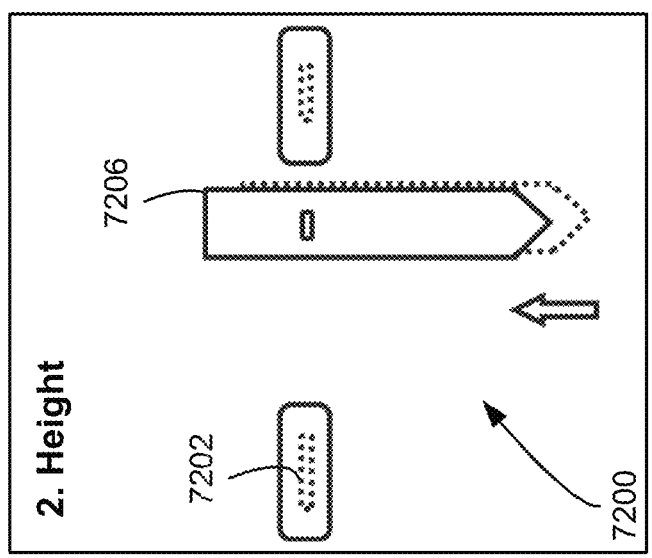
Figure 72A:
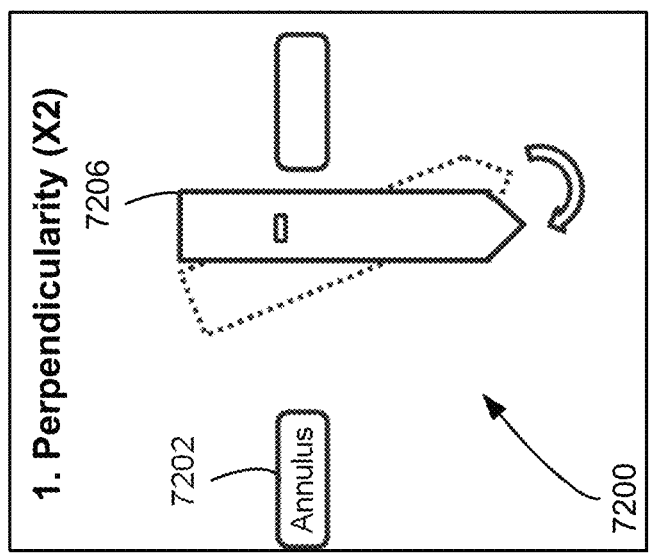

Each of these relationships is shown in FIGS. 72A-72C, which illustrate a simplified mitral valve environment 7200 including a mitral valve annulus 7202 and a simplified mitral valve implant 7206. The criticality of each DOF shown in FIGS. 72A-72C may vary across implant designs with specific implants being more tolerant of or able to self-align despite offsets in one of the DOFs. For example, the implant of U.S. Pat. No. 11,197,755 (incorporated herein by reference) is relatively tolerant of and can self-center despite centrality offsets during deployment but is less tolerant of offsets in depth and perpendicularity.

Substantial difficulties can arise when a clinician wants to change the position of an implant relative to the mitral valve annulus but is limited to controlling movement of the implant by actuating joints of the delivery system. Although certain theoretical configurations and exceptions exist, from a practical perspective, single joint controls rarely correspond directly to the key DOFs relative to the mitral valve. As a result, achieving movement that changes just one of perpendicularity, centrality, and depth often requires changes in multiple DOFs of the delivery system and complex, coordinated actuation of the corresponding joints.

Figure 73C:
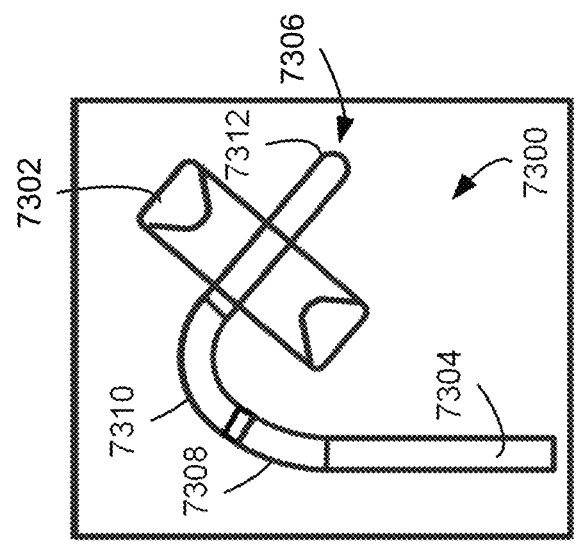
FIGS. 73A-73C illustrate an example delivery and implantation procedure.
Figure 73B:
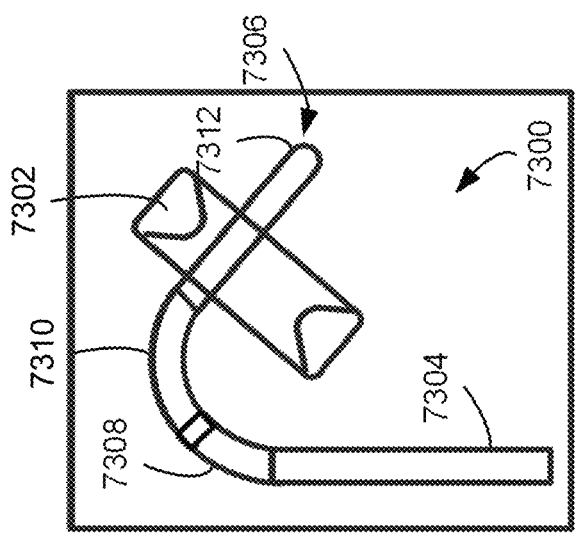
Figure 73A:
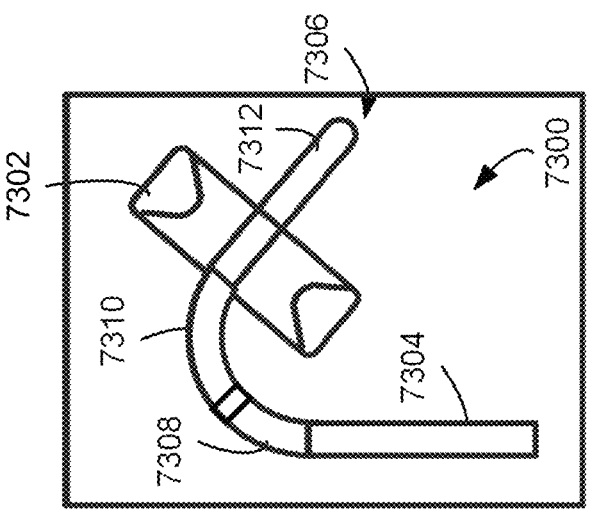

By way of example, FIGS. 73A-73C illustrate a mitral valve environment 7300 including a valve annulus 7302. As shown, a distal end 7306 of an example implant delivery catheter 7304 having each of a proximal steering section 7308 and a distal steering section 7310 is positioned across valve annulus 7302 with distal end 7306 terminating in an implant 7312. FIG. 73A illustrates an initial state in which good perpendicularity and centrality of implant 7312 relative to valve annulus 7302 have been achieved but that requires atrial translation of implant 7312 for proper deployment and implantation of implant 7312. Unfortunately, such translation is not achievable through a change in a single DOF of implant delivery catheter 7304. The closest single movement for achieving the desired change in depth is further insertion of implant delivery catheter 7304. However, as shown in FIG. 73B, further inserting implant delivery catheter 7304 negatively impacts centrality. Depending on how critical centrality is to deployment of the implant, this trade-off may range from being acceptable but suboptimal to completely precluding proper deployment and placement, the latter requiring further adjustments and repositioning by the clinician.

FIG. 73C illustrates implant 7312 subject to the desired atrial translation. Notably, achieving this result from the state illustrated in FIG. 73A requires a complex compound motion including each of device insertion and articulation of each of proximal steering section 7308 and distal steering section 7310. Such a coordinated movement can be challenging to visualize and execute for even the most experienced and trained clinicians, often leading to a substantial amount of trial-and-error by the clinician, increased operating times, suboptimal implant placements, and the potential for inadvertently contacting and damaging cardiac structures with implant delivery catheter 7304 and its components.

The example illustrated in FIGS. 73A-73C is a specific case of a more general problem for clinicians. Specifically, clinicians often know precisely how they would like an implant to move relative to a particular frame of reference, e.g., a frame of reference corresponding to a valve annulus or other anatomy. However, converting a desired movement in the frame of reference to corresponding joint inputs of a delivery system can be extremely challenging and unintuitive. Such challenges are compounded as delivery approach complexity and the number of DOFs for a delivery system increase.

To address the foregoing issues and others, implementations of the present disclosure include enhanced drive modes and other functionality for improved robotic implant delivery systems and procedures. Among other things, this disclosure provides control interfaces that permit clinicians to input movement commands to a robotic delivery system in frames of reference that are more meaningful and intuitive than joint-based control modalities. For example, in one implementation, a clinician may input movement commands that map directly to changes in perpendicularity, centricity, and depth of a mitral valve implant relative to the mitral valve annulus. The robotic delivery system then determines and executes the necessary joint actuations to achieve the movement input by the clinician.

For purposes of the present disclosure, the foregoing approach of providing robotic delivery system inputs with reference to an anatomical structure is referred to as providing inputs in an anatomical frame of reference. More specifically, providing inputs in an anatomical frame of reference involves providing changes in positional parameters that map directly to relevant DOFs of the anatomical structure. As noted above, in the context of mitral valve placement, such DOFs include perpendicularity, depth, and centrality.

While this disclosure focuses primarily on mitral valve implant-related applications, use of an anatomical frame of reference is not necessarily limited to mitral valve applications. Rather, the anatomical frame of reference may be readily adapted to other anatomical structures and procedures with corresponding modifications to the DOFs mapped to inputs available to the clinician.

This disclosure also contemplates that the approach of mapping inputs provided in an intuitive frame of reference to facilitate complex, compound robotic movements can be readily modified for other frames of reference. For example, in one implementation, the robotic delivery system receives inputs from the clinician in a frame of reference corresponding to the implant as coupled to a distal end of the robotic delivery system. So, for example, the frame of reference may have an x-, y-, and z-axis with defined directions and an origin at a centroid, tip, fixation feature, or similar point of interest of the implant and the clinician may be permitted to provide inputs to move the implant linearly along one or more of the axes and rotationally about one or more of the axes. Such a frame of reference may be particularly useful during delivery and navigation of the implant to the implantation site.

In another implementation, the clinician may provide inputs for movement of a distal portion of the robotic delivery system in a frame of reference based on the implant following implantation. So, for example, once implanted, a frame of reference for the implant may be established in which the x- and y-axis extend along the annular plane with the z-axis extending normal to the plane. As in the previous example, the clinician may then provide inputs to move a distal segment of the robotic delivery system linearly along or rotationally about one or more of the defined axes. Among other uses, the post-delivery implant frame of reference can facilitate disengagement and clearing of the implant by the distal segment of the robotic delivery device by permitting movement of the distal segment directly normal to the annular plan (e.g., along the z-axis).

As a final example, the clinician may provide inputs for movement with respect to a frame of reference based on a current perspective or view of a visualization presented to the clinician. So, for example, the clinician may be permitted to provide inputs that move an implant or other component of the robotic delivery system presented on a screen directly vertically, directly horizontally, or normal to the screen (i.e., into/out of the screen) or about corresponding axes of rotation.

Notably, this disclosure contemplates that a clinician may change between frames of references throughout a procedure. So, for example, the clinician may begin by providing inputs within a frame of reference corresponding to a distal end of the robotic implantation system. During navigation to the implantation site, the clinician may periodically switch between the distal end-based frame and a visualization-based frame. As the clinician approaches the implantation site, the clinician may switch again to an anatomical frame of reference based on the anatomical structure associated with the implant. Following implantation, the clinician may opt for a frame of reference based on the delivered implant to facilitate clearing the implant and initiating removal of the delivery system.

Figure 74A:
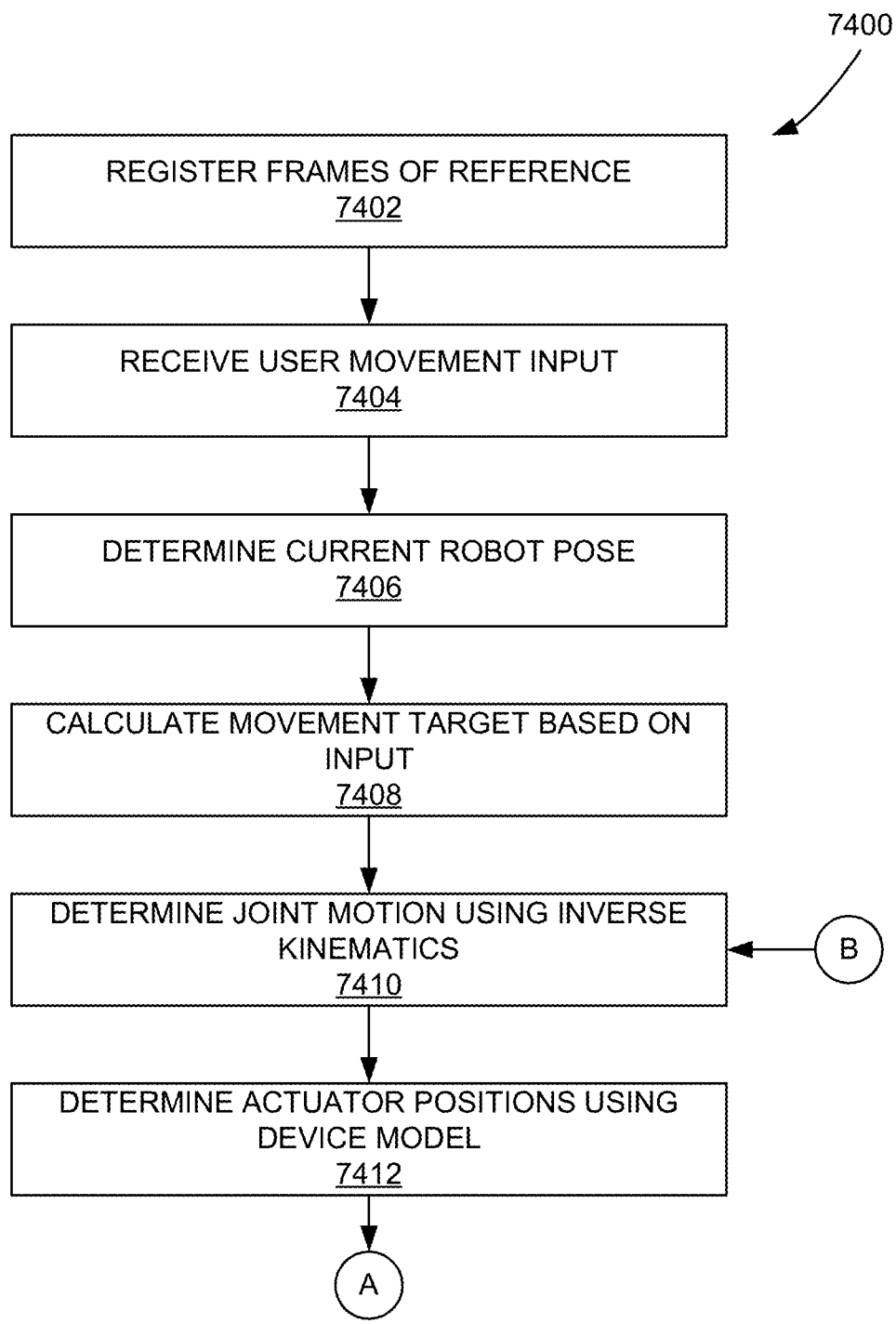
FIGS. 74A and 74B depict a flow chart for drive and control of a robotic implantation system according to the present disclosure.
Figure 74B:
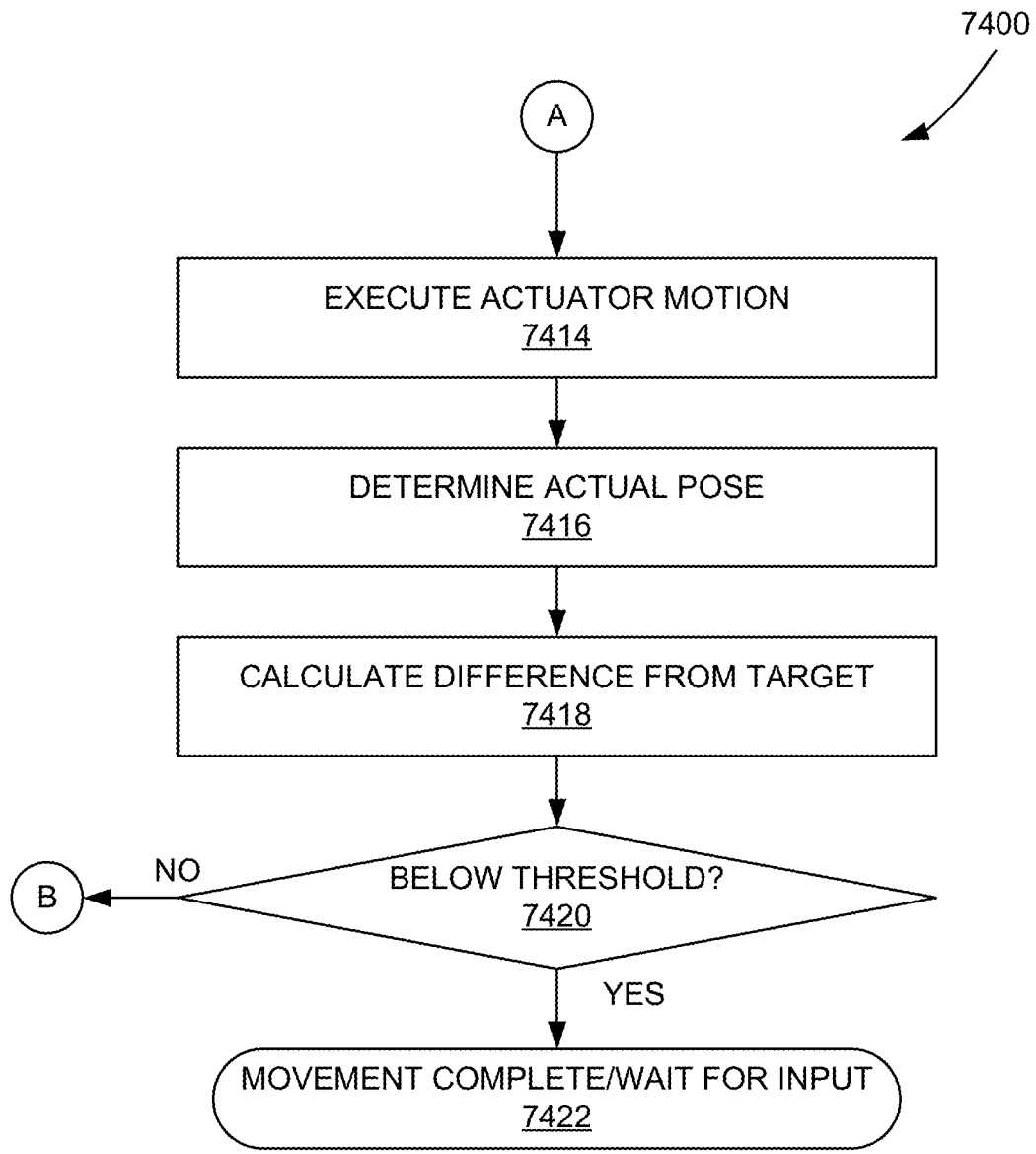

FIGS. 74A and 74B illustrate a flow chart for an example method 7400 of operating a robotic implantation system. The following discussion regarding operation of the robotic implantation system relies on a mitral valve implant as a primary example implementation. Nevertheless, concepts in the following discussion may be readily adapted for other applications. For example, while the following discussion relies on an anatomical frame of reference (namely a frame of reference corresponding to the mitral valve annulus) in which the clinician provides input, the same general concepts may be applied any of the other frames of reference noted above.

At step 7402, the robotic implantation system registers relevant frames of reference. Registration generally refers to the process of spatially aligning and determining the relationship between different frames of reference relevant to the implantation procedure.

In most cases, the registration process will include establishing a spatial relationship between primary frames of reference corresponding to the robotic implantation system (or a component of the robotic implantation system), the anatomical feature of interest (e.g., the mitral valve annulus), and a preoperative plan represented by a computer model. To the extent the clinician may rely on additional frames of reference, the registration process may further include establishing spatial relationships between the additional frames of reference and one or more of the primary frames.

At least some registration may be performed pre-operatively; however, this disclosure contemplates that registration of certain frames of reference may occur during the course of a procedure. For example, as noted above, this disclosure contemplates that the clinician may operate the robotic delivery system in a frame of reference based on a delivered implant. Such a frame of reference necessarily requires placement of the implant prior registration.

Among potential frames of reference that may be included in the registration are, without limitation, frames of reference corresponding to one or more features of the patient (including, but not limited to, the primary anatomical feature of interest for the procedure), any component of the robotic implantation system or capital equipment related to the robotic implantation system (e.g., a stand or structural support on which the robotic implantation system is supported), the implant itself or specific feature of the implant, a controller or input device for use by the clinician (particularly if fixed within the operating theater), the clinician or a location where the clinician stands during the procedure, an environmental feature or other capital equipment within the operating theater (regardless of whether it is involved in the procedure), any imaging equipment or perspective of imaging equipment, any reported patient relative image plane from an imaging device (e.g. an angle of a C-arm), a visualization generated by pre- or intraoperative imaging, a 3D computer-generated model, and the like.

Regarding anatomical registration in particular, this disclosure contemplates that such registration may be performed using a variety of techniques including pre-operative scanning (e.g., computer tomography (CT) scans and corresponding models generated from such scans), live scanning (including contrast-type scanning, fluoroscopy, and CT scans alone or in combination), rigid anatomical landmarks (e.g., ribs or other bony structures), coordinate data from capital equipment with fixed relationships to the patient, and external fiducials/markers that may be placed onto the patient, among other techniques. Anatomical registration may also be achieved using an internal reference. Such registration may be achieved using a global location sensor positioned within the patient and with a known relationship to an anatomical structure of the patient. Examples of such sensors include, without limitation, shape sensing catheters or guidewires positioned within a known section of the vasculature and that can be referenced during a corresponding preoperative procedure (e.g., using electromagnetic, fiber, or other sensing techniques).

In certain cases, registration may include collecting sensor data and processing the sensor data to identify a corresponding frame of reference. For example, certain capital equipment (e.g., imaging systems) may include internal sensors configured to measure position and orientation of a component of the equipment. As another example, particular device locations or features may include markers (e.g., radiopaque markers or fiducials) that can be captured by imaging systems and analyzed to determine the orientation and position of the feature. Device locations and orientations may also be based on the relationships between features of the device and known anatomical landmarks within a given image (e.g., known boney structures in fluoroscopic images or known tissue structures in ultrasonographic images).

In one example registration process, an operator may input a C-arm angle to align the C-arm to a nominal plane of the patient or robotic implantation system. The operator may then adjust a base coordinate system of the robotic system represented in a visualization of the robotic system until the virtually represented coordinate system of the robotic system aligns with the nominal plane (e.g., by aligning the virtual representation with a corresponding fluoroscopic image obtained using an imaging system mounted on the C-arm and presented to the operator) to calibrate the robotic system. This process may be repeated multiple times (e.g., using different C-arm angles/orientations) to improve registration.

In a similar implementations, alignment of the base coordinate system of the robotic implantation system may be automatically aligned to the nominal plane using an algorithm that extracts a pose of the robotic implantation system using images (e.g., fluoroscopic images) captured using equipment mounted to the C-arm. For example, following positioning of the C-arm, an image may be capture using an imaging system mounted on the C-arm with features of the robotic implantation system visible in the fluoroscopic image. Based on the appearance of the features and the relationship between features, the system determines a pose of the robotic implantation system and a corresponding coordinate system which can then be registered to the coordinate system of the C-arm.

Following registration, the robotic implantation system is generally capable of transforming positions, vectors, trajectories, and similar geometric elements from one registered frame of reference to another. Accordingly, following registration, the robotic implantation system receives a motion-related input from a user/clinician at step 7404. As previously noted, the motion-related input generally corresponds to a movement of a defined feature or element relative to a current frame of reference.

While this disclosure contemplates that the robotic implantation system may be operable in a mode in which a clinician can directly drive one or more actuators of the robotic implantation system, for purposes of the current discussion of method 7400, the input received at step 7404 is considered to be provided by the clinician with respect to an anatomical frame of reference and, in particular, a frame of reference based on the mitral valve annulus. In certain implementations, the frame of reference based on the mitral valve annulus may be aligned to a fluoroscopic or other image. So, for example, a roll of the coordinate system of the robotic implantation system may be aligned along an axis of the mitral valve projected to the plane of a fluoroscopic image. Subsequently, and with such alignment established, the operator may command changes in pitch and translation about the valve similarly relative to the plane of the fluoroscopic image.

As previously discussed, in at least certain implementations, positioning of an implant within the mitral valve annulus may include manipulating the implant perpendicularity, depth, and centricity with respect to an annular plane. In such implementations, the clinician may be provided with an input device (e.g., a joystick, controller, touchscreen, keyboard, haptic device, etc.) that, when actuated by the clinician, causes a change in value with respect to one of the noted DOFs. To facilitate placement and manipulation of the implant, the clinician may also be presented with a visualization (e.g., a 3D model) of the valve annulus, implant, and distal portion of the robotic implantation system on which the implant is retained.

In certain implementations, the input device may be configured to "jog" the corresponding DOF. So, as long as the clinician maintains a control stick in a certain direction, holds a button, etc., the value of the corresponding DOF will continue to change. In such implementations, holding the control of the input device may cause the change in value to accelerate. The control of the input device may also be analog in nature such that the degree to which a control is held, moved, etc., by the clinician dictates the rate of change of the corresponding DOF.

This disclosure contemplates that actuation of a control of an input device may control jogging across multiple DOFs. In one specific example, a control stick may be configured to jog in a first DOF when tilted along a first plane; a second DOF when tilted along a second, perpendicular plane; and a combination of the first DOF and second DOF when tilted at an intermediate angle between the two planes. Stated differently, the single movement of the control stick may result in a blended input of the two DOFs that the system divides/decomposes and applies to control jogging of each of the DOFs. This general approach may be applied to any simultaneous inputs received from the input device, limited only by the number of DOFs mapped to inputs of the input device.

At step 7406 and following receipt of a motion-related input by the clinician, the robotic implantation system determines a current pose of the robot. In certain implementations, the current pose of the robot may be sufficiently determinable using onboard sensors of the robot. For example, the robotic implantation system may access data including encoder readings collected since the robotic implantation system and, based on a model of the robot and corresponding forward kinematic equations, determine a current state of the robot. Other examples of onboard sensor data that may be used to determine a current pose of the robotic implantation system include tension readings from pull wire spools and strain gauge readings which, again, may be used with a corresponding model of the robotic implantation system to determine the current pose of the robot.

This disclosure also contemplates that the current pose of the robotic implantation system may be determined, at least in part, by an imaging system and corresponding analysis software for extracting pose data from images captured using the imaging system. Further pose data may be obtained using supplemental sensors of the robotic implantation system including, but not limited to, electromagnetic sensors, inertial measurement units, fiber optic sensors, and shape-sensing components. In certain implementations, the pose of the robotic implantation system may be determined from a single sensor (e.g., a shape sensing fiber optic cable extending along the length of the robotic implantation system) or a single set of sensors. In other implementations, the position of the robotic implantation system may be determined by fusing measurements from multiple sensors or sensor sets. So, for example, the robotic implantation system may execute an algorithm that determines the pose of the robotic implantation system by averaging measurements obtained by multiple sensors, applying weights and combining measurements from multiple sensors, applying a voting scheme to multiple sensors, applying a corresponding filter (e.g., a Kalman filter) for fusing sensor measurements, or otherwise combining sensor measurements to more accurately and reliable determine the pose of the robotic implantation system.

At step 7408, the robotic implantation system calculates a movement target based on the input received in step 7404 for the DOF being manipulated by the clinician. So, for example, the robotic implantation system may determine that the current input corresponds to a 5 unit decrease in depth and a 4-degree change in perpendicularity relative to the mitral valve annulus. More generally, step 7408 includes determining a change in the location or orientation of a given feature subject to manipulation by the clinician using the input device.

At step 7410, the robotic implantation system determines the necessary joint motion for achieving the target pose using an inverse kinematic model of the robotic implantation system. More specifically, the robotic implantation system uses known geometric properties of the robotic implantation system to determine a state of the robot for achieving the change captured in step 7408.

Certain implementations of the present disclosure may include features and functionality directed to automatically or manually limiting the solution space available to the inverse kinematic model or otherwise prioritizing certain solutions for actuation of the robotic implantation system.

In one example, the inverse kinematic solutions available in step 7410 may be limited by one or more anatomical boundaries or volumes defined relative to anatomical features. For example, when performing mitral valve implant delivery and when the distal portion of the robotic delivery system is within the atrium, the inverse kinematic model may be restricted to solutions in which the robotic delivery system remains within a volume substantially smaller than the atrium to avoid contact between the robotic delivery system and cardiac tissue.

As another example, the solution space for the inverse kinematic model may also be restricted by requiring that the robotic implantation system pass through a specific location. For example, mitral valve replacement and repair may include a transseptal approach and, as a result, may include piercing through the atrial septum. Following piercing of the septum, movement of the portion of the robotic implantation system extending through the septum may put undue stress on the septum and enlarge the passage created by the transseptal approach. Accordingly, to avoid such stress on the septum, the inverse kinematic model may be restricted to solutions in which the robotic implantation system passes through the septum in substantially the same location or within a volume about the original piercing location.

As yet another example, the inverse kinematic model may be restricted by locking or restricting movement in one or more DOFs. For example, once an implant is positioned and oriented with good perpendicularity, the clinician may "lock" the perpendicularity DOF, thereby maintaining the perpendicularity of the implant while centricity and depth may be adjusted.

This disclosure also contemplates that the inverse kinematic model may prioritize certain inverse kinematic solutions over others. For example, once the robotic implantation system has entered the heart, inverse kinematic solutions that rely exclusively on movement of a distal tip of the robotic implantation system (as opposed to gross movements of a proximal portion of the system) may be favored. Failing that, the system may consider solutions that permit movement of the distal tip in combination with roll or insertion and, if necessary, movement of a proximal segment of the robotic implantation system catheter. To the extent an implementation prioritizes or selects from multiple inverse kinematic solutions, the availability of multiple inverse kinematic solutions generally results from the presence of redundant degrees of freedom, thus permitting the system to optimize the null space for secondary constraints.

At step 7412, the robotic implantation system determines actuator positions corresponding to the necessary joint motions identified in step 7410 and, in step 7414, executes the corresponding actuator motions.

In at least certain implementations, the robotic implantation system may be configured to synchronize movements, at least in part, to heart activity, e.g., heart beats. For example, the robotic implantation system may be configured to move its distal tip during diastole when the mitral valve is open. Among other things doing so can prevent collision with the valve leaflets during implantation.

Following actuation, the robotic implantation system may enter a feedback loop in which it measures the updated actual pose of the robot following execution of the actuator motions (step 7416, e.g., using similar approaches as described above in the context of step 7406) and calculates a deviation between the actual pose of the robot (step 7418) and the target determined in step 7410. If that difference is below a threshold (step 7420), the movement initiated in step 7404 is considered complete (step 7422) and the robotic implantation system waits for further input from the clinician. Alternatively, if the difference in poses is outside the permissible range, the robotic implantation system may execute an additional loop (e.g., step 7410 to step 7420) to refine the pose of the robot.

In other implementations, the operator of the robotic implantation system may provide direct feedback following movement of the robot. Stated differently, the operator provides the necessary feedback to converge or close the control loop. So, for example, following execution of a movement by the robotic implantation system the operator may observe the updated pose and position of the robot (e.g., using an image generated by a suitable imaging system) and may provide the robotic implantation system with a command indicating whether the movement/pose is within a target range or threshold or requires correction.

More generally, implementations of this disclosure include receiving a control input from an input device operated by a clinician. The control input may be provided using any suitable input device but is provided in a frame of reference other than direct joint control. Among other things, such frames of reference include those based on anatomical features, visualizations presented to the clinician, and the like.

The control input generally corresponds to a transition of an implant coupled to a robotic delivery system or other feature of the robotic delivery system from a first pose to a second pose with each pose corresponding to a different configuration of the robotic delivery system.

In response to receiving the control input, the robotic delivery system generates a control signal (e.g., one or more actuator control signals) for transitioning the robotic delivery system from the first configuration into a second configuration corresponding to the second pose. The system then transmits the control signal to a drive system of the robotic delivery system, such that, when received by the drive system, the control signal causes the drive system to actuate the robotic delivery system toward the second configuration resulting in movement of the implant toward the second pose.

An anatomical frame of reference within which the clinician may provide control inputs may include a frame of reference based on a cardiac valve annulus of a patient. In such applications, the control input provided by the clinician may correspond to specialized degrees of freedom specifically relevant to delivery and implantation of valve implants. For example, in certain implementations, the control input provided by the clinician may correspond to a change in perpendicularity of the implant relative to the cardiac valve annulus, a change in centrality of the implant relative to the cardiac valve annulus, a change in depth of the implant relative to the cardiac valve annulus, or a rotation of the implant relative to a normal of the cardiac valve annulus.

In another example, the anatomical frame of reference may correspond to an anatomical surface of a patient, such as the atrial septum. In such applications, the clinician may provide control inputs corresponding to translation along the anatomical surface, movement perpendicular to the anatomical surface, and rotation relative to a normal of the anatomical surface, among others.

This disclosure contemplates that the input provided by the clinician may be a velocity-based input. For example, in implementations in which the clinician input device includes an analog control stick or similar joystick-style control, leaving the control stick in a neutral position may correspond to zero velocity and no movement in the corresponding DOF. When the control input is moved from the neutral position, a corresponding velocity value for the DOF is changed, resulting in movement until the control input is returned to its neutral position with the degree of change corresponding to variations in the velocity value. Depending on the DOF mapped to the control input, the control input may correspond to a linear velocity or a rotational velocity. This disclosure also contemplates that a given control input may result in simultaneous velocity changes for multiple DOFs. So, for example, a joystick-style control may be configured to control movement along a first axis (e.g., an x-axis) when moved horizontally and a second axis (e.g., a y-axis) when moved vertically y-axis. In such a configuration, diagonal movement of the joystick-style control may simultaneously change velocity along each axis.

Alternatively, the control input may be a displacement-based input or may be changeable from a velocity-based to displacement-based mode. In displacement-based control, the output of the control input is mapped directly to a location within a frame of reference. For example, the clinician may provide input via a touch pad or screen where locations on the pad or screen are mapped to locations presented in a visualization to the clinician. Accordingly, when the clinician selects a location of the pad, the resulting control input is for a movement of the implant or feature of interest to the location as presented in the visualization and mapped to the input device.

As yet another example the control input device may be a multi-DOF positional input device, such as a haptic user input device, in which movement of the device results in corresponding movement of a portion of the robotic implantation system (e.g., an end effector or an implant coupled to a distal end of the system). In one specific example implementation, an operator may be permitted to switch between multiple modes that dictate how the robotic implantation system behaves in response to movement of the haptic input device. For example, the haptic input device may be configured to manipulate a distal end of the robotic implantation system and the operator may be able to switch between at least two modes of operation. In a first "following" mode, the robotic implantation system may operate such that manipulation of the haptic user input device results in corresponding (either 1:1 or scaled) movement of the distal end of the robotic implantation system. In a second "non-following" mode, the haptic input device would hold alignment to the robotic implantation system pose. In at least certain implementations, the coordinate system of a haptic input device may be further registered to the image/patient coordinate system or other coordinate system relevant to operation of the robotic implantation system.

Drive and control systems of this disclosure may include various features for improving the usability of the system, safety, and, ultimately, patient outcomes. For example, in at least certain implementations, the robotic implantation system may provide clinicians with controls related to locking DOFs. So, for example, a clinician may determine that an implant is positioned with satisfactory centrality relative to the valve annulus and may lock a centrality related DOF as the clinician refines perpendicularity and depth. In response to a lock command, the robotic implantation system may apply a corresponding condition or restriction when identifying inverse kinematic solutions for achieving desired movement.

Implementations of this disclosure may also support defined volumes for use during implantation and delivery. Defined volumes, for example, may provide a workspace for the robot. In the case of automatic movement, the defined volume may limit the inverse kinematic solution space. When operated manually or semi-manually, the defined volume may similarly provide a workspace for the clinician with the robotic implantation system configured to provide feedback (e.g., an audial, visual, or haptic alert or alarm) as the clinician approaches the limits of the volume.

Similarly, the system may support defined paths. Such paths may be automatically or manually generated and may be used to define automatic movement of the robot or to provide guidance and feedback to the clinician. In at least certain implementations, the system may operate in a semi-autonomous mode in which the system executes a movement along a defined path in response to approval by the clinician or based on a "jog" input by the clinician that causes the robot to move along the defined path.

This disclosure also contemplates that the clinician may provide input based on other frames of reference and may switch between frames of reference during the course of a procedure. For example, in addition to or as an alternative to an anatomical frame of reference, the clinician may provide input based on a frame of reference corresponding to a perspective of a visualization presented to the clinician. Examples of such visualizations may include, without limitation, fluoroscopic images, ultrasonic images, computerized tomography (CT) images, and computer-generated 3D or 2D models. The switches in between frames may mirror the switches between fluoroscopic imaging planes. Such switching may occur such that the reference frame of control follows the image plane of the fluoroscopy image displayed.

This disclosure further contemplates that the control input may be provided in a frame of reference defined relative to the implant, whether coupled to a distal end of the delivery system or following implantation.

T. PRE-OPERATIVE PLANNING, PATH GENERATION, AND NAVIGATIONAL AIDS

As previously noted, use of robotic implantation systems according to this disclosure generally rely on an initial collection of anatomical data for a patient. While the specific methods for collecting the anatomical data may vary, the goal of collecting such data is to generate at least a partial model of the patient's anatomy, which may then be used for pre-operative planning.

In certain cases, pre-operative planning may include generating a planned or optimal path for implant delivery. Once generated, such a path may be used to help guide the clinician during delivery and implantation. For example, the path may be presented to the clinician as a visualization that further includes the distal portion of the robotic implantation system, relevant patient anatomy, and the like. The clinician may then use the pre-determined path as a guide for performing the delivery and implantation procedure.

This disclosure contemplates that in addition to simply presenting the path identified during pre-operative planning, the robotic implantation system may also use such a path to provide direct feedback and suggestions to the clinician.

Figure 75:
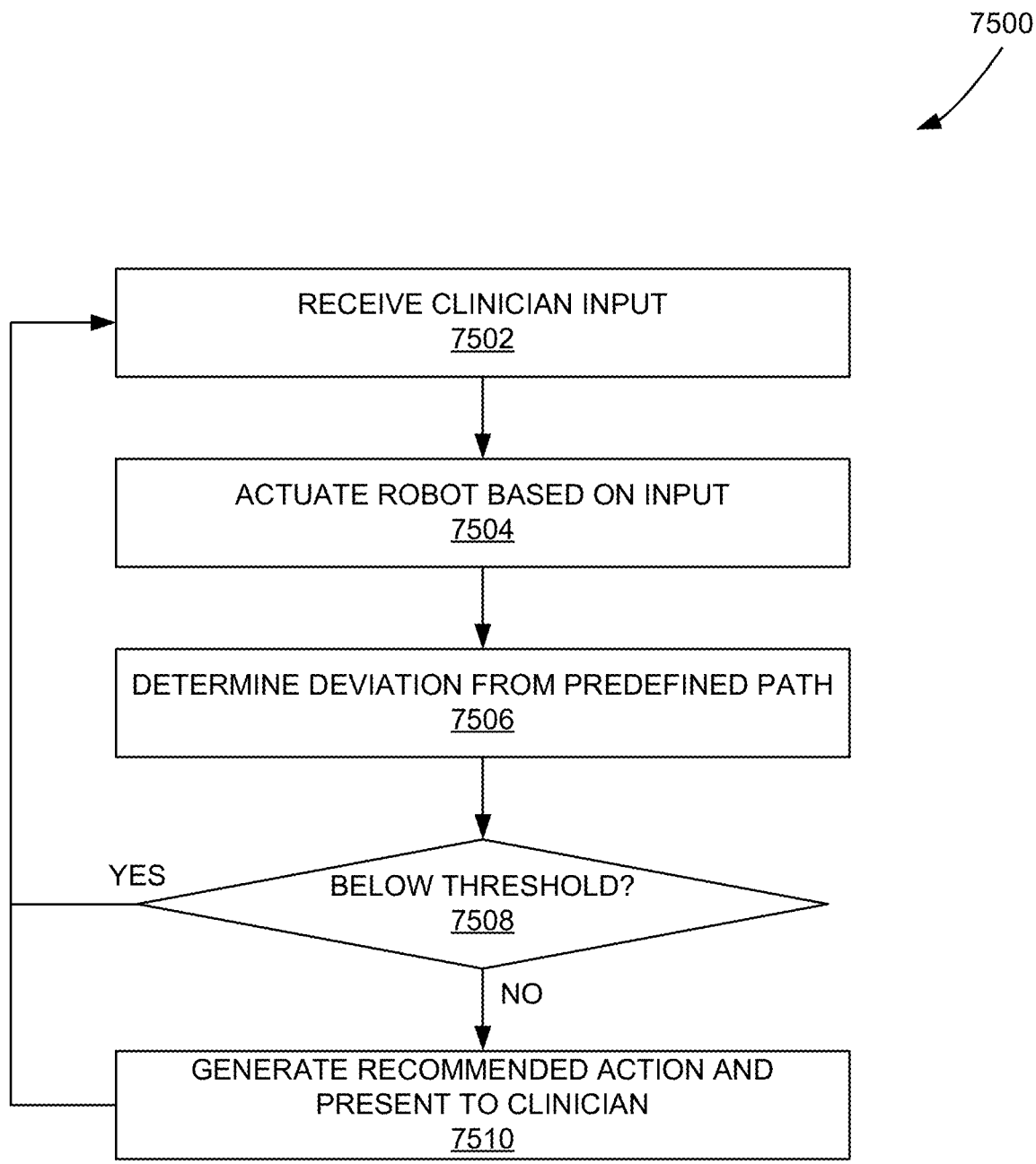
FIG. 75 is a flow chart illustrating a method for path-based control of robotic movement.

FIG. 75, for example, illustrates a method 7500 for providing feedback to a clinician during an implantation procedure using a robotic implantation system of this disclosure. At step 7502, the robotic implantation system receives a motion-related input from the clinician and, at step 7504, actuates the robot in accordance with the received input.

Following a certain number of movements, a period of time, or in substantially real time, the robotic implantation system may compare a current location of an implant (or similar feature of interest) and determine a deviation of the current location from the predefined (e.g., preoperatively generated) path (step 7506).

At step 7508, the system determines whether any deviation between the current location of the implant/feature exceeds a threshold, indicating that the clinician has substantially steered the implant off of the predefined path. If the implant is still on path, the system simply continues to accept input from the clinician and drive the robot.

If, on the other hand, the implant is off path, the system may take remedial action. In certain implementations, the system may provide auditory, visual, haptic, or similar feedback to notify the clinician of the deviation. The system may also slow or stop driving the robot.

In method 7500 and at step 7510, the system generates a recommended action (e.g., a combination of one or more inputs) for the clinician and presents the recommended action to the clinician. In one implementation, the system may generate a recommended action by determining an on-path location for the implant and, using an inverse kinematic model and device actuator model, determining the necessary actuation of the robot to achieve the on-path location.

In certain implementations, the recommended actions may be presented to the clinician such that the clinician may provide the corresponding inputs to the robotic implantation system. Alternatively, the system may request permission from the clinician to automatically execute the recommended action in order to place the implant back on path. As an intermediate alternative, the system may present a corrective action/path to the clinician and the clinician may then provide an input to jog the robot through the corrective action. Once the implant is on path, normal operation may resume with the system receiving and executing clinician inputs.

In a related concept, pre-operative planning may establish one or more volumes within the patient within which the implant may be positioned and moved. As in the case of path deviation, the clinician may be provided with feedback, suggested corrective action, or may have inputs overridden if and when the clinician steers the implant out of or near a boundary of the one or more volumes.

In the specific context of mitral valve implant delivery, the foregoing concepts of path-tracking and volume limitations can be particularly useful in critical stages of the delivery and implantation procedures. Retraction of the robotic delivery system following placement of the mitral valve implant, for example, can be a critical part of the implantation procedure due to the risk that the distal end of the robotic delivery system may contact and dislodge or damage the now-deployed implant.

Figure 76:
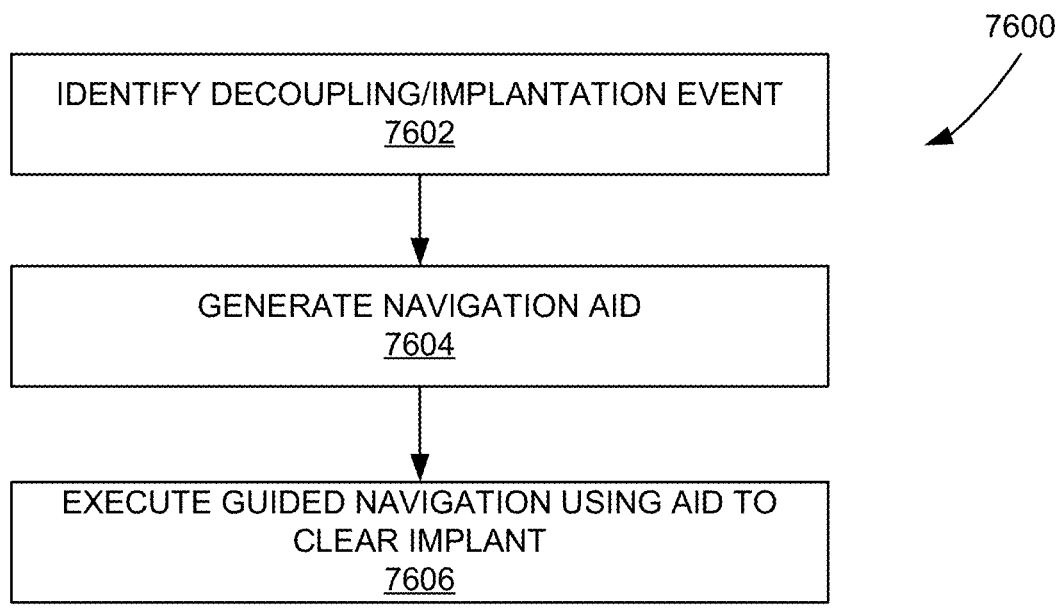
FIG. 76 is a flow chart illustrating a method for robotic movement including generation and application of navigational aids.

FIG. 76 is a flow chart of a method 7600 for facilitating removal of the robotic delivery system following implant deployment and decoupling.

Method 7600 begins with step 7602 of identifying a decoupling/implantation event. In certain implementations, the clinician may manually perform acknowledgement of decoupling/implantation. Alternatively, the robotic implantation system may include sensors for detecting the presence of the implant on the distal end of the system. As another alternative, implantation and decoupling may be identified and verified by an auxiliary imaging system.

Following decoupling and at step 7604, the system generates one or more navigation aids to facilitate removal of the distal end of the robotic implantation system from the valve annulus and clearing of the implant. In certain implementations, the navigation aid may be in the form of a path or trajectory that extends substantially normal to the annular plane and a sufficient distance to clear the implant. Alternatively, the navigation aid may be a volume extending from the valve annulus. For example, the volume may have a conical shape extending normal to the annular plane.

At step 7606, a guided navigation process is executed until the implant has been successfully cleared. Such a process may be similar to that shown in FIG. 75 in which movement of the distal end of the robotic implantation system is compared to the navigation aid and, if substantial deviation occurs, the system may intervene or provide recommended corrective action. In other implementations, the system may automatically execute an initial retraction process, e.g., by moving the distal end of the robotic implantation system according to the boundaries and parameters of the navigation aids generated in step 7604. In certain implementations, the retraction process may include at least some clinician involvement, e.g., by confirming execution of the retraction process for automatic execution by the system or by providing a "jogging" input that moves the distal end of the system away from the valve annulus according to the navigation aids.

The foregoing approach can be readily modified for other parts of the mitral valve delivery and implantation procedure. For example, in addition to retraction following implantation, piercing of the atrial septum is considered a critical step given that it has substantial impact on the final approach trajectory toward the valve annulus. Accordingly, this disclosure contemplates that navigational aids, as described above in the context of retraction, may be similarly and readily adapted for use when piercing the septum.

U. COMMAND HISTORIES AND BACKTRACKING

Many situations may arise during a delivery and implantation procedure that necessitate backtracking or otherwise "undoing" recent commands executed by the robotic implantation system. For example, inputs provided by a clinician may result in an unintended or suboptimal movement of the system and/or implant and the clinician may wish to backtrack and reattempt the movement. In at least certain circumstances, unintended movement of the system and/or implant may result in the robotic implantation system or implant negatively impacting heart function. For example, the robotic implantation system or implant coupled to the system may impinge on movement of or hold open a valve leaflet or press against cardiac tissue to disrupt electrical flow through the tissue. Accordingly, in such circumstances, an operator may be required to quickly backtrack the robotic implantation system to a known and safe location in order to restore cardiac function.

This disclosure contemplates various approaches to facilitating backtracking of commands issued to and executed by the robotic implantation system. For example, in a first implementation, the system may log inputs received from the clinician and other drive-related events. The clinician may then be provided with the option to back track through the logged events, where backtracking essentially conducts the logged input or event in reverse.

Alternatively, or in addition to the input-based approach noted above, the system may instead relay on a location- or path-based approach to backtracking during a procedure. So, for example, the system may log discrete locations or a path of the implant or other feature of the system and may permit the clinician to revert to previous locations included in the log. While reverting to a prior location may include reversing previously provided inputs, this disclosure contemplates that the location-based approach may instead rely on the robotic implantation system determining the best way to transition back to the earlier state. Stated differently, in at least some location-based approaches, the robotic implantation system may be configured to determine the inverse kinematics and corresponding actuation to move from a current location to a previous location and to execute the actuation.

In general, each of the foregoing approaches to enabling backtracking include storing a state of the robot and subsequently reverting back to that state. Capturing the initial state may occur in various ways. For example, the system may automatically store/log the state of the robot when a clinician applies an input but prior to actual actuation based on the received input. Alternatively, the system may periodically store the state of the robot independent of any input provided by the clinician. As yet another alternative, the state of the robot may be logged in response to corresponding input provided by the clinician such that the clinician can generate custom waypoints/markers, etc.

In at least certain implementations, the system may automatically capture the state of the robot in response to various events. For example, the system may log the state of the robot on each of entering the heart, piercing the septum, deploying/unfurling the implant, crossing the valve annulus with the implant, and implantation/decoupling of the implant. Alternatively, the robotic implantation system may continually log its state. In implementations in which continuous logging is used, key locations and events may still be marked or otherwise identified in the logging stream.

Among other advantages, doing so permits return to the locations corresponding to the key events and identification of the key events in the logged data, e.g., during post-operative review and analysis.

As in other examples of robot actuation covered in this disclosure, backtracking may be an entirely automated process, may require relatively minimal clinician intervention (e.g., confirming a backtrack is to occur or "jogging" the robot along a path generated by the system), or may be performed substantially by the clinician with help and feedback provided by the system.

This disclosure contemplates that the robotic implantation system may backtrack in one or more modes and, in certain implementations, an operator may change backtracking modes based on the operator's needs. For example, in certain implementations and in one mode of operation, input commands provided by the operator may be treated as discrete driving events with backtracking consisting of reverting previous driving events. In this particular backtracking mode, backtracking essentially undoes previous driving events. In an alternative mode of operation, backtracking may be more continuous. So, for example, an operator may mark a first location or pose of the robotic implantation system and provide an input to transition the robotic implantation system into a second pose or location. The operator may then backtrack to the first pose/location by providing a corresponding input. In response to the input, the robotic implantation system may reverse along the path defined between the two poses/locations.

In addition to backtracking, this disclosure also contemplates that the robotic implantation system may also be configured to execute previous movements and transitions. Stated differently, in addition to "undoing" inputs, the robotic implantation system may support "redoing" inputs. More generally, this disclosure contemplates that an operator may transition forward or backward through a history of inputs provided to the robotic implantation system and corresponding movements and transitions by the system.

In addition to facilitating backtracking during a procedure, logged robot states can also serve as a record of a given procedure. Such records may be used for various purposes including, but not limited to, clinician evaluation and education.

V. COMPUTING SYSTEM

Figure 77:
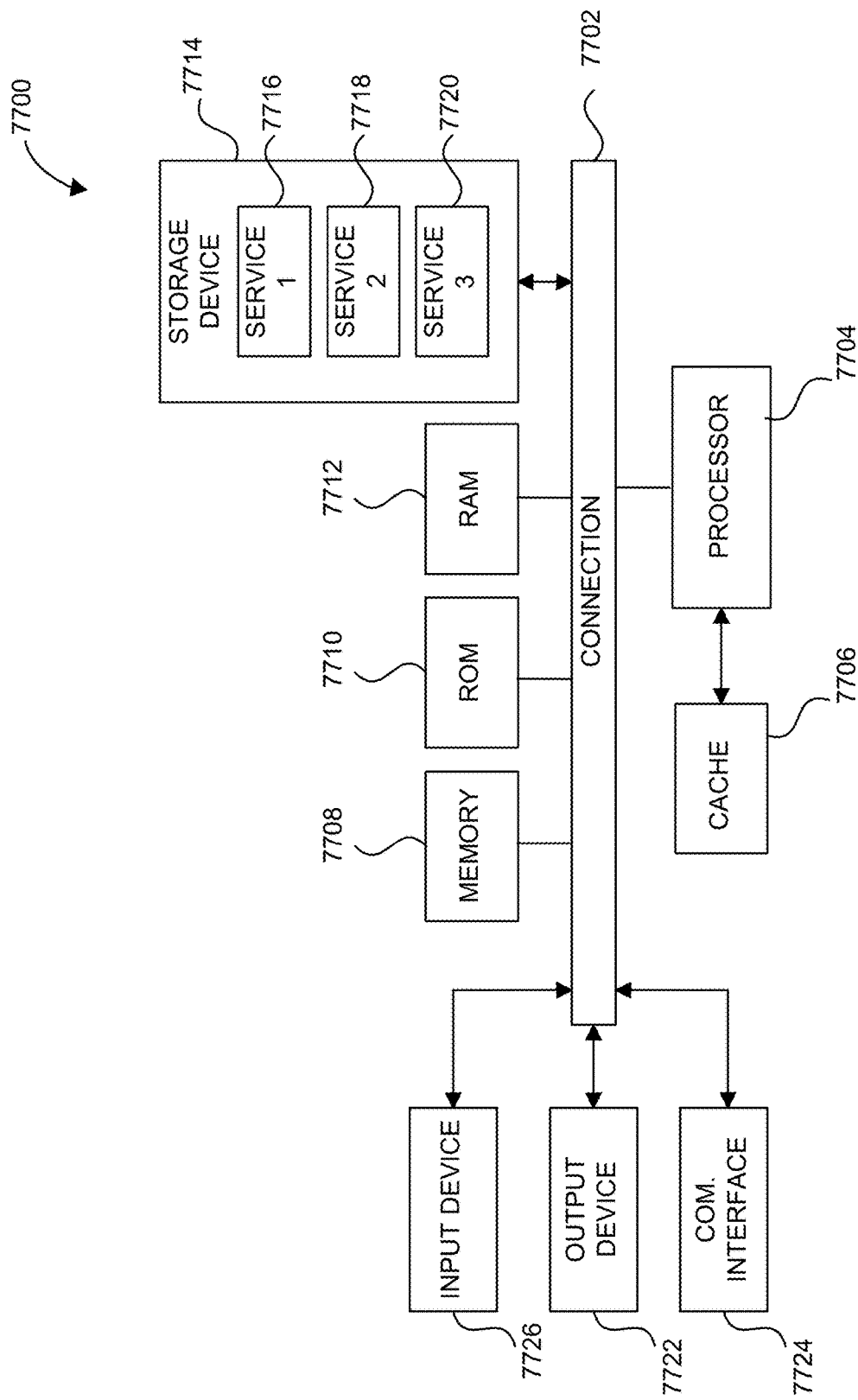
FIG. 77 is a block diagram of an example computing system for use in implementations of this disclosure.

FIG. 77 shows an example of computing system 7700, which can be for example any computing device making up the systems of the previously discussed figures, or any component thereof in which the components of the system are in communication with each other using connection 7702. Connection 7702 can be a physical connection via a bus, or a direct connection into processor 7704, such as in a chipset architecture. Connection 7702 can also be a virtual connection, networked connection, or logical connection.

In some embodiments, computing system 7700 is a distributed system in which the functions described in this disclosure can be distributed within a datacenter, multiple data centers, a peer network, etc. In some embodiments, one or more of the described system components represents many such components each performing some or all of the function for which the component is described. In some embodiments, the components can be physical or virtual devices.

Example computing system 7700 includes at least one processing unit (CPU or processor) 7704 and connection 7702 that couples various system components including system memory 7708, such as read-only memory (ROM) 7710 and random-access memory (RAM) 7712 to processor 7704. Computing system 7700 can include a cache of high-speed memory 7706 connected directly with, in close proximity to, or integrated as part of processor 7704.

Processor 7704 can include any general-purpose processor and a hardware service or software service, such as services 7716, 7718, and 7720 stored in storage device 7714, configured to control processor 7704 as well as a special-purpose processor where software instructions are incorporated into the actual processor design. Processor 7704 may essentially be a completely self-contained computing system, containing multiple cores or processors, a bus, memory controller, cache, etc. A multi-core processor may be symmetric or asymmetric.

To enable user interaction, computing system 7700 includes an input device 7726, which can represent any number of input mechanisms, such as a microphone for speech, a touch-sensitive screen for gesture or graphical input, keyboard, mouse, motion input, speech, etc. Computing system 7700 can also include output device 7722, which can be one or more of a number of output mechanisms known to those of skill in the art. In some instances, multimodal systems can enable a user to provide multiple types of input/output to communicate with computing system 7700. Computing system 7700 can include communication interface 7724, which can generally govern and manage the user input and system output and facilitate communication with other computing systems, devices, sensors, actuators, and the like. There is no restriction on operating on any particular hardware arrangement, and therefore the basic features here may easily be substituted for improved hardware or firmware arrangements as they are developed.

Storage device 7714 can be a non-volatile memory device and can be a hard disk or other types of computer readable media which can store data that are accessible by a computer, such as magnetic cassettes, flash memory cards, solid state memory devices, digital versatile disks, cartridges, random access memories (RAMs), read-only memory (ROM), and/or some combination of these devices.

The storage device 7714 can include software services, servers, services, etc., that when the code that defines such software is executed by the processor 7704, it causes the system to perform a function. In some embodiments, a hardware service that performs a particular function can include the software component stored in a computer-readable medium in connection with the necessary hardware components, such as processor 7704, connection 7702, output device 7722, etc., to carry out the function.

For clarity of explanation, in some instances, the present technology may be presented as including individual functional blocks including functional blocks including devices, device components, steps or routines in a method embodied in software, or combinations of hardware and software.

Any of the steps, operations, functions, or processes described herein may be performed or implemented by a combination of hardware and software services or services, alone or in combination with other devices. In some embodiments, a service can be software that resides in memory of a client device and/or one or more servers of a content management system and perform one or more functions when a processor executes the software associated with the service. In some embodiments, a service is a program or a collection of programs that carry out a specific function. In some embodiments, a service can be considered a server. The memory can be a non-transitory computer-readable medium.

In some embodiments, the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer-readable media. Such instructions can include, for example, instructions and data which cause or otherwise configure a general-purpose computer, special-purpose computer, or special-purpose processing device to perform a certain function or group of functions. Portions of computer resources used can be accessible over a network. The executable computer instructions may be, for example, binaries, intermediate format instructions such as assembly language, firmware, or source code. Examples of computer-readable media that may be used to store instructions, information used, and/or information created during methods according to described examples include magnetic or optical disks, solid-state memory devices, flash memory, USB devices provided with non-volatile memory, networked storage devices, and so on.

Devices implementing methods according to these disclosures can include hardware, firmware and/or software, and can take any of a variety of form factors. Typical examples of such form factors include servers, laptops, smartphones, small form factor personal computers, personal digital assistants, and so on. The functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

W. ASPECTS OF THE DISCLOSURE

Illustrative examples of this disclosure include, but are not limited to the following:

Aspect 1-1: A catheter including: a handle assembly; and a tubular body assembly extending distally from the handle assembly, wherein: the handle assembly includes a cable control assembly operable to deflect a portion of the tubular body assembly, and the handle assembly is configured to be coupleable to a robot such that, when coupled to the robot, the cable control assembly interfaces with a drive motor assembly of the robot to facilitate operation of the cable control assembly to deflect the portion of the tubular body.

Aspect 1-2: The catheter of Aspect 1-1, wherein the tubular body assembly includes: a rotor defining a working lumen; and a stator coaxially surrounding the rotor, wherein the rotor is configured to rotate relative to the stator to control deployment of an implant disposed on a distal end of the tubular body assembly.

Aspect 1-3: The catheter of Aspect 1-2, wherein the rotor is configured to control deployment of the implant by selectively furling the implant.

Aspect 1-4: The catheter of Aspect 1-2, wherein the tubular body assembly further includes a steering shaft coaxially surrounding the stator and configured to be steered by the cable control assembly to deflect the portion of the tubular body assembly.

Aspect 1-5: The catheter of Aspect 1-2, wherein the stator is coupled to a proximal stator key configured to prevent rotation of the stator.

Aspect 1-6: The catheter of Aspect 1-1, wherein the cable control assembly is one of a plurality of cable control assemblies.

Aspect 1-7: The catheter of Aspect 1-6, wherein each cable control assembly of the plurality of cable control assemblies is configured to deflect a respective portion of the tubular body.

Aspect 1-8: The catheter of Aspect 1-1, wherein the handle assembly includes four cable control assemblies including the cable control assembly.

Aspect 1-9: The catheter of Aspect 1-1, wherein the cable control assembly includes is operable to control extension and retraction of a first actuation cable and a second actuation cable.

Aspect 1-10: The catheter of Aspect 1-9, wherein the first actuation cable and the second actuation cable are routed from the cable control assembly at least partially along the tubular body assembly.

Aspect 1-11: The catheter of Aspect 1-10, wherein the tubular body assembly includes a steering shaft to facilitate steering of the tubular body assembly and a stator disposed within the steering shaft, and wherein the first actuation cable and the second actuation cable are routed between the steering shaft and the stator.

Aspect 1-12: The catheter of Aspect 1-11, further including a shaft plate coupled to a proximal end of the steering shaft and including a passthrough plate, wherein each of the first actuation cable, the second actuation cable, and the stator extend through the passthrough plate.

Aspect 1-13: The catheter of Aspect 1-9, wherein the cable control assembly includes: a first control spindle coupled to the first actuation cable and operable to extend and retract the first actuation cable; and a second control spindle coupled to the second actuation cable and operable to extend and retract the second actuation cable.

Aspect 1-14: The catheter of Aspect 1-13, wherein the first control spindle and the second control spindle are each coupled to a bearing cap.

Aspect 1-15: The catheter of Aspect 1-14, wherein each of the first control spindle and the second control spindle are supported by a first respective bearing disposed within the bearing cap and a second respective bearing supported within a handle frame of the handle assembly.

Aspect 1-16: The catheter of Aspect 1-14, wherein each of the first control spindle and the second control spindle is coupled to respective torque springs to maintain torque on the first control spindle and second control spindle during operation.

Aspect 1-17: The catheter of Aspect 1-16, wherein the respective torque springs are configured to maintain a constant torque on the first control spindle and the second control spindle.

Aspect 1-18: The catheter of Aspect 1-13, wherein each of the first control spindle and the second control spindle includes a top having a coupling for attaching the first control spindle and the second control spindle to a manual pull wire assembly.

Aspect 1-19: The catheter of Aspect 1-18 further including the manual pull wire assembly, wherein the manual pull wire assembly is removably interfaceable with the coupling of each of the first control spindle and the second control spindle and to simultaneously apply torque to the first control spindle and the second control spindle.

Aspect 1-20: The catheter of Aspect 1-19, wherein the manual pull wire assembly includes a gear train coupled to a lever and configured to simultaneously drive a first drive shaft mated with the first control spindle and a second drive shaft mated with the second control spindle.

Aspect 1-21: The catheter of Aspect 1-20, wherein the gear train includes: a lever gear coupled to the lever; an intermediate gear interfacing with the lever gear; a first drive gear interfacing with the intermediate gear and coupled to the first drive shaft; and a second drive gear interfacing with the lever gear and coupled to the second drive shaft.

Aspect 1-22: The catheter of Aspect 1-21, wherein each of the first drive shaft and the second drive shaft are further coupled to respective dog plate assemblies.

Aspect 1-23: The catheter of Aspect 1-13, wherein the handle assembly includes a handle frame and each of the first control spindle and the second control spindle extends through a bottom of the handle frame such that a bottom of each of the first control spindle and the second control spindle is coupleable to a respective cable control assembly drive element of the robot.

Aspect 1-24: The catheter of Aspect 1-23, wherein the bottom of each of the first control spindle and the second control spindle includes a coupling for interfacing with its respective cable control assembly drive element of the robot.

Aspect 1-25: The catheter of Aspect 1-24, wherein the coupling includes an Oldham floating disk coupling.

Aspect 1-26: The catheter of Aspect 1-9, wherein the cable control assembly further includes an idler pulley about which each of the first actuation cable and the second actuation cable are routed.

Aspect 1-27: The catheter of Aspect 1-1, wherein the handle assembly includes a handle frame supporting the cable control assembly.

Aspect 1-28: The catheter of Aspect 1-1 further including a housing shell disposed on a top of the handle assembly.

Aspect 1-29: The catheter of Aspect 1-1, wherein the handle assembly further includes a pair of latch tie bars to facilitate coupling of the handle assembly to the robot.

Aspect 1-30: The catheter of Aspect 1-28, wherein each latch tie bar of the pair of latch tie bars is operable to simultaneously release a respective set of handle latches disposed on an underside of the handle assembly.

Aspect 1-31: The catheter of Aspect 1-1, wherein the handle assembly includes a furl assembly configured to facilitate selective deployment of an implant coupled to a distal end of the tubular body assembly.

Aspect 1-32: The catheter of Aspect 1-31, wherein: the furl assembly includes a capstan gear coupled to a rotor of the tubular body assembly, rotation of the capstan gear results in rotation of the rotor, and the rotor is configured to interface with the implant such that rotation of the rotor results in selective deployment of the implant.

Aspect 1-33: The catheter of Aspect 1-32, wherein: the handle assembly includes a handle frame, a portion of the capstan gear protrudes from an underside of the handle frame, and the capstan gear and the handle frame are configured such that, when the handle assembly is coupled to the robot, the portion of the capstan gear interfaces with a motor of the robot for driving the capstan gear.

Aspect 1-34: The catheter of Aspect 1-32, wherein the furl assembly further includes an indicator gear simultaneously drivable with the capstan gear and visible through a housing shell of the handle assembly to facilitate monitoring of furling of the implant.

Aspect 1-35: The catheter of Aspect 1-32, wherein the furl assembly further includes a furl lock lever movable between a first position in which the capstan gear is free to rotate and a second position in which rotation of the capstan gear is restricted.

Aspect 1-36: The catheter of Aspect 1-35, wherein the furl lock lever is ratcheting such that, when the furl lock lever is in the second position, the furl lock lever engages the capstan gear and is movable to permit rotation of the capstan gear in a first direction while preventing rotation of the capstan gear in a second direction opposite the first direction.

Aspect 1-37: The catheter of Aspect 1-36, wherein the first direction corresponds to furling of the implant and the second direction corresponds to unfurling of the implant.

Aspect 1-38: The catheter of Aspect 1-36, wherein the furl assembly further includes a furl lock release pin that selectively engages the furl lock lever to prevent movement of the furl lock lever, thereby preventing rotation of the capstan gear in the first direction.

Aspect 1-39: The catheter of Aspect 1-1, wherein: the handle assembly includes a working channel fitting disposed on a proximal end of the handle assembly, and the working channel fitting is in communication with a lumen defined by the tubular body assembly.

Aspect 1-40: The catheter of Aspect 1-1, wherein the control cable assembly is further coupleable to a manual pull wire assembly to manually operate the cable control assembly.

Aspect 1-41: The catheter of Aspect 1-40, wherein the manual pull wire assembly is coupleable to a top of the cable control assembly.

Aspect 1-42: The catheter of Aspect 1-41, wherein the manual pull wire assembly includes a lever operable to drive the cable control assembly when the manual pull wire assembly is coupled to the cable control assembly.

Aspect 1-43: The catheter of Aspect 1-40, wherein the manual pull wire assembly is coupleable to the cable control assembly when the handle assembly is coupled to the robot.

Aspect 1-44: The catheter of Aspect 1-1, wherein the tubular body assembly includes an inner tubular body providing a distal tip.

Aspect 1-45: The catheter of Aspect 1-44, wherein the inner tubular body further includes a deflectable region extending proximal the distal tip, wherein the portion of the tubular body is the deflectable region.

Aspect 1-46: The catheter of Aspect 1-44, wherein the tubular body assembly further includes a sheath, wherein the sheath is linearly displaceable along the inner tubular body such that a distal end of the sheath is displaceable relative to the distal tip of the inner tubular body.

Aspect 1-47: The catheter of Aspect 1-46, wherein: handle assembly further includes a sheath retraction assembly coupled to a proximal end of the tubular body assembly, and when the handle assembly is coupled to the robot, the sheath retraction assembly is driveable by a motor assembly of the robot.

Aspect 1-48: The catheter of Aspect 1-47, wherein the sheath retraction assembly includes: a sheath nose block coupled to a proximal end of the sheath; one or more guide shafts; a sheath mount block coupled to and supporting the sheath nose block, the one or more guide shafts extending through the sheath mount block; and a lead screw coupled to the sheath mount block and configured to drive the sheath mount block along the one or more guide shafts in response to rotation of the lead screw.

Aspect 1-49: The catheter of Aspect 1-47, wherein the sheath mount block is coupled to the lead screw by a fast travel flange and ball bearing assembly.

Aspect 1-50: The catheter of Aspect 1-47, wherein the lead screw is an ultra-precision lead screw.

Aspect 1-51: The catheter of Aspect 1-47, wherein the lead screw is a single start lead screw.

Aspect 1-52: The catheter of Aspect 1-47, wherein the lead screw is a multi-start lead screw.

Aspect 1-53: The catheter of Aspect 1-47, wherein the sheath mount block includes a fitting.

Aspect 1-54: The catheter of Aspect 1-53, wherein the fitting is one of a Luer lock fitting, a Tuohy-Borst fitting, and a quick connect fitting.

Aspect 1-55: The catheter of Aspect 1-48, wherein: the sheath retraction assembly further includes a lead screw gear coupled to the lead screw supported within a handle frame of the handle assembly, a portion of the lead screw gear protrudes from an underside of the handle frame, and the lead screw gear and the handle frame are configured such that, when the handle assembly is coupled to the robot, the portion of the lead screw gear interfaces with a motor of the robot for driving the lead screw.

Aspect 1-56: The catheter of Aspect 1-1, wherein the cable control assembly includes: a first control spindle spool and a first cable extending from the first control spindle to a first location of the tubular body assembly, wherein the first control spindle is operable to deflect a portion of the tubular body assembly by selectively spooling and unspooling the first cable; a second control spindle and a second cable extending from the second control spindle to a second location of the tubular body assembly, wherein the second control spindle is operable such that the second cable is antagonistic to the first cable.

Aspect 1-57: The catheter of Aspect 1-1, wherein: the handle assembly includes a plurality of cable control assemblies including the cable control assembly, and each cable control assembly includes respective cables for controlling deflection of a respective section of the tubular body assembly.

Aspect 1-58: The catheter of Aspect 1-1, wherein the tubular body assembly includes a distal portion including a proximal steering section and a distal steering section and wherein the plurality of cable control assemblies includes a first cable control assembly for controlling deflection of the proximal steering section along a lateral plane, a second cable control assembly for controlling deflection of the distal steering section along the lateral plane, and a third cable control assembly for controlling deflection of the distal steering section along an anterior-posterior plane orthogonal to the lateral plane.

Aspect 1-59: The catheter of Aspect 1-1, wherein the tubular body assembly includes an articulable distal section, the articulable distal section includes a proximal deflectable section and a distal deflectable section, and the articulable distal section further includes a plurality of sensors distributed along the articulable distal section, the plurality of sensors configured to provide position data for the articulable distal section.

Aspect 2-1: A robot for use with a catheter-based surgical system including: a linear displacement platform; and a carriage coupled to the linear displacement platform, wherein: the carriage is linearly displaceable along the linear displacement platform and rotatable relative to the linear displacement platform, and the carriage includes a drive motor assembly such that, when a handle assembly of a catheter is received by the carriage, the drive motor assembly interfaces with a cable control assembly of the catheter.

Aspect 2-2: The robot of Aspect 2-1, wherein the carriage is one of a plurality of carriages.

Aspect 2-3: The robot of Aspect 2-2, wherein each carriage of the plurality of carriages is independently movable along the linear displacement platform and independently rotatable relative to the linear displacement platform.

Aspect 2-4: The robot of Aspect 2-2, wherein a first carriage of the plurality of carriages and a second carriage of the plurality of carriages are configured to move simultaneously along the linear displacement platform and to rotate simultaneously relative to the linear displacement platform.

Aspect 2-5: The robot of Aspect 2-2, wherein the handle assembly is received by the plurality of carriages.

Aspect 2-6: The robot of Aspect 2-1, wherein the carriage includes a nesting side configured to receive a bottom surface of the handle assembly.

Aspect 2-7: The robot of Aspect 2-6, wherein the carriage includes a drive motor assembly and the nesting side includes a coupling configured to mechanically interface with a corresponding coupling of a cable control assembly of the handle assembly and to transmit torque from the drive motor assembly to cable control assembly when the handle assembly is received by the carriage.

Aspect 2-8: The robot of Aspect 2-7, wherein the coupling is an Oldham floating disk.

Aspect 2-9: The robot of Aspect 2-7, wherein: the nesting side includes a plurality of drive motor assemblies and the nesting side includes a plurality of couplings, each coupling corresponding to a respective one of the plurality of drive motor assemblies, and wherein each coupling of the plurality of couplings is configured to mechanically interface with a respective coupling of a cable control assembly of the handle assembly and to transmit torque from the drive motor assembly to cable control assembly when the handle assembly is received by the carriage.

Aspect 2-10: The robot of Aspect 2-9, wherein the plurality of couplings includes four couplings.

Aspect 2-11: The robot of Aspect 2-7, wherein the nesting side further includes a drive gear protruding from the nesting side of the carriage.

Aspect 2-12: The robot of Aspect 2-11, wherein the drive gear has an axis of rotation parallel to a direction of the longitudinal displacement along the linear displacement platform.

Aspect 2-13: The robot of Aspect 2-11, wherein the carriage further includes a combination motor gear box coupled to the drive gear and configured to drive the drive gear.

Aspect 2-14: The robot of Aspect 2-7, wherein the nesting side further includes a latch configured to retain the handle assembly on the carriage when the handle assembly is received by the carriage.

Aspect 2-15: The robot of Aspect 2-14, wherein the latch is one of a plurality of latches disposed on the nesting side.

Aspect 2-16: The robot of Aspect 2-7, wherein: the carriage includes a drive motor assembly, the nesting side includes a coupling configured to mechanically interface with a corresponding coupling of a cable control assembly of the handle assembly and to transmit torque from the drive motor assembly to cable control assembly when the handle assembly is received by the carriage, and the latch includes a disengagement plate that, when depressed, causes the coupling to retract into the carriage.

Aspect 2-17: The robot of Aspect 2-1, wherein the carriage includes a drive motor assembly including a drive motor configured to drive a cable axis rotor, and wherein the cable axis rotor is configured to be aligned with a control spindle of a control cable assembly of the handle assembly when the handle assembly is received by the carriage.

Aspect 2-18: The robot of Aspect 2-17, wherein the drive motor assembly further includes a brake.

Aspect 2-19: The robot of Aspect 2-18, wherein the brake is a power off brake configured to brake the cable axis rotor when power is not provided to the brake.

Aspect 2-20: The robot of Aspect 2-18, wherein the brake is configured to automatically engage in response to a fault condition.

Aspect 2-21: The robot of Aspect 2-17, wherein the drive motor assembly further includes a motor encoder.

Aspect 2-22: The robot of Aspect 2-1 further including a C-arm, wherein: the carriage is coupled to and supported within the C-arm, and the C-arm is movably supported by a linear displacement block movable along the linear displacement platform.

Aspect 2-23: The robot of Aspect 2-22, wherein the C-arm defines an arcuate channel opening outwardly and extending along an outer circumference of the C-arm.

Aspect 2-24: The robot of Aspect 2-22 further including a roller assembly disposed within the arcuate channel and coupled to the linear displacement block.

Aspect 2-25: The robot of Aspect 2-23, wherein the roller assembly includes side rollers configured to be received by the C-arm to permit rotation of the C-arm relative to the linear displacement platform.

Aspect 2-26: The robot of Aspect 2-25, wherein the rollers are received in C-arm roller channels defined on each of a proximal surface and a distal surface of the arcuate channel.

Aspect 2-27: The robot of Aspect 2-22, wherein the roller assembly includes bottom rollers configured to be received within channels of a rail of the linear displacement platform, thereby permitting linear displacement of the C-arm.

Aspect 2-28: The robot of Aspect 2-22, wherein: the linear displacement platform includes a lead screw extending longitudinally within an elongated frame of the linear displacement platform, and the lead screw is threadably coupled to the linear displacement block such that rotation of the lead screw drives the linear displacement block along the elongated frame.

Aspect 2-29: The robot of Aspect 2-22, wherein: the linear displacement platform includes a C-arm drive shaft extending longitudinally within an elongated frame of the linear displacement platform, and the C-arm drive shaft is coupled to a C-arm drive drum such that that rotation of the C-arm drive shaft rotates the C-arm drive drum to rotate the C-arm relative to the linear displacement platform.

Aspect 2-30: The robot of Aspect 2-29, wherein the C-arm drive shaft is a spline shaft.

Aspect 2-31: The robot of Aspect 2-29 further including cables extending between the C-arm drive drum and extents of the C-arm such that rotation of the C-arm drive drum causes the cables to wind out and wind up, thereby rotating the C-arm.

Aspect 2-32: The robot of Aspect 2-1, further including a plurality of carriages including the carriage, wherein: each carriage is supported by a respective C-arm, each C-arm is movably supported by a respective linear displacement block movable along the linear displacement platform, and for each C-arm, the linear displacement platform includes a lead screw and a C-arm drive shaft extending along an elongated frame of the linear displacement platform, the lead screw configured to longitudinally translate the C-arm when rotated and the C-arm drive shaft configured to rotate the C-arm when rotated.

Aspect 2-33: The robot of Aspect 2-32, wherein the linear displacement platform includes independently controllable motors for driving each lead screw and each C-arm drive.

Aspect 3-1: A system including: a catheter according to any of Aspect 1-1 to Aspect 1-58; and a robot according to any of Aspect 2-1 to Aspect 2-33.

Aspect 4-1: A system including: a catheter as described in this disclosure; and a robot as described in this disclosure.

Aspect 5-1: A system including: a catheter including: a handle assembly including a cable control assembly; and a tubular body assembly extending distally from the handle assembly and deflectable by operation of the cable control assembly; and a robot including: a linear displacement platform; and a carriage coupled to the linear displacement platform and including a drive motor assembly, the carriage at least one of linearly displaceable along the linear displacement platform and rotatable relative to the linear displacement platform, wherein the handle assembly is coupled to the carriage such that the cable control assembly interfaces with the drive motor assembly of the carriage to facilitate operation of the cable control assembly by the robot.

Aspect 5-2: The system of Aspect 5-1 further including a stand coupled to the linear displacement platform.

Aspect 5-3: The system of Aspect 5-1, wherein the stand is adjustable to modify a vertical position of the linear displacement platform.

Aspect 5-4: The system of Aspect 5-3, wherein the stand includes: one or more vertically oriented members; a mounting plate coupled to the linear displacement platform and slidingly coupled to the one or more vertically oriented members; and one or more constant force springs configured to apply a vertical force on the mounting plate to at least partially offset a combined weight of the catheter and the robot.

Aspect 5-5: The system of Aspect 5-1, wherein the carriage is one of a plurality of carriages and the handle assembly is coupled to the plurality of carriages.

Aspect 5-6: The system of Aspect 5-1, wherein the catheter is supported by the robot such that the catheter is rotatable about a longitudinal axis of rotation extending coaxially with a center axis of a working lumen defined by the tubular body assembly.

Aspect 6-1: A method operating a robotic implant delivery system, the method including identifying a stop condition; depowering one or more motors of the robotic implant delivery system; engaging a brake of a motor of the one or more motors of the robotic implant delivery system; and manually coupling a pull wire assembly to a cable control assembly of a handle assembly of the robotic implant delivery system, wherein the manual pull wire assembly is configured to simultaneously drive multiple control spindles of the cable control assembly.

Aspect 6-2: The method of Aspect 6-1, wherein the stop condition is activation of an emergency stop button.

Aspect 6-3: The method of Aspect 6-1, wherein the stop condition is a loss of control of a motor axis.

Aspect 6-4: The method of Aspect 6-1, wherein the stop condition is a loss of power to a motor controller.

Aspect 6-5: The method of Aspect 6-1 further including, in response to identifying the stop condition, placing motor controllers of the one or more motors into a safe torque off mode.

Aspect 6-6: The method of Aspect 6-1, wherein depowering one or more motors includes depowering all motors of the robotic implant delivery system.

Aspect 6-7: The method of Aspect 6-1, wherein the brake is manually engaged.

Aspect 6-8: The method of Aspect 6-1, wherein the brake is automatically engaged.

Aspect 6-9: The method of Aspect 6-1, wherein the brake is a friction brake.

Aspect 6-10: The method of Aspect 6-1, wherein the brake is a toothed brake.

Aspect 6-11: The method of Aspect 6-1, wherein the brake is biased into a braking state such that, when deenergized, the brake is applied to the motor.

Aspect 6-12: The method of Aspect 6-1, further including, subsequent to attaching the pull wire assembly to the cable control assembly of the robotic implant delivery system, manually controlling the cable control assembly to complete an implantation procedure.

Aspect 6-13: The method of Aspect 6-1, further including, subsequent to attaching the pull wire assembly to the cable control assembly of the robotic implant delivery system, manually controlling the cable control assembly to perform a manual bailout procedure in which the robotic implant delivery system is at least partially removed from a patient.

Aspect 6-14: The method of Aspect 6-1, further including, subsequent to attaching the pull wire assembly to the cable control assembly of the robotic implant delivery system, locking the pull wire assembly to at least partially lock operation of the handle assembly.

Aspect 6-15: The method of Aspect 6-1, further including, subsequent to attaching the pull wire assembly to the cable control assembly of the robotic implant delivery system, disabling automatic control of the cable control assembly by the robotic implant delivery system.

Aspect 7-1: A method including: receiving a control input from a user input device for a transition of an implant coupled to a robotic delivery system, wherein the transition is from a first pose to a second pose and the robotic delivery system has a first configuration when the implant is in the first pose; generating a control signal for transitioning the robotic delivery system from the first configuration into a second configuration, the second configuration resulting in the second pose of the implant; and transmitting the control signal to a drive system of the robotic delivery system, such that, when received by the drive system, the control signal causes the drive system to actuate the robotic delivery system toward the second configuration resulting in movement of the implant toward the second pose, wherein the control input indicates the movement of the implant relative to an anatomical frame of reference.

Aspect 7-2: The method of Aspect 7-1, wherein the anatomical frame of reference corresponds to a cardiac valve annulus of a patient.

Aspect 7-3: The method of Aspect 7-2, wherein the control input includes a value corresponding to a change in perpendicularity of the implant relative to the cardiac valve annulus.

Aspect 7-4: The method of Aspect 7-2, wherein the control input includes a value corresponding to a change in centrality of the implant relative to the cardiac valve annulus.

Aspect 7-5: The method of Aspect 7-2, wherein the control input includes a value corresponding to a change in depth of the implant relative to the cardiac valve annulus.

Aspect 7-6: The method of Aspect 7-2, wherein the control input includes a value corresponding to a rotation of the implant relative to a normal of the cardiac valve annulus.

Aspect 7-7: The method of Aspect 7-1, wherein the anatomical frame of reference corresponds to an anatomical surface of a patient.

Aspect 7-8: The method of Aspect 7-7, wherein the control input includes a value corresponding to at least one of a translation along the anatomical surface, a movement perpendicular to the anatomical surface, and rotation relative to a normal of the anatomical surface.

Aspect 7-9: The method of Aspect 7-7, wherein the anatomical surface corresponds to an atrial septum of the patient.

Aspect 7-10: The method of Aspect 7-1, wherein the control input corresponds to a change in at least one of linear velocity and rotational velocity of the implant relative to the anatomical frame of reference.

Aspect 7-11: The method of Aspect 7-1, wherein the control input corresponds to a change in at least one of linear displacement and rotational displacement relative to the anatomical frame of reference.

Aspect 7-12: The method of Aspect 7-1, further including receiving a lock command corresponding to a degree of freedom of the implant relative to the anatomical frame of reference, wherein the control signal is for transitioning the robotic delivery system from the first configuration into the second configuration while constraining the degree of freedom.

Aspect 7-13: The method of Aspect 7-1, further including receiving a lock command corresponding to a degree of freedom of the robotic delivery system, wherein the control signal is for transitioning the robotic delivery system from the first configuration into the second configuration while constraining the degree of freedom.

Aspect 7-14: The method of Aspect 7-1, further including receiving a path constraint command including a location, wherein the control signal is for transitioning the robotic delivery system from the first configuration into the second configuration while maintaining the robotic delivery system extending through an envelope about the location.

Aspect 7-15: The method of Aspect 7-14, wherein the location corresponds to an atrial septum of a patient.

Aspect 7-16: The method of Aspect 7-1, further including receiving a path constraint command including a location, wherein the control signal is for transitioning the robotic delivery system from the first configuration into the second configuration while maintaining the robotic delivery system extending through the location.

Aspect 7-17: The method of Aspect 7-16, wherein the location corresponds to an atrial septum of a patient.

Aspect 7-18: The method of Aspect 7-1, further including receiving a path constraint command including a location, wherein the control signal is for transitioning the robotic delivery system from the first configuration into the second configuration while maintaining the robotic delivery system at an offset from the location.

Aspect 7-19: The method of Aspect 7-1, wherein transmitting the control signal to the drive system is in response to receiving a confirmation command.

Aspect 7-20: The method of Aspect 7-1, wherein generating the control signal includes determining the second configuration by calculating an inverse kinematic solution for the robotic delivery system for achieving the second pose.

Aspect 7-21: The method of Aspect 7-20, wherein generating the control signal further includes calculating actuator positions using a model of the robotic delivery system.

Aspect 7-22: The method of Aspect 7-21, further including: subsequent to actuating the robotic delivery system toward the second configuration, receiving a measurement corresponding to a current configuration of the robotic delivery system; calculating a difference between the current configuration and the second configuration; and when the difference exceeds a predetermined threshold, generating and transmitting a second control signal to the drive system of the robotic delivery system, such that, when received by the drive system, the second control signal causes the drive system to further actuate the robotic delivery system toward the second configuration.

Aspect 7-23: The method of Aspect 7-21, further including: subsequent to actuating the robotic delivery system toward the second configuration, receiving a measurement corresponding to a current pose of the implant; calculating a difference between the current pose and the second pose; and when the difference exceeds a predetermined threshold, generating and transmitting a second control signal to the drive system of the robotic delivery system, such that, when received by the drive system, the second control signal causes the drive system to further actuate the robotic delivery system resulting in further movement of the implant toward the second pose.

Aspect 7-24: The method of Aspect 7-21 further including: receiving a selection corresponding to a second frame of reference different from the anatomical frame of reference; receiving a second control input from the user input device for a second transition of the implant, the second transition being relative to the second frame of reference; and operating the robotic delivery system to perform the second transition.

Aspect 7-25: The method of Aspect 7-24, wherein the second frame of reference corresponds to one of a device frame of reference corresponding to a portion of the robotic delivery system and a visualization frame of reference corresponding to a perspective of a visualization presented on a computing device display.

Aspect 8-1: A method including: receiving a control input from a user input device for a transition of an implant coupled to a robotic delivery system, wherein the transition is from a first pose to a second pose and the robotic delivery system has a first configuration when the implant is in the first pose; generating a control signal for transitioning the robotic delivery system from the first configuration into a second configuration, the second configuration resulting in the second pose of the implant; and transmitting the control signal to a drive system of the robotic delivery system, such that, when received by the drive system, the control signal causes the drive system to actuate the robotic delivery system toward the second configuration resulting in movement of the implant toward the second pose, wherein the control input indicates the movement of the implant relative to a visualization frame of reference for a visualization presented on a computing device display, the visualization frame of reference corresponding to a perspective of the visualization as presented on the computing device display.

Aspect 8-2: The method of Aspect 8-1, wherein the visualization is a fluoroscopic image.

Aspect 8-3: The method of Aspect 8-1, wherein the visualization is a computerized tomography (CT) image.

Aspect 8-4: The method of Aspect 8-1, wherein the visualization is an image captured by a medical imaging system.

Aspect 8-5: The method of Aspect 8-1, wherein the visualization is a computer-generated visualization.

Aspect 8-6 The method of Aspect 8-1 further including updating the visualization frame of reference in response to a change in the perspective of the visualization as presented on the computing device display to an updated perspective of the visualization, wherein updating the visualization frame of reference includes updating the visualization frame of reference to correspond to the updated perspective.

Aspect 8-7: The method of Aspect 8-1, wherein the visualization is an ultrasonic image.

Aspect 9-1: A method including: receiving a control input from a user input device for a transition of an implant coupled to a robotic delivery system, wherein the transition is from a first pose to a second pose and the robotic delivery system has a first configuration when the implant is in the first pose; generating a control signal for transitioning the robotic delivery system from the first configuration into a second configuration, the second configuration resulting in the second pose of the implant; and transmitting the control signal to a drive system of the robotic delivery system, such that, when received by the drive system, the control signal causes the drive system to actuate the robotic delivery system toward the second configuration resulting in movement of the implant toward the second pose, wherein the control input indicates the movement of the implant relative to a frame of reference defined relative to the implant.

Aspect 9-2: The method of Aspect 9-1, wherein the implant is a mitral valve replacement implant.

Aspect 9-3: The method of Aspect 9-1, wherein the robotic delivery system is a catheter-based delivery system including an actuatable catheter and the implant is coupled to a distal end of the actuatable catheter.

Aspect 9-4: The method of Aspect 9-1, further including measuring a pose of the implant, wherein measuring the pose of the implant includes locating one or more features of the implant and determining the pose of the implant based on locations of the one or more features of the implant.

Aspect 9-5: The method of Aspect 9-4, wherein locating the one or more features of the implant includes locating the one or more features in image data generated by a medical imaging system.

Aspect 9-6: The method of Aspect 9-1, further including measuring a pose of the implant, wherein measuring the pose of the implant includes locating one or more features of the robotic delivery system and determining the pose of the implant based on locations of the one or more features of the robotic delivery system and known geometric relationships between the implant and the robotic delivery system.

Aspect 9-7: The method of Aspect 9-6, wherein identifying the one or more features of the robotic delivery system includes locating the one or more features of the robotic delivery system in image data generated by a medical imaging system.

Aspect 9-8: The method of Aspect 9-6, wherein identifying the one or more features of the robotic delivery system include locating the one or more features of the robotic delivery system using positional sensor data collected from positional sensors of the robotic delivery system.

Aspect 9-9: The method of Aspect 9-1, wherein the frame of reference is defined relative to a centroid of the implant.

Aspect 10-1: A method including: subsequent to deploying an implant within a patient using an implant deployment section of a robotic delivery system and prior to actuation of the robotic delivery system to move the implant deployment section, determining a limited workspace for the robotic delivery system; and restricting movement of the implant deployment section to the limited workspace.

Aspect 10-2: The method of Aspect 10-1, wherein the limited workspace is defined to reduce contact between the implant deployment section and at least one of the implant and anatomical structures adjacent the implant during retraction of the implant deployment section.

Aspect 10-3: The method of Aspect 10-1, wherein determining the limited workspace includes determining a pose of the implant and the limited workspace is based on a location relative to the implant and the pose.

Aspect 10-4: The method of Aspect 10-3, wherein determining the pose of the implant includes capturing an image of the implant after deployment using a medical imaging system and determining the pose of the implant from the image.

Aspect 10-5: The method of Aspect 10-3, wherein the implant has a longitudinal axis and the location relative to the implant is relative to the longitudinal axis.

Aspect 10-6: The method of Aspect 10-3, wherein the location is relative to a centroid of the implant.

Aspect 10-7: The method of Aspect 10-3, wherein the location is relative to one or more markers of the implant, the one or more markers configured to be visible in images generated by medical imaging systems.

Aspect 10-8: The method of Aspect 10-3, wherein the location is relative to a structural element of the implant.

Aspect 10-9: The method of Aspect 10-3, wherein the limited workspace is a path extending from the location.

Aspect 10-10: The method of Aspect 10-3, wherein the limited workspace is a volume defined relative to the location.

Aspect 10-11: The method of Aspect 10-10, wherein the volume includes an axis extending from the location and the volume increases in lateral cross-section proximally along the axis.

Aspect 10-12: The method of Aspect 10-1, wherein determining the limited workspace includes determining a pose of the implant deployment section.

Aspect 10-13: The method of Aspect 10-1, wherein the limited workspace includes a path extending along a longitudinal axis of the implant deployment section.

Aspect 10-14: The method of Aspect 10-1, wherein the limited workspace includes a volume defined by a longitudinal axis of the implant deployment section.

Aspect 10-15: The method of Aspect 10-14, wherein the volume increases in lateral cross-section proximally along the longitudinal axis.

Aspect 10-16: The method of Aspect 10-1, wherein the limited workspace is a predefined path defined relative to the implant.

Aspect 10-17: The method of Aspect 10-1, wherein the limited workspace is a predefined volume defined relative to the implant.

Aspect 10-18: The method of Aspect 10-1, wherein the implant is a mitral valve replacement implant deployed within a mitral valve of a patient.

Aspect 10-19: The method of Aspect 10-18, wherein the mitral valve replacement implant has a longitudinal axis, the mitral valve replacement implant defines an annulus plane perpendicular to the longitudinal axis, and the limited workspace includes a path segment extending along the longitudinal axis.

Aspect 10-20: The method of Aspect 10-18, wherein the mitral valve replacement implant has a longitudinal axis, the mitral valve replacement implant defines an annulus plane perpendicular to the longitudinal axis, and the limited workspace includes a volume extending around the longitudinal axis.

Aspect 10-21: The method of Aspect 10-20, wherein the volume includes an axis extending from the annulus plane and the volume increases in lateral cross-section proximally along the axis.

Aspect 10-22: The method of Aspect 10-20, wherein the limited workspace is a predefined path defined relative to the mitral valve replacement implant.

Aspect 10-23: The method of Aspect 10-20, wherein the limited workspace is a predefined volume defined relative to the mitral valve replacement implant.

Aspect 10-24: The method of Aspect 10-1, further including: prior to deployment of the implant, coordinating movement of the implant by the robotic delivery system based on a first frame of reference; and subsequent to deployment of the implant, coordinating movement of the implant by the robotic delivery system based on a second frame of reference different from the first frame of reference.

Aspect 11-1: A system for delivering a cardiac valve replacement implant, the system including: a catheter assembly including a catheter; a handle assembly coupled to the catheter, the handle assembly including a spool and a tendon extending from the spool to a location of the catheter for steering the catheter; and a drive assembly, the drive assembly including: a motor module including a motor having a motor shaft, the motor shaft coupleable to the spool such that actuation of the motor rotates the spool to steer the catheter; a carriage coupled to and supporting the motor module; and a carriage base, wherein the carriage is each of longitudinally translatable along the carriage base to control insertion of the catheter assembly and rotatable relative to the carriage base to control rotation of the catheter assembly.

Aspect 11-2: The system of Aspect 11-1, wherein the tendon is a first tendon, the handle assembly further including a second spool and a second tendon extending from the second spool to a second location of the catheter, the second tendon operable to be antagonistic to the first tendon.

Aspect 11-3: The system of Aspect 11-1, wherein the handle assembly includes the spool is part of a spool pair and the handle assembly includes a plurality of spool pairs, each spool pair including respective tendons for controlling a respective steering action of the catheter.

Aspect 11-4: The system of Aspect 11-3, wherein the catheter includes a distal portion including a proximal steering section and a distal steering section and wherein the plurality of spool pairs includes: a first spool pair for controlling steering of the proximal steering section along a lateral plane, a second spool pair for controlling steering of the distal steering section along the lateral plane, and a third spool pair for controlling steering of the distal steering section along an anterior-posterior plane orthogonal to the lateral plane.

Aspect 11-5: The system of Aspect 11-1, wherein: the catheter includes a catheter body and an articulable distal section coupled to a distal end of the catheter body, the articulable distal section including a proximal steering section and a distal steering section, and the articulable distal section further includes a plurality of sensors distributed along the articulable distal section, the plurality of sensors configured to provide position data for the articulable distal section Aspect 11-6: The system of Aspect 11-1, wherein the motor includes a braking system configured to lock rotation of the motor shaft in response to a fault of the system.

Aspect 11-7: The system of Aspect 11-1, wherein the motor includes an absolute encoder configured to measure absolute rotational position of the motor shaft during operation.

X. CONCLUSION

Various modifications and additions can be made to the exemplary implementations discussed without departing from the scope of the present invention. For example, while the implementations described above refer to particular features, the scope of this invention also includes embodiments having different combinations of features and implementations that do not include all of the described features. Accordingly, the scope of the present invention is intended to embrace all such alternatives, modifications, and variations together with all equivalents thereof.

While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an implementation in the present disclosure can be references to the same implementation or any implementation; and such references mean at least one of the implementations.

Reference to "one implementation" or "an implementation" means that a particular feature, structure, or characteristic described in connection with the implementation is included in at least one implementation of the disclosure. The appearances of the phrase "in one implementation" in various places in the specification are not necessarily all referring to the same implementation, nor are separate or alternative implementations mutually exclusive of other implementations.

Moreover, various features are described which may be exhibited by some implementations and not by others.

The terms used in this specification generally have their ordinary meanings in the art, within the context of the disclosure, and in the specific context where each term is used.

Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any example term. Likewise, the disclosure is not limited to various implementations given in this specification.

Without intent to limit the scope of the disclosure, examples of instruments, apparatus, methods, and their related results according to the implementations of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

What is claimed:

1. A system for delivery of a cardiac implant, the system comprising:
    a catheter including:
        a handle assembly including a cable control assembly and a furl assembly;
        a tubular body assembly extending distally from the handle assembly and deflectable by operation of the cable control assembly, the tubular body assembly including a sheath, an inner tubular body and a rotor configured to interface with the cardiac implant; and
        a sheath retraction assembly coupled to a proximal end of the tubular body assembly and configured to selectively retract the sheath of the tubular body assembly, wherein the furl assembly is configured to rotate the rotor of the tubular body;
    a robot including:

a linear displacement platform; and
a carriage coupled to the linear displacement platform and including a drive motor assembly, the carriage at least one of linearly displaceable along the linear displacement platform and rotatable relative to the linear displacement platform; and
a manual pull wire assembly,
wherein the handle assembly couples to the carriage such that the cable control assembly interfaces with the drive motor assembly of the carriage to facilitate operation of the cable control assembly by the robot, and
wherein the cable control assembly of the handle assembly interfaces with the manual pull wire assembly to facilitate alternative operation of the cable control assembly by the manual pull wire assembly, and
wherein the cable control assembly must be disengaged from the carriage of the robot to operate the cable control assembly with the manual pull wire assembly.

2. The system of claim 1, wherein:
the drive motor assembly is a first drive motor assembly,
the carriage further includes a second drive motor assembly,
the handle assembly includes a handle frame, and
the cable control assembly includes:
  a first control spindle extending through the handle frame and coupled to a first actuation cable, the first control spindle rotatable by the first drive motor assembly to wind and unwind the first actuation cable to deflect a portion of the tubular body assembly, and
  a second control spindle extending through the handle frame and coupled to a second actuation cable, the second control spindle rotatable by the second drive motor assembly to wind and unwind the second actuation cable.

3. The system of claim 2, wherein the second drive motor assembly is configured to operate such that the second actuation cable is antagonistic to the first actuation cable.

4. The system of claim 2, wherein the first control spindle is further rotatable by the manual pull wire assembly to wind and unwind the first actuation cable to deflect a portion of the tubular body assembly, and the second control spindle is further rotatable by the manual pull wire assembly to wind and unwind the second actuation cable.

5. The system of claim 4, wherein the manual pull wire assembly is configured to operate such that the second actuation cable is antagonistic to the first actuation cable.

6. The system of claim 4, wherein torque remains constant across operation of the first and second actuation cables.

7. The system of claim 4, wherein one of the first and second actuation cables may be operated by the manual pull wire assembly and another of the first and second actuation cables may be operated by the respective drive motor assembly of the carriage.

8. The system of claim 1, wherein the sheath is linearly displaceable along the inner tubular body such that a distal end of the sheath is displaceable relative to a distal tip of the inner tubular body.

9. The system of claim 8, wherein the sheath retraction assembly includes:
the sheath,
a sheath nose block coupled to a proximal end of the sheath,
one or more guide shafts,
a sheath mount block coupled to and supporting the sheath nose block, the one or more guide shafts extending through the sheath mount block, and
a lead screw coupled to the sheath mount block and configured to drive the sheath mount block along the one or more guide shafts in response to rotation of the lead screw.

10. The system of claim 9, wherein:
the lead screw includes a lead screw gear protruding from an underside of a handle frame of the handle assembly, and
the carriage includes a motor gear box including a drive gear, the motor gear box configured to be actuated to rotate the drive gear and drive the lead screw.

11. The system of claim 1, wherein the furl assembly includes a capstan gear coupled to the rotor such that rotation of the capstan gear results in rotation of the rotor.

12. The system of claim 11, wherein:
the capstan gear protrudes from an underside of a handle frame of the handle assembly, and
the carriage includes a motor gear box including a drive gear, the motor gear box configured to be actuated to rotate the drive gear and drive the capstan gear.

13. The system of claim 11, wherein the furl assembly further includes a furl indicator configured to be drivable with the capstan gear and visible at the handle assembly.

14. The system of claim 11, wherein the furl assembly further includes a furl lock movable between a first position in which the which the capstan gear is free to rotate and a second position in which rotation of the capstan gear is restricted.

15. The system of claim 14, wherein the furl lock comprises a ratcheting lever such that, when the furl lock is in the second position, the ratcheting lever engages the capstan gear and is movable to permit rotation of the capstan gear in a first direction while preventing rotation of the capstan gear in a second direction opposite the first direction.

16. The system of claim 14, wherein the furl lock assembly further includes a furl lock release pin that selectively engages the furl lock to prevent movement of the furl lock, thereby preventing rotation of the capstan gear in the first direction.

17. The system of claim 1, wherein:
the cable control assembly is a first cable control assembly operable to deflect a first portion of the tubular body assembly,
the handle assembly includes a second cable control assembly operable to deflect a second portion of the tubular body assembly,
the carriage includes a second drive motor assembly, and
the handle assembly is coupled to the carriage such that the second cable control assembly interfaces with the second drive motor assembly of the carriage to facilitate operation of the second cable control assembly by the robot.

18. The system of claim 1, wherein:
the cable control assembly is a first cable control assembly operable to deflect a first portion of the tubular body assembly,
the handle assembly includes a second cable control assembly operable to deflect a second portion of the tubular body assembly,
the carriage is a first carriage,
the robot includes a second carriage coupled to the linear displacement platform and including a second drive motor assembly, the second carriage at least one of linearly displaceable along the linear displacement platform and rotatable relative to the linear displacement platform, and the handle assembly is further coupled to the second carriage such that the second cable control assembly interfaces with the second drive motor assembly of the second carriage to facilitate operation of the second cable control assembly by the robot.

19. The system of claim 18, wherein:
the sheath retraction assembly is operable to selectively retract the sheath of the tubular body assembly by rotation of a lead screw,
the lead screw includes a lead screw gear driven by a motor gear box of the first carriage,
the furl assembly includes a capstan gear coupled to a rotor of the tubular body assembly such that rotation of the capstan gear results in rotation of the rotor, and
the capstan gear is driven by a motor gear box of the second carriage.

20. The system of claim 1, wherein the manual pull wire assembly is removably interfaceable with the handle assembly.

21. The system of claim 1, wherein at least one of the manual pull wire assembly and the handle assembly comprise a brake assembly to lock operation of the handle assembly and prevent deflection of the catheter.

22. The system of claim 1, wherein the manual pull wire assembly is operable to control the handle assembly to deliver the catheter and a cardiac implant within a patient.

23. The system of claim 1, wherein the manual pull wire assembly is operable to remove the catheter and a cardiac implant from a patient.

24. The system of claim 1, wherein the cable control assembly may be operated along one or more axes by the drive motor assembly of the carriage and along one or more alternate axes by the manual pull wire assembly.

25. A system for delivery of a cardiac implant, the system comprising:
a catheter including:
a handle assembly including a cable control assembly and a furl assembly;
a tubular body assembly extending distally from the handle assembly and deflectable by operation of the cable control assembly, the tubular body assembly including a sheath, an inner tubular body and a rotor configured to interface with the cardiac implant; and
a sheath retraction assembly coupled to a proximal end of the tubular body assembly and configured to selectively retract the sheath of the tubular body assembly, wherein the furl assembly is configured to rotate the rotor of the tubular body;
a robot including:
a linear displacement platform; and
a carriage coupled to the linear displacement platform and including a drive motor assembly, the carriage at least one of linearly displaceable along the linear displacement platform and rotatable relative to the linear displacement platform; and
a manual pull wire assembly,
wherein the handle assembly couples to the carriage such that the cable control assembly interfaces with the drive motor assembly of the carriage to facilitate operation of the cable control assembly by the robot,
wherein the sheath is linearly displaceable along the inner tubular body such that a distal end of the sheath is displaceable relative to a distal tip of the inner tubular body; and
wherein the cable control assembly of the handle assembly interfaces with the manual pull wire assembly to facilitate alternative operation of the cable control assembly by the manual pull wire assembly, and
wherein the sheath retraction assembly includes:
the sheath,
a sheath nose block coupled to a proximal end of the sheath,
one or more guide shafts,
a sheath mount block coupled to and supporting the sheath nose block, the one or more guide shafts extending through the sheath mount block, and
a lead screw coupled to the sheath mount block and configured to drive the sheath mount block along the one or more guide shafts in response to rotation of the lead screw.

26. The system of claim 25, wherein:
the lead screw includes a lead screw gear protruding from an underside of a handle frame of the handle assembly, and
the carriage includes a motor gear box including a drive gear, the motor gear box configured to be actuated to rotate the drive gear and drive the lead screw.

27. A system for delivery of a cardiac implant, the system comprising:
a catheter including:
a handle assembly including a cable control assembly and a furl assembly;
a tubular body assembly extending distally from the handle assembly and deflectable by operation of the cable control assembly, the tubular body assembly including a sheath, an inner tubular body and a rotor configured to interface with the cardiac implant; and
a sheath retraction assembly coupled to a proximal end of the tubular body assembly and configured to selectively retract the sheath of the tubular body assembly, wherein the furl assembly is configured to rotate the rotor of the tubular body;
a robot including:
a linear displacement platform; and
a carriage coupled to the linear displacement platform and including a drive motor assembly, the carriage at least one of linearly displaceable along the linear displacement platform and rotatable relative to the linear displacement platform; and
a manual pull wire assembly,
wherein the handle assembly couples to the carriage such that the cable control assembly interfaces with the drive motor assembly of the carriage to facilitate operation of the cable control assembly by the robot, and
wherein the cable control assembly of the handle assembly interfaces with the manual pull wire assembly to facilitate alternative operation of the cable control assembly by the manual pull wire assembly, and
wherein the furl assembly includes a capstan gear coupled to the rotor such that rotation of the capstan gear results in rotation of the rotor.

28. The system of claim 27, wherein the furl assembly further includes a furl indicator configured to be drivable with the capstan gear and visible at the handle assembly.

29. The system of claim 27, wherein the furl assembly further includes a furl lock movable between a first position in which the which the capstan gear is free to rotate and a second position in which rotation of the capstan gear is restricted.

30. A system for delivery of a cardiac implant, the system comprising:

a catheter including:
- a handle assembly including a cable control assembly and a furl assembly;
- a tubular body assembly extending distally from the handle assembly and deflectable by operation of the cable control assembly, the tubular body assembly including a sheath, an inner tubular body and a rotor configured to interface with the cardiac implant; and
- a sheath retraction assembly coupled to a proximal end of the tubular body assembly and configured to selectively retract the sheath of the tubular body assembly, wherein the furl assembly is configured to rotate the rotor of the tubular body;

a robot including:
- a linear displacement platform; and
- a carriage coupled to the linear displacement platform and including a drive motor assembly, the carriage at least one of linearly displaceable along the linear displacement platform and rotatable relative to the linear displacement platform; and a manual pull wire assembly, wherein the handle assembly couples to the carriage such that the cable control assembly interfaces with the drive motor assembly of the carriage to facilitate operation of the cable control assembly by the robot, and wherein the cable control assembly of the handle assembly interfaces with the manual pull wire assembly to facilitate alternative operation of the cable control assembly by the manual pull wire assembly, wherein:
- the cable control assembly is a first cable control assembly operable to deflect a first portion of the tubular body assembly,
- the handle assembly includes a second cable control assembly operable to deflect a second portion of the tubular body assembly,
- the carriage is a first carriage,
- the robot includes a second carriage coupled to the linear displacement platform and including a second drive motor assembly, the second carriage at least one of linearly displaceable along the linear displacement platform and rotatable relative to the linear displacement platform, and
- the handle assembly is further coupled to the second carriage such that the second cable control assembly interfaces with the second drive motor assembly of the second carriage to facilitate operation of the second cable control assembly by the robot, and wherein:
- the sheath retraction assembly is operable to selectively retract the sheath of the tubular body assembly by rotation of a lead screw,
- the lead screw includes a lead screw gear driven by a motor gear box of the first carriage,
- the furl assembly includes a capstan gear coupled to a rotor of the tubular body assembly such that rotation of the capstan gear results in rotation of the rotor, and
- the capstan gear is driven by a motor gear box of the second carriage.

* * * * *